US009816097B2

(12) United States Patent
Raab et al.

(10) Patent No.: US 9,816,097 B2
(45) Date of Patent: Nov. 14, 2017

(54) STRONG CONSTITUTIVE PROMOTERS FOR HETEROLOGOUS EXPRESSION OF PROTEINS IN PLANTS

(71) Applicant: AGRIVIDA, INC., Medford, MA (US)

(72) Inventors: R. Michael Raab, Arlington, MA (US); Oleg Bougri, Boise, ID (US)

(73) Assignee: AGRIVIDA, INC., Medford, MA (US)

( * ) Notice: Subject to any disclaimer, the term of this patent is extended or adjusted under 35 U.S.C. 154(b) by 180 days.

(21) Appl. No.: 14/400,600

(22) PCT Filed: May 29, 2013

(86) PCT No.: PCT/US2013/043148
§ 371 (c)(1),
(2) Date: Nov. 12, 2014

(87) PCT Pub. No.: WO2013/181271
PCT Pub. Date: Dec. 5, 2013

(65) Prior Publication Data

US 2015/0225735 A1 Aug. 13, 2015

Related U.S. Application Data

(60) Provisional application No. 61/652,628, filed on May 29, 2012.

(51) Int. Cl.

*C12N 15/113* (2010.01)
*C12N 15/82* (2006.01)
*C12N 9/42* (2006.01)

(52) U.S. Cl.
CPC ....... *C12N 15/8216* (2013.01); *C12N 9/2437* (2013.01); *C12N 15/113* (2013.01); *C12N 15/8251* (2013.01)

(58) Field of Classification Search
None
See application file for complete search history.

(56) References Cited

U.S. PATENT DOCUMENTS

| | | | | |
|---|---|---|---|---|
| 8,604,276 B2 | 12/2013 | Stewart et al. | | |
| 2011/0111442 A1* | 5/2011 | Shen | C12N 9/2437 | 435/18 |
| 2011/0167514 A1* | 7/2011 | Brover | A23L 1/10 | 800/278 |
| 2012/0040409 A1* | 2/2012 | Hau | C12N 15/74 | 435/99 |
| 2012/0258503 A1* | 10/2012 | Raab | C12N 9/2437 | 435/99 |
| 2013/0340116 A1* | 12/2013 | Stewart | C07K 14/415 | 800/279 |

OTHER PUBLICATIONS

Clontech. GenomeWalker Universal Kit User Manual. Clontech Laboratories. 2007. pp. 1-30.*

(Continued)

*Primary Examiner* — Ashley K Buran
(74) *Attorney, Agent, or Firm* — Volpe and Koenig, P.C.

(57) ABSTRACT

Nucleic acid promoters isolated from *Panicum virgatum* capable of transcriptional activation of heterologous nucleic acids are provided. Constructs, vectors and transgenic plants that include nucleic acid promoters are described. Methods for producing heterologous proteins in transgenic plants by transforming the plants with vectors and constructs are also provided.

28 Claims, 22 Drawing Sheets

Normalized GUS expression

WT | ZmUbi1:GUS | PvUbi3:GUS | PvUbi4:GUS | PvUbi4s:GUS

(56) References Cited

OTHER PUBLICATIONS

Coll et al., "Lack of repeatable differential expression patterns between MON810 and comparable commercial varieties of maize", Plant Mol Biol (2008) 68: pp. 105-117.

Mann et al.; "Switchgrass (*Panicum virgatum* L.) polyubiquitin gene (PvUbi1 and PvUbi2) promoters for use in plant transformation", BMC Biotechnology (2011) 11: pp. 74.

Manoli et al.; "Evaluation of candidate reference genes for qPCR in maize", Journal of Plant Physiology 169 (2012) pp. 807-815.

Hubert Sytykiewicz; "Expression Patterns of Glutathione Transferase Gene (Gstl) in Maize Seedlings Under Juglone-Induced Oxidative Stress", Int. J. Mol. Sci. (2011) vol. 12, pp. 7982-7995.

Vyroubalova et al., "Characterization of New Maize Genes Putatively Involved in Cytokinin Metabolism and Their Expression during Osmotic Stress in Relation to Cytokinin Levels1[W]", Plant Physiol. (2009) vol. 151, pp. 433-447.

* cited by examiner

SEQUENCE LISTING

```
<160> NUMBER OF SEQ ID NOS: 37

<210> SEQ ID NO 1
<211> LENGTH: 2267
<212> TYPE: DNA
<213> ORGANISM: Panicum virgatum
<220> FEATURE:
<221> NAME/KEY: promoter
<222> LOCATION: (1)..(2267)
<223> OTHER INFORMATION: PvUbi3

<400> SEQUENCE: 1

acgaccggag gagagattct ttgctttgct tgtggctgcg aaggaggagg agaaaccacg      60

ccgcggataa gaaggaaacc gcctttgcaa aaccagaaca tcttttctga tgaagaaatc     120

cgcgttgcct cctgtgagaa gaatgcgacc cttttttat actctattat atctttatta      180
```

```
ttattgtcaa tttgtcatgt cactgagaaa tgaccctgat acgaacggtc atttttgata    240
attcttgttt ctattgtctt gacgattcta atgccatgtc cttttgtctt gacagctcta    300
gtgccatgtc tatttgtcat gttatcattt gttcttttta tttcaaggaa aattattaca    360
tcaaaaaatt gattttcgaa gttcacggtc atcttcacca tcactctcta ccgcattggt    420
ggcgagaagc atatctagtg gtttcattct ggtaagcctc gctcaaatga aatttgtaat    480
aaaatactat atttctttat caaggttata agatatggag agaaatggtc tgcttcataa    540
atttgactta catagagcct ttaaaaagga ataccatgta atctaaactc tataacataa    600
agagctttgc gcttttaaaa atatgctaac ctatataaat cgcttttgct agagacaggt    660
catgtatgat tgaagcgtca ccataacgcc gttaatcttc cgtccagcca ttaacggcca    720
cctaccgcag gaaacaaacg gcgtcaccat cctcgatatc tccgcggcgg ccgctggctt    780
ttttcggaga aattgcgcgg tggggacgga gtccacgaga gcctctcgcc gctgggcccc    840
acaatcaatg gcgtgacctc acgggacgcc tccctccctc taccctcccc ccgtgtataa    900
atagcacccc tccctcgcct cttccgcatc cagtattcca gtccccaatc cgtcgagaaa    960
ttctcgcgag cgatcgaaat ctaagcgaag cgaagaggcc tccccagatc ctctcaaggt   1020
atgcgagagc atcgatcccc ttccgatcta tatcgcgtgt cctccctgtt cttgttcttc   1080
gtcgatctag tttagggttt gatttggttc tgaatcgaac ccttttcctg cttgcgttcg   1140
atttgtactc gatcctcggg tagaggtgtg gatctgcggg gcgtgatgag gtagtttggt   1200
gtagatttgt tctgggcgtt cgatttgcca ctagggttcg gctgctgttg gcattcctga   1260
tcgagcggcc ggataggatt gtttttccct ttttatatgt tggatgcgtg atggttcctg   1320
tgtgttgggt tagattgctg gtacgattca tctaggtggt gatttgcaga ggaacaactt   1380
tgctgttgaa tattggtagg tctatctaga tttattactt ttgattatcg cctgataagg   1440
atcaccgatt cgtgtagaat aaattatttc attgttgggt catgtagata tagctgcaca   1500
atttcttact tggctcctta ctgtgtgaat tgtagaataa actgtgttac tctatgagtt   1560
tttctggatt gctggatcca gttaggccag tgctgtcaat ttgttatggc tgttaatgta   1620
ataattttct ggattgttgg cctgcttctc ttcatgttta atcacgtgat ggttcatgat   1680
gcctgttggg ttagattgtt tgttcaattc atctaggcag tgctgtgcag agtacaactc   1740
gattgatgtt taatcttggt agcttcatct agatttgtac aaattttggt cacctgatga   1800
tgatcaccga ttgttgtgga attatttctt aactggttcg ttgttagtca ccaccttact   1860
tgtagaataa cctgtggtac tgcttttctg ttctgtttta ggccacatca tatgattgtc   1920
aaaaatttac atggtagttt aatgataaaa ttagttcagc ttacttcagt ttgatttgct   1980
tcatattttg ttttctgttc tattaatgat acttcatgaa atgtttgttt tttctctgtt   2040
cagatttgac atgtttcagt atcataataa taatattctg tatcctttat agtttgttgg   2100
catgatttgc tttgaattta gttagcctat tctgttaata taggatgata agctgtgagg   2160
cgttcattct cttcagtcca gagttatcat tttcagtgtt ttaatgttgt ttatcaagct   2220
ggatgtatat ggtggtttaa ctcttttctg tttcttactg tttgcag                 2267
```

<210> SEQ ID NO 2
<211> LENGTH: 3581
<212> TYPE: DNA
<213> ORGANISM: Panicum virgatum
<220> FEATURE:
<221> NAME/KEY: promoter
<222> LOCATION: (1)..(3581)

<223> OTHER INFORMATION: PvUbi4

<400> SEQUENCE: 2

```
ctggcctaac ctaaaatcag ttcttgctgc tgggtggttg ggtacattat ctgacaacta     60
ggatccacat caaaaaaaaa aagactacta cgatcatcat ggagtccttc gcaacggcag    120
ctgggcagac accttcagag ttcagagtcc acgcacacac taataaaggg gtccatttgc    180
ctgcttcgtt ccggctgaaa tttttacgaa ccggtcatcc gtaaccacga taatcgatat    240
ggaccaagag agacaaaaat aatctcggaa catcgttagc aagtccaaat ggaacgcaac    300
cagagacatg ttgtttgcct tcatccttca tacacaaccc acctggccac ctccatgtcc    360
atgatttttt ttccccaatc gaccttggac aaccaccaag gaattccttg tcagttgtta    420
gcatggatga cagttcaagc cgggcagctg gcgtgtccgt tcagacatca tcgtcctgcc    480
agaactccat ccacgcgagc ccgctgaacc aagggagcct ttgcgtttgc cctttggcca    540
cggcatcgtt cagctcattc cctcaacaga tcaactgaac ccagcgcgcg aagttagcac    600
cggagcgcaa tgcgagccgt gcccgtgtct tcctcccagc tcctccagcg caagcaagac    660
gacgaccgga ggagagattc tttgctttgc ttgtggctgc gaaggaggag gagaaaccac    720
gcagcggata agaaggaagc cgcctttgca aaaccagagc atcttttctg atgaagaaat    780
ccgcgttgcc tcctgtgaga agaatgcgac ccttttttta tactctattc tatctttatt    840
attattgtca atttgtcatg tcactgagaa atggccctga tacgaacgct aagatccaat    900
catacacctt ttatttattt atacataagt acgtaaataa gatgaaaata aaaaaaatgt    960
catggacgaa aacaacgtcc acaaggacgg caaagatgga ggaccgcagg agcacaacgg   1020
atggatgttc tttttttgtt atcaaacaac ggatggatgt ttccgagcag gtgcagcgtc   1080
tcctccgttt actcgccgtg cacatcacgg cgtccaaacg ggcgtttgcc ggcgaggaca   1140
cggtagattt tgccgacatg gtagatttta tcaagatatt ccggtcgagt ttggagtact   1200
agctccatca tgtataacca ccaatgattg agtggtgacc atatcataat cgttggtcag   1260
ctttccttcc attacttttt aattcagtaa taataatccc taaagcctaa tcaagtaaat   1320
tcaacttccg aattcaatag ggatcatcag ggcacgacct gattgtaaag acatacaata   1380
gctttcaaac aacattttca cttatggtaa aatcttaatt aaggtcttaa tattataatt   1440
atttttttca ctgccgtgag ggaatggaga tttcagaaag ggactttttg gtatcatcat   1500
tgtatatgat ccacggtttt tagttagggc gactttaatt tcttattttt gataattctt   1560
gtttctattg tcttgacgat tctaatgcca tgtccttttg tcttgacagc tctagtgcca   1620
tgtctatttg tcatgttatc atttgttctt tttatttcaa ggaaaattat tacatcaaaa   1680
aattgatttt cgaagttcac ggtcatcttc accatcactc tctatcgcat tggtggcgag   1740
aagcatatct agtggtttca ttctggtaag cctcgctcaa atgaaatttg taataaaata   1800
ctatatttct ttatcaaggt tataagatat ggagagaaat ggtctgcttc ataaatttga   1860
cttacctaga gcctttaaaa aggaatacca tgtaatctaa actctataac ataaagagct   1920
ttgcgctttt aaaaatatgc taacctatat aaatcgcttt tgctagagac aggtcatgta   1980
tgattgaagc gtcaccataa cgccgttaat cttccgtcca gccattaacg gccacctacc   2040
gcaggaaaca aacggcgtca ccatcctcga tatctccgcg gcggccgctg gctttttttcg   2100
gagaaattgc gcggtgggga cggagtccac gagagcctct cgccgctggg ccccacaatc   2160
aatggcgtga cctcacggga cggctccctc cctctaccct ccccccgtgt ataaatagca   2220
cccctccctc gcctcttccg catccagtat tccagtcccc aatccgtcga gaaattctcg   2280
```

```
cgagcgatcg aaatctaagc gaagcgaaga ggcctcccca gatcctctca aggtatgcga   2340
gagcatcgat ccccttccga tctatatcgc gtgtcctccc tgttcttgtt cttcgtcgat   2400
ctagtttagg gtttgatttg gttctgaatc gaacccttttt cctgcttgcg ttcgatttgt  2460
actcgatcct cgggtagagg tgtggatctg cggggcgtga tgaggtagtt tggtgtagat   2520
ttgttctggg cgttcgattt gccactaggg ttcggctgct gttggcattc ctgatcgagc   2580
ggccggatag gattgttttt ccctttttat atgttggatg cgtgatggtt cctgtgtgtt   2640
gggttagatt gctggtacga ttcatctagg tggtgatttg cagaggaaca actttgctgt   2700
tgaatattgg taggtctatc tagatttatt actttttgatt atcgcctgat aaggatcacc  2760
gattcgtgta gaataaatta tttcattgtt gggtcatgta gatatagctg cacaatttct   2820
tacttggctc cttactgtgt gaattgtaga ataaactgtg ttactctatg agtttttctg   2880
gattgctgga tccagttagg ccagtgctgt caatttgtta tggctgttaa tgtaataatt   2940
ttctggattg ttggcctgct tctcttcatg tttaatcacg tgatggttca tgatgcctgt   3000
tgggttagat tgtttgttca attcatctag gcagtgctgt gcagagtaca actcgattga   3060
tgtttaatct tggtagcttc atctagattt gtacaaattt tggtcacctg atgatgatca   3120
ccgattgttg tggaattatt tcttaactgg ttcgttgtta gtcaccacct tacttgtaga   3180
ataacctgtg gtactgcttt tctgttctgt tttaggccac atcatatgat tgtcaaaaat   3240
ttacatggta gtttaatgat aaaattagtt cagcttactt cagtttgatt tgcttcatat   3300
tttgttttct gttctattaa tgatacttca tgaaatgttt gttttttctc tgttcagatt   3360
tgacatgttt cagtatcata ataataatat tctgtatcct ttatagtttg ttggcatgat   3420
ttgctttgaa tttagttagc ctattctgtt aatataggat gataagctgt gaggcgttca   3480
ttctcttcag tccagagtta tcattttcag tgttttaatg ttgtttatca agctggatgt   3540
atatggtggt ttaactcttt tctgtttctt actgtttgca g                        3581
```

<210> SEQ ID NO 3
<211> LENGTH: 2920
<212> TYPE: DNA
<213> ORGANISM: Panicum virgatum
<220> FEATURE:
<221> NAME/KEY: promoter
<222> LOCATION: (1)..(2920)
<223> OTHER INFORMATION: PvUbi4s

<400> SEQUENCE: 3

```
acgaccggag gagagattct ttgctttgct tgtggctgcg aaggaggagg agaaaccacg     60
cagcggataa gaaggaagcc gcctttgcaa aaccagagca tcttttctga tgaagaaatc    120
cgcgttgcct cctgtgagaa gaatgcgacc cttttttat actctattct atctttatta     180
ttattgtcaa tttgtcatgt cactgagaaa tggccctgat acgaacgcta agatccaatc    240
atacaccttt tatttattta tacataagta cgtaaataag atgaaaataa aaaaaatgtc    300
atggacgaaa acaacgtcca caaggacggc aaagatggag gaccgcagga gcacaacgga    360
tggatgttct ttttttgtta tcaaacaacg gatggatgtt tccgagcagg tgcagcgtct    420
cctccgttta ctcgccgtgc acatcacggc gtccaaacgg gcgtttgccg gcgaggacac    480
ggtagatttt gccgacatgg tagattttat caagatattc cggtcgagtt tggagtacta    540
gctccatcat gtataaccac caatgattga gtggtgacca tatcataatc gttggtcagc    600
tttccttcca ttacttttta attcagtaat aataatccct aaagcctaat caagtaaatt    660
```

```
caacttccga attcaatagg gatcatcagg gcacgacctg attgtaaaga catacaatag    720

ctttcaaaca acattttcac ttatggtaaa atcttaatta aggtcttaat attataatta    780

tttttttcac tgccgtgagg gaatggagat ttcagaaagg gactttttgg tatcatcatt    840

gtatatgatc cacggttttt agttagggcg actttaattt cttatttttg ataattcttg    900

tttctattgt cttgacgatt ctaatgccat gtccttttgt cttgacagct ctagtgccat    960

gtctatttgt catgttatca tttgttcttt ttatttcaag gaaaattatt acatcaaaaa   1020

attgattttc gaagttcacg gtcatcttca ccatcactct ctatcgcatt ggtggcgaga   1080

agcatatcta gtggtttcat tctggtaagc ctcgctcaaa tgaaatttgt aataaaatac   1140

tatatttctt tatcaaggtt ataagatatg gagagaaatg gtctgcttca taaatttgac   1200

ttacctagag cctttaaaaa ggaataccat gtaatctaaa ctctataaca taaagagctt   1260

tgcgctttta aaaatatgct aacctatata aatcgctttt gctagagaca ggtcatgtat   1320

gattgaagcg tcaccataac gccgttaatc ttccgtccag ccattaacgg ccacctaccg   1380

caggaaacaa acggcgtcac catcctcgat atctccgcgg cggccgctgg ctttttttcgg   1440

agaaattgcg cggtggggac ggagtccacg agagcctctc gccgctgggc cccacaatca   1500

atggcgtgac ctcacgggac ggctccctcc ctctaccctc cccccgtgta taaatagcac   1560

ccctccctcg cctcttccgc atccagtatt ccagtcccca atccgtcgag aaattctcgc   1620

gagcgatcga aatctaagcg aagcgaagag gcctccccag atcctctcaa ggtatgcgag   1680

agcatcgatc cccttccgat ctatatcgcg tgtcctccct gttcttgttc ttcgtcgatc   1740

tagtttaggg tttgatttgg ttctgaatcg aaccctttc ctgcttgcgt tcgatttgta   1800

ctcgatcctc gggtagaggt gtggatctgc ggggcgtgat gaggtagttt ggtgtagatt   1860

tgttctgggc gttcgatttg ccactagggt tcggctgctg ttggcattcc tgatcgagcg   1920

gccggatagg attgtttttc cctttttata tgttggatgc gtgatggttc ctgtgtgttg   1980

ggttagattg ctggtacgat tcatctaggt ggtgatttgc agaggaacaa ctttgctgtt   2040

gaatattggt aggtctatct agatttatta cttttgatta tcgcctgata aggatcaccg   2100

attcgtgtag aataaattat ttcattgttg ggtcatgtag atatagctgc acaatttctt   2160

acttggctcc ttactgtgtg aattgtagaa taaactgtgt tactctatga gtttttctgg   2220

attgctggat ccagttaggc cagtgctgtc aatttgttat ggctgttaat gtaataattt   2280

tctggattgt tggcctgctt ctcttcatgt ttaatcacgt gatggttcat gatgcctgtt   2340

gggttagatt gtttgttcaa ttcatctagg cagtgctgtg cagagtacaa ctcgattgat   2400

gtttaatctt ggtagcttca tctagatttg tacaaatttt ggtcacctga tgatgatcac   2460

cgattgttgt ggaattattt cttaactggt tcgttgttag tcaccacctt acttgtagaa   2520

taacctgtgg tactgctttt ctgttctgtt ttaggccaca tcatatgatt gtcaaaaatt   2580

tacatggtag tttaatgata aaattagttc agcttacttc agtttgattt gcttcatatt   2640

ttgttttctg ttctattaat gatacttcat gaaatgtttg ttttttctct gttcagattt   2700

gacatgtttc agtatcataa taataatatt ctgtatcctt tatagtttgt tggcatgatt   2760

tgctttgaat ttagttagcc tattctgtta atataggatg ataagctgtg aggcgttcat   2820

tctcttcagt ccagagttat cattttcagt gttttaatgt tgtttatcaa gctggatgta   2880

tatggtggtt taactctttt ctgtttctta ctgtttgcag                          2920
```

<210> SEQ ID NO 4
<211> LENGTH: 2037

<212> TYPE: DNA
<213> ORGANISM: Panicum virgatum
<220> FEATURE:
<221> NAME/KEY: misc_feature
<222> LOCATION: (1)..(2037)
<223> OTHER INFORMATION: 2037bp region PvUbi3

<400> SEQUENCE: 4

```
atttttgata attcttgttt ctattgtctt gacgattcta atgccatgtc cttttgtctt     60
gacagctcta gtgccatgtc tatttgtcat gttatcattt gttcttttta tttcaaggaa    120
aattattaca tcaaaaaatt gattttcgaa gttcacggtc atcttcacca tcactctcta    180
ccgcattggt ggcgagaagc atatctagtg gtttcattct ggtaagcctc gctcaaatga    240
aatttgtaat aaaatactat atttctttat caaggttata agatatggag agaaatggtc    300
tgcttcataa atttgactta catagagcct ttaaaaagga ataccatgta atctaaactc    360
tataacataa agagctttgc gcttttaaaa atatgctaac ctatataaat cgcttttgct    420
agagacaggt catgtatgat tgaagcgtca ccataacgcc gttaatcttc cgtccagcca    480
ttaacggcca cctaccgcag gaaacaaacg gcgtcaccat cctcgatatc tccgcggcgg    540
ccgctggctt ttttcggaga aattgcgcgg tggggacgga gtccacgaga gcctctcgcc    600
gctgggcccc acaatcaatg gcgtgacctc acgggacgcc tccctccctc taccctcccc    660
ccgtgtataa atagcacccc tccctcgcct cttccgcatc cagtattcca gtccccaatc    720
cgtcgagaaa ttctcgcgag cgatcgaaat ctaagcgaag cgaagaggcc tccccagatc    780
ctctcaaggt atgcgagagc atcgatcccc ttccgatcta tatcgcgtgt cctccctgtt    840
cttgttcttc gtcgatctag tttagggttt gatttggttc tgaatcgaac ccttttcctg    900
cttgcgttcg atttgtactc gatcctcggg tagaggtgtg gatctgcggg gcgtgatgag    960
gtagtttggt gtagatttgt tctgggcgtt cgatttgcca ctagggttcg gctgctgttg   1020
gcattcctga tcgagcggcc ggataggatt gtttttccct ttttatatgt tggatgcgtg   1080
atggttcctg tgtgttgggt tagattgctg gtacgattca tctaggtggt gatttgcaga   1140
ggaacaactt tgctgttgaa tattggtagg tctatctaga tttattactt ttgattatcg   1200
cctgataagg atcaccgatt cgtgtagaat aaattatttc attgttgggt catgtagata   1260
tagctgcaca atttcttact tggctcctta ctgtgtgaat tgtagaataa actgtgttac   1320
tctatgagtt tttctggatt gctggatcca gttaggccag tgctgtcaat ttgttatggc   1380
tgttaatgta ataattttct ggattgttgg cctgcttctc ttcatgttta atcacgtgat   1440
ggttcatgat gcctgttggg ttagattgtt tgttcaattc atctaggcag tgctgtgcag   1500
agtacaactc gattgatgtt taatcttggt agcttcatct agatttgtac aaattttggt   1560
cacctgatga tgatcaccga ttgttgtgga attatttctt aactggttcg ttgttagtca   1620
ccaccttact tgtagaataa cctgtggtac tgcttttctg ttctgtttta ggccacatca   1680
tatgattgtc aaaaatttac atggtagttt aatgataaaa ttagttcagc ttacttcagt   1740
ttgatttgct tcatattttg ttttctgttc tattaatgat acttcatgaa atgtttgttt   1800
tttctctgtt cagatttgac atgtttcagt atcataataa taatattctg tatcctttat   1860
agtttgttgg catgatttgc tttgaattta gttagcctat tctgttaata taggatgata   1920
agctgtgagg cgttcattct cttcagtcca gagttatcat tttcagtgtt ttaatgttgt   1980
ttatcaagct ggatgtatat ggtggtttaa ctcttttctg tttcttactg tttgcag      2037
```

<210> SEQ ID NO 5

```
<211> LENGTH: 2037
<212> TYPE: DNA
<213> ORGANISM: Panicum virgatum
<220> FEATURE:
<221> NAME/KEY: misc_feature
<222> LOCATION: (1)..(2037)
<223> OTHER INFORMATION: 2037bp Region PvUbi4

<400> SEQUENCE: 5

atttttgata attcttgttt ctattgtctt gacgattcta atgccatgtc cttttgtctt     60

gacagctcta gtgccatgtc tatttgtcat gttatcattt gttcttttta tttcaaggaa    120

aattattaca tcaaaaaatt gattttcgaa gttcacggtc atcttcacca tcactctcta    180

tcgcattggt ggcgagaagc atatctagtg gtttcattct ggtaagcctc gctcaaatga    240

aatttgtaat aaaatactat atttctttat caaggttata agatatggag agaaatggtc    300

tgcttcataa atttgactta cctagagcct ttaaaaagga ataccatgta atctaaactc    360

tataacataa agagctttgc gcttttaaaa atatgctaac ctatataaat cgcttttgct    420

agagacaggt catgtatgat tgaagcgtca ccataacgcc gttaatcttc cgtccagcca    480

ttaacggcca cctaccgcag gaaacaaacg gcgtcaccat cctcgatatc tccgcggcgg    540

ccgctggctt ttttcggaga aattgcgcgg tggggacgga gtccacgaga gcctctcgcc    600

gctgggcccc acaatcaatg gcgtgacctc acgggacggc tccctccctc taccctcccc    660

ccgtgtataa atagcacccc tccctcgcct cttccgcatc cagtattcca gtccccaatc    720

cgtcgagaaa ttctcgcgag cgatcgaaat ctaagcgaag cgaagaggcc tccccagatc    780

ctctcaaggt atgcgagagc atcgatcccc ttccgatcta tatcgcgtgt cctccctgtt    840

cttgttcttc gtcgatctag tttagggttt gatttggttc tgaatcgaac ccttttcctg    900

cttgcgttcg atttgtactc gatcctcggg tagaggtgtg gatctgcggg gcgtgatgag    960

gtagtttggt gtagatttgt tctgggcgtt cgatttgcca ctagggttcg gctgctgttg   1020

gcattcctga tcgagcggcc ggataggatt gtttttccct ttttatatgt tggatgcgtg   1080

atggttcctg tgtgttgggt tagattgctg gtacgattca tctaggtggt gatttgcaga   1140

ggaacaactt tgctgttgaa tattggtagg tctatctaga tttattactt ttgattatcg   1200

cctgataagg atcaccgatt cgtgtagaat aaattatttc attgttgggt catgtagata   1260

tagctgcaca atttcttact tggctcctta ctgtgtgaat tgtagaataa actgtgttac   1320

tctatgagtt tttctggatt gctggatcca gttaggccag tgctgtcaat ttgttatggc   1380

tgttaatgta ataattttct ggattgttgg cctgcttctc ttcatgttta atcacgtgat   1440

ggttcatgat gcctgttggg ttagattgtt tgttcaattc atctaggcag tgctgtgcag   1500

agtacaactc gattgatgtt taatcttggt agcttcatct agatttgtac aaattttggt   1560

cacctgatga tgatcaccga ttgttgtgga attatttctt aactggttcg ttgttagtca   1620

ccaccttact tgtagaataa cctgtggtac tgcttttctg ttctgtttta ggccacatca   1680

tatgattgtc aaaaatttac atggtagttt aatgataaaa ttagttcagc ttacttcagt   1740

ttgatttgct tcatattttg ttttctgttc tattaatgat acttcatgaa atgtttgttt   1800

tttctctgtt cagatttgac atgtttcagt atcataataa taatattctg tatcctttat   1860

agtttgttgg catgatttgc tttgaattta gttagcctat tctgttaata taggatgata   1920

agctgtgagg cgttcattct cttcagtcca gagttatcat tttcagtgtt ttaatgttgt   1980

ttatcaagct ggatgtatat ggtggtttaa ctcttttctg tttcttactg tttgcag      2037
```

<210> SEQ ID NO 6
<211> LENGTH: 230
<212> TYPE: DNA
<213> ORGANISM: Panicum virgatum
<220> FEATURE:
<221> NAME/KEY: misc_feature
<222> LOCATION: (1)..(230)
<223> OTHER INFORMATION: 230bp Region PvUbi3

<400> SEQUENCE: 6

```
acgaccggag gagagattct ttgctttgct tgtggctgcg aaggaggagg agaaaccacg     60

ccgcggataa gaaggaaacc gcctttgcaa aaccagaaca tcttttctga tgaagaaatc    120

cgcgttgcct cctgtgagaa gaatgcgacc cttttttat actctattat atctttatta     180

ttattgtcaa tttgtcatgt cactgagaaa tgaccctgat acgaacggtc               230
```

<210> SEQ ID NO 7
<211> LENGTH: 230
<212> TYPE: DNA
<213> ORGANISM: Panicum virgatum
<220> FEATURE:
<221> NAME/KEY: misc_feature
<222> LOCATION: (1)..(230)
<223> OTHER INFORMATION: 230bp Region PvUbi4

<400> SEQUENCE: 7

```
acgaccggag gagagattct ttgctttgct tgtggctgcg aaggaggagg agaaaccacg     60

cagcggataa gaaggaagcc gcctttgcaa aaccagagca tcttttctga tgaagaaatc    120

cgcgttgcct cctgtgagaa gaatgcgacc cttttttat actctattct atctttatta     180

ttattgtcaa tttgtcatgt cactgagaaa tggccctgat acgaacgcta               230
```

<210> SEQ ID NO 8
<211> LENGTH: 653
<212> TYPE: DNA
<213> ORGANISM: Panicum virgatum
<220> FEATURE:
<221> NAME/KEY: misc_feature
<222> LOCATION: (1)..(653)
<223> OTHER INFORMATION: 653bp “Unique” Region PvUbi4

<400> SEQUENCE: 8

```
agatccaatc atacaccttt tatttattta tacataagta cgtaaataag atgaaaataa     60

aaaaaatgtc atggacgaaa acaacgtcca caaggacggc aaagatggag gaccgcagga    120

gcacaacgga tggatgttct ttttttgtta tcaaacaacg gatggatgtt tccgagcagg    180

tgcagcgtct cctccgttta ctcgccgtgc acatcacggc gtccaaacgg gcgtttgccg    240

gcgaggacac ggtagatttt gccgacatgg tagattttat caagatattc cggtcgagtt    300

tggagtacta gctccatcat gtataaccac caatgattga gtggtgacca tatcataatc    360

gttggtcagc tttccttcca ttactttta attcagtaat aataatccct aaagcctaat     420

caagtaaatt caacttccga attcaatagg gatcatcagg gcacgacctg attgtaaaga    480

catacaatag ctttcaaaca acattttcac ttatggtaaa atcttaatta aggtcttaat    540

attataatta tttttttcac tgccgtgagg gaatggagat ttcagaaagg gactttttgg    600

tatcatcatt gtatatgatc cacggttttt agttagggcg actttaattt ctt           653
```

<210> SEQ ID NO 9
<211> LENGTH: 91
<212> TYPE: DNA
<213> ORGANISM: Panicum virgatum
<220> FEATURE:

```
<221> NAME/KEY: exon
<222> LOCATION: (1)..(91)
<223> OTHER INFORMATION: 91bp non-coding exon

<400> SEQUENCE: 9

atc cag tat tcc agt ccc caa tcc gtc gag aaa ttc tcg cga gcg atc      48
Ile Gln Tyr Ser Ser Pro Gln Ser Val Glu Lys Phe Ser Arg Ala Ile
1               5                   10                  15

gaa atc taa gcg aag cga aga ggc ctc ccc aga tcc tct caa g            91
Glu Ile     Ala Lys Arg Arg Gly Leu Pro Arg Ser Ser Gln
                20                  25


<210> SEQ ID NO 10
<211> LENGTH: 1249
<212> TYPE: DNA
<213> ORGANISM: Panicum virgatum
<220> FEATURE:
<221> NAME/KEY: Intron
<222> LOCATION: (1)..(1249)
<223> OTHER INFORMATION: 1249bp intron

<400> SEQUENCE: 10

gtatgcgaga gcatcgatcc ccttccgatc tatatcgcgt gtcctccctg ttcttgttct     60

tcgtcgatct agtttagggt ttgatttggt tctgaatcga accctttttcc tgcttgcgtt    120

cgatttgtac tcgatcctcg ggtagaggtg tggatctgcg gggcgtgatg aggtagtttg    180

gtgtagattt gttctgggcg ttcgatttgc cactagggtt cggctgctgt tggcattcct    240

gatcgagcgg ccggatagga ttgtttttcc ctttttatat gttggatgcg tgatggttcc    300

tgtgtgttgg gttagattgc tggtacgatt catctaggtg gtgatttgca gaggaacaac    360

tttgctgttg aatattggta ggtctatcta gatttattac ttttgattat cgcctgataa    420

ggatcaccga ttcgtgtaga ataaattatt tcattgttgg gtcatgtaga tatagctgca    480

caatttctta cttggctcct tactgtgtga attgtagaat aaactgtgtt actctatgag    540

tttttctgga ttgctggatc cagttaggcc agtgctgtca atttgttatg gctgttaatg    600

taataatttt ctggattgtt ggcctgcttc tcttcatgtt taatcacgtg atggttcatg    660

atgcctgttg ggttagattg tttgttcaat tcatctaggc agtgctgtgc agagtacaac    720

tcgattgatg tttaatcttg gtagcttcat ctagatttgt acaaattttg gtcacctgat    780

gatgatcacc gattgttgtg gaattatttc ttaactggtt cgttgttagt caccacctta    840

cttgtagaat aacctgtggt actgcttttc tgttctgttt taggccacat catatgattg    900

tcaaaaattt acatggtagt ttaatgataa aattagttca gcttacttca gtttgatttg    960

cttcatattt tgttttctgt tctattaatg atacttcatg aaatgtttgt tttttctctg   1020

ttcagatttg acatgtttca gtatcataat aataatattc tgtatccttt atagtttgtt   1080

ggcatgattt gctttgaatt tagttagcct attctgttaa tataggatga taagctgtga   1140

ggcgttcatt ctcttcagtc cagagttatc attttcagtg ttttaatgtt gtttatcaag   1200

ctggatgtat atggtggttt aactcttttc tgtttcttac tgtttgcag               1249


<210> SEQ ID NO 11
<211> LENGTH: 14428
<212> TYPE: DNA
<213> ORGANISM: Artificial Sequence
<220> FEATURE:
<223> OTHER INFORMATION: Synthetic construct, pAG4008

<400> SEQUENCE: 11

gatccccggg tagtcagtcc cttatgttac gtcctgtaga aaccccaacc cgtgaaatca     60
```

```
aaaaactcga cggcctgtgg gcattcagtc tggatcgcga aaactgtgga attggtcagc    120
gttggtggga aagcgcgtta caagaaagcc gggcaattgc tgtgccaggc agttttaacg    180
atcagttcgc cgatgcagat attcgtaatt atgcgggcaa cgtctggtat cagcgcgaag    240
tctttatacc gaaaggttgg gcaggccagc gtatcgtgct gcgtttcgat gcggtcactc    300
attacggcaa agtgtgggtc aataatcagg aagtgatgga gcatcagggc ggctatacgc    360
catttgaagc cgatgtcacg ccgtatgtta ttgccgggaa aagtgtacgt aagtttctgc    420
ttctaccttt gatatatata taataattat cattaattag tagtaatata atatttcaaa    480
tatttttttc aaaataaaag aatgtagtat atagcaattg cttttctgta gtttataagt    540
gtgtatattt taatttataa cttttctaat atatgaccaa aatttgttga tgtgcaggta    600
tcaccgtttg tgtgaacaac gaactgaact ggcagactat cccgccggga atggtgatta    660
ccgacgaaaa cggcaagaaa aagcagtctt acttccatga tttctttaac tatgccggaa    720
tccatcgcag cgtaatgctc tacaccacgc cgaacacctg ggtggacgat atcaccgtgg    780
tgacgcatgt cgcgcaagac tgtaaccacg cgtctgttga ctggcaggtg gtggccaatg    840
gtgatgtcag cgttgaactg cgtgatgcgg atcaacaggt ggttgcaact ggacaaggca    900
ctagcgggac tttgcaagtg gtgaatccgc acctctggca accgggtgaa ggttatctct    960
atgaactgtg cgtcacagcc aaaagccaga cagagtgtga tatctacccg cttcgcgtcg   1020
gcatccggtc agtggcagtg aagggcgaac agttcctgat taaccacaaa ccgttctact   1080
ttactggctt tggtcgtcat gaagatgcgg acttacgtgg caaaggattc gataacgtgc   1140
tgatggtgca cgaccacgca ttaatggact ggattggggc caactcctac cgtacctcgc   1200
attaccctta cgctgaagag atgctcgact gggcagatga acatggcatc gtggtgattg   1260
atgaaactgc tgctgtcggc tttaacctct ctttaggcat tggtttcgaa gcgggcaaca   1320
agccgaaaga actgtacagc gaagaggcag tcaacgggga aactcagcaa gcgcacttac   1380
aggcgattaa agagctgata gcgcgtgaca aaaaccaccc aagcgtggtg atgtggagta   1440
ttgccaacga accggatacc cgtccgcaag gtgcacggga atatttcgcg ccactggcgg   1500
aagcaacgcg taaactcgac ccgacgcgtc cgatcacctg cgtcaatgta atgttctgcg   1560
acgctcacac cgataccatc agcgatctct ttgatgtgct gtgcctgaac cgttattacg   1620
gatggtatgt ccaaagcggc gatttggaaa cggcagagaa ggtactggaa aaagaacttc   1680
tggcctggca ggagaaactg catcagccga ttatcatcac cgaatacggc gtggatacgt   1740
tagccgggct gcactcaatg tacaccgaca tgtggagtga agagtatcag tgtgcatggc   1800
tggatatgta tcaccgcgtc tttgatcgcg tcagcgccgt cgtcggtgaa caggtatgga   1860
atttcgccga ttttgcgacc tcgcaaggca tattgcgcgt tggcggtaac aagaaaggga   1920
tcttcactcg cgaccgcaaa ccgaagtcgg cggcttttct gctgcaaaaa cgctggactg   1980
gcatgaactt cggtgaaaaa ccgcagcagg gaggcaaaca atgacctagg tccccgaatt   2040
tccccgatcg ttcaaacatt tggcaataaa gtttcttaag attgaatcct gttgccggtc   2100
ttgcgatgat tatcatataa tttctgttga attacgttaa gcatgtaata attaacatgt   2160
aatgcatgac gttatttatg agatgggttt ttatgattag agtcccgcaa ttatacattt   2220
aatacgcgat agaaaacaaa atatagcgcg caaactagga taaattatcg cgcgcggtgt   2280
catctatgtt actagatcgg gaattggaat tcctgcagtg cagcgtgacc cggtcgtgcc   2340
cctctctaga gataatgagc attgcatgtc taagttataa aaaattacca catatttttt   2400
```

-continued

```
ttgtcacact tgtttgaagt gcagtttatc tatctttata catatattta aactttactc   2460
tacgaataat ataatctata gtactacaat aatatcagtg ttttagagaa tcatataaat   2520
gaacagttag acatggtcta aaggacaatt gagtattttg acaacaggac tctacagttt   2580
tatcttttta gtgtgcatgt gttctccttt ttttttgcaa atagcttcac ctatataata   2640
cttcatccat tttattagta catccattta gggtttaggg ttaatggttt ttatagacta   2700
atttttttag tacatctatt ttattctatt ttagcctcta aattaagaaa actaaaactc   2760
tattttagtt tttttattta ataatttaga tataaaatag aataaaataa agtgactaaa   2820
aattaaacaa ataccettta agaaattaaa aaaactaagg aaacattttt cttgtttcga   2880
gtagataatg ccagcctgtt aaacgccgtc gacgagtcta acggacacca accagcgaac   2940
cagcagcgtc gcgtcgggcc aagcgaagca gacggcacgg catctctgtc gctgcctctg   3000
gacccctctc gagagttccg ctccaccgtt ggacttgctc cgctgtcggc atccagaaat   3060
tgcgtggcgg agcggcagac gtgagccggc acggcaggcg gcctcctcct cctctcacgg   3120
cacggcagct acgggggatt cctttcccac cgctccttcg ctttcccttc ctcgcccgcc   3180
gtaataaata gacacccct ccacaccctc tttccccaac ctcgtgttgt tcggagcgca   3240
cacacacaca accagatctc ccccaaatcc acccgtcggc acctccgctt caaggtacgc   3300
cgctcgtcct cccccccccc ccctctctac cttctctaga tcggcgttcc ggtccatggt   3360
tagggcccgg tagttctact tctgttcatg tttgtgttag atccgtgttt gtgttagatc   3420
cgtgctgcta gcgttcgtac acggatgcga cctgtacgtc agacacgttc tgattgctaa   3480
cttgccagtg tttctctttg gggaatcctg ggatggctct agccgttccg cagacgggat   3540
cgatttcatg atttttttg tttcgttgca tagggtttgg tttgcccttt tcctttattt   3600
caatatatgc cgtgcacttg tttgtcgggt catcttttca tgcttttttt tgtcttggtt   3660
gtgatgatgt ggtctggttg ggcggtcgtt ctagatcgga gtagaattct gtttcaaact   3720
acctggtgga tttattaatt ttggatctgt atgtgtgtgc catacatatt catagttacg   3780
aattgaagat gatggatgga aatatcgatc taggataggt atacatgttg atgcgggttt   3840
tactgatgca tatacagaga tgctttttgt tcgcttggtt gtgatgatgt ggtgtggttg   3900
ggcggtcgtt cattcgttct agatcggagt agaatactgt ttcaaactac ctggtgtatt   3960
tattaatttt ggaactgtat gtgtgtgtca tacatcttca tagttacgag tttaagatgg   4020
atggaaatat cgatctagga taggtataca tgttgatgtg ggttttactg atgcatatac   4080
atgatggcat atgcagcatc tattcatatg ctctaacctt gagtacctat ctattataat   4140
aaacaagtat gttttataat tattttgatc ttgatatact tggatgatgg catatgcagc   4200
agctatatgt ggattttttt agccctgcct tcatacgcta tttatttgct tggtactgtt   4260
tcttttgtcg atgctcaccc tgttgtttgg tgttacttct gcagatgcag aaactcatta   4320
actcagtgca aaactatgcc tggggcagca aaacggcgtt gactgaactt tatggtatgg   4380
aaaatccgtc cagccagccg atggccgagc tgtggatggg cgcacatccg aaaagcagtt   4440
cacgagtgca gaatgccgcc ggagatatcg tttcactgcg tgatgtgatt gagagtgata   4500
aatcgactct gctcggagag gccgttgcca aacgctttgg cgaactgcct ttcctgttca   4560
aagtattatg cgcagcacag ccactctcca ttcaggttca tccaaacaaa cacaattctg   4620
aaatcggttt tgccaaagaa aatgccgcag gtatcccgat ggatgccgcc gagcgtaact   4680
ataaagatcc taaccacaag ccggagctgg tttttgcgct gacgcctttc cttgcgatga   4740
acgcgtttcg tgaattttcc gagattgtct ccctactcca gccggtcgca ggtgcacatc   4800
```

```
cggcgattgc tcacttttta caacagcctg atgccgaacg tttaagcgaa ctgttcgcca   4860
gcctgttgaa tatgcagggt gaagaaaaat cccgcgcgct ggcgatttta aaatcggccc   4920
tcgatagcca gcagggtgaa ccgtggcaaa cgattcgttt aatttctgaa ttttacccgg   4980
aagacagcgg tctgttctcc ccgctattgc tgaatgtggt gaaattgaac cctggcgaag   5040
cgatgttcct gttcgctgaa acaccgcacg cttacctgca aggcgtggcg ctggaagtga   5100
tggcaaactc cgataacgtg ctgcgtgcgg gtctgacgcc taaatacatt gatattccgg   5160
aactggttgc caatgtgaaa ttcgaagcca aaccggctaa ccagttgttg acccagccgg   5220
tgaaacaagg tgcagaactg gacttcccga ttccagtgga tgattttgcc ttctcgctgc   5280
atgaccttag tgataaagaa accaccatta gccagcagag tgccgccatt ttgttctgcg   5340
tcgaaggcga tgcaacgttg tggaaaggtt ctcagcagtt acagcttaaa ccgggtgaat   5400
cagcgtttat tgccgccaac gaatcaccgg tgactgtcaa aggccacggc cgtttagcgc   5460
gtgtttacaa caagctgtaa gagcttactg aaaaaattaa catctcttgc taagctggga   5520
gctctagatc cccgaatttc cccgatcgtt caaacatttg gcaataaagt ttcttaagat   5580
tgaatcctgt tgccggtctt gcgatgatta tcatataatt tctgttgaat tacgttaagc   5640
atgtaataat taacatgtaa tgcatgacgt tatttatgag atgggttttt atgattagag   5700
tcccgcaatt atacatttaa tacgcgatag aaaacaaaat atagcgcgca aactaggata   5760
aattatcgcg cgcggtgtca tctatgttac tagatcggga attggcgagc tcgaattaat   5820
tcagtacatt aaaaacgtcc gcaatgtgtt attaagttgt ctaagcgtca atttgtttac   5880
accacaatat atcctgccac cagccagcca acagctcccc gaccggcagc tcggcacaaa   5940
atcaccactc gatacaggca gcccatcagt ccgggacggc gtcagcggga gagccgttgt   6000
aaggcggcag actttgctca tgttaccgat gctattcgga agaacggcaa ctaagctgcc   6060
gggtttgaaa cacggatgat ctcgcggagg gtagcatgtt gattgtaacg atgacagagc   6120
gttgctgcct gtgatcaaat atcatctccc tcgcagagat ccgaattatc agccttctta   6180
ttcatttctc gcttaaccgt gacaggctgt cgatcttgag aactatgccg acataatagg   6240
aaatcgctgg ataaagccgc tgaggaagct gagtggcgct atttctttag aagtgaacgt   6300
tgacgatcgt cgaccgtacc ccgatgaatt aattcggacg tacgttctga acacagctgg   6360
atacttactt gggcgattgt catacatgac atcaacaatg tacccgtttg tgtaaccgtc   6420
tcttggaggt tcgtatgaca ctagtggttc ccctcagctt gcgactagat gttgaggcct   6480
aacattttat tagagagcag gctagttgct tagatacatg atcttcaggc cgttatctgt   6540
cagggcaagc gaaaattggc catttatgac gaccaatgcc ccgcagaagc tcccatcttt   6600
gccgccatag acgccgcgcc ccccttttgg ggtgtagaac atccttttgc cagatgtgga   6660
aaagaagttc gttgtcccat tgttggcaat gacgtagtag ccggcgaaag tgcgagaccc   6720
atttgcgcta tatataagcc tacgatttcc gttgcgacta ttgtcgtaat tggatgaact   6780
attatcgtag ttgctctcag agttgtcgta atttgatgga ctattgtcgt aattgcttat   6840
ggagttgtcg tagttgcttg gagaaatgtc gtagttggat ggggagtagt catagggaag   6900
acgagcttca tccactaaaa caattggcag gtcagcaagt gcctgccccg atgccatcgc   6960
aagtacgagg cttagaacca ccttcaacag atcgcgcata gtcttcccca gctctctaac   7020
gcttgagtta agccgcgccg cgaagcggcg tcggcttgaa cgaattgtta gacattattt   7080
gccgactacc ttggtgatct cgcctttcac gtagtgaaca aattcttcca actgatctgc   7140
```

-continued

```
gcgcgaggcc aagcgatctt cttgtccaag ataagcctgc ctagcttcaa gtatgacggg   7200
ctgatactgg gccggcaggc gctccattgc ccagtcggca gcgacatcct tcggcgcgat   7260
tttgccggtt actgcgctgt accaaatgcg ggacaacgta agcactacat ttcgctcatc   7320
gccagcccag tcgggcggcg agttccatag cgttaaggtt tcatttagcg cctcaaatag   7380
atcctgttca ggaaccggat caaagagttc ctccgccgct ggacctacca aggcaacgct   7440
atgttctctt gcttttgtca gcaagatagc cagatcaatg tcgatcgtgg ctggctcgaa   7500
gatacctgca agaatgtcat tgcgctgcca ttctccaaat tgcagttcgc gcttagctgg   7560
ataacgccac ggaatgatgt cgtcgtgcac aacaatggtg acttctacag cgcggagaat   7620
ctcgctctct ccaggggaag ccgaagtttc caaaaggtcg ttgatcaaag ctcgccgcgt   7680
tgtttcatca agccttacgg tcaccgtaac cagcaaatca atatcactgt gtggcttcag   7740
gccgccatcc actgcggagc cgtacaaatg tacggccagc aacgtcggtt cgagatggcg   7800
ctcgatgacg ccaactacct ctgatagttg agtcgatact tcggcgatca ccgcttccct   7860
catgatgttt aactcctgaa ttaagccgcg ccgcgaagcg gtgtcggctt gaatgaattg   7920
ttaggcgtca tcctgtgctc ccgagaacca gtaccagtac atcgctgttt cgttcgagac   7980
ttgaggtcta gttttatacg tgaacaggtc aatgccgccg agagtaaagc cacattttgc   8040
gtacaaattg caggcaggta cattgttcgt ttgtgtctct aatcgtatgc caaggagctg   8100
tctgcttagt gcccactttt tcgcaaattc gatgagactg tgcgcgactc ctttgcctcg   8160
gtgcgtgtgc gacacaacaa tgtgttcgat agaggctaga tcgttccatg ttgagttgag   8220
ttcaatcttc ccgacaagct cttggtcgat gaatgcgcca tagcaagcag agtcttcatc   8280
agagtcatca tccgagatgt aatccttccg gtaggggctc acacttctgg tagatagttc   8340
aaagccttgg tcggataggt gcacatcgaa cacttcacga acaatgaaat ggttctcagc   8400
atccaatgtt tccgccacct gctcagggat caccgaaatc ttcatatgac gcctaacgcc   8460
tggcacagcg gatcgcaaac ctggcgcggc ttttggcaca aaaggcgtga caggtttgcg   8520
aatccgttgc tgccacttgt taaccctttt gccagatttg gtaactataa tttatgttag   8580
aggcgaagtc ttgggtaaaa actggcctaa aattgctggg gatttcagga aagtaaacat   8640
caccttccgg ctcgatgtct attgtagata tatgtagtgt atctacttga tcgggggatc   8700
tgctgcctcg cgcgtttcgg tgatgacggt gaaaacctct gacacatgca gctcccggag   8760
acggtcacag cttgtctgta agcggatgcc gggagcagac aagcccgtca gggcgcgtca   8820
gcgggtgttg gcgggtgtcg gggcgcagcc atgacccagt cacgtagcga tagcggagtg   8880
tatactggct taactatgcg gcatcagagc agattgtact gagagtgcac catatgcggt   8940
gtgaaatacc gcacagatgc gtaaggagaa aataccgcat caggcgctct tccgcttcct   9000
cgctcactga ctcgctgcgc tcggtcgttc ggctgcggcg agcggtatca gctcactcaa   9060
aggcggtaat acggttatcc acagaatcag gggataacgc aggaaagaac atgtgagcaa   9120
aaggccagca aaaggccagg aaccgtaaaa aggccgcgtt gctggcgttt ttccataggc   9180
tccgcccccc tgacgagcat cacaaaaatc gacgctcaag tcagaggtgg cgaaacccga   9240
caggactata aagataccag gcgtttcccc ctggaagctc cctcgtgcgc tctcctgttc   9300
cgaccctgcc gcttaccgga tacctgtccg cctttctccc ttcgggaagc gtggcgcttt   9360
ctcatagctc acgctgtagg tatctcagtt cggtgtaggt cgttcgctcc aagctgggct   9420
gtgtgcacga accccccgtt cagcccgacc gctgcgcctt atccggtaac tatcgtcttg   9480
agtccaaccc ggtaagacac gacttatcgc cactggcagc agccactggt aacaggatta   9540
```

```
gcagagcgag gtatgtaggc ggtgctacag agttcttgaa gtggtggcct aactacggct   9600
acactagaag gacagtattt ggtatctgcg ctctgctgaa gccagttacc ttcggaaaaa   9660
gagttggtag ctcttgatcc ggcaaacaaa ccaccgctgg tagcggtggt ttttttgttt   9720
gcaagcagca gattacgcgc agaaaaaaag gatctcaaga agatcctttg atcttttcta   9780
cggggtctga cgctcagtgg aacgaaaact cacgttaagg gattttggtc atgagattat   9840
caaaaaggat cttcacctag atccttttaa attaaaaatg aagttttaaa tcaatctaaa   9900
gtatatatga gtaaacttgg tctgacagtt accaatgctt aatcagtgag gcacctatct   9960
cagcgatctg tctatttcgt tcatccatag ttgcctgact ccccgtcgtg tagataacta  10020
cgatacggga gggcttacca tctggcccca gtgctgcaat gataccgcga gacccacgct  10080
caccggctcc agatttatca gcaataaacc agccagccgg aagggccgag cgcagaagtg  10140
gtcctgcaac tttatccgcc tccatccagt ctattaattg ttgccgggaa gctagagtaa  10200
gtagttcgcc agttaatagt ttgcgcaacg ttgttgccat tgctgcaggg gggggggggg  10260
gggggttcca ttgttcattc cacggacaaa aacagagaaa ggaaacgaca gaggccaaaa  10320
agctcgcttt cagcacctgt cgtttccttt cttttcagag ggtattttaa ataaaaacat  10380
taagttatga cgaagaagaa cggaaacgcc ttaaaccgga aattttcat aaatagcgaa  10440
aacccgcgag gtcgccgccc cgtaacctgt cggatcaccg gaaaggaccc gtaaagtgat  10500
aatgattatc atctacatat cacaacgtgc gtggaggcca tcaaaccacg tcaaataatc  10560
aattatgacg caggtatcgt attaattgat ctgcatcaac ttaacgtaaa aacaacttca  10620
gacaatacaa atcagcgaca ctgaatacgg ggcaacctca tgtccccccc cccccccccc  10680
tgcaggcatc gtggtgtcac gctcgtcgtt tggtatggct tcattcagct ccggttccca  10740
acgatcaagg cgagttacat gatcccccat gttgtgcaaa aaagcggtta gctccttcgg  10800
tcctccgatc gttgtcagaa gtaagttggc cgcagtgtta tcactcatgg ttatggcagc  10860
actgcataat tctcttactg tcatgccatc cgtaagatgc ttttctgtga ctggtgagta  10920
ctcaaccaag tcattctgag aatagtgtat gcggcgaccg agttgctctt gcccggcgtc  10980
aacacgggat aataccgcgc cacatagcag aactttaaaa gtgctcatca ttggaaaacg  11040
ttcttcgggg cgaaaactct caaggatctt accgctgttg agatccagtt cgatgtaacc  11100
cactcgtgca cccaactgat cttcagcatc ttttactttc accagcgttt ctgggtgagc  11160
aaaaacagga aggcaaaatg ccgcaaaaaa gggaataagg gcgacacgga aatgttgaat  11220
actcatactc ttcctttttc aatattattg aagcatttat cagggttatt gtctcatgag  11280
cggatacata tttgaatgta tttagaaaaa taaacaaata ggggttccgc gcacatttcc  11340
ccgaaaagtg ccacctgacg tctaagaaac cattattatc atgacattaa cctataaaaa  11400
taggcgtatc acgaggccct ttcgtcttca agaattggtc gacgatcttg ctgcgttcgg  11460
atattttcgt ggagttcccg ccacagaccc ggattgaagg cgagatccag caactcgcgc  11520
cagatcatcc tgtgacggaa ctttggcgcg tgatgactgg ccaggacgtc ggccgaaaga  11580
gcgacaagca gatcacgctt ttcgacagcg tcggatttgc gatcgaggat ttttcggcgc  11640
tgcgctacgt ccgcgaccgc gttgagggat caagccacag cagcccactc gaccttctag  11700
ccgacccaga cgagccaagg gatctttttg gaatgctgct ccgtcgtcag gctttccgac  11760
gtttgggtgg ttgaacagaa gtcattatcg cacggaatgc caagcactcc cgaggggaac  11820
cctgtggttg gcatgcacat acaaatggac gaacggataa accttttcac gccctttttaa  11880
```

```
atatccgatt attctaataa acgctctttt ctcttaggtt tacccgccaa tatatcctgt  11940
caaacactga tagtttaaac tgaaggcggg aaacgacaac ctgatcatga gcggagaatt  12000
aagggagtca cgttatgacc cccgccgatg acgcgggaca agccgtttta cgtttggaac  12060
tgacagaacc gcaacgttga aggagccact cagcttaatt aagtctaact cgagttactg  12120
gtacgtacca aatccatgga atcaaggtac cacgaccgga ggagagattc tttgctttgc  12180
ttgtggctgc gaaggaggag gagaaaccac gccgcggata agaaggaaac cgcctttgca  12240
aaaccagaac atcttttctg atgaagaaat ccgcgttgcc tcctgtgaga agaatgcgac  12300
cctttttta tactctatta tatctttatt attattgtca atttgtcatg tcactgagaa  12360
atgaccctga tacgaacggt catttttgat aattcttgtt tctattgtct tgacgattct  12420
aatgccatgt ccttttgtct tgacagctct agtgccatgt ctatttgtca tgttatcatt  12480
tgttcttttt atttcaagga aaattattac atcaaaaaat tgattttcga agttcacggt  12540
catcttcacc atcactctct accgcattgg tggcgagaag catatctagt ggtttcattc  12600
tggtaagcct cgctcaaatg aaatttgtaa taaaatacta tatttcttta tcaaggttat  12660
aagatatgga gagaaatggt ctgcttcata aatttgactt acatagagcc tttaaaaagg  12720
aataccatgt aatctaaact ctataacata aagagctttg cgcttttaaa aatatgctaa  12780
cctatataaa tcgcttttgc tagagacagg tcatgtatga ttgaagcgtc accataacgc  12840
cgttaatctt ccgtccagcc attaacggcc acctaccgca ggaaacaaac ggcgtcacca  12900
tcctcgatat ctccgcggcg gccgctggct tttttcggag aaattgcgcg gtggggacgg  12960
agtccacgag agcctctcgc cgctgggccc cacaatcaat ggcgtgacct cacgggacgc  13020
ctccctccct ctaccctccc cccgtgtata aatagcaccc ctccctcgcc tcttccgcat  13080
ccagtattcc agtccccaat ccgtcgagaa attctcgcga gcgatcgaaa tctaagcgaa  13140
gcgaagaggc ctccccagat cctctcaagg tatgcgagag catcgatccc cttccgatct  13200
atatcgcgtg tcctccctgt tcttgttctt cgtcgatcta gtttagggtt tgatttggtt  13260
ctgaatcgaa cccttttcct gcttgcgttc gatttgtact cgatcctcgg gtagaggtgt  13320
ggatctgcgg ggcgtgatga ggtagtttgg tgtagatttg ttctgggcgt tcgatttgcc  13380
actagggttc ggctgctgtt ggcattcctg atcgagcggc cggataggat tgtttttccc  13440
tttttatatg ttggatgcgt gatggttcct gtgtgttggg ttagattgct ggtacgattc  13500
atctaggtgg tgatttgcag aggaacaact ttgctgttga atattggtag gtctatctag  13560
atttattact tttgattatc gcctgataag gatcaccgat tcgtgtagaa taaattattt  13620
cattgttggg tcatgtagat atagctgcac aatttcttac ttggctcctt actgtgtgaa  13680
ttgtagaata aactgtgtta ctctatgagt tttctggat tgctggatcc agttaggcca  13740
gtgctgtcaa tttgttatgg ctgttaatgt aataattttc tggattgttg gcctgcttct  13800
cttcatgttt aatcacgtga tggttcatga tgcctgttgg gttagattgt ttgttcaatt  13860
catctaggca gtgctgtgca gagtacaact cgattgatgt ttaatcttgg tagcttcatc  13920
tagatttgta caaattttgg tcacctgatg atgatcaccg attgttgtgg aattatttct  13980
taactggttc gttgttagtc accaccttac ttgtagaata acctgtggta ctgcttttct  14040
gttctgtttt aggccacatc atatgattgt caaaaattta catggtagtt taatgataaa  14100
attagttcag cttacttcag tttgatttgc ttcatatttt gttttctgtt ctattaatga  14160
tacttcatga aatgtttgtt ttttctctgt tcagatttga catgtttcag tatcataata  14220
ataatattct gtatccttta tagtttgttg gcatgatttg ctttgaattt agttagccta  14280
```

ttctgttaat ataggatgat aagctgtgag gcgttcattc tcttcagtcc agagttatca 14340
ttttcagtgt tttaatgttg tttatcaagc tggatgtata tggtggttta actcttttct 14400
gtttcttact gtttgcagat ccagatcg 14428

<210> SEQ ID NO 12
<211> LENGTH: 15742
<212> TYPE: DNA
<213> ORGANISM: Artificial Sequence
<220> FEATURE:
<223> OTHER INFORMATION: Synthetic construct, pAG4009

<400> SEQUENCE: 12
gatccccggg tagtcagtcc cttatgttac gtcctgtaga aaccccaacc cgtgaaatca 60
aaaaactcga cggcctgtgg gcattcagtc tggatcgcga aaactgtgga attggtcagc 120
gttggtggga aagcgcgtta caagaaagcc gggcaattgc tgtgccaggc agttttaacg 180
atcagttcgc cgatgcagat attcgtaatt atgcgggcaa cgtctggtat cagcgcgaag 240
tctttatacc gaaaggttgg gcaggccagc gtatcgtgct gcgtttcgat gcggtcactc 300
attacggcaa agtgtgggtc aataatcagg aagtgatgga gcatcagggc ggctatacgc 360
catttgaagc cgatgtcacg ccgtatgtta ttgccgggaa aagtgtacgt aagtttctgc 420
ttctaccttt gatatatata taataattat cattaattag tagtaatata atatttcaaa 480
tatttttttc aaaataaaag aatgtagtat atagcaattg cttttctgta gtttataagt 540
gtgtatattt taatttataa cttttctaat atatgaccaa aatttgttga tgtgcaggta 600
tcaccgtttg tgtgaacaac gaactgaact ggcagactat cccgccggga atggtgatta 660
ccgacgaaaa cggcaagaaa aagcagtctt acttccatga tttctttaac tatgccggaa 720
tccatcgcag cgtaatgctc tacaccacgc cgaacacctg ggtggacgat atcaccgtgg 780
tgacgcatgt cgcgcaagac tgtaaccacg cgtctgttga ctggcaggtg gtggccaatg 840
gtgatgtcag cgttgaactg cgtgatgcgg atcaacaggt ggttgcaact ggacaaggca 900
ctagcgggac tttgcaagtg gtgaatccgc acctctggca accgggtgaa ggttatctct 960
atgaactgtg cgtcacagcc aaaagccaga cagagtgtga tatctacccg cttcgcgtcg 1020
gcatccggtc agtggcagtg aagggcgaac agttcctgat taaccacaaa ccgttctact 1080
ttactggctt tggtcgtcat gaagatgcgg acttacgtgg caaaggattc gataacgtgc 1140
tgatggtgca cgaccacgca ttaatggact ggattggggc caactcctac cgtacctcgc 1200
attaccctta cgctgaagag atgctcgact gggcagatga acatggcatc gtggtgattg 1260
atgaaactgc tgctgtcggc tttaacctct ctttaggcat tggtttcgaa gcgggcaaca 1320
agccgaaaga actgtacagc gaagaggcag tcaacgggga aactcagcaa gcgcacttac 1380
aggcgattaa agagctgata gcgcgtgaca aaaaccaccc aagcgtggtg atgtggagta 1440
ttgccaacga accggatacc cgtccgcaag gtgcacggga atatttcgcg ccactggcgg 1500
aagcaacgcg taaactcgac ccgacgcgtc cgatcacctg cgtcaatgta atgttctgcg 1560
acgctcacac cgataccatc agcgatctct ttgatgtgct gtgcctgaac cgttattacg 1620
gatggtatgt ccaaagcggc gatttggaaa cggcagagaa ggtactggaa aaagaacttc 1680
tggcctggca ggagaaactg catcagccga ttatcatcac cgaatacggc gtggatacgt 1740
tagccgggct gcactcaatg tacaccgaca tgtggagtga agagtatcag tgtgcatggc 1800
tggatatgta tcaccgcgtc tttgatcgcg tcagcgccgt cgtcggtgaa caggtatgga 1860

-continued

```
atttcgccga ttttgcgacc tcgcaaggca tattgcgcgt tggcggtaac aagaaaggga   1920
tcttcactcg cgaccgcaaa ccgaagtcgg cggcttttct gctgcaaaaa cgctggactg   1980
gcatgaactt cggtgaaaaa ccgcagcagg gaggcaaaca atgacctagg tccccgaatt   2040
tccccgatcg ttcaaacatt tggcaataaa gtttcttaag attgaatcct gttgccggtc   2100
ttgcgatgat tatcatataa tttctgttga attacgttaa gcatgtaata attaacatgt   2160
aatgcatgac gttatttatg agatgggttt ttatgattag agtcccgcaa ttatacattt   2220
aatacgcgat agaaaacaaa atatagcgcg caaactagga taaattatcg cgcgcggtgt   2280
catctatgtt actagatcgg gaattggaat tcctgcagtg cagcgtgacc cggtcgtgcc   2340
cctctctaga gataatgagc attgcatgtc taagttataa aaaattacca catatttttt   2400
ttgtcacact tgtttgaagt gcagtttatc tatctttata catatattta aactttactc   2460
tacgaataat ataatctata gtactacaat aatatcagtg ttttagagaa tcatataaat   2520
gaacagttag acatggtcta aaggacaatt gagtattttg acaacaggac tctacagttt   2580
tatcttttta gtgtgcatgt gttctccttt ttttttgcaa atagcttcac ctatataata   2640
cttcatccat tttattagta catccattta gggtttaggg ttaatggttt ttatagacta   2700
attttttag tacatctatt ttattctatt ttagcctcta aattaagaaa actaaaactc    2760
tattttagtt tttttattta ataatttaga tataaaatag aataaaataa agtgactaaa   2820
aattaaacaa ataccettta agaaattaaa aaaactaagg aaacattttt cttgtttcga   2880
gtagataatg ccagcctgtt aaacgccgtc gacgagtcta acggacacca accagcgaac   2940
cagcagcgtc gcgtcgggcc aagcgaagca gacggcacgg catctctgtc gctgcctctg   3000
gacccctctc gagagttccg ctccaccgtt ggacttgctc cgctgtcggc atccagaaat   3060
tgcgtggcgg agcggcagac gtgagccggc acggcaggcg gcctcctcct cctctcacgg   3120
cacggcagct acgggggatt cctttcccac cgctccttcg ctttcccttc ctcgcccgcc   3180
gtaataaata gacacccct ccacaccctc tttccccaac ctcgtgttgt tcggagcgca    3240
cacacacaca accagatctc ccccaaatcc acccgtcggc acctccgctt caaggtacgc   3300
cgctcgtcct cccccccccc ccctctctac cttctctaga tcggcgttcc ggtccatggt   3360
tagggcccgg tagttctact tctgttcatg tttgtgttag atccgtgttt gtgttagatc   3420
cgtgctgcta gcgttcgtac acggatgcga cctgtacgtc agacacgttc tgattgctaa   3480
cttgccagtg tttctctttg gggaatcctg ggatggctct agccgttccg cagacgggat   3540
cgatttcatg atttttttg tttcgttgca tagggtttgg tttgcccttt tcctttattt    3600
caatatatgc cgtgcacttg tttgtcgggt catcttttca tgcttttttt tgtcttggtt   3660
gtgatgatgt ggtctggttg ggcggtcgtt ctagatcgga gtagaattct gtttcaaact   3720
acctggtgga tttattaatt ttggatctgt atgtgtgtgc catacatatt catagttacg   3780
aattgaagat gatggatgga aatatcgatc taggataggt atacatgttg atgcgggttt   3840
tactgatgca tatacagaga tgctttttgt tcgcttggtt gtgatgatgt ggtgtggttg   3900
ggcggtcgtt cattcgttct agatcggagt agaatactgt ttcaaactac ctggtgtatt   3960
tattaatttt ggaactgtat gtgtgtgtca tacatcttca tagttacgag tttaagatgg   4020
atggaaatat cgatctagga taggtataca tgttgatgtg ggttttactg atgcatatac   4080
atgatggcat atgcagcatc tattcatatg ctctaacctt gagtacctat ctattataat   4140
aaacaagtat gttttataat tattttgatc ttgatatact tggatgatgg catatgcagc   4200
agctatatgt ggattttttt agccctgcct tcatacgcta tttatttgct tggtactgtt   4260
```

```
tcttttgtcg atgctcaccc tgttgtttgg tgttacttct gcagatgcag aaactcatta   4320
actcagtgca aaactatgcc tggggcagca aaacggcgtt gactgaactt tatggtatgg   4380
aaaatccgtc cagccagccg atggccgagc tgtggatggg cgcacatccg aaaagcagtt   4440
cacgagtgca gaatgccgcc ggagatatcg tttcactgcg tgatgtgatt gagagtgata   4500
aatcgactct gctcggagag gccgttgcca aacgctttgg cgaactgcct ttcctgttca   4560
aagtattatg cgcagcacag ccactctcca ttcaggttca tccaaacaaa cacaattctg   4620
aaatcggttt tgccaaagaa aatgccgcag gtatcccgat ggatgccgcc gagcgtaact   4680
ataaagatcc taaccacaag ccggagctgg tttttgcgct gacgcctttc cttgcgatga   4740
acgcgtttcg tgaattttcc gagattgtct ccctactcca gccggtcgca ggtgcacatc   4800
cggcgattgc tcacttttta caacagcctg atgccgaacg tttaagcgaa ctgttcgcca   4860
gcctgttgaa tatgcagggt gaagaaaaat cccgcgcgct ggcgatttta aaatcggccc   4920
tcgatagcca gcagggtgaa ccgtggcaaa cgattcgttt aatttctgaa ttttacccgg   4980
aagacagcgg tctgttctcc ccgctattgc tgaatgtggt gaaattgaac cctggcgaag   5040
cgatgttcct gttcgctgaa acaccgcacg cttacctgca aggcgtggcg ctggaagtga   5100
tggcaaactc cgataacgtg ctgcgtgcgg gtctgacgcc taaatacatt gatattccgg   5160
aactggttgc caatgtgaaa ttcgaagcca aaccggctaa ccagttgttg acccagccgg   5220
tgaaacaagg tgcagaactg gacttcccga ttccagtgga tgattttgcc ttctcgctgc   5280
atgaccttag tgataaagaa accaccatta gccagcagag tgccgccatt ttgttctgcg   5340
tcgaaggcga tgcaacgttg tggaaaggtt ctcagcagtt acagcttaaa ccgggtgaat   5400
cagcgtttat tgccgccaac gaatcaccgg tgactgtcaa aggccacggc cgtttagcgc   5460
gtgtttacaa caagctgtaa gagcttactg aaaaaattaa catctcttgc taagctggga   5520
gctctagatc cccgaatttc cccgatcgtt caaacatttg gcaataaagt ttcttaagat   5580
tgaatcctgt tgccggtctt gcgatgatta tcatataatt tctgttgaat tacgttaagc   5640
atgtaataat taacatgtaa tgcatgacgt tatttatgag atgggttttt atgattagag   5700
tcccgcaatt atacatttaa tacgcgatag aaaacaaaat atagcgcgca aactaggata   5760
aattatcgcg cgcggtgtca tctatgttac tagatcggga attggcgagc tcgaattaat   5820
tcagtacatt aaaaacgtcc gcaatgtgtt attaagttgt ctaagcgtca atttgtttac   5880
accacaatat atcctgccac cagccagcca acagctcccc gaccggcagc tcggcacaaa   5940
atcaccactc gatacaggca gcccatcagt ccgggacggc gtcagcggga gagccgttgt   6000
aaggcggcag actttgctca tgttaccgat gctattcgga agaacggcaa ctaagctgcc   6060
gggtttgaaa cacggatgat ctcgcggagg gtagcatgtt gattgtaacg atgacagagc   6120
gttgctgcct gtgatcaaat atcatctccc tcgcagagat ccgaattatc agccttctta   6180
ttcatttctc gcttaaccgt gacaggctgt cgatcttgag aactatgccg acataatagg   6240
aaatcgctgg ataaagccgc tgaggaagct gagtggcgct atttctttag aagtgaacgt   6300
tgacgatcgt cgaccgtacc ccgatgaatt aattcggacg tacgttctga acacagctgg   6360
atacttactt gggcgattgt catacatgac atcaacaatg tacccgtttg tgtaaccgtc   6420
tcttggaggt tcgtatgaca ctagtggttc ccctcagctt gcgactagat gttgaggcct   6480
aacattttat tagagagcag gctagttgct tagatacatg atcttcaggc cgttatctgt   6540
cagggcaagc gaaaattggc catttatgac gaccaatgcc ccgcagaagc tcccatcttt   6600
```

```
gccgccatag acgccgcgcc cccttttgg ggtgtagaac atccttttgc cagatgtgga   6660
aaagaagttc gttgtcccat tgttggcaat gacgtagtag ccggcgaaag tgcgagaccc   6720
atttgcgcta tatataagcc tacgatttcc gttgcgacta ttgtcgtaat tggatgaact   6780
attatcgtag ttgctctcag agttgtcgta atttgatgga ctattgtcgt aattgcttat   6840
ggagttgtcg tagttgcttg gagaaatgtc gtagttggat ggggagtagt catagggaag   6900
acgagcttca tccactaaaa caattggcag gtcagcaagt gcctgccccg atgccatcgc   6960
aagtacgagg cttagaacca ccttcaacag atcgcgcata gtcttcccca gctctctaac   7020
gcttgagtta agccgcgccg cgaagcggcg tcggcttgaa cgaattgtta gacattattt   7080
gccgactacc ttggtgatct cgcctttcac gtagtgaaca aattcttcca actgatctgc   7140
gcgcgaggcc aagcgatctt cttgtccaag ataagcctgc ctagcttcaa gtatgacggg   7200
ctgatactgg gccggcaggc gctccattgc ccagtcggca gcgacatcct tcggcgcgat   7260
tttgccggtt actgcgctgt accaaatgcg ggacaacgta agcactacat ttcgctcatc   7320
gccagcccag tcgggcggcg agttccatag cgttaaggtt tcatttagcg cctcaaatag   7380
atcctgttca ggaaccggat caaagagttc ctccgccgct ggacctacca aggcaacgct   7440
atgttctctt gcttttgtca gcaagatagc cagatcaatg tcgatcgtgg ctggctcgaa   7500
gatacctgca agaatgtcat tgcgctgcca ttctccaaat tgcagttcgc gcttagctgg   7560
ataacgccac ggaatgatgt cgtcgtgcac aacaatggtg acttctacag cgcggagaat   7620
ctcgctctct ccaggggaag ccgaagtttc caaaaggtcg ttgatcaaag ctcgccgcgt   7680
tgtttcatca agccttacgg tcaccgtaac cagcaaatca atatcactgt gtggcttcag   7740
gccgccatcc actgcggagc cgtacaaatg tacggccagc aacgtcggtt cgagatggcg   7800
ctcgatgacg ccaactacct ctgatagttg agtcgatact tcggcgatca ccgcttccct   7860
catgatgttt aactcctgaa ttaagccgcg ccgcgaagcg gtgtcggctt gaatgaattg   7920
ttaggcgtca tcctgtgctc ccgagaacca gtaccagtac atcgctgttt cgttcgagac   7980
ttgaggtcta gttttatacg tgaacaggtc aatgccgccg agagtaaagc cacattttgc   8040
gtacaaattg caggcaggta cattgttcgt ttgtgtctct aatcgtatgc caaggagctg   8100
tctgcttagt gcccactttt tcgcaaattc gatgagactg tgcgcgactc ctttgcctcg   8160
gtgcgtgtgc gacacaacaa tgtgttcgat agaggctaga tcgttccatg ttgagttgag   8220
ttcaatcttc ccgacaagct cttggtcgat gaatgcgcca tagcaagcag agtcttcatc   8280
agagtcatca tccgagatgt aatccttccg gtaggggctc acacttctgg tagatagttc   8340
aaagccttgg tcggataggt gcacatcgaa cacttcacga acaatgaaat ggttctcagc   8400
atccaatgtt tccgccacct gctcagggat caccgaaatc ttcatatgac gcctaacgcc   8460
tggcacagcg gatcgcaaac ctggcgcggc ttttggcaca aaaggcgtga caggtttgcg   8520
aatccgttgc tgccacttgt taaccctttt gccagatttg gtaactataa tttatgttag   8580
aggcgaagtc ttgggtaaaa actggcctaa aattgctggg gatttcagga aagtaaacat   8640
caccttccgg ctcgatgtct attgtagata tatgtagtgt atctacttga tcgggggatc   8700
tgctgcctcg cgcgtttcgg tgatgacggt gaaaacctct gacacatgca gctcccggag   8760
acggtcacag cttgtctgta agcggatgcc gggagcagac aagcccgtca gggcgcgtca   8820
gcgggtgttg gcgggtgtcg gggcgcagcc atgacccagt cacgtagcga tagcggagtg   8880
tatactggct taactatgcg gcatcagagc agattgtact gagagtgcac catatgcggt   8940
gtgaaatacc gcacagatgc gtaaggagaa aataccgcat caggcgctct tccgcttcct   9000
```

```
cgctcactga ctcgctgcgc tcggtcgttc ggctgcggcg agcggtatca gctcactcaa   9060
aggcggtaat acggttatcc acagaatcag gggataacgc aggaaagaac atgtgagcaa   9120
aaggccagca aaaggccagg aaccgtaaaa aggccgcgtt gctggcgttt ttccataggc   9180
tccgcccccc tgacgagcat cacaaaaatc gacgctcaag tcagaggtgg cgaaacccga   9240
caggactata aagataccag gcgtttcccc ctggaagctc cctcgtgcgc tctcctgttc   9300
cgaccctgcc gcttaccgga tacctgtccg cctttctccc ttcgggaagc gtggcgcttt   9360
ctcatagctc acgctgtagg tatctcagtt cggtgtaggt cgttcgctcc aagctgggct   9420
gtgtgcacga accccccgtt cagcccgacc gctgcgcctt atccggtaac tatcgtcttg   9480
agtccaaccc ggtaagacac gacttatcgc cactggcagc agccactggt aacaggatta   9540
gcagagcgag gtatgtaggc ggtgctacag agttcttgaa gtggtggcct aactacggct   9600
acactagaag gacagtattt ggtatctgcg ctctgctgaa gccagttacc ttcggaaaaa   9660
gagttggtag ctcttgatcc ggcaaacaaa ccaccgctgg tagcggtggt ttttttgttt   9720
gcaagcagca gattacgcgc agaaaaaaag gatctcaaga agatcctttg atcttttcta   9780
cggggtctga cgctcagtgg aacgaaaact cacgttaagg gattttggtc atgagattat   9840
caaaaaggat cttcacctag atccttttaa attaaaaatg aagttttaaa tcaatctaaa   9900
gtatatatga gtaaacttgg tctgacagtt accaatgctt aatcagtgag gcacctatct   9960
cagcgatctg tctatttcgt tcatccatag ttgcctgact ccccgtcgtg tagataacta  10020
cgatacggga gggcttacca tctggcccca gtgctgcaat gataccgcga gacccacgct  10080
caccggctcc agatttatca gcaataaacc agccagccgg aagggccgag cgcagaagtg  10140
gtcctgcaac tttatccgcc tccatccagt ctattaattg ttgccgggaa gctagagtaa  10200
gtagttcgcc agttaatagt ttgcgcaacg ttgttgccat tgctgcaggg gggggggggg  10260
gggggttcca ttgttcattc cacggacaaa aacagagaaa ggaaacgaca gaggccaaaa  10320
agctcgcttt cagcacctgt cgtttccttt cttttcagag ggtattttaa ataaaaacat  10380
taagttatga cgaagaagaa cggaaacgcc ttaaaccgga aattttcat aaatagcgaa  10440
aacccgcgag gtcgccgccc cgtaacctgt cggatcaccg gaaaggaccc gtaaagtgat  10500
aatgattatc atctacatat cacaacgtgc gtggaggcca tcaaaccacg tcaaataatc  10560
aattatgacg caggtatcgt attaattgat ctgcatcaac ttaacgtaaa aacaacttca  10620
gacaatacaa atcagcgaca ctgaatacgg ggcaacctca tgtccccccc cccccccccc  10680
tgcaggcatc gtggtgtcac gctcgtcgtt tggtatggct tcattcagct ccggttccca  10740
acgatcaagg cgagttacat gatcccccat gttgtgcaaa aaagcggtta gctccttcgg  10800
tcctccgatc gttgtcagaa gtaagttggc cgcagtgtta tcactcatgg ttatggcagc  10860
actgcataat tctcttactg tcatgccatc cgtaagatgc ttttctgtga ctggtgagta  10920
ctcaaccaag tcattctgag aatagtgtat gcggcgaccg agttgctctt gcccggcgtc  10980
aacacgggat aataccgcgc cacatagcag aactttaaaa gtgctcatca ttggaaaacg  11040
ttcttcgggg cgaaaactct caaggatctt accgctgttg agatccagtt cgatgtaacc  11100
cactcgtgca cccaactgat cttcagcatc ttttactttc accagcgttt ctgggtgagc  11160
aaaaacagga aggcaaaatg ccgcaaaaaa gggaataagg gcgacacgga aatgttgaat  11220
actcatactc ttcctttttc aatattattg aagcatttat cagggttatt gtctcatgag  11280
cggatacata tttgaatgta tttagaaaaa taaacaaata ggggttccgc gcacatttcc  11340
```

```
ccgaaaagtg ccacctgacg tctaagaaac cattattatc atgacattaa cctataaaaa  11400
taggcgtatc acgaggccct ttcgtcttca agaattggtc gacgatcttg ctgcgttcgg  11460
atattttcgt ggagttcccg ccacagaccc ggattgaagg cgagatccag caactcgcgc  11520
cagatcatcc tgtgacggaa ctttggcgcg tgatgactgg ccaggacgtc ggccgaaaga  11580
gcgacaagca gatcacgctt ttcgacagcg tcggatttgc gatcgaggat tttcggcgc  11640
tgcgctacgt ccgcgaccgc gttgagggat caagccacag cagcccactc gaccttctag  11700
ccgacccaga cgagccaagg gatcttttg gaatgctgct ccgtcgtcag gctttccgac  11760
gtttgggtgg ttgaacagaa gtcattatcg cacggaatgc caagcactcc cgaggggaac  11820
cctgtggttg gcatgcacat acaaatggac gaacggataa accttttcac gccctttaa  11880
atatccgatt attctaataa acgctctttt ctcttaggtt tacccgccaa tatatcctgt  11940
caaacactga tagtttaaac tgaaggcggg aaacgacaac ctgatcatga gcggagaatt  12000
aagggagtca cgttatgacc cccgccgatg acgcgggaca agccgtttta cgtttggaac  12060
tgacagaacc gcaacgttga aggagccact cagcttaatt aagtctaact cgagttactg  12120
gtacgtacca aatccatgga atcaaggtac cctggcctaa cctaaaatca gttcttgctg  12180
ctgggtggtt gggtacatta tctgacaact aggatccaca tcaaaaaaaa aaagactact  12240
acgatcatca tggagtcctt cgcaacggca gctgggcaga caccttcaga gttcagagtc  12300
cacgcacaca ctaataaagg ggtccatttg cctgcttcgt tccggctgaa atttttacga  12360
accggtcatc cgtaaccacg ataatcgata tggaccaaga gagacaaaaa taatctcgga  12420
acatcgttag caagtccaaa tggaacgcaa ccagagacat gttgtttgcc ttcatccttc  12480
atacacaacc cacctggcca cctccatgtc catgattttt tttccccaat cgaccttgga  12540
caaccaccaa ggaattcctt gtcagttgtt agcatggatg acagttcaag ccgggcagct  12600
ggcgtgtccg ttcagacatc atcgtcctgc cagaactcca tccacgcgag cccgctgaac  12660
caagggagcc tttgcgtttg ccctttggcc acggcatcgt tcagctcatt ccctcaacag  12720
atcaactgaa cccagcgcgc gaagttagca ccggagcgca atgcgagccg tgcccgtgtc  12780
ttcctcccag ctcctccagc gcaagcaaga cgacgaccgg aggagagatt ctttgctttg  12840
cttgtggctg cgaaggagga ggagaaacca cgcagcggat aagaaggaag ccgcctttgc  12900
aaaaccagag catcttttct gatgaagaaa tccgcgttgc ctcctgtgag aagaatgcga  12960
ccctttttt atactctatt ctatctttat tattattgtc aatttgtcat gtcactgaga  13020
aatggccctg atacgaacgc taagatccaa tcatacacct tttatttatt tatacataag  13080
tacgtaaata agatgaaaat aaaaaaaatg tcatggacga aaacaacgtc cacaaggacg  13140
gcaaagatgg aggaccgcag gagcacaacg gatggatgtt cttttttgt tatcaaacaa  13200
cggatggatg tttccgagca ggtgcagcgt ctcctccgtt tactcgccgt gcacatcacg  13260
gcgtccaaac gggcgtttgc cggcgaggac acggtagatt ttgccgacat ggtagatttt  13320
atcaagatat tccggtcgag tttggagtac tagctccatc atgtataacc accaatgatt  13380
gagtggtgac catatcataa tcgttggtca gctttccttc cattactttt taattcagta  13440
ataataatcc ctaaagccta atcaagtaaa ttcaacttcc gaattcaata gggatcatca  13500
gggcacgacc tgattgtaaa gacatacaat agctttcaaa caacattttc acttatggta  13560
aaatcttaat taaggtctta atattataat tattttttc actgccgtga gggaatggag  13620
atttcagaaa gggacttttt ggtatcatca ttgtatatga tccacggttt ttagttaggg  13680
cgactttaat ttcttatttt tgataattct tgtttctatt gtcttgacga ttctaatgcc  13740
```

atgtcctttt gtcttgacag ctctagtgcc atgtctattt gtcatgttat catttgttct 13800
ttttatttca aggaaaatta ttacatcaaa aaattgattt tcgaagttca cggtcatctt 13860
caccatcact ctctatcgca ttggtggcga gaagcatatc tagtggtttc attctggtaa 13920
gcctcgctca aatgaaattt gtaataaaat actatatttc tttatcaagg ttataagata 13980
tggagagaaa tggtctgctt cataaatttg acttacctag agcctttaaa aaggaatacc 14040
atgtaatcta aactctataa cataaagagc tttgcgcttt taaaaatatg ctaacctata 14100
taaatcgctt ttgctagaga caggtcatgt atgattgaag cgtcaccata acgccgttaa 14160
tcttccgtcc agccattaac ggccacctac cgcaggaaac aaacggcgtc accatcctcg 14220
atatctccgc ggcggccgct ggcttttttc ggagaaattg cgcggtgggg acggagtcca 14280
cgagagcctc tcgccgctgg gccccacaat caatggcgtg acctcacggg acggctccct 14340
ccctctaccc tccccccgtg tataaatagc acccctccct cgcctcttcc gcatccagta 14400
ttccagtccc caatccgtcg agaaattctc gcgagcgatc gaaatctaag cgaagcgaag 14460
aggcctcccc agatcctctc aaggtatgcg agagcatcga tccccttccg atctatatcg 14520
cgtgtcctcc ctgttcttgt tcttcgtcga tctagtttag ggtttgattt ggttctgaat 14580
cgaacccttt tcctgcttgc gttcgatttg tactcgatcc tcgggtagag gtgtggatct 14640
gcggggcgtg atgaggtagt ttggtgtaga tttgttctgg gcgttcgatt tgccactagg 14700
gttcggctgc tgttggcatt cctgatcgag cggccggata ggattgtttt tcccttttta 14760
tatgttggat gcgtgatggt tcctgtgtgt tgggttagat tgctggtacg attcatctag 14820
gtggtgattt gcagaggaac aactttgctg ttgaatattg gtaggtctat ctagatttat 14880
tacttttgat tatcgcctga taaggatcac cgattcgtgt agaataaatt atttcattgt 14940
tgggtcatgt agatatagct gcacaatttc ttacttggct ccttactgtg tgaattgtag 15000
aataaactgt gttactctat gagtttttct ggattgctgg atccagttag gccagtgctg 15060
tcaatttgtt atggctgtta atgtaataat tttctggatt gttggcctgc ttctcttcat 15120
gtttaatcac gtgatggttc atgatgcctg ttgggttaga ttgtttgttc aattcatcta 15180
ggcagtgctg tgcagagtac aactcgattg atgtttaatc ttggtagctt catctagatt 15240
tgtacaaatt ttggtcacct gatgatgatc accgattgtt gtggaattat ttcttaactg 15300
gttcgttgtt agtcaccacc ttacttgtag aataacctgt ggtactgctt ttctgttctg 15360
ttttaggcca catcatatga ttgtcaaaaa tttacatggt agtttaatga taaaattagt 15420
tcagcttact tcagtttgat ttgcttcata ttttgttttc tgttctatta atgatacttc 15480
atgaaatgtt tgttttttct ctgttcagat ttgacatgtt tcagtatcat aataataata 15540
ttctgtatcc tttatagttt gttggcatga tttgctttga atttagttag cctattctgt 15600
taatatagga tgataagctg tgaggcgttc attctcttca gtccagagtt atcattttca 15660
gtgttttaat gttgtttatc aagctggatg tatatggtgg tttaactctt ttctgtttct 15720
tactgtttgc agatccagat cg 15742

<210> SEQ ID NO 13
<211> LENGTH: 15081
<212> TYPE: DNA
<213> ORGANISM: Artificial Sequence
<220> FEATURE:
<223> OTHER INFORMATION: Synthetic construct, pAG4010

<400> SEQUENCE: 13

```
tatgattgtc aaaaatttac atggtagttt aatgataaaa ttagttcagc ttacttcagt     60
ttgatttgct tcatattttg ttttctgttc tattaatgat acttcatgaa atgtttgttt    120
tttctctgtt cagatttgac atgtttcagt atcataataa taatattctg tatcctttat    180
agtttgttgg catgatttgc tttgaattta gttagcctat tctgttaata taggatgata    240
agctgtgagg cgttcattct cttcagtcca gagttatcat tttcagtgtt ttaatgttgt    300
ttatcaagct ggatgtatat ggtggtttaa ctcttttctg tttcttactg tttgcagatc    360
cagatcggat ccccgggtag tcagtccctt atgttacgtc ctgtagaaac cccaacccgt    420
gaaatcaaaa aactcgacgg cctgtgggca ttcagtctgg atcgcgaaaa ctgtggaatt    480
ggtcagcgtt ggtgggaaag cgcgttacaa gaaagccggg caattgctgt gccaggcagt    540
tttaacgatc agttcgccga tgcagatatt cgtaattatg cgggcaacgt ctggtatcag    600
cgcgaagtct ttataccgaa aggttgggca ggccagcgta tcgtgctgcg tttcgatgcg    660
gtcactcatt acggcaaagt gtgggtcaat aatcaggaag tgatggagca tcagggcggc    720
tatacgccat ttgaagccga tgtcacgccg tatgttattg ccgggaaaag tgtacgtaag    780
tttctgcttc tacctttgat atatatataa taattatcat taattagtag taatataata    840
tttcaaatat ttttttcaaa ataaaagaat gtagtatata gcaattgctt ttctgtagtt    900
tataagtgtg tatattttaa tttataactt ttctaatata tgaccaaaat ttgttgatgt    960
gcaggtatca ccgtttgtgt gaacaacgaa ctgaactggc agactatccc gccgggaatg   1020
gtgattaccg acgaaaacgg caagaaaaag cagtcttact tccatgattt ctttaactat   1080
gccggaatcc atcgcagcgt aatgctctac accacgccga acacctgggt ggacgatatc   1140
accgtggtga cgcatgtcgc gcaagactgt aaccacgcgt ctgttgactg gcaggtggtg   1200
gccaatggtg atgtcagcgt tgaactgcgt gatgcggatc aacaggtggt tgcaactgga   1260
caaggcacta gcgggacttt gcaagtggtg aatccgcacc tctggcaacc gggtgaaggt   1320
tatctctatg aactgtgcgt cacagccaaa agccagacag agtgtgatat ctacccgctt   1380
cgcgtcggca tccggtcagt ggcagtgaag ggcgaacagt tcctgattaa ccacaaaccg   1440
ttctacttta ctggctttgg tcgtcatgaa gatgcggact tacgtggcaa aggattcgat   1500
aacgtgctga tggtgcacga ccacgcatta atggactgga ttggggccaa ctcctaccgt   1560
acctcgcatt acccttacgc tgaagagatg ctcgactggg cagatgaaca tggcatcgtg   1620
gtgattgatg aaactgctgc tgtcggcttt aacctctctt taggcattgg tttcgaagcg   1680
ggcaacaagc cgaaagaact gtacagcgaa gaggcagtca acggggaaac tcagcaagcg   1740
cacttacagg cgattaaaga gctgatagcg cgtgacaaaa accacccaag cgtggtgatg   1800
tggagtattg ccaacgaacc ggatacccgt ccgcaaggtg cacgggaata tttcgcgcca   1860
ctggcggaag caacgcgtaa actcgacccg acgcgtccga tcacctgcgt caatgtaatg   1920
ttctgcgacg ctcacaccga taccatcagc gatctctttg atgtgctgtg cctgaaccgt   1980
tattacggat ggtatgtcca aagcggcgat ttggaaacgg cagagaaggt actggaaaaa   2040
gaacttctgg cctggcagga gaaactgcat cagccgatta tcatcaccga atacggcgtg   2100
gatacgttag ccgggctgca ctcaatgtac accgacatgt ggagtgaaga gtatcagtgt   2160
gcatggctgg atatgtatca ccgcgtcttt gatcgcgtca gcgccgtcgt cggtgaacag   2220
gtatggaatt tcgccgattt tgcgacctcg caaggcatat tgcgcgttgg cggtaacaag   2280
aaagggatct tcactcgcga ccgcaaaccg aagtcggcgg cttttctgct gcaaaaacgc   2340
tggactggca tgaacttcgg tgaaaaaccg cagcagggag gcaaacaatg acctaggtcc   2400
```

```
ccgaatttcc ccgatcgttc aaacatttgg caataaagtt tcttaagatt gaatcctgtt   2460
gccggtcttg cgatgattat catataattt ctgttgaatt acgttaagca tgtaataatt   2520
aacatgtaat gcatgacgtt atttatgaga tgggttttta tgattagagt cccgcaatta   2580
tacatttaat acgcgataga aaacaaaata tagcgcgcaa actaggataa attatcgcgc   2640
gcggtgtcat ctatgttact agatcgggaa ttggaattcc tgcagtgcag cgtgacccgg   2700
tcgtgcccct ctctagagat aatgagcatt gcatgtctaa gttataaaaa attaccacat   2760
atttttttg tcacacttgt ttgaagtgca gtttatctat ctttatacat atatttaaac   2820
tttactctac gaataatata atctatagta ctacaataat atcagtgttt tagagaatca   2880
tataaatgaa cagttagaca tggtctaaag gacaattgag tattttgaca acaggactct   2940
acagttttat ctttttagtg tgcatgtgtt ctcctttttt tttgcaaata gcttcaccta   3000
tataatactt catccatttt attagtacat ccatttaggg tttagggtta atggttttta   3060
tagactaatt tttttagtac atctatttta ttctatttta gcctctaaat taagaaaact   3120
aaaactctat tttagttttt ttatttaata atttagatat aaaatagaat aaaataaagt   3180
gactaaaaat taaacaaata ccctttaaga aattaaaaaa actaaggaaa catttttctt   3240
gtttcgagta gataatgcca gcctgttaaa cgccgtcgac gagtctaacg gacaccaacc   3300
agcgaaccag cagcgtcgcg tcgggccaag cgaagcagac ggcacggcat ctctgtcgct   3360
gcctctggac ccctctcgag agttccgctc caccgttgga cttgctccgc tgtcggcatc   3420
cagaaattgc gtggcggagc ggcagacgtg agccggcacg gcaggcggcc tcctcctcct   3480
ctcacggcac ggcagctacg gggggattcct ttcccaccgc tccttcgctt tcccttcctc   3540
gcccgccgta ataaatagac acccccctcca caccctcttt ccccaacctc gtgttgttcg   3600
gagcgcacac acacacaacc agatctcccc caaatccacc cgtcggcacc tccgcttcaa   3660
ggtacgccgc tcgtcctccc cccccccccc tctctacctt ctctagatcg gcgttccggt   3720
ccatggttag ggcccggtag ttctacttct gttcatgttt gtgttagatc cgtgtttgtg   3780
ttagatccgt gctgctagcg ttcgtacacg gatgcgacct gtacgtcaga cacgttctga   3840
ttgctaactt gccagtgttt ctctttgggg aatcctggga tggctctagc cgttccgcag   3900
acgggatcga tttcatgatt ttttttgttt cgttgcatag ggtttggttt gccctttttcc   3960
tttatttcaa tatatgccgt gcacttgttt gtcgggtcat cttttcatgc ttttttttgt   4020
cttggttgtg atgatgtggt ctggttgggc ggtcgttcta gatcggagta gaattctgtt   4080
tcaaactacc tggtggattt attaattttg gatctgtatg tgtgtgccat acatattcat   4140
agttacgaat tgaagatgat ggatggaaat atcgatctag gataggtata catgttgatg   4200
cgggttttac tgatgcatat acagagatgc tttttgttcg cttggttgtg atgatgtggt   4260
gtggttgggc ggtcgttcat tcgttctaga tcggagtaga atactgtttc aaactacctg   4320
gtgtatttat taattttgga actgtatgtg tgtgtcatac atcttcatag ttacgagttt   4380
aagatggatg gaaatatcga tctaggatag gtatacatgt tgatgtgggt tttactgatg   4440
catatacatg atggcatatg cagcatctat tcatatgctc taaccttgag tacctatcta   4500
ttataataaa caagtatgtt ttataattat tttgatcttg atatacttgg atgatggcat   4560
atgcagcagc tatatgtgga tttttttagc cctgccttca tacgctattt atttgcttgg   4620
tactgtttct tttgtcgatg ctcaccctgt tgtttggtgt tacttctgca gatgcagaaa   4680
ctcattaact cagtgcaaaa ctatgcctgg ggcagcaaaa cggcgttgac tgaactttat   4740
```

```
ggtatggaaa atccgtccag ccagccgatg gccgagctgt ggatgggcgc acatccgaaa   4800
agcagttcac gagtgcagaa tgccgccgga gatatcgttt cactgcgtga tgtgattgag   4860
agtgataaat cgactctgct cggagaggcc gttgccaaac gctttggcga actgcctttc   4920
ctgttcaaag tattatgcgc agcacagcca ctctccattc aggttcatcc aaacaaacac   4980
aattctgaaa tcggttttgc caaagaaaat gccgcaggta tcccgatgga tgccgccgag   5040
cgtaactata aagatcctaa ccacaagccg gagctggttt ttgcgctgac gcctttcctt   5100
gcgatgaacg cgtttcgtga attttccgag attgtctccc tactccagcc ggtcgcaggt   5160
gcacatccgg cgattgctca ctttttacaa cagcctgatg ccgaacgttt aagcgaactg   5220
ttcgccagcc tgttgaatat gcagggtgaa gaaaaatccc gcgcgctggc gattttaaaa   5280
tcggccctcg atagccagca gggtgaaccg tggcaaacga ttcgtttaat ttctgaattt   5340
tacccggaag acagcggtct gttctccccg ctattgctga atgtggtgaa attgaaccct   5400
ggcgaagcga tgttcctgtt cgctgaaaca ccgcacgctt acctgcaagg cgtggcgctg   5460
gaagtgatgg caaactccga taacgtgctg cgtgcgggtc tgacgcctaa atacattgat   5520
attccggaac tggttgccaa tgtgaaattc gaagccaaac cggctaacca gttgttgacc   5580
cagccggtga aacaaggtgc agaactggac ttcccgattc cagtggatga ttttgccttc   5640
tcgctgcatg accttagtga taaagaaacc accattagcc agcagagtgc cgccattttg   5700
ttctgcgtcg aaggcgatgc aacgttgtgg aaaggttctc agcagttaca gcttaaaccg   5760
ggtgaatcag cgtttattgc cgccaacgaa tcaccggtga ctgtcaaagg ccacggccgt   5820
ttagcgcgtg tttacaacaa gctgtaagag cttactgaaa aaattaacat ctcttgctaa   5880
gctgggagct ctagatcccc gaatttcccc gatcgttcaa acatttggca ataaagtttc   5940
ttaagattga atcctgttgc cggtcttgcg atgattatca tataatttct gttgaattac   6000
gttaagcatg taataattaa catgtaatgc atgacgttat ttatgagatg ggtttttatg   6060
attagagtcc cgcaattata catttaatac gcgatagaaa acaaaatata gcgcgcaaac   6120
taggataaat tatcgcgcgc ggtgtcatct atgttactag atcgggaatt ggcgagctcg   6180
aattaattca gtacattaaa aacgtccgca atgtgttatt aagttgtcta agcgtcaatt   6240
tgtttacacc acaatatatc ctgccaccag ccagccaaca gctccccgac cggcagctcg   6300
gcacaaaatc accactcgat acaggcagcc catcagtccg ggacggcgtc agcgggagag   6360
ccgttgtaag gcggcagact ttgctcatgt taccgatgct attcggaaga acggcaacta   6420
agctgccggg tttgaaacac ggatgatctc gcggagggta gcatgttgat tgtaacgatg   6480
acagagcgtt gctgcctgtg atcaaatatc atctccctcg cagagatccg aattatcagc   6540
cttcttattc atttctcgct taaccgtgac aggctgtcga tcttgagaac tatgccgaca   6600
taataggaaa tcgctggata aagccgctga ggaagctgag tggcgctatt tctttagaag   6660
tgaacgttga cgatcgtcga ccgtaccccg atgaattaat tcggacgtac gttctgaaca   6720
cagctggata cttacttggg cgattgtcat acatgacatc aacaatgtac ccgtttgtgt   6780
aaccgtctct tggaggttcg tatgacacta gtggttcccc tcagcttgcg actagatgtt   6840
gaggcctaac attttattag agagcaggct agttgcttag atacatgatc ttcaggccgt   6900
tatctgtcag ggcaagcgaa aattggccat ttatgacgac caatgccccg cagaagctcc   6960
catctttgcc gccatagacg ccgcgccccc cttttggggt gtagaacatc cttttgccag   7020
atgtggaaaa gaagttcgtt gtcccattgt tggcaatgac gtagtagccg gcgaaagtgc   7080
gagacccatt tgcgctatat ataagcctac gatttccgtt gcgactattg tcgtaattgg   7140
```

```
atgaactatt atcgtagttg ctctcagagt tgtcgtaatt tgatggacta ttgtcgtaat   7200
tgcttatgga gttgtcgtag ttgcttggag aaatgtcgta gttggatggg gagtagtcat   7260
agggaagacg agcttcatcc actaaaacaa ttggcaggtc agcaagtgcc tgccccgatg   7320
ccatcgcaag tacgaggctt agaaccacct tcaacagatc gcgcatagtc ttccccagct   7380
ctctaacgct tgagttaagc cgcgccgcga agcggcgtcg gcttgaacga attgttagac   7440
attatttgcc gactaccttg gtgatctcgc ctttcacgta gtgaacaaat tcttccaact   7500
gatctgcgcg cgaggccaag cgatcttctt gtccaagata agcctgccta gcttcaagta   7560
tgacgggctg atactgggcc ggcaggcgct ccattgccca gtcggcagcg acatccttcg   7620
gcgcgatttt gccggttact gcgctgtacc aaatgcggga caacgtaagc actacatttc   7680
gctcatcgcc agcccagtcg ggcggcgagt tccatagcgt taaggtttca tttagcgcct   7740
caaatagatc ctgttcagga accggatcaa agagttcctc cgccgctgga cctaccaagg   7800
caacgctatg ttctcttgct tttgtcagca agatagccag atcaatgtcg atcgtggctg   7860
gctcgaagat acctgcaaga atgtcattgc gctgccattc tccaaattgc agttcgcgct   7920
tagctggata acgccacgga atgatgtcgt cgtgcacaac aatggtgact tctacagcgc   7980
ggagaatctc gctctctcca ggggaagccg aagtttccaa aaggtcgttg atcaaagctc   8040
gccgcgttgt ttcatcaagc cttacggtca ccgtaaccag caaatcaata tcactgtgtg   8100
gcttcaggcc gccatccact gcggagccgt acaaatgtac ggccagcaac gtcggttcga   8160
gatggcgctc gatgacgcca actacctctg atagttgagt cgatacttcg gcgatcaccg   8220
cttccctcat gatgtttaac tcctgaatta agccgcgccg cgaagcggtg tcggcttgaa   8280
tgaattgtta ggcgtcatcc tgtgctcccg agaaccagta ccagtacatc gctgtttcgt   8340
tcgagacttg aggtctagtt ttatacgtga acaggtcaat gccgccgaga gtaaagccac   8400
attttgcgta caaattgcag gcaggtacat tgttcgtttg tgtctctaat cgtatgccaa   8460
ggagctgtct gcttagtgcc cactttttcg caaattcgat gagactgtgc gcgactcctt   8520
tgcctcggtg cgtgtgcgac acaacaatgt gttcgataga ggctagatcg ttccatgttg   8580
agttgagttc aatcttcccg acaagctctt ggtcgatgaa tgcgccatag caagcagagt   8640
cttcatcaga gtcatcatcc gagatgtaat ccttccggta ggggctcaca cttctggtag   8700
atagttcaaa gccttggtcg gataggtgca catcgaacac ttcacgaaca atgaaatggt   8760
tctcagcatc caatgtttcc gccacctgct cagggatcac cgaaatcttc atatgacgcc   8820
taacgcctgg cacagcggat cgcaaacctg gcgcggcttt tggcacaaaa ggcgtgacag   8880
gtttgcgaat ccgttgctgc cacttgttaa ccccttttgcc agatttggta actataattt   8940
atgttagagg cgaagtcttg ggtaaaaact ggcctaaaat tgctggggat ttcaggaaag   9000
taaacatcac cttccggctc gatgtctatt gtagatatat gtagtgtatc tacttgatcg   9060
ggggatctgc tgcctcgcgc gtttcggtga tgacggtgaa aacctctgac acatgcagct   9120
cccggagacg gtcacagctt gtctgtaagc ggatgccggg agcagacaag cccgtcaggg   9180
cgcgtcagcg ggtgttggcg ggtgtcgggg cgcagccatg acccagtcac gtagcgatag   9240
cggagtgtat actggcttaa ctatgcggca tcagagcaga ttgtactgag agtgcaccat   9300
atgcggtgtg aaataccgca cagatgcgta aggagaaaat accgcatcag gcgctcttcc   9360
gcttcctcgc tcactgactc gctgcgctcg gtcgttcggc tgcggcgagc ggtatcagct   9420
cactcaaagg cggtaatacg gttatccaca gaatcagggg ataacgcagg aaagaacatg   9480
```

tgagcaaaag gccagcaaaa ggccaggaac cgtaaaaagg ccgcgttgct ggcgtttttc 9540
cataggctcc gcccccctga cgagcatcac aaaaatcgac gctcaagtca gaggtggcga 9600
aacccgacag gactataaag ataccaggcg tttccccctg gaagctccct cgtgcgctct 9660
cctgttccga ccctgccgct taccggatac ctgtccgcct ttctcccttc gggaagcgtg 9720
gcgctttctc atagctcacg ctgtaggtat ctcagttcgg tgtaggtcgt tcgctccaag 9780
ctgggctgtg tgcacgaacc ccccgttcag cccgaccgct gcgccttatc cggtaactat 9840
cgtcttgagt ccaacccggt aagacacgac ttatcgccac tggcagcagc cactggtaac 9900
aggattagca gagcgaggta tgtaggcggt gctacagagt tcttgaagtg gtggcctaac 9960
tacggctaca ctagaaggac agtatttggt atctgcgctc tgctgaagcc agttaccttc 10020
ggaaaaagag ttggtagctc ttgatccggc aaacaaacca ccgctggtag cggtggtttt 10080
tttgtttgca agcagcagat tacgcgcaga aaaaaaggat ctcaagaaga tcctttgatc 10140
ttttctacgg ggtctgacgc tcagtggaac gaaaactcac gttaagggat tttggtcatg 10200
agattatcaa aaaggatctt cacctagatc cttttaaatt aaaaatgaag ttttaaatca 10260
atctaaagta tatatgagta aacttggtct gacagttacc aatgcttaat cagtgaggca 10320
cctatctcag cgatctgtct atttcgttca tccatagttg cctgactccc cgtcgtgtag 10380
ataactacga tacgggaggg cttaccatct ggccccagtg ctgcaatgat accgcgagac 10440
ccacgctcac cggctccaga tttatcagca ataaaccagc cagccggaag ggccgagcgc 10500
agaagtggtc ctgcaacttt atccgcctcc atccagtcta ttaattgttg ccgggaagct 10560
agagtaagta gttcgccagt taatagtttg cgcaacgttg ttgccattgc tgcagggggg 10620
gggggggggg ggttccattg ttcattccac ggacaaaaac agagaaagga aacgacagag 10680
gccaaaaagc tcgctttcag cacctgtcgt ttcctttctt ttcagagggt attttaaata 10740
aaaacattaa gttatgacga agaagaacgg aaacgcctta aaccggaaaa ttttcataaa 10800
tagcgaaaac ccgcgaggtc gccgccccgt aacctgtcgg atcaccggaa aggacccgta 10860
aagtgataat gattatcatc tacatatcac aacgtgcgtg gaggccatca aaccacgtca 10920
aataatcaat tatgacgcag gtatcgtatt aattgatctg catcaactta acgtaaaaac 10980
aacttcagac aatacaaatc agcgacactg aatacggggc aacctcatgt cccccccccc 11040 cccccctgc aggcatcgtg gtgtcacgct cgtcgtttgg tatggcttca ttcagctccg 11100
gttcccaacg atcaaggcga gttacatgat cccccatgtt gtgcaaaaaa gcggttagct 11160
ccttcggtcc tccgatcgtt gtcagaagta agttggccgc agtgttatca ctcatggtta 11220
tggcagcact gcataattct cttactgtca tgccatccgt aagatgcttt tctgtgactg 11280
gtgagtactc aaccaagtca ttctgagaat agtgtatgcg gcgaccgagt tgctcttgcc 11340
cggcgtcaac acgggataat accgcgccac atagcagaac tttaaaagtg ctcatcattg 11400
gaaaacgttc ttcggggcga aaactctcaa ggatcttacc gctgttgaga tccagttcga 11460
tgtaacccac tcgtgcaccc aactgatctt cagcatcttt tactttcacc agcgtttctg 11520
ggtgagcaaa aacaggaagg caaaatgccg caaaaaaggg aataagggcg acacggaaat 11580
gttgaatact catactcttc ctttttcaat attattgaag catttatcag ggttattgtc 11640
tcatgagcgg atacatattt gaatgtattt agaaaaataa acaaataggg gttccgcgca 11700
catttccccg aaaagtgcca cctgacgtct aagaaaccat tattatcatg acattaacct 11760
ataaaaatag gcgtatcacg aggccctttc gtcttcaaga attggtcgac gatcttgctg 11820
cgttcggata ttttcgtgga gttcccgcca cagacccgga ttgaaggcga gatccagcaa 11880

```
ctcgcgccag atcatcctgt gacggaactt tggcgcgtga tgactggcca ggacgtcggc  11940
cgaaagagcg acaagcagat cacgcttttc gacagcgtcg gatttgcgat cgaggatttt  12000
tcggcgctgc gctacgtccg cgaccgcgtt gagggatcaa gccacagcag cccactcgac  12060
cttctagccg acccagacga gccaagggat ctttttggaa tgctgctccg tcgtcaggct  12120
ttccgacgtt tgggtggttg aacagaagtc attatcgcac ggaatgccaa gcactcccga  12180
ggggaaccct gtggttggca tgcacataca aatggacgaa cggataaacc ttttcacgcc  12240
cttttaaata tccgattatt ctaataaacg ctcttttctc ttaggtttac ccgccaatat  12300
atcctgtcaa acactgatag tttaaactga aggcgggaaa cgacaacctg atcatgagcg  12360
gagaattaag ggagtcacgt tatgaccccc gccgatgacg cgggacaagc cgttttacgt  12420
ttggaactga cagaaccgca acgttgaagg agccactcag cttaattaag tctaactcga  12480
gttactggta cgtaccaaat ccatggaatc aaggtaccac gaccggagga gagattcttt  12540
gctttgcttg tggctgcgaa ggaggaggag aaaccacgca gcggataaga aggaagccgc  12600
ctttgcaaaa ccagagcatc ttttctgatg aagaaatccg cgttgcctcc tgtgagaaga  12660
atgcgaccct ttttttatac tctattctat ctttattatt attgtcaatt tgtcatgtca  12720
ctgagaaatg gccctgatac gaacgctaag atccaatcat acacctttta tttatttata  12780
cataagtacg taaataagat gaaaataaaa aaaatgtcat ggacgaaaac aacgtccaca  12840
aggacggcaa agatggagga ccgcaggagc acaacggatg gatgttcttt ttttgttatc  12900
aaacaacgga tggatgtttc cgagcaggtg cagcgtctcc tccgtttact cgccgtgcac  12960
atcacggcgt ccaaacgggc gtttgccggc gaggacacgg tagattttgc cgacatggta  13020
gattttatca agatattccg gtcgagtttg gagtactagc tccatcatgt ataaccacca  13080
atgattgagt ggtgaccata tcataatcgt tggtcagctt tccttccatt acttttttaat  13140
tcagtaataa taatccctaa agcctaatca agtaaattca acttccgaat tcaataggga  13200
tcatcagggc acgacctgat tgtaaagaca tacaatagct ttcaaacaac attttcactt  13260
atggtaaaat cttaattaag gtcttaatat tataattatt tttttcactg ccgtgaggga  13320
atggagattt cagaaaggga ctttttggta tcatcattgt atatgatcca cggtttttag  13380
ttagggcgac tttaatttct tatttttgat aattcttgtt tctattgtct tgacgattct  13440
aatgccatgt ccttttgtct tgacagctct agtgccatgt ctatttgtca tgttatcatt  13500
tgttcttttt atttcaagga aaattattac atcaaaaaat tgattttcga agttcacggt  13560
catcttcacc atcactctct atcgcattgg tggcgagaag catatctagt ggtttcattc  13620
tggtaagcct cgctcaaatg aaatttgtaa taaaatacta tatttcttta tcaaggttat  13680
aagatatgga gagaaatggt ctgcttcata aatttgactt acctagagcc tttaaaaagg  13740
aataccatgt aatctaaact ctataacata aagagctttg cgcttttaaa aatatgctaa  13800
cctatataaa tcgcttttgc tagagacagg tcatgtatga ttgaagcgtc accataacgc  13860
cgttaatctt ccgtccagcc attaacggcc acctaccgca ggaaacaaac ggcgtcacca  13920
tcctcgatat ctccgcggcg gccgctggct tttttcggag aaattgcgcg gtggggacgg  13980
agtccacgag agcctctcgc cgctgggccc cacaatcaat ggcgtgacct cacgggacgg  14040
ctccctccct ctaccctccc cccgtgtata aatagcaccc ctccctcgcc tcttccgcat  14100
ccagtattcc agtccccaat ccgtcgagaa attctcgcga gcgatcgaaa tctaagcgaa  14160
gcgaagaggc ctccccagat cctctcaagg tatgcgagag catcgatccc cttccgatct  14220
```

```
atatcgcgtg tcctccctgt tcttgttctt cgtcgatcta gtttagggtt tgatttggtt  14280

ctgaatcgaa cccttttcct gcttgcgttc gatttgtact cgatcctcgg gtagaggtgt  14340

ggatctgcgg ggcgtgatga ggtagtttgg tgtagatttg ttctgggcgt tcgatttgcc  14400

actagggttc ggctgctgtt ggcattcctg atcgagcggc cggataggat tgtttttccc  14460

tttttatatg ttggatgcgt gatggttcct gtgtgttggg ttagattgct ggtacgattc  14520

atctaggtgg tgatttgcag aggaacaact ttgctgttga atattggtag gtctatctag  14580

atttattact tttgattatc gcctgataag gatcaccgat tcgtgtagaa taaattattt  14640

cattgttggg tcatgtagat atagctgcac aatttcttac ttggctcctt actgtgtgaa  14700

ttgtagaata aactgtgtta ctctatgagt ttttctggat tgctggatcc agttaggcca  14760

gtgctgtcaa tttgttatgg ctgttaatgt aataattttc tggattgttg gcctgcttct  14820

cttcatgttt aatcacgtga tggttcatga tgcctgttgg gttagattgt ttgttcaatt  14880

catctaggca gtgctgtgca gagtacaact cgattgatgt ttaatcttgg tagcttcatc  14940

tagatttgta caaattttgg tcacctgatg atgatcaccg attgttgtgg aattatttct  15000

taactggttc gttgttagtc accaccttac ttgtagaata acctgtggta ctgcttttct  15060

gttctgtttt aggccacatc a                                            15081
```

<210> SEQ ID NO 14
<211> LENGTH: 12427
<212> TYPE: DNA
<213> ORGANISM: Artificial Sequence
<220> FEATURE:
<223> OTHER INFORMATION: Synthetic construct, pAG4008b

<400> SEQUENCE: 14

```
gatccccggg tagtcagtcc cttcctaggt ccccgaattt ccccgatcgt tcaaacattt     60

ggcaataaag tttcttaaga ttgaatcctg ttgccggtct tgcgatgatt atcatataat    120

ttctgttgaa ttacgttaag catgtaataa ttaacatgta atgcatgacg ttatttatga    180

gatgggtttt tatgattaga gtcccgcaat tatacattta atacgcgata gaaaacaaaa    240

tatagcgcgc aaactaggat aaattatcgc gcgcggtgtc atctatgtta ctagatcggg    300

aattggaatt cctgcagtgc agcgtgaccc ggtcgtgccc ctctctagag ataatgagca    360

ttgcatgtct aagttataaa aaattaccac atattttttt tgtcacactt gtttgaagtg    420

cagtttatct atctttatac atatatttaa actttactct acgaataata taatctatag    480

tactacaata atatcagtgt tttagagaat catataaatg aacagttaga catggtctaa    540

aggacaattg agtattttga caacaggact ctacagtttt atctttttag tgtgcatgtg    600

ttctcctttt tttttgcaaa tagcttcacc tatataatac ttcatccatt ttattagtac    660

atccatttag ggtttagggt taatggtttt tatagactaa tttttttagt acatctattt    720

tattctattt tagcctctaa attaagaaaa ctaaaactct attttagttt ttttatttaa    780

taatttagat ataaaataga ataaaataaa gtgactaaaa attaaacaaa taccctttaa    840

gaaattaaaa aaactaagga aacatttttc ttgtttcgag tagataatgc cagcctgtta    900

aacgccgtcg acgagtctaa cggacaccaa ccagcgaacc agcagcgtcg cgtcgggcca    960

agcgaagcag acggcacggc atctctgtcg ctgcctctgg acccctctcg agagttccgc   1020

tccaccgttg gacttgctcc gctgtcggca tccagaaatt gcgtggcgga gcggcagacg   1080

tgagccggca cggcaggcgg cctcctcctc ctctcacggc acggcagcta cgggggattc   1140

ctttcccacc gctccttcgc tttcccttcc tcgcccgccg taataaatag acaccccctc   1200
```

```
cacaccctct ttccccaacc tcgtgttgtt cggagcgcac acacacacaa ccagatctcc   1260
cccaaatcca cccgtcggca cctccgcttc aaggtacgcc gctcgtcctc cccccccccc   1320
cctctctacc ttctctagat cggcgttccg gtccatggtt agggcccggt agttctactt   1380
ctgttcatgt ttgtgttaga tccgtgtttg tgttagatcc gtgctgctag cgttcgtaca   1440
cggatgcgac ctgtacgtca gacacgttct gattgctaac ttgccagtgt ttctctttgg   1500
ggaatcctgg gatggctcta gccgttccgc agacgggatc gatttcatga ttttttttgt   1560
ttcgttgcat agggtttggt ttgccctttt cctttatttc aatatatgcc gtgcacttgt   1620
ttgtcgggtc atcttttcat gctttttttt gtcttggttg tgatgatgtg gtctggttgg   1680
gcggtcgttc tagatcggag tagaattctg tttcaaacta cctggtggat ttattaattt   1740
tggatctgta tgtgtgtgcc atacatattc atagttacga attgaagatg atggatggaa   1800
atatcgatct aggataggta tacatgttga tgcgggtttt actgatgcat atacagagat   1860
gctttttgtt cgcttggttg tgatgatgtg gtgtggttgg gcggtcgttc attcgttcta   1920
gatcggagta gaatactgtt tcaaactacc tggtgtattt attaattttg gaactgtatg   1980
tgtgtgtcat acatcttcat agttacgagt ttaagatgga tggaaatatc gatctaggat   2040
aggtatacat gttgatgtgg gttttactga tgcatataca tgatggcata tgcagcatct   2100
attcatatgc tctaaccttg agtacctatc tattataata aacaagtatg ttttataatt   2160
attttgatct tgatatactt ggatgatggc atatgcagca gctatatgtg gattttttta   2220
gccctgcctt catacgctat ttatttgctt ggtactgttt cttttgtcga tgctcaccct   2280
gttgtttggt gttacttctg cagatgcaga aactcattaa ctcagtgcaa aactatgcct   2340
ggggcagcaa aacggcgttg actgaacttt atggtatgga aaatccgtcc agccagccga   2400
tggccgagct gtggatgggc gcacatccga aaagcagttc acgagtgcag aatgccgccg   2460
gagatatcgt ttcactgcgt gatgtgattg agagtgataa atcgactctg ctcggagagg   2520
ccgttgccaa acgctttggc gaactgcctt tcctgttcaa agtattatgc gcagcacagc   2580
cactctccat tcaggttcat ccaaacaaac acaattctga aatcggtttt gccaaagaaa   2640
atgccgcagg tatcccgatg gatgccgccg agcgtaacta taaagatcct aaccacaagc   2700
cggagctggt ttttgcgctg acgcctttcc ttgcgatgaa cgcgtttcgt gaattttccg   2760
agattgtctc cctactccag ccggtcgcag gtgcacatcc ggcgattgct cactttttac   2820
aacagcctga tgccgaacgt ttaagcgaac tgttcgccag cctgttgaat atgcagggtg   2880
aagaaaaatc ccgcgcgctg gcgattttaa aatcggccct cgatagccag cagggtgaac   2940
cgtggcaaac gattcgttta atttctgaat tttacccgga agacagcggt ctgttctccc   3000
cgctattgct gaatgtggtg aaattgaacc ctggcgaagc gatgttcctg ttcgctgaaa   3060
caccgcacgc ttacctgcaa ggcgtggcgc tggaagtgat ggcaaactcc gataacgtgc   3120
tgcgtgcggg tctgacgcct aaatacattg atattccgga actggttgcc aatgtgaaat   3180
tcgaagccaa accggctaac cagttgttga cccagccggt gaaacaaggt gcagaactgg   3240
acttcccgat tccagtggat gattttgcct tctcgctgca tgaccttagt gataaagaaa   3300
ccaccattag ccagcagagt gccgccattt tgttctgcgt cgaaggcgat gcaacgttgt   3360
ggaaaggttc tcagcagtta cagcttaaac cgggtgaatc agcgtttatt gccgccaacg   3420
aatcaccggt gactgtcaaa ggccacggcc gtttagcgcg tgtttacaac aagctgtaag   3480
agcttactga aaaaattaac atctcttgct aagctgggag ctctagatcc ccgaatttcc   3540
```

```
ccgatcgttc aaacatttgg caataaagtt tcttaagatt gaatcctgtt gccggtcttg   3600
cgatgattat catataattt ctgttgaatt acgttaagca tgtaataatt aacatgtaat   3660
gcatgacgtt atttatgaga tgggttttta tgattagagt cccgcaatta tacatttaat   3720
acgcgataga aaacaaaata tagcgcgcaa actaggataa attatcgcgc gcggtgtcat   3780
ctatgttact agatcgggaa ttggcgagct cgaattaatt cagtacatta aaaacgtccg   3840
caatgtgtta ttaagttgtc taagcgtcaa tttgtttaca ccacaatata tcctgccacc   3900
agccagccaa cagctccccg accggcagct cggcacaaaa tcaccactcg atacaggcag   3960
cccatcagtc cgggacggcg tcagcgggag agccgttgta aggcggcaga ctttgctcat   4020
gttaccgatg ctattcggaa gaacggcaac taagctgccg ggtttgaaac acggatgatc   4080
tcgcggaggg tagcatgttg attgtaacga tgacagagcg ttgctgcctg tgatcaaata   4140
tcatctccct cgcagagatc cgaattatca gccttcttat tcatttctcg cttaaccgtg   4200
acaggctgtc gatcttgaga actatgccga cataatagga aatcgctgga taaagccgct   4260
gaggaagctg agtggcgcta tttctttaga agtgaacgtt gacgatcgtc gaccgtaccc   4320
cgatgaatta attcggacgt acgttctgaa cacagctgga tacttacttg ggcgattgtc   4380
atacatgaca tcaacaatgt acccgtttgt gtaaccgtct cttggaggtt cgtatgacac   4440
tagtggttcc cctcagcttg cgactagatg ttgaggccta acattttatt agagagcagg   4500
ctagttgctt agatacatga tcttcaggcc gttatctgtc agggcaagcg aaaattggcc   4560
atttatgacg accaatgccc cgcagaagct cccatctttg ccgccataga cgccgcgccc   4620
ccttttgggg gtgtagaaca tccttttgcc agatgtggaa aagaagttcg ttgtcccatt   4680
gttggcaatg acgtagtagc cggcgaaagt gcgagaccca tttgcgctat atataagcct   4740
acgatttccg ttgcgactat tgtcgtaatt ggatgaacta ttatcgtagt tgctctcaga   4800
gttgtcgtaa tttgatggac tattgtcgta attgcttatg gagttgtcgt agttgcttgg   4860
agaaatgtcg tagttggatg gggagtagtc atagggaaga cgagcttcat ccactaaaac   4920
aattggcagg tcagcaagtg cctgccccga tgccatcgca agtacgaggc ttagaaccac   4980
cttcaacaga tcgcgcatag tcttccccag ctctctaacg cttgagttaa gccgcgccgc   5040
gaagcggcgt cggcttgaac gaattgttag acattatttg ccgactacct tggtgatctc   5100
gcctttcacg tagtgaacaa attcttccaa ctgatctgcg cgcgaggcca agcgatcttc   5160
ttgtccaaga taagcctgcc tagcttcaag tatgacgggc tgatactggg ccggcaggcg   5220
ctccattgcc cagtcggcag cgacatcctt cggcgcgatt ttgccggtta ctgcgctgta   5280
ccaaatgcgg gacaacgtaa gcactacatt tcgctcatcg ccagcccagt cgggcggcga   5340
gttccatagc gttaaggttt catttagcgc ctcaaataga tcctgttcag gaaccggatc   5400
aaagagttcc tccgccgctg gacctaccaa ggcaacgcta tgttctcttg cttttgtcag   5460
caagatagcc agatcaatgt cgatcgtggc tggctcgaag atacctgcaa gaatgtcatt   5520
gcgctgccat tctccaaatt gcagttcgcg cttagctgga taacgccacg gaatgatgtc   5580
gtcgtgcaca acaatggtga cttctacagc gcggagaatc tcgctctctc caggggaagc   5640
cgaagtttcc aaaaggtcgt tgatcaaagc tcgccgcgtt gtttcatcaa gccttacggt   5700
caccgtaacc agcaaatcaa tatcactgtg tggcttcagg ccgccatcca ctgcggagcc   5760
gtacaaatgt acggccagca acgtcggttc gagatggcgc tcgatgacgc caactacctc   5820
tgatagttga gtcgatactt cggcgatcac cgcttccctc atgatgttta actcctgaat   5880
taagccgcgc cgcgaagcgg tgtcggcttg aatgaattgt taggcgtcat cctgtgctcc   5940
```

```
cgagaaccag taccagtaca tcgctgtttc gttcgagact tgaggtctag ttttatacgt   6000
gaacaggtca atgccgccga gagtaaagcc acattttgcg tacaaattgc aggcaggtac   6060
attgttcgtt tgtgtctcta atcgtatgcc aaggagctgt ctgcttagtg cccacttttt   6120
cgcaaattcg atgagactgt gcgcgactcc tttgcctcgg tgcgtgtgcg acacaacaat   6180
gtgttcgata gaggctagat cgttccatgt tgagttgagt tcaatcttcc cgacaagctc   6240
ttggtcgatg aatgcgccat agcaagcaga gtcttcatca gagtcatcat ccgagatgta   6300
atccttccgg taggggctca cacttctggt agatagttca aagccttggt cggataggtg   6360
cacatcgaac acttcacgaa caatgaaatg gttctcagca tccaatgttt ccgccacctg   6420
ctcagggatc accgaaatct tcatatgacg cctaacgcct ggcacagcgg atcgcaaacc   6480
tggcgcggct tttggcacaa aaggcgtgac aggtttgcga atccgttgct gccacttgtt   6540
aaccctttg ccagatttgg taactataat ttatgttaga ggcgaagtct tgggtaaaaa    6600
ctggcctaaa attgctgggg atttcaggaa agtaaacatc accttccggc tcgatgtcta   6660
ttgtagatat atgtagtgta tctacttgat cgggggatct gctgcctcgc gcgtttcggt   6720
gatgacggtg aaaacctctg acacatgcag ctcccggaga cggtcacagc ttgtctgtaa   6780
gcggatgccg ggagcagaca agcccgtcag ggcgcgtcag cgggtgttgg cgggtgtcgg   6840
ggcgcagcca tgacccagtc acgtagcgat agcggagtgt atactggctt aactatgcgg   6900
catcagagca gattgtactg agagtgcacc atatgcggtg tgaaataccg cacagatgcg   6960
taaggagaaa ataccgcatc aggcgctctt ccgcttcctc gctcactgac tcgctgcgct   7020
cggtcgttcg gctgcggcga gcggtatcag ctcactcaaa ggcggtaata cggttatcca   7080
cagaatcagg ggataacgca ggaaagaaca tgtgagcaaa aggccagcaa aaggccagga   7140
accgtaaaaa ggccgcgttg ctggcgtttt tccataggct ccgcccccct gacgagcatc   7200
acaaaaatcg acgctcaagt cagaggtggc gaaacccgac aggactataa agataccagg   7260
cgtttccccc tggaagctcc ctcgtgcgct ctcctgttcc gaccctgccg cttaccggat   7320
acctgtccgc ctttctccct tcgggaagcg tggcgctttc tcatagctca cgctgtaggt   7380
atctcagttc ggtgtaggtc gttcgctcca agctgggctg tgtgcacgaa ccccccgttc   7440
agcccgaccg ctgcgcctta tccggtaact atcgtcttga gtccaacccg gtaagacacg   7500
acttatcgcc actggcagca gccactggta acaggattag cagagcgagg tatgtaggcg   7560
gtgctacaga gttcttgaag tggtggccta actacggcta cactagaagg acagtatttg   7620
gtatctgcgc tctgctgaag ccagttacct tcggaaaaag agttggtagc tcttgatccg   7680
gcaaacaaac caccgctggt agcggtggtt tttttgtttg caagcagcag attacgcgca   7740
gaaaaaaagg atctcaagaa gatcctttga tcttttctac ggggtctgac gctcagtgga   7800
acgaaaactc acgttaaggg attttggtca tgagattatc aaaaaggatc ttcacctaga   7860
tccttttaaa ttaaaaatga agttttaaat caatctaaag tatatatgag taaacttggt   7920
ctgacagtta ccaatgctta atcagtgagg cacctatctc agcgatctgt ctatttcgtt   7980
catccatagt tgcctgactc cccgtcgtgt agataactac gatacgggag ggcttaccat   8040
ctggccccag tgctgcaatg ataccgcgag acccacgctc accggctcca gatttatcag   8100
caataaacca gccagccgga agggccgagc gcagaagtgg tcctgcaact ttatccgcct   8160
ccatccagtc tattaattgt tgccgggaag ctagagtaag tagttcgcca gttaatagtt   8220
tgcgcaacgt tgttgccatt gctgcagggg gggggggggg ggggttccat tgttcattcc   8280
```

```
acggacaaaa acagagaaag gaaacgacag aggccaaaaa gctcgctttc agcacctgtc   8340

gtttcctttc ttttcagagg gtattttaaa taaaaacatt aagttatgac gaagaagaac   8400

ggaaacgcct taaaccggaa aattttcata aatagcgaaa acccgcgagg tcgccgcccc   8460

gtaacctgtc ggatcaccgg aaaggacccg taaagtgata atgattatca tctacatatc   8520

acaacgtgcg tggaggccat caaaccacgt caaataatca attatgacgc aggtatcgta   8580

ttaattgatc tgcatcaact taacgtaaaa acaacttcag acaatacaaa tcagcgacac   8640

tgaatacggg gcaacctcat gtcccccccc cccccccct gcaggcatcg tggtgtcacg   8700

ctcgtcgttt ggtatggctt cattcagctc cggttcccaa cgatcaaggc gagttacatg   8760

atcccccatg ttgtgcaaaa aagcggttag ctccttcggt cctccgatcg ttgtcagaag   8820

taagttggcc gcagtgttat cactcatggt tatggcagca ctgcataatt ctcttactgt   8880

catgccatcc gtaagatgct tttctgtgac tggtgagtac tcaaccaagt cattctgaga   8940

atagtgtatg cggcgaccga gttgctcttg cccggcgtca acacgggata ataccgcgcc   9000

acatagcaga actttaaaag tgctcatcat tggaaaacgt tcttcggggc gaaaactctc   9060

aaggatctta ccgctgttga gatccagttc gatgtaaccc actcgtgcac ccaactgatc   9120

ttcagcatct tttactttca ccagcgtttc tgggtgagca aaaacaggaa ggcaaaatgc   9180

cgcaaaaaag ggaataaggg cgacacggaa atgttgaata ctcatactct tcctttttca   9240

atattattga agcatttatc agggttattg tctcatgagc ggatacatat ttgaatgtat   9300

ttagaaaaat aaacaaatag gggttccgcg cacatttccc cgaaaagtgc cacctgacgt   9360

ctaagaaacc attattatca tgacattaac ctataaaaat aggcgtatca cgaggccctt   9420

tcgtcttcaa gaattggtcg acgatcttgc tgcgttcgga tattttcgtg gagttcccgc   9480

cacagacccg gattgaaggc gagatccagc aactcgcgcc agatcatcct gtgacggaac   9540

tttggcgcgt gatgactggc caggacgtcg gccgaaagag cgacaagcag atcacgcttt   9600

tcgacagcgt cggatttgcg atcgaggatt tttcggcgct gcgctacgtc cgcgaccgcg   9660

ttgagggatc aagccacagc agcccactcg accttctagc cgacccagac gagccaaggg   9720

atctttttgg aatgctgctc cgtcgtcagg ctttccgacg tttgggtggt tgaacagaag   9780

tcattatcgc acggaatgcc aagcactccc gaggggaacc ctgtggttgg catgcacata   9840

caaatggacg aacggataaa ccttttcacg ccctttttaaa tatccgatta ttctaataaa   9900

cgctcttttc tcttaggttt acccgccaat atatcctgtc aaacactgat agtttaaact   9960

gaaggcggga aacgacaacc tgatcatgag cggagaatta agggagtcac gttatgaccc  10020

ccgccgatga cgcgggacaa gccgttttac gtttggaact gacagaaccg caacgttgaa  10080

ggagccactc agcttaatta agtctaactc gagttactgg tacgtaccaa atccatggaa  10140

tcaaggtacc acgaccggag gagagattct ttgctttgct tgtggctgcg aaggaggagg  10200

agaaaccacg ccgcggataa gaaggaaacc gcctttgcaa aaccagaaca tcttttctga  10260

tgaagaaatc cgcgttgcct cctgtgagaa gaatgcgacc ctttttttat actctattat  10320

atctttatta ttattgtcaa tttgtcatgt cactgagaaa tgaccctgat acgaacggtc  10380

atttttgata attcttgttt ctattgtctt gacgattcta atgccatgtc cttttgtctt  10440

gacagctcta gtgccatgtc tatttgtcat gttatcattt gttctttttta tttcaaggaa  10500

aattattaca tcaaaaaatt gattttcgaa gttcacggtc atcttcacca tcactctcta  10560

ccgcattggt ggcgagaagc atatctagtg gtttcattct ggtaagcctc gctcaaatga  10620

aatttgtaat aaaatactat atttctttat caaggttata agatatggag agaaatggtc  10680
```

tgcttcataa atttgactta catagagcct ttaaaaagga ataccatgta atctaaactc 10740
tataacataa agagctttgc gcttttaaaa atatgctaac ctatataaat cgcttttgct 10800
agagacaggt catgtatgat tgaagcgtca ccataacgcc gttaatcttc cgtccagcca 10860
ttaacggcca cctaccgcag gaaacaaacg gcgtcaccat cctcgatatc tccgcggcgg 10920
ccgctggctt ttttcggaga aattgcgcgg tggggacgga gtccacgaga gcctctcgcc 10980
gctgggcccc acaatcaatg gcgtgacctc acgggacgcc tccctccctc taccctcccc 11040
ccgtgtataa atagcacccc tccctcgcct cttccgcatc cagtattcca gtccccaatc 11100
cgtcgagaaa ttctcgcgag cgatcgaaat ctaagcgaag cgaagaggcc tccccagatc 11160
ctctcaaggt atgcgagagc atcgatcccc ttccgatcta tatcgcgtgt cctccctgtt 11220
cttgttcttc gtcgatctag tttagggttt gatttggttc tgaatcgaac ccttttcctg 11280
cttgcgttcg atttgtactc gatcctcggg tagaggtgtg gatctgcggg gcgtgatgag 11340
gtagtttggt gtagatttgt tctgggcgtt cgatttgcca ctagggttcg gctgctgttg 11400
gcattcctga tcgagcggcc ggataggatt gtttttccct ttttatatgt tggatgcgtg 11460
atggttcctg tgtgttgggt tagattgctg gtacgattca tctaggtggt gatttgcaga 11520
ggaacaactt tgctgttgaa tattggtagg tctatctaga tttattactt ttgattatcg 11580
cctgataagg atcaccgatt cgtgtagaat aaattatttc attgttgggt catgtagata 11640
tagctgcaca atttcttact tggctcctta ctgtgtgaat tgtagaataa actgtgttac 11700
tctatgagtt tttctggatt gctggatcca gttaggccag tgctgtcaat ttgttatggc 11760
tgttaatgta ataattttct ggattgttgg cctgcttctc ttcatgttta atcacgtgat 11820
ggttcatgat gcctgttggg ttagattgtt tgttcaattc atctaggcag tgctgtgcag 11880
agtacaactc gattgatgtt taatcttggt agcttcatct agatttgtac aaattttggt 11940
cacctgatga tgatcaccga ttgttgtgga attatttctt aactggttcg ttgttagtca 12000
ccaccttact tgtagaataa cctgtggtac tgcttttctg ttctgtttta ggccacatca 12060
tatgattgtc aaaaatttac atggtagttt aatgataaaa ttagttcagc ttacttcagt 12120
ttgatttgct tcatattttg ttttctgttc tattaatgat acttcatgaa atgtttgttt 12180
tttctctgtt cagatttgac atgtttcagt atcataataa taatattctg tatcctttat 12240
agtttgttgg catgatttgc tttgaattta gttagcctat tctgttaata taggatgata 12300
agctgtgagg cgttcattct cttcagtcca gagttatcat tttcagtgtt ttaatgttgt 12360
ttatcaagct ggatgtatat ggtggtttaa ctcttttctg tttcttactg tttgcagatc 12420
cagatcg 12427

<210> SEQ ID NO 15
<211> LENGTH: 13741
<212> TYPE: DNA
<213> ORGANISM: Artificial Sequence
<220> FEATURE:
<223> OTHER INFORMATION: Synthetic construct, pAG4009b

<400> SEQUENCE: 15
gatccccggg tagtcagtcc cttcctaggt ccccgaattt ccccgatcgt tcaaacattt 60
ggcaataaag tttcttaaga ttgaatcctg ttgccggtct tgcgatgatt atcatataat 120
ttctgttgaa ttacgttaag catgtaataa ttaacatgta atgcatgacg ttatttatga 180
gatgggtttt tatgattaga gtcccgcaat tatacattta atacgcgata gaaaacaaaa 240

```
tatagcgcgc aaactaggat aaattatcgc gcgcggtgtc atctatgtta ctagatcggg    300
aattggaatt cctgcagtgc agcgtgaccc ggtcgtgccc ctctctagag ataatgagca    360
ttgcatgtct aagttataaa aaattaccac atattttttt tgtcacactt gtttgaagtg    420
cagtttatct atctttatac atatatttaa actttactct acgaataata taatctatag    480
tactacaata atatcagtgt tttagagaat catataaatg aacagttaga catggtctaa    540
aggacaattg agtattttga caacaggact ctacagtttt atctttttag tgtgcatgtg    600
ttctcctttt tttttgcaaa tagcttcacc tatataatac ttcatccatt ttattagtac    660
atccatttag ggtttagggt taatggtttt tatagactaa ttttttagt acatctattt     720
tattctattt tagcctctaa attaagaaaa ctaaaactct attttagttt ttttatttaa    780
taatttagat ataaaataga ataaaataaa gtgactaaaa attaaacaaa taccctttaa    840
gaaattaaaa aaactaagga aacatttttc ttgtttcgag tagataatgc cagcctgtta    900
aacgccgtcg acgagtctaa cggacaccaa ccagcgaacc agcagcgtcg cgtcgggcca    960
agcgaagcag acggcacggc atctctgtcg ctgcctctgg acccctctcg agagttccgc   1020
tccaccgttg gacttgctcc gctgtcggca tccagaaatt gcgtggcgga gcggcagacg   1080
tgagccggca cggcaggcgg cctcctcctc ctctcacggc acggcagcta cgggggattc   1140
ctttcccacc gctccttcgc tttcccttcc tcgcccgccg taataaatag acacccccctc  1200
cacaccctct ttccccaacc tcgtgttgtt cggagcgcac acacacacaa ccagatctcc   1260
cccaaatcca cccgtcggca cctccgcttc aaggtacgcc gctcgtcctc cccccccccc   1320
cctctctacc ttctctagat cggcgttccg gtccatggtt agggcccggt agttctactt   1380
ctgttcatgt ttgtgttaga tccgtgtttg tgttagatcc gtgctgctag cgttcgtaca   1440
cggatgcgac ctgtacgtca gacacgttct gattgctaac ttgccagtgt ttctctttgg   1500
ggaatcctgg gatggctcta gccgttccgc agacgggatc gatttcatga ttttttttgt   1560
ttcgttgcat agggtttggt ttgccctttt cctttatttc aatatatgcc gtgcacttgt   1620
ttgtcgggtc atcttttcat gctttttttt gtcttggttg tgatgatgtg gtctggttgg   1680
gcggtcgttc tagatcggag tagaattctg tttcaaacta cctggtggat ttattaattt   1740
tggatctgta tgtgtgtgcc atacatattc atagttacga attgaagatg atggatggaa   1800
atatcgatct aggataggta tacatgttga tgcgggtttt actgatgcat atacagagat   1860
gctttttgtt cgcttggttg tgatgatgtg gtgtggttgg gcggtcgttc attcgttcta   1920
gatcggagta gaatactgtt tcaaactacc tggtgtattt attaattttg gaactgtatg   1980
tgtgtgtcat acatcttcat agttacgagt ttaagatgga tggaaatatc gatctaggat   2040
aggtatacat gttgatgtgg gttttactga tgcatataca tgatggcata tgcagcatct   2100
attcatatgc tctaaccttg agtacctatc tattataata aacaagtatg ttttataatt   2160
attttgatct tgatatactt ggatgatggc atatgcagca gctatatgtg gattttttta   2220
gccctgcctt catacgctat ttatttgctt ggtactgttt cttttgtcga tgctcaccct   2280
gttgtttggt gttacttctg cagatgcaga aactcattaa ctcagtgcaa aactatgcct   2340
ggggcagcaa aacggcgttg actgaacttt atggtatgga aaatccgtcc agccagccga   2400
tggccgagct gtggatgggc gcacatccga aaagcagttc acgagtgcag aatgccgccg   2460
gagatatcgt ttcactgcgt gatgtgattg agagtgataa atcgactctg ctcggagagg   2520
ccgttgccaa acgctttggc gaactgcctt tcctgttcaa agtattatgc gcagcacagc   2580
cactctccat tcaggttcat ccaaacaaac acaattctga aatcggtttt gccaaagaaa   2640
```

```
atgccgcagg tatcccgatg gatgccgccg agcgtaacta taaagatcct aaccacaagc   2700
cggagctggt ttttgcgctg acgcctttcc ttgcgatgaa cgcgtttcgt gaattttccg   2760
agattgtctc cctactccag ccggtcgcag gtgcacatcc ggcgattgct cactttttac   2820
aacagcctga tgccgaacgt ttaagcgaac tgttcgccag cctgttgaat atgcagggtg   2880
aagaaaaatc ccgcgcgctg gcgattttaa aatcggccct cgatagccag cagggtgaac   2940
cgtggcaaac gattcgttta atttctgaat tttacccgga agacagcggt ctgttctccc   3000
cgctattgct gaatgtggtg aaattgaacc ctggcgaagc gatgttcctg ttcgctgaaa   3060
caccgcacgc ttacctgcaa ggcgtggcgc tggaagtgat ggcaaactcc gataacgtgc   3120
tgcgtgcggg tctgacgcct aaatacattg atattccgga actggttgcc aatgtgaaat   3180
tcgaagccaa accggctaac cagttgttga cccagccggt gaaacaaggt gcagaactgg   3240
acttcccgat tccagtggat gattttgcct tctcgctgca tgaccttagt gataaagaaa   3300
ccaccattag ccagcagagt gccgccattt tgttctgcgt cgaaggcgat gcaacgttgt   3360
ggaaaggttc tcagcagtta cagcttaaac cgggtgaatc agcgtttatt gccgccaacg   3420
aatcaccggt gactgtcaaa ggccacggcc gtttagcgcg tgtttacaac aagctgtaag   3480
agcttactga aaaaattaac atctcttgct aagctgggag ctctagatcc ccgaatttcc   3540
ccgatcgttc aaacatttgg caataaagtt tcttaagatt gaatcctgtt gccggtcttg   3600
cgatgattat catataattt ctgttgaatt acgttaagca tgtaataatt aacatgtaat   3660
gcatgacgtt atttatgaga tgggttttta tgattagagt cccgcaatta tacatttaat   3720
acgcgataga aaacaaaata tagcgcgcaa actaggataa attatcgcgc gcggtgtcat   3780
ctatgttact agatcgggaa ttggcgagct cgaattaatt cagtacatta aaaacgtccg   3840
caatgtgtta ttaagttgtc taagcgtcaa tttgtttaca ccacaatata tcctgccacc   3900
agccagccaa cagctccccg accggcagct cggcacaaaa tcaccactcg atacaggcag   3960
cccatcagtc cgggacggcg tcagcgggag agccgttgta aggcggcaga ctttgctcat   4020
gttaccgatg ctattcggaa gaacggcaac taagctgccg ggtttgaaac acggatgatc   4080
tcgcggaggg tagcatgttg attgtaacga tgacagagcg ttgctgcctg tgatcaaata   4140
tcatctccct cgcagagatc cgaattatca gccttcttat tcatttctcg cttaaccgtg   4200
acaggctgtc gatcttgaga actatgccga cataatagga aatcgctgga taaagccgct   4260
gaggaagctg agtggcgcta tttctttaga agtgaacgtt gacgatcgtc gaccgtaccc   4320
cgatgaatta attcggacgt acgttctgaa cacagctgga tacttacttg ggcgattgtc   4380
atacatgaca tcaacaatgt acccgtttgt gtaaccgtct cttggaggtt cgtatgacac   4440
tagtggttcc cctcagcttg cgactagatg ttgaggccta acattttatt agagagcagg   4500
ctagttgctt agatacatga tcttcaggcc gttatctgtc agggcaagcg aaaattggcc   4560
atttatgacg accaatgccc cgcagaagct cccatctttg ccgccataga cgccgcgccc   4620
ccctttttggg gtgtagaaca tcctttttgcc agatgtggaa aagaagttcg ttgtcccatt   4680
gttggcaatg acgtagtagc cggcgaaagt gcgagaccca tttgcgctat atataagcct   4740
acgatttccg ttgcgactat tgtcgtaatt ggatgaacta ttatcgtagt tgctctcaga   4800
gttgtcgtaa tttgatggac tattgtcgta attgcttatg gagttgtcgt agttgcttgg   4860
agaaatgtcg tagttggatg gggagtagtc atagggaaga cgagcttcat ccactaaaac   4920
aattggcagg tcagcaagtg cctgccccga tgccatcgca agtacgaggc ttagaaccac   4980
```

```
cttcaacaga tcgcgcatag tcttccccag ctctctaacg cttgagttaa gccgcgccgc   5040

gaagcggcgt cggcttgaac gaattgttag acattatttg ccgactacct tggtgatctc   5100

gcctttcacg tagtgaacaa attcttccaa ctgatctgcg cgcgaggcca agcgatcttc   5160

ttgtccaaga taagcctgcc tagcttcaag tatgacgggc tgatactggg ccggcaggcg   5220

ctccattgcc cagtcggcag cgacatcctt cggcgcgatt ttgccggtta ctgcgctgta   5280

ccaaatgcgg gacaacgtaa gcactacatt tcgctcatcg ccagcccagt cgggcggcga   5340

gttccatagc gttaaggttt catttagcgc ctcaaataga tcctgttcag gaaccggatc   5400

aaagagttcc tccgccgctg gacctaccaa ggcaacgcta tgttctcttg cttttgtcag   5460

caagatagcc agatcaatgt cgatcgtggc tggctcgaag atacctgcaa gaatgtcatt   5520

gcgctgccat tctccaaatt gcagttcgcg cttagctgga taacgccacg gaatgatgtc   5580

gtcgtgcaca acaatggtga cttctacagc gcggagaatc tcgctctctc caggggaagc   5640

cgaagtttcc aaaaggtcgt tgatcaaagc tcgccgcgtt gtttcatcaa gccttacggt   5700

caccgtaacc agcaaatcaa tatcactgtg tggcttcagg ccgccatcca ctgcggagcc   5760

gtacaaatgt acggccagca acgtcggttc gagatggcgc tcgatgacgc caactacctc   5820

tgatagttga gtcgatactt cggcgatcac cgcttccctc atgatgttta actcctgaat   5880

taagccgcgc cgcgaagcgg tgtcggcttg aatgaattgt taggcgtcat cctgtgctcc   5940

cgagaaccag taccagtaca tcgctgtttc gttcgagact tgaggtctag ttttatacgt   6000

gaacaggtca atgccgccga gagtaaagcc acattttgcg tacaaattgc aggcaggtac   6060

attgttcgtt tgtgtctcta atcgtatgcc aaggagctgt ctgcttagtg cccacttttt   6120

cgcaaattcg atgagactgt gcgcgactcc tttgcctcgg tgcgtgtgcg acacaacaat   6180

gtgttcgata gaggctagat cgttccatgt tgagttgagt tcaatcttcc cgacaagctc   6240

ttggtcgatg aatgcgccat agcaagcaga gtcttcatca gagtcatcat ccgagatgta   6300

atccttccgg taggggctca cacttctggt agatagttca aagccttggt cggataggtg   6360

cacatcgaac acttcacgaa caatgaaatg gttctcagca tccaatgttt ccgccacctg   6420

ctcagggatc accgaaatct tcatatgacg cctaacgcct ggcacagcgg atcgcaaacc   6480

tggcgcggct tttggcacaa aaggcgtgac aggtttgcga atccgttgct gccacttgtt   6540

aaccctttg ccagatttgg taactataat ttatgttaga ggcgaagtct tgggtaaaaa   6600

ctggcctaaa attgctgggg atttcaggaa agtaaacatc accttccggc tcgatgtcta   6660

ttgtagatat atgtagtgta tctacttgat cgggggatct gctgcctcgc gcgtttcggt   6720

gatgacggtg aaaacctctg acacatgcag ctcccggaga cggtcacagc ttgtctgtaa   6780

gcggatgccg ggagcagaca agcccgtcag ggcgcgtcag cgggtgttgg cgggtgtcgg   6840

ggcgcagcca tgacccagtc acgtagcgat agcggagtgt atactggctt aactatgcgg   6900

catcagagca gattgtactg agagtgcacc atatgcggtg tgaaataccg cacagatgcg   6960

taaggagaaa ataccgcatc aggcgctctt ccgcttcctc gctcactgac tcgctgcgct   7020

cggtcgttcg gctgcggcga gcggtatcag ctcactcaaa ggcggtaata cggttatcca   7080

cagaatcagg ggataacgca ggaaagaaca tgtgagcaaa aggccagcaa aaggccagga   7140

accgtaaaaa ggccgcgttg ctggcgtttt tccataggct ccgcccccct gacgagcatc   7200

acaaaaatcg acgctcaagt cagaggtggc gaaacccgac aggactataa agataccagg   7260

cgtttccccc tggaagctcc ctcgtgcgct ctcctgttcc gaccctgccg cttaccggat   7320

acctgtccgc ctttctccct tcgggaagcg tggcgctttc tcatagctca cgctgtaggt   7380
```

```
atctcagttc ggtgtaggtc gttcgctcca agctgggctg tgtgcacgaa ccccccgttc   7440
agcccgaccg ctgcgcctta tccggtaact atcgtcttga gtccaacccg gtaagacacg   7500
acttatcgcc actggcagca gccactggta acaggattag cagagcgagg tatgtaggcg   7560
gtgctacaga gttcttgaag tggtggccta actacggcta cactagaagg acagtatttg   7620
gtatctgcgc tctgctgaag ccagttacct tcggaaaaag agttggtagc tcttgatccg   7680
gcaaacaaac caccgctggt agcggtggtt tttttgtttg caagcagcag attacgcgca   7740
gaaaaaaagg atctcaagaa gatcctttga tcttttctac ggggtctgac gctcagtgga   7800
acgaaaactc acgttaaggg attttggtca tgagattatc aaaaaggatc ttcacctaga   7860
tccttttaaa ttaaaaatga agttttaaat caatctaaag tatatatgag taaacttggt   7920
ctgacagtta ccaatgctta atcagtgagg cacctatctc agcgatctgt ctatttcgtt   7980
catccatagt tgcctgactc cccgtcgtgt agataactac gatacgggag ggcttaccat   8040
ctggccccag tgctgcaatg ataccgcgag acccacgctc accggctcca gatttatcag   8100
caataaacca gccagccgga agggccgagc gcagaagtgg tcctgcaact ttatccgcct   8160
ccatccagtc tattaattgt tgccgggaag ctagagtaag tagttcgcca gttaatagtt   8220
tgcgcaacgt tgttgccatt gctgcagggg gggggggggg ggggttccat tgttcattcc   8280
acggacaaaa acagagaaag gaaacgacag aggccaaaaa gctcgctttc agcacctgtc   8340
gtttcctttc ttttcagagg gtattttaaa taaaaacatt aagttatgac gaagaagaac   8400
ggaaacgcct taaaccggaa aattttcata aatagcgaaa acccgcgagg tcgccgcccc   8460
gtaacctgtc ggatcaccgg aaaggacccg taaagtgata atgattatca tctacatatc   8520
acaacgtgcg tggaggccat caaaccacgt caaataatca attatgacgc aggtatcgta   8580
ttaattgatc tgcatcaact taacgtaaaa acaacttcag acaatacaaa tcagcgacac   8640
tgaatacggg gcaacctcat gtcccccccc cccccccccct gcaggcatcg tggtgtcacg   8700
ctcgtcgttt ggtatggctt cattcagctc cggttcccaa cgatcaaggc gagttacatg   8760
atcccccatg ttgtgcaaaa aagcggttag ctccttcggt cctccgatcg ttgtcagaag   8820
taagttggcc gcagtgttat cactcatggt tatggcagca ctgcataatt ctcttactgt   8880
catgccatcc gtaagatgct tttctgtgac tggtgagtac tcaaccaagt cattctgaga   8940
atagtgtatg cggcgaccga gttgctcttg cccggcgtca acacgggata ataccgcgcc   9000
acatagcaga actttaaaag tgctcatcat tggaaaacgt tcttcggggc gaaaactctc   9060
aaggatctta ccgctgttga gatccagttc gatgtaaccc actcgtgcac ccaactgatc   9120
ttcagcatct tttactttca ccagcgtttc tgggtgagca aaaacaggaa ggcaaaatgc   9180
cgcaaaaaag ggaataaggg cgacacggaa atgttgaata ctcatactct tcctttttca   9240
atattattga agcatttatc agggttattg tctcatgagc ggatacatat ttgaatgtat   9300
ttagaaaaat aaacaaatag gggttccgcg cacatttccc cgaaaagtgc cacctgacgt   9360
ctaagaaacc attattatca tgacattaac ctataaaaat aggcgtatca cgaggccctt   9420
tcgtcttcaa gaattggtcg acgatcttgc tgcgttcgga tattttcgtg gagttcccgc   9480
cacagacccg gattgaaggc gagatccagc aactcgcgcc agatcatcct gtgacggaac   9540
tttggcgcgt gatgactggc caggacgtcg gccgaaagag cgacaagcag atcacgcttt   9600
tcgacagcgt cggatttgcg atcgaggatt tttcggcgct gcgctacgtc cgcgaccgcg   9660
ttgagggatc aagccacagc agcccactcg accttctagc cgacccagac gagccaaggg   9720
```

```
atctttttgg aatgctgctc cgtcgtcagg ctttccgacg tttgggtggt tgaacagaag   9780
tcattatcgc acggaatgcc aagcactccc gaggggaacc ctgtggttgg catgcacata   9840
caaatggacg aacggataaa ccttttcacg cccttttaaa tatccgatta ttctaataaa   9900
cgctcttttc tcttaggttt acccgccaat atatcctgtc aaacactgat agtttaaact   9960
gaaggcggga aacgacaacc tgatcatgag cggagaatta agggagtcac gttatgaccc  10020
ccgccgatga cgcgggacaa gccgttttac gtttggaact gacagaaccg caacgttgaa  10080
ggagccactc agcttaatta agtctaactc gagttactgg tacgtaccaa atccatggaa  10140
tcaaggtacc ctggcctaac ctaaaatcag ttcttgctgc tgggtggttg ggtacattat  10200
ctgacaacta ggatccacat caaaaaaaaa aagactacta cgatcatcat ggagtccttc  10260
gcaacggcag ctgggcagac accttcagag ttcagagtcc acgcacacac taataaaggg  10320
gtccatttgc ctgcttcgtt ccggctgaaa tttttacgaa ccggtcatcc gtaaccacga  10380
taatcgatat ggaccaagag agacaaaaat aatctcggaa catcgttagc aagtccaaat  10440
ggaacgcaac cagagacatg ttgtttgcct tcatccttca tacacaaccc acctggccac  10500
ctccatgtcc atgatttttt ttccccaatc gaccttggac aaccaccaag gaattccttg  10560
tcagttgtta gcatggatga cagttcaagc cgggcagctg gcgtgtccgt tcagacatca  10620
tcgtcctgcc agaactccat ccacgcgagc ccgctgaacc aagggagcct ttgcgtttgc  10680
cctttggcca cggcatcgtt cagctcattc cctcaacaga tcaactgaac ccagcgcgcg  10740
aagttagcac cggagcgcaa tgcgagccgt gcccgtgtct tcctcccagc tcctccagcg  10800
caagcaagac gacgaccgga ggagagattc tttgctttgc ttgtggctgc gaaggaggag  10860
gagaaaccac gcagcggata agaaggaagc cgcctttgca aaaccagagc atcttttctg  10920
atgaagaaat ccgcgttgcc tcctgtgaga agaatgcgac ccttttttta tactctattc  10980
tatctttatt attattgtca atttgtcatg tcactgagaa atggccctga tacgaacgct  11040
aagatccaat catacacctt ttatttattt atacataagt acgtaaataa gatgaaaata  11100
aaaaaaatgt catggacgaa aacaacgtcc acaaggacgg caaagatgga ggaccgcagg  11160
agcacaacgg atggatgttc ttttttttgtt atcaaacaac ggatggatgt ttccgagcag  11220
gtgcagcgtc tcctccgttt actcgccgtg cacatcacgg cgtccaaacg ggcgtttgcc  11280
ggcgaggaca cggtagattt tgccgacatg gtagatttta tcaagatatt ccggtcgagt  11340
ttggagtact agctccatca tgtataacca ccaatgattg agtggtgacc atatcataat  11400
cgttggtcag ctttccttcc attacttttt aattcagtaa taataatccc taaagcctaa  11460
tcaagtaaat tcaacttccg aattcaatag ggatcatcag ggcacgacct gattgtaaag  11520
acatacaata gctttcaaac aacattttca cttatggtaa aatcttaatt aaggtcttaa  11580
tattataatt attttttca ctgccgtgag ggaatggaga tttcagaaag ggactttttg  11640
gtatcatcat tgtatatgat ccacggtttt tagttagggc gactttaatt tcttattttt  11700
gataattctt gtttctattg tcttgacgat tctaatgcca tgtccttttg tcttgacagc  11760
tctagtgcca tgtctatttg tcatgttatc atttgttctt tttatttcaa ggaaaattat  11820
tacatcaaaa aattgatttt cgaagttcac ggtcatcttc accatcactc tctatcgcat  11880
tggtggcgag aagcatatct agtggtttca ttctggtaag cctcgctcaa atgaaatttg  11940
taataaaata ctatatttct ttatcaaggt tataagatat ggagagaaat ggtctgcttc  12000
ataaatttga cttacctaga gcctttaaaa aggaatacca tgtaatctaa actctataac  12060
ataaagagct ttgcgctttt aaaaatatgc taacctatat aaatcgcttt tgctagagac  12120
```

aggtcatgta tgattgaagc gtcaccataa cgccgttaat cttccgtcca gccattaacg 12180
gccacctacc gcaggaaaca aacggcgtca ccatcctcga tatctccgcg gcggccgctg 12240
gcttttttcg gagaaattgc gcggtgggga cggagtccac gagagcctct cgccgctggg 12300
ccccacaatc aatggcgtga cctcacggga cggctccctc cctctaccct ccccccgtgt 12360
ataaatagca cccctccctc gcctcttccg catccagtat tccagtcccc aatccgtcga 12420
gaaattctcg cgagcgatcg aaatctaagc gaagcgaaga ggcctcccca gatcctctca 12480
aggtatgcga gagcatcgat ccccttccga tctatatcgc gtgtcctccc tgttcttgtt 12540
cttcgtcgat ctagtttagg gtttgatttg gttctgaatc gaaccctttt cctgcttgcg 12600
ttcgatttgt actcgatcct cgggtagagg tgtggatctg cggggcgtga tgaggtagtt 12660
tggtgtagat ttgttctggg cgttcgattt gccactaggg ttcggctgct gttggcattc 12720
ctgatcgagc ggccggatag gattgttttt ccctttttat atgttggatg cgtgatggtt 12780
cctgtgtgtt gggttagatt gctggtacga ttcatctagg tggtgatttg cagaggaaca 12840
actttgctgt tgaatattgg taggtctatc tagatttatt acttttgatt atcgcctgat 12900
aaggatcacc gattcgtgta gaataaatta tttcattgtt gggtcatgta gatatagctg 12960
cacaatttct tacttggctc cttactgtgt gaattgtaga ataaactgtg ttactctatg 13020
agtttttctg gattgctgga tccagttagg ccagtgctgt caatttgtta tggctgttaa 13080
tgtaataatt ttctggattg ttggcctgct tctcttcatg tttaatcacg tgatggttca 13140
tgatgcctgt tgggttagat tgtttgttca attcatctag gcagtgctgt gcagagtaca 13200
actcgattga tgtttaatct tggtagcttc atctagattt gtacaaattt tggtcacctg 13260
atgatgatca ccgattgttg tggaattatt tcttaactgg ttcgttgtta gtcaccacct 13320
tacttgtaga ataacctgtg gtactgcttt tctgttctgt tttaggccac atcatatgat 13380
tgtcaaaaat ttacatggta gtttaatgat aaaattagtt cagcttactt cagtttgatt 13440
tgcttcatat tttgttttct gttctattaa tgatacttca tgaaatgttt gtttttttctc 13500 tgttcagatt tgacatgttt cagtatcata ataataatat tctgtatcct ttatagtttg 13560
ttggcatgat ttgctttgaa tttagttagc ctattctgtt aatataggat gataagctgt 13620
gaggcgttca ttctcttcag tccagagtta tcattttcag tgttttaatg ttgtttatca 13680
agctggatgt atatggtggt ttaactcttt tctgtttctt actgtttgca gatccagatc 13740
g 13741

<210> SEQ ID NO 16
<211> LENGTH: 13080
<212> TYPE: DNA
<213> ORGANISM: Artificial Sequence
<220> FEATURE:
<223> OTHER INFORMATION: Synthetic construct, pAG4010b

<400> SEQUENCE: 16
tatgattgtc aaaaatttac atggtagttt aatgataaaa ttagttcagc ttacttcagt 60
ttgatttgct tcatattttg ttttctgttc tattaatgat acttcatgaa atgtttgttt 120
tttctctgtt cagatttgac atgtttcagt atcataataa taatattctg tatcctttat 180
agtttgttgg catgatttgc tttgaattta gttagcctat tctgttaata taggatgata 240
agctgtgagg cgttcattct cttcagtcca gagttatcat tttcagtgtt ttaatgttgt 300
ttatcaagct ggatgtatat ggtggtttaa ctcttttctg tttcttactg tttgcagatc 360

-continued

```
cagatcggat ccccgggtag tcagtccctt cctaggtccc cgaatttccc cgatcgttca    420
aacatttggc aataaagttt cttaagattg aatcctgttg ccggtcttgc gatgattatc    480
atataatttc tgttgaatta cgttaagcat gtaataatta acatgtaatg catgacgtta    540
tttatgagat gggtttttat gattagagtc ccgcaattat acatttaata cgcgatagaa    600
aacaaaatat agcgcgcaaa ctaggataaa ttatcgcgcg cggtgtcatc tatgttacta    660
gatcgggaat tggaattcct gcagtgcagc gtgacccggt cgtgcccctc tctagagata    720
atgagcattg catgtctaag ttataaaaaa ttaccacata ttttttttgt cacacttgtt    780
tgaagtgcag tttatctatc tttatacata tatttaaact ttactctacg aataatataa    840
tctatagtac tacaataata tcagtgtttt agagaatcat ataaatgaac agttagacat    900
ggtctaaagg acaattgagt attttgacaa caggactcta cagttttatc tttttagtgt    960
gcatgtgttc tccttttttt ttgcaaatag cttcacctat ataatacttc atccatttta   1020
ttagtacatc catttagggt ttagggttaa tggtttttat agactaattt ttttagtaca   1080
tctattttat tctattttag cctctaaatt aagaaaacta aaactctatt ttagtttttt   1140
tatttaataa tttagatata aaatagaata aaataaagtg actaaaaatt aaacaaatac   1200
cctttaagaa attaaaaaaa ctaaggaaac atttttcttg tttcgagtag ataatgccag   1260
cctgttaaac gccgtcgacg agtctaacgg acaccaacca gcgaaccagc agcgtcgcgt   1320
cgggccaagc gaagcagacg gcacggcatc tctgtcgctg cctctggacc cctctcgaga   1380
gttccgctcc accgttggac ttgctccgct gtcggcatcc agaaattgcg tggcggagcg   1440
gcagacgtga gccggcacgg caggcggcct cctcctcctc tcacggcacg gcagctacgg   1500
gggattcctt tcccaccgct ccttcgcttt cccttcctcg cccgccgtaa taaatagaca   1560
ccccctccac accctctttc cccaacctcg tgttgttcgg agcgcacaca cacacaacca   1620
gatctccccc aaatccaccc gtcggcacct ccgcttcaag gtacgccgct cgtcctcccc   1680
cccccccct ctctaccttc tctagatcgg cgttccggtc catggttagg gcccggtagt    1740
tctacttctg ttcatgtttg tgttagatcc gtgtttgtgt tagatccgtg ctgctagcgt   1800
tcgtacacgg atgcgacctg tacgtcagac acgttctgat tgctaacttg ccagtgtttc   1860
tctttgggga atcctgggat ggctctagcc gttccgcaga cgggatcgat ttcatgattt   1920
tttttgtttc gttgcatagg gtttggtttg cccttttcct ttatttcaat atatgccgtg   1980
cacttgtttg tcgggtcatc ttttcatgct ttttttgtc ttggttgtga tgatgtggtc    2040
tggttgggcg gtcgttctag atcggagtag aattctgttt caaactacct ggtggattta   2100
ttaattttgg atctgtatgt gtgtgccata catattcata gttacgaatt gaagatgatg   2160
gatggaaata tcgatctagg ataggtatac atgttgatgc gggttttact gatgcatata   2220
cagagatgct tttgttcgc ttggttgtga tgatgtggtg tggttgggcg gtcgttcatt    2280
cgttctagat cggagtagaa tactgtttca aactacctgg tgtatttatt aattttggaa   2340
ctgtatgtgt gtgtcataca tcttcatagt tacgagttta agatggatgg aaatatcgat   2400
ctaggatagg tatacatgtt gatgtgggtt ttactgatgc atatacatga tggcatatgc   2460
agcatctatt catatgctct aaccttgagt acctatctat tataataaac aagtatgttt   2520
tataattatt ttgatcttga tatacttgga tgatggcata tgcagcagct atatgtggat   2580
ttttttagcc ctgccttcat acgctattta tttgcttggt actgtttctt ttgtcgatgc   2640
tcaccctgtt gtttggtgtt acttctgcag atgcagaaac tcattaactc agtgcaaaac   2700
tatgcctggg gcagcaaaac ggcgttgact gaactttatg gtatggaaaa tccgtccagc   2760
```

```
cagccgatgg ccgagctgtg gatgggcgca catccgaaaa gcagttcacg agtgcagaat   2820
gccgccggag atatcgtttc actgcgtgat gtgattgaga gtgataaatc gactctgctc   2880
ggagaggccg ttgccaaacg ctttggcgaa ctgcctttcc tgttcaaagt attatgcgca   2940
gcacagccac tctccattca ggttcatcca aacaaacaca attctgaaat cggttttgcc   3000
aaagaaaatg ccgcaggtat cccgatggat gccgccgagc gtaactataa agatcctaac   3060
cacaagccgg agctggtttt tgcgctgacg cctttccttg cgatgaacgc gtttcgtgaa   3120
ttttccgaga ttgtctccct actccagccg gtcgcaggtg cacatccggc gattgctcac   3180
tttttacaac agcctgatgc cgaacgttta agcgaactgt tcgccagcct gttgaatatg   3240
cagggtgaag aaaaatcccg cgcgctggcg attttaaaat cggccctcga tagccagcag   3300
ggtgaaccgt ggcaaacgat tcgtttaatt tctgaatttt acccggaaga cagcggtctg   3360
ttctccccgc tattgctgaa tgtggtgaaa ttgaaccctg gcgaagcgat gttcctgttc   3420
gctgaaacac cgcacgctta cctgcaaggc gtggcgctgg aagtgatggc aaactccgat   3480
aacgtgctgc gtgcgggtct gacgcctaaa tacattgata ttccggaact ggttgccaat   3540
gtgaaattcg aagccaaacc ggctaaccag ttgttgaccc agccggtgaa acaaggtgca   3600
gaactggact tcccgattcc agtggatgat tttgccttct cgctgcatga ccttagtgat   3660
aaagaaacca ccattagcca gcagagtgcc gccattttgt tctgcgtcga aggcgatgca   3720
acgttgtgga aaggttctca gcagttacag cttaaaccgg gtgaatcagc gtttattgcc   3780
gccaacgaat caccggtgac tgtcaaaggc cacggccgtt tagcgcgtgt ttacaacaag   3840
ctgtaagagc ttactgaaaa aattaacatc tcttgctaag ctgggagctc tagatccccg   3900
aatttccccg atcgttcaaa catttggcaa taaagtttct taagattgaa tcctgttgcc   3960
ggtcttgcga tgattatcat ataatttctg ttgaattacg ttaagcatgt aataattaac   4020
atgtaatgca tgacgttatt tatgagatgg gtttttatga ttagagtccc gcaattatac   4080
atttaatacg cgatagaaaa caaaatatag cgcgcaaact aggataaatt atcgcgcgcg   4140
gtgtcatcta tgttactaga tcgggaattg gcgagctcga attaattcag tacattaaaa   4200
acgtccgcaa tgtgttatta agttgtctaa gcgtcaattt gtttacacca caatatatcc   4260
tgccaccagc cagccaacag ctccccgacc ggcagctcgg cacaaaatca ccactcgata   4320
caggcagccc atcagtccgg gacggcgtca gcgggagagc cgttgtaagg cggcagactt   4380
tgctcatgtt accgatgcta ttcggaagaa cggcaactaa gctgccgggt ttgaaacacg   4440
gatgatctcg cggagggtag catgttgatt gtaacgatga cagagcgttg ctgcctgtga   4500
tcaaatatca tctccctcgc agagatccga attatcagcc ttcttattca tttctcgctt   4560
aaccgtgaca ggctgtcgat cttgagaact atgccgacat aataggaaat cgctggataa   4620
agccgctgag gaagctgagt ggcgctattt ctttagaagt gaacgttgac gatcgtcgac   4680
cgtaccccga tgaattaatt cggacgtacg ttctgaacac agctggatac ttacttgggc   4740
gattgtcata catgacatca acaatgtacc cgtttgtgta accgtctctt ggaggttcgt   4800
atgacactag tggttcccct cagcttgcga ctagatgttg aggcctaaca ttttattaga   4860
gagcaggcta gttgcttaga tacatgatct tcaggccgtt atctgtcagg gcaagcgaaa   4920
attggccatt tatgacgacc aatgccccgc agaagctccc atctttgccg ccatagacgc   4980
cgcgcccccc ttttggggtg tagaacatcc ttttgccaga tgtggaaaag aagttcgttg   5040
tcccattgtt ggcaatgacg tagtagccgg cgaaagtgcg agacccattt gcgctatata   5100
```

```
taagcctacg atttccgttg cgactattgt cgtaattgga tgaactatta tcgtagttgc   5160
tctcagagtt gtcgtaattt gatggactat tgtcgtaatt gcttatggag ttgtcgtagt   5220
tgcttggaga aatgtcgtag ttggatgggg agtagtcata gggaagacga gcttcatcca   5280
ctaaaacaat tggcaggtca gcaagtgcct gccccgatgc catcgcaagt acgaggctta   5340
gaaccacctt caacagatcg cgcatagtct tccccagctc tctaacgctt gagttaagcc   5400
gcgccgcgaa gcggcgtcgg cttgaacgaa ttgttagaca ttatttgccg actaccttgg   5460
tgatctcgcc tttcacgtag tgaacaaatt cttccaactg atctgcgcgc gaggccaagc   5520
gatcttcttg tccaagataa gcctgcctag cttcaagtat gacgggctga tactgggccg   5580
gcaggcgctc cattgcccag tcggcagcga catccttcgg cgcgattttg ccggttactg   5640
cgctgtacca aatgcgggac aacgtaagca ctacatttcg ctcatcgcca gcccagtcgg   5700
gcggcgagtt ccatagcgtt aaggtttcat ttagcgcctc aaatagatcc tgttcaggaa   5760
ccggatcaaa gagttcctcc gccgctggac ctaccaaggc aacgctatgt tctcttgctt   5820
ttgtcagcaa gatagccaga tcaatgtcga tcgtggctgg ctcgaagata cctgcaagaa   5880
tgtcattgcg ctgccattct ccaaattgca gttcgcgctt agctggataa cgccacggaa   5940
tgatgtcgtc gtgcacaaca atggtgactt ctacagcgcg gagaatctcg ctctctccag   6000
gggaagccga agtttccaaa aggtcgttga tcaaagctcg ccgcgttgtt tcatcaagcc   6060
ttacggtcac cgtaaccagc aaatcaatat cactgtgtgg cttcaggccg ccatccactg   6120
cggagccgta caaatgtacg gccagcaacg tcggttcgag atggcgctcg atgacgccaa   6180
ctacctctga tagttgagtc gatacttcgg cgatcaccgc ttccctcatg atgtttaact   6240
cctgaattaa gccgcgccgc gaagcggtgt cggcttgaat gaattgttag gcgtcatcct   6300
gtgctcccga gaaccagtac cagtacatcg ctgtttcgtt cgagacttga ggtctagttt   6360
tatacgtgaa caggtcaatg ccgccgagag taaagccaca ttttgcgtac aaattgcagg   6420
caggtacatt gttcgtttgt gtctctaatc gtatgccaag gagctgtctg cttagtgccc   6480
actttttcgc aaattcgatg agactgtgcg cgactccttt gcctcggtgc gtgtgcgaca   6540
caacaatgtg ttcgatagag gctagatcgt tccatgttga gttgagttca atcttcccga   6600
caagctcttg gtcgatgaat gcgccatagc aagcagagtc ttcatcagag tcatcatccg   6660
agatgtaatc cttccggtag ggctcacac ttctggtaga tagttcaaag ccttggtcgg   6720
ataggtgcac atcgaacact tcacgaacaa tgaaatggtt ctcagcatcc aatgtttccg   6780
ccacctgctc agggatcacc gaaatcttca tatgacgcct aacgcctggc acagcggatc   6840
gcaaacctgg cgcggctttt ggcacaaaag gcgtgacagg tttgcgaatc cgttgctgcc   6900
acttgttaac ccttttgcca gatttggtaa ctataattta tgttagaggc gaagtcttgg   6960
gtaaaaactg gcctaaaatt gctggggatt tcaggaaagt aaacatcacc ttccggctcg   7020
atgtctattg tagatatatg tagtgtatct acttgatcgg gggatctgct gcctcgcgcg   7080
tttcggtgat gacggtgaaa acctctgaca catgcagctc ccggagacgg tcacagcttg   7140
tctgtaagcg gatgccggga gcagacaagc ccgtcagggc gcgtcagcgg gtgttggcgg   7200
gtgtcggggc gcagccatga cccagtcacg tagcgatagc ggagtgtata ctggcttaac   7260
tatgcggcat cagagcagat tgtactgaga gtgcaccata tgcggtgtga aataccgcac   7320
agatgcgtaa ggagaaaata ccgcatcagg cgctcttccg cttcctcgct cactgactcg   7380
ctgcgctcgg tcgttcggct gcggcgagcg gtatcagctc actcaaaggc ggtaatacgg   7440
ttatccacag aatcagggga taacgcagga aagaacatgt gagcaaaagg ccagcaaaag   7500
```

```
gccaggaacc gtaaaaaggc cgcgttgctg gcgtttttcc ataggctccg cccccctgac   7560
gagcatcaca aaaatcgacg ctcaagtcag aggtggcgaa acccgacagg actataaaga   7620
taccaggcgt ttccccctgg aagctccctc gtgcgctctc ctgttccgac cctgccgctt   7680
accggatacc tgtccgcctt tctcccttcg ggaagcgtgg cgctttctca tagctcacgc   7740
tgtaggtatc tcagttcggt gtaggtcgtt cgctccaagc tgggctgtgt gcacgaaccc   7800
cccgttcagc ccgaccgctg cgccttatcc ggtaactatc gtcttgagtc caacccggta   7860
agacacgact tatcgccact ggcagcagcc actggtaaca ggattagcag agcgaggtat   7920
gtaggcggtg ctacagagtt cttgaagtgg tggcctaact acggctacac tagaaggaca   7980
gtatttggta tctgcgctct gctgaagcca gttaccttcg gaaaaagagt tggtagctct   8040
tgatccggca aacaaaccac cgctggtagc ggtggttttt ttgtttgcaa gcagcagatt   8100
acgcgcagaa aaaaaggatc tcaagaagat cctttgatct tttctacggg gtctgacgct   8160
cagtggaacg aaaactcacg ttaagggatt ttggtcatga gattatcaaa aaggatcttc   8220
acctagatcc ttttaaatta aaaatgaagt tttaaatcaa tctaaagtat atatgagtaa   8280
acttggtctg acagttacca atgcttaatc agtgaggcac ctatctcagc gatctgtcta   8340
tttcgttcat ccatagttgc ctgactcccc gtcgtgtaga taactacgat acgggagggc   8400
ttaccatctg gccccagtgc tgcaatgata ccgcgagacc cacgctcacc ggctccagat   8460
ttatcagcaa taaaccagcc agccggaagg gccgagcgca gaagtggtcc tgcaacttta   8520
tccgcctcca tccagtctat taattgttgc cgggaagcta gagtaagtag ttcgccagtt   8580
aatagtttgc gcaacgttgt tgccattgct gcaggggggg gggggggggg gttccattgt   8640
tcattccacg gacaaaaaca gagaaaggaa acgacagagg ccaaaaagct cgctttcagc   8700
acctgtcgtt tcctttcttt tcagagggta ttttaaataa aaacattaag ttatgacgaa   8760
gaagaacgga aacgccttaa accggaaaat tttcataaat agcgaaaacc cgcgaggtcg   8820
ccgccccgta acctgtcgga tcaccggaaa ggacccgtaa agtgataatg attatcatct   8880
acatatcaca acgtgcgtgg aggccatcaa accacgtcaa ataatcaatt atgacgcagg   8940
tatcgtatta attgatctgc atcaacttaa cgtaaaaaca acttcagaca atacaaatca   9000
gcgacactga atacggggca acctcatgtc cccccccccc ccccccctgca ggcatcgtgg   9060
tgtcacgctc gtcgtttggt atggcttcat tcagctccgg ttcccaacga tcaaggcgag   9120
ttacatgatc ccccatgttg tgcaaaaaag cggttagctc cttcggtcct ccgatcgttg   9180
tcagaagtaa gttggccgca gtgttatcac tcatggttat ggcagcactg cataattctc   9240
ttactgtcat gccatccgta agatgctttt ctgtgactgg tgagtactca accaagtcat   9300
tctgagaata gtgtatgcgg cgaccgagtt gctcttgccc ggcgtcaaca cgggataata   9360
ccgcgccaca tagcagaact ttaaaagtgc tcatcattgg aaaacgttct tcggggcgaa   9420
aactctcaag gatcttaccg ctgttgagat ccagttcgat gtaacccact cgtgcaccca   9480
actgatcttc agcatctttt actttcacca gcgtttctgg gtgagcaaaa acaggaaggc   9540
aaaatgccgc aaaaaaggga ataagggcga cacggaaatg ttgaatactc atactcttcc   9600
tttttcaata ttattgaagc atttatcagg gttattgtct catgagcgga tacatatttg   9660
aatgtattta gaaaaataaa caaatagggg ttccgcgcac atttccccga aaagtgccac   9720
ctgacgtcta agaaaccatt attatcatga cattaaccta taaaaatagg cgtatcacga   9780
ggccctttcg tcttcaagaa ttggtcgacg atcttgctgc gttcggatat tttcgtggag   9840
```

```
ttcccgccac agacccggat tgaaggcgag atccagcaac tcgcgccaga tcatcctgtg   9900
acggaacttt ggcgcgtgat gactggccag gacgtcggcc gaaagagcga caagcagatc   9960
acgcttttcg acagcgtcgg atttgcgatc gaggattttt cggcgctgcg ctacgtccgc  10020
gaccgcgttg agggatcaag ccacagcagc ccactcgacc ttctagccga cccagacgag  10080
ccaagggatc tttttggaat gctgctccgt cgtcaggctt tccgacgttt gggtggttga  10140
acagaagtca ttatcgcacg gaatgccaag cactcccgag gggaaccctg tggttggcat  10200
gcacatacaa atggacgaac ggataaacct tttcacgccc ttttaaatat ccgattattc  10260
taataaacgc tcttttctct taggtttacc cgccaatata tcctgtcaaa cactgatagt  10320
ttaaactgaa ggcgggaaac gacaacctga tcatgagcgg agaattaagg gagtcacgtt  10380
atgacccccg ccgatgacgc gggacaagcc gttttacgtt tggaactgac agaaccgcaa  10440
cgttgaagga gccactcagc ttaattaagt ctaactcgag ttactggtac gtaccaaatc  10500
catggaatca aggtaccacg accggaggag agattctttg ctttgcttgt ggctgcgaag  10560
gaggaggaga aaccacgcag cggataagaa ggaagccgcc tttgcaaaac cagagcatct  10620
tttctgatga agaaatccgc gttgcctcct gtgagaagaa tgcgaccctt tttttatact  10680
ctattctatc tttattatta ttgtcaattt gtcatgtcac tgagaaatgg ccctgatacg  10740
aacgctaaga tccaatcata caccttttat ttatttatac ataagtacgt aaataagatg  10800
aaaataaaaa aaatgtcatg gacgaaaaca acgtccacaa ggacggcaaa gatggaggac  10860
cgcaggagca caacggatgg atgttctttt tttgttatca aacaacggat ggatgtttcc  10920
gagcaggtgc agcgtctcct ccgtttactc gccgtgcaca tcacggcgtc caaacgggcg  10980
tttgccggcg aggacacggt agattttgcc gacatggtag attttatcaa gatattccgg  11040
tcgagtttgg agtactagct ccatcatgta taaccaccaa tgattgagtg gtgaccatat  11100
cataatcgtt ggtcagcttt ccttccatta ctttttaatt cagtaataat aatccctaaa  11160
gcctaatcaa gtaaattcaa cttccgaatt caatagggat catcagggca cgacctgatt  11220
gtaaagacat acaatagctt tcaaacaaca ttttcactta tggtaaaatc ttaattaagg  11280
tcttaatatt ataattattt ttttcactgc cgtgagggaa tggagatttc agaaagggac  11340
tttttggtat catcattgta tatgatccac ggtttttagt tagggcgact ttaatttctt  11400
atttttgata attcttgttt ctattgtctt gacgattcta atgccatgtc cttttgtctt  11460
gacagctcta gtgccatgtc tatttgtcat gttatcattt gttcttttta tttcaaggaa  11520
aattattaca tcaaaaaatt gattttcgaa gttcacggtc atcttcacca tcactctcta  11580
tcgcattggt ggcgagaagc atatctagtg gtttcattct ggtaagcctc gctcaaatga  11640
aatttgtaat aaaatactat atttctttat caaggttata agatatggag agaaatggtc  11700
tgcttcataa atttgactta cctagagcct ttaaaaagga ataccatgta atctaaactc  11760
tataacataa agagctttgc gcttttaaaa atatgctaac ctatataaat cgcttttgct  11820
agagacaggt catgtatgat tgaagcgtca ccataacgcc gttaatcttc cgtccagcca  11880
ttaacggcca cctaccgcag gaaacaaacg gcgtcaccat cctcgatatc tccgcggcgg  11940
ccgctggctt ttttcggaga aattgcgcgg tggggacgga gtccacgaga gcctctcgcc  12000
gctgggcccc acaatcaatg gcgtgacctc acgggacggc tccctccctc taccctcccc  12060
ccgtgtataa atagcacccc tccctcgcct cttccgcatc cagtattcca gtccccaatc  12120
cgtcgagaaa ttctcgcgag cgatcgaaat ctaagcgaag cgaagaggcc tccccagatc  12180
ctctcaaggt atgcgagagc atcgatcccc ttccgatcta tatcgcgtgt cctccctgtt  12240
```

```
cttgttcttc gtcgatctag tttagggttt gatttggttc tgaatcgaac ccttttcctg  12300

cttgcgttcg atttgtactc gatcctcggg tagaggtgtg gatctgcggg gcgtgatgag  12360

gtagtttggt gtagatttgt tctgggcgtt cgatttgcca ctagggttcg gctgctgttg  12420

gcattcctga tcgagcggcc ggataggatt gtttttccct tttatatgt tggatgcgtg  12480

atggttcctg tgtgttgggt tagattgctg gtacgattca tctaggtggt gatttgcaga  12540

ggaacaactt tgctgttgaa tattggtagg tctatctaga tttattactt ttgattatcg  12600

cctgataagg atcaccgatt cgtgtagaat aaattatttc attgttgggt catgtagata  12660

tagctgcaca atttcttact tggctcctta ctgtgtgaat tgtagaataa actgtgttac  12720

tctatgagtt tttctggatt gctggatcca gttaggccag tgctgtcaat ttgttatggc  12780

tgttaatgta ataattttct ggattgttgg cctgcttctc ttcatgttta atcacgtgat  12840

ggttcatgat gcctgttggg ttagattgtt tgttcaattc atctaggcag tgctgtgcag  12900

agtacaactc gattgatgtt taatcttggt agcttcatct agatttgtac aaattttggt  12960

cacctgatga tgatcaccga ttgttgtgga attatttctt aactggttcg ttgttagtca  13020

ccaccttact tgtagaataa cctgtggtac tgcttttctg ttctgtttta ggccacatca  13080
```

```
<210> SEQ ID NO 17
<211> LENGTH: 10146
<212> TYPE: DNA
<213> ORGANISM: Artificial Sequence
<220> FEATURE:
<223> OTHER INFORMATION: Synthetic construct, pAG4000

<400> SEQUENCE: 17

aattcctgca gtgcagcgtg acccggtcgt gcccctctct agagataatg agcattgcat     60

gtctaagtta taaaaaatta ccacatattt tttttgtcac acttgtttga agtgcagttt    120

atctatcttt atacatatat ttaaacttta ctctacgaat aatataatct atagtactac    180

aataatatca gtgttttaga gaatcatata aatgaacagt tagacatggt ctaaaggaca    240

attgagtatt ttgacaacag gactctacag ttttatcttt ttagtgtgca tgtgttctcc    300

tttttttttg caaatagctt cacctatata atacttcatc cattttatta gtacatccat    360

ttagggttta gggttaatgg tttttataga ctaatttttt tagtacatct attttattct    420

attttagcct ctaaattaag aaaactaaaa ctctatttta gttttttat ttaataattt    480

agatataaaa tagaataaaa taaagtgact aaaaattaaa caaataccct ttaagaaatt    540

aaaaaaacta aggaaacatt tttcttgttt cgagtagata atgccagcct gttaaacgcc    600

gtcgacgagt ctaacggaca ccaaccagcg aaccagcagc gtcgcgtcgg gccaagcgaa    660

gcagacggca cggcatctct gtcgctgcct ctggacccct ctcgagagtt ccgctccacc    720

gttggacttg ctccgctgtc ggcatccaga aattgcgtgg cggagcggca gacgtgagcc    780

ggcacggcag gcggcctcct cctcctctca cggcacggca gctacggggg attcctttcc    840

caccgctcct tcgctttccc ttcctcgccc gccgtaataa atagacaccc cctccacacc    900

ctctttcccc aacctcgtgt tgttcggagc gcacacacac acaaccagat ctcccccaaa    960

tccacccgtc ggcacctccg cttcaaggta cgccgctcgt cctccccccc cccccctctc   1020

taccttctct agatcggcgt tccggtccat ggttagggcc cggtagttct acttctgttc   1080

atgtttgtgt tagatccgtg tttgtgttag atccgtgctg ctagcgttcg tacacggatg   1140

cgacctgtac gtcagacacg ttctgattgc taacttgcca gtgtttctct ttggggaatc   1200
```

-continued

```
ctgggatggc tctagccgtt ccgcagacgg gatcgatttc atgatttttt ttgtttcgtt   1260
gcatagggtt tggtttgccc ttttccttta tttcaatata tgccgtgcac ttgtttgtcg   1320
ggtcatcttt tcatgctttt ttttgtcttg gttgtgatga tgtggtctgg ttgggcggtc   1380
gttctagatc ggagtagaat tctgtttcaa actacctggt ggatttatta attttggatc   1440
tgtatgtgtg tgccatacat attcatagtt acgaattgaa gatgatggat ggaaatatcg   1500
atctaggata ggtatacatg ttgatgcggg ttttactgat gcatatacag agatgctttt   1560
tgttcgcttg gttgtgatga tgtggtgtgg ttgggcggtc gttcattcgt tctagatcgg   1620
agtagaatac tgtttcaaac tacctggtgt atttattaat tttggaactg tatgtgtgtg   1680
tcatacatct tcatagttac gagtttaaga tggatggaaa tatcgatcta ggataggtat   1740
acatgttgat gtgggtttta ctgatgcata tacatgatgg catatgcagc atctattcat   1800
atgctctaac cttgagtacc tatctattat aataaacaag tatgttttat aattattttg   1860
atcttgatat acttggatga tggcatatgc agcagctata tgtggatttt tttagccctg   1920
ccttcatacg ctatttattt gcttggtact gtttcttttg tcgatgctca ccctgttgtt   1980
tggtgttact tctgcagatg cagaaactca ttaactcagt gcaaaactat gcctggggca   2040
gcaaaacggc gttgactgaa ctttatggta tggaaaatcc gtccagccag ccgatggccg   2100
agctgtggat gggcgcacat ccgaaaagca gttcacgagt gcagaatgcc gccggagata   2160
tcgtttcact gcgtgatgtg attgagagtg ataaatcgac tctgctcgga gaggccgttg   2220
ccaaacgctt tggcgaactg cctttcctgt tcaaagtatt atgcgcagca cagccactct   2280
ccattcaggt tcatccaaac aaacacaatt ctgaaatcgg ttttgccaaa gaaaatgccg   2340
caggtatccc gatggatgcc gccgagcgta actataaaga tcctaaccac aagccggagc   2400
tggtttttgc gctgacgcct ttccttgcga tgaacgcgtt tcgtgaattt tccgagattg   2460
tctccctact ccagccggtc gcaggtgcac atccggcgat tgctcacttt ttacaacagc   2520
ctgatgccga acgtttaagc gaactgttcg ccagcctgtt gaatatgcag ggtgaagaaa   2580
aatcccgcgc gctggcgatt ttaaaatcgg ccctcgatag ccagcagggt gaaccgtggc   2640
aaacgattcg tttaatttct gaattttacc cggaagacag cggtctgttc tccccgctat   2700
tgctgaatgt ggtgaaattg aaccctggcg aagcgatgtt cctgttcgct gaaacaccgc   2760
acgcttacct gcaaggcgtg gcgctggaag tgatggcaaa ctccgataac gtgctgcgtg   2820
cgggtctgac gcctaaatac attgatattc cggaactggt tgccaatgtg aaattcgaag   2880
ccaaaccggc taaccagttg ttgacccagc cggtgaaaca aggtgcagaa ctggacttcc   2940
cgattccagt ggatgatttt gccttctcgc tgcatgacct tagtgataaa gaaaccacca   3000
ttagccagca gagtgccgcc attttgttct gcgtcgaagg cgatgcaacg ttgtggaaag   3060
gttctcagca gttacagctt aaaccgggtg aatcagcgtt tattgccgcc aacgaatcac   3120
cggtgactgt caaaggccac ggccgtttag cgcgtgttta caacaagctg taagagctta   3180
ctgaaaaaat taacatctct tgctaagctg ggagctctag atccccgaat ttccccgatc   3240
gttcaaacat ttggcaataa agtttcttaa gattgaatcc tgttgccggt cttgcgatga   3300
ttatcatata atttctgttg aattacgtta agcatgtaat aattaacatg taatgcatga   3360
cgttatttat gagatgggtt tttatgatta gagtcccgca attatacatt taatacgcga   3420
tagaaaacaa aatatagcgc gcaaactagg ataaattatc gcgcgcggtg tcatctatgt   3480
tactagatcg ggaattggcg agctcgaatt aattcagtac attaaaaacg tccgcaatgt   3540
gttattaagt tgtctaagcg tcaatttgtt tacaccacaa tatatcctgc caccagccag   3600
```

```
ccaacagctc cccgaccggc agctcggcac aaaatcacca ctcgatacag gcagcccatc   3660
agtccgggac ggcgtcagcg ggagagccgt tgtaaggcgg cagactttgc tcatgttacc   3720
gatgctattc ggaagaacgg caactaagct gccgggtttg aaacacggat gatctcgcgg   3780
agggtagcat gttgattgta acgatgacag agcgttgctg cctgtgatca aatatcatct   3840
ccctcgcaga gatccgaatt atcagccttc ttattcattt ctcgcttaac cgtgacaggc   3900
tgtcgatctt gagaactatg ccgacataat aggaaatcgc tggataaagc cgctgaggaa   3960
gctgagtggc gctatttctt tagaagtgaa cgttgacgat cgtcgaccgt accccgatga   4020
attaattcgg acgtacgttc tgaacacagc tggatactta cttgggcgat tgtcatacat   4080
gacatcaaca atgtacccgt ttgtgtaacc gtctcttgga ggttcgtatg acactagtgg   4140
ttcccctcag cttgcgacta gatgttgagg cctaacattt tattagagag caggctagtt   4200
gcttagatac atgatcttca ggccgttatc tgtcagggca agcgaaaatt ggccatttat   4260
gacgaccaat gccccgcaga agctcccatc tttgccgcca tagacgccgc gcccccccttt   4320
tggggtgtag aacatccttt tgccagatgt ggaaaagaag ttcgttgtcc cattgttggc   4380
aatgacgtag tagccggcga aagtgcgaga cccatttgcg ctatatataa gcctacgatt   4440
tccgttgcga ctattgtcgt aattggatga actattatcg tagttgctct cagagttgtc   4500
gtaatttgat ggactattgt cgtaattgct tatggagttg tcgtagttgc ttggagaaat   4560
gtcgtagttg gatggggagt agtcataggg aagacgagct tcatccacta aaacaattgg   4620
caggtcagca agtgcctgcc ccgatgccat cgcaagtacg aggcttagaa ccaccttcaa   4680
cagatcgcgc atagtcttcc ccagctctct aacgcttgag ttaagccgcg ccgcgaagcg   4740
gcgtcggctt gaacgaattg ttagacatta tttgccgact accttggtga tctcgccttt   4800
cacgtagtga acaaattctt ccaactgatc tgcgcgcgag gccaagcgat cttcttgtcc   4860
aagataagcc tgcctagctt caagtatgac gggctgatac tgggccggca ggcgctccat   4920
tgcccagtcg gcagcgacat ccttcggcgc gattttgccg gttactgcgc tgtaccaaat   4980
gcgggacaac gtaagcacta catttcgctc atcgccagcc cagtcgggcg gcgagttcca   5040
tagcgttaag gtttcattta gcgcctcaaa tagatcctgt tcaggaaccg gatcaaagag   5100
ttcctccgcc gctggaccta ccaaggcaac gctatgttct cttgcttttg tcagcaagat   5160
agccagatca atgtcgatcg tggctggctc gaagatacct gcaagaatgt cattgcgctg   5220
ccattctcca aattgcagtt cgcgcttagc tggataacgc cacggaatga tgtcgtcgtg   5280
cacaacaatg gtgacttcta cagcgcggag aatctcgctc tctccagggg aagccgaagt   5340
ttccaaaagg tcgttgatca aagctcgccg cgttgtttca tcaagcctta cggtcaccgt   5400
aaccagcaaa tcaatatcac tgtgtggctt caggccgcca tccactgcgg agccgtacaa   5460
atgtacggcc agcaacgtcg gttcgagatg gcgctcgatg acgccaacta cctctgatag   5520
ttgagtcgat acttcggcga tcaccgcttc cctcatgatg tttaactcct gaattaagcc   5580
gcgccgcgaa gcggtgtcgg cttgaatgaa ttgttaggcg tcatcctgtg ctcccgagaa   5640
ccagtaccag tacatcgctg tttcgttcga gacttgaggt ctagttttat acgtgaacag   5700
gtcaatgccg ccgagagtaa agccacattt tgcgtacaaa ttgcaggcag gtacattgtt   5760
cgtttgtgtc tctaatcgta tgccaaggag ctgtctgctt agtgcccact tttcgcaaa    5820
ttcgatgaga ctgtgcgcga ctcctttgcc tcggtgcgtg tgcgacacaa caatgtgttc   5880
gatagaggct agatcgttcc atgttgagtt gagttcaatc ttcccgacaa gctcttggtc   5940
```

```
gatgaatgcg ccatagcaag cagagtcttc atcagagtca tcatccgaga tgtaatcctt   6000
ccggtagggg ctcacacttc tggtagatag ttcaaagcct tggtcggata ggtgcacatc   6060
gaacacttca cgaacaatga aatggttctc agcatccaat gtttccgcca cctgctcagg   6120
gatcaccgaa atcttcatat gacgcctaac gcctggcaca gcggatcgca aacctggcgc   6180
ggcttttggc acaaaaggcg tgacaggttt gcgaatccgt tgctgccact tgttaaccct   6240
tttgccagat ttggtaacta taatttatgt tagaggcgaa gtcttgggta aaaactggcc   6300
taaaattgct ggggatttca ggaaagtaaa catcaccttc cggctcgatg tctattgtag   6360
atatatgtag tgtatctact tgatcggggg atctgctgcc tcgcgcgttt cggtgatgac   6420
ggtgaaaacc tctgacacat gcagctcccg gagacggtca cagcttgtct gtaagcggat   6480
gccgggagca gacaagcccg tcagggcgcg tcagcgggtg ttggcgggtg tcggggcgca   6540
gccatgaccc agtcacgtag cgatagcgga gtgtatactg gcttaactat gcggcatcag   6600
agcagattgt actgagagtg caccatatgc ggtgtgaaat accgcacaga tgcgtaagga   6660
gaaaataccg catcaggcgc tcttccgctt cctcgctcac tgactcgctg cgctcggtcg   6720
ttcggctgcg gcgagcggta tcagctcact caaaggcggt aatacggtta tccacagaat   6780
caggggataa cgcaggaaag aacatgtgag caaaaggcca gcaaaaggcc aggaaccgta   6840
aaaaggccgc gttgctggcg tttttccata ggctccgccc ccctgacgag catcacaaaa   6900
atcgacgctc aagtcagagg tggcgaaacc cgacaggact ataaagatac caggcgtttc   6960
cccctggaag ctccctcgtg cgctctcctg ttccgaccct gccgcttacc ggatacctgt   7020
ccgcctttct cccttcggga agcgtggcgc tttctcatag ctcacgctgt aggtatctca   7080
gttcggtgta ggtcgttcgc tccaagctgg gctgtgtgca cgaacccccc gttcagcccg   7140
accgctgcgc cttatccggt aactatcgtc ttgagtccaa cccggtaaga cacgacttat   7200
cgccactggc agcagccact ggtaacagga ttagcagagc gaggtatgta ggcggtgcta   7260
cagagttctt gaagtggtgg cctaactacg gctacactag aaggacagta tttggtatct   7320
gcgctctgct gaagccagtt accttcggaa aaagagttgg tagctcttga tccggcaaac   7380
aaaccaccgc tggtagcggt ggtttttttg tttgcaagca gcagattacg cgcagaaaaa   7440
aaggatctca agaagatcct ttgatctttt ctacggggtc tgacgctcag tggaacgaaa   7500
actcacgtta agggattttg gtcatgagat tatcaaaaag gatcttcacc tagatccttt   7560
taaattaaaa atgaagtttt aaatcaatct aaagtatata tgagtaaact tggtctgaca   7620
gttaccaatg cttaatcagt gaggcaccta tctcagcgat ctgtctattt cgttcatcca   7680
tagttgcctg actccccgtc gtgtagataa ctacgatacg ggagggctta ccatctggcc   7740
ccagtgctgc aatgataccg cgagacccac gctcaccggc tccagattta tcagcaataa   7800
accagccagc cggaagggcc gagcgcagaa gtggtcctgc aactttatcc gcctccatcc   7860
agtctattaa ttgttgccgg gaagctagag taagtagttc gccagttaat agtttgcgca   7920
acgttgttgc cattgctgca gggggggggg gggggggggtt ccattgttca ttccacggac   7980
aaaaacagag aaaggaaacg acagaggcca aaaagctcgc tttcagcacc tgtcgtttcc   8040
tttcttttca gagggtattt taaataaaaa cattaagtta tgacgaagaa gaacggaaac   8100
gccttaaacc ggaaaatttt cataaatagc gaaaacccgc gaggtcgccg ccccgtaacc   8160
tgtcggatca ccggaaagga cccgtaaagt gataatgatt atcatctaca tatcacaacg   8220
tgcgtggagg ccatcaaacc acgtcaaata atcaattatg acgcaggtat cgtattaatt   8280
gatctgcatc aacttaacgt aaaaacaact tcagacaata caaatcagcg acactgaata   8340
```

```
cggggcaacc tcatgtcccc cccccccccc ccctgcaggc atcgtggtgt cacgctcgtc   8400
gtttggtatg gcttcattca gctccggttc ccaacgatca aggcgagtta catgatcccc   8460
catgttgtgc aaaaaagcgg ttagctcctt cggtcctccg atcgttgtca gaagtaagtt   8520
ggccgcagtg ttatcactca tggttatggc agcactgcat aattctctta ctgtcatgcc   8580
atccgtaaga tgcttttctg tgactggtga gtactcaacc aagtcattct gagaatagtg   8640
tatgcggcga ccgagttgct cttgcccggc gtcaacacgg gataataccg cgccacatag   8700
cagaacttta aaagtgctca tcattggaaa acgttcttcg gggcgaaaac tctcaaggat   8760
cttaccgctg ttgagatcca gttcgatgta acccactcgt gcacccaact gatcttcagc   8820
atcttttact ttcaccagcg tttctgggtg agcaaaaaca ggaaggcaaa atgccgcaaa   8880
aaagggaata agggcgacac ggaaatgttg aatactcata ctcttccttt ttcaatatta   8940
ttgaagcatt tatcagggtt attgtctcat gagcggatac atatttgaat gtatttagaa   9000
aaataaacaa ataggggttc cgcgcacatt tccccgaaaa gtgccacctg acgtctaaga   9060
aaccattatt atcatgacat taacctataa aaataggcgt atcacgaggc cctttcgtct   9120
tcaagaattg gtcgacgatc ttgctgcgtt cggatatttt cgtggagttc ccgccacaga   9180
cccggattga aggcgagatc cagcaactcg cgccagatca tcctgtgacg gaactttggc   9240
gcgtgatgac tggccaggac gtcggccgaa agagcgacaa gcagatcacg cttttcgaca   9300
gcgtcggatt tgcgatcgag gatttttcgg cgctgcgcta cgtccgcgac cgcgttgagg   9360
gatcaagcca cagcagccca ctcgaccttc tagccgaccc agacgagcca agggatcttt   9420
ttggaatgct gctccgtcgt caggctttcc gacgtttggg tggttgaaca gaagtcatta   9480
tcgcacggaa tgccaagcac tcccgagggg aaccctgtgg ttggcatgca catacaaatg   9540
gacgaacgga taaacctttt cacgcccttt taaatatccg attattctaa taaacgctct   9600
tttctcttag gtttacccgc caatatatcc tgtcaaacac tgatagttta aactgaaggc   9660
gggaaacgac aacctgatca tgagcggaga attaagggag tcacgttatg acccccgccg   9720
atgacgcggg acaagccgtt ttacgtttgg aactgacaga accgcaacgt tgaaggagcc   9780
actcagctta attaagtcta actcgagtta ctggtacgta ccaaatccat ggaatcaagg   9840
taccatcaat cccgggtatt catcctaggt ccccgaattt ccccgatcgt tcaaacattt   9900
ggcaataaag tttcttaaga ttgaatcctg ttgccggtct tgcgatgatt atcatataat   9960
ttctgttgaa ttacgttaag catgtaataa ttaacatgta atgcatgacg ttatttatga  10020
gatgggtttt tatgattaga gtcccgcaat tatacattta atacgcgata gaaaacaaaa  10080
tatagcgcgc aaactaggat aaattatcgc gcgcggtgtc atctatgtta ctagatcggg  10140
aattgg                                                             10146
```

<210> SEQ ID NO 18
<211> LENGTH: 14126
<212> TYPE: DNA
<213> ORGANISM: Artificial Sequence
<220> FEATURE:
<223> OTHER INFORMATION: Synthetic construct, pAG4001

<400> SEQUENCE: 18

```
ctaggtcccc gaatttcccc gatcgttcaa acatttggca ataaagtttc ttaagattga     60
atcctgttgc cggtcttgcg atgattatca tataatttct gttgaattac gttaagcatg    120
taataattaa catgtaatgc atgacgttat ttatgagatg ggtttttatg attagagtcc    180
```

```
cgcaattata catttaatac gcgatagaaa acaaaatata gcgcgcaaac taggataaat    240
tatcgcgcgc ggtgtcatct atgttactag atcgggaatt ggaattcctg cagtgcagcg    300
tgacccggtc gtgcccctct ctagagataa tgagcattgc atgtctaagt tataaaaaat    360
taccacatat ttttttgtc acacttgttt gaagtgcagt ttatctatct ttatacatat    420
atttaaactt tactctacga ataatataat ctatagtact acaataatat cagtgtttta    480
gagaatcata taaatgaaca gttagacatg gtctaaagga caattgagta ttttgacaac    540
aggactctac agttttatct ttttagtgtg catgtgttct ccttttttt tgcaaatagc    600
ttcacctata taatacttca tccattttat tagtacatcc atttagggtt tagggttaat    660
ggtttttata gactaatttt tttagtacat ctattttatt ctattttagc ctctaaatta    720
agaaaactaa aactctattt tagtttttt atttaataat ttagatataa aatagaataa    780
aataaagtga ctaaaaatta aacaaatacc ctttaagaaa ttaaaaaaac taaggaaaca    840
tttttcttgt ttcgagtaga taatgccagc ctgttaaacg ccgtcgacga gtctaacgga    900
caccaaccag cgaaccagca gcgtcgcgtc gggccaagcg aagcagacgg cacggcatct    960
ctgtcgctgc ctctggaccc ctctcgagag ttccgctcca ccgttggact tgctccgctg   1020
tcggcatcca gaaattgcgt ggcggagcgg cagacgtgag ccggcacggc aggcggcctc   1080
ctcctcctct cacggcacgg cagctacggg ggattccttt cccaccgctc cttcgctttc   1140
ccttcctcgc ccgccgtaat aaatagacac cccctccaca ccctctttcc ccaacctcgt   1200
gttgttcgga gcgcacacac acacaaccag atctccccca aatccacccg tcggcacctc   1260
cgcttcaagg tacgccgctc gtcctccccc ccccccctc tctaccttct ctagatcggc   1320
gttccggtcc atggttaggg cccggtagtt ctacttctgt tcatgtttgt gttagatccg   1380
tgtttgtgtt agatccgtgc tgctagcgtt cgtacacgga tgcgacctgt acgtcagaca   1440
cgttctgatt gctaacttgc cagtgtttct ctttggggaa tcctgggatg gctctagccg   1500
ttccgcagac gggatcgatt tcatgatttt ttttgtttcg ttgcataggg tttggtttgc   1560
ccttttcctt tatttcaata tatgccgtgc acttgtttgt cgggtcatct tttcatgctt   1620
tttttgtct tggttgtgat gatgtggtct ggttgggcgg tcgttctaga tcggagtaga   1680
attctgtttc aaactacctg gtggatttat taattttgga tctgtatgtg tgtgccatac   1740
atattcatag ttacgaattg aagatgatgg atggaaatat cgatctagga taggtataca   1800
tgttgatgcg ggttttactg atgcatatac agagatgctt tttgttcgct tggttgtgat   1860
gatgtggtgt ggttgggcgg tcgttcattc gttctagatc ggagtagaat actgtttcaa   1920
actacctggt gtatttatta attttggaac tgtatgtgtg tgtcatacat cttcatagtt   1980
acgagtttaa gatggatgga aatatcgatc taggataggt atacatgttg atgtgggttt   2040
tactgatgca tatacatgat ggcatatgca gcatctattc atatgctcta accttgagta   2100
cctatctatt ataataaaca agtatgtttt ataattattt tgatcttgat atacttggat   2160
gatggcatat gcagcagcta tatgtggatt tttttagccc tgccttcata cgctatttat   2220
ttgcttggta ctgtttcttt tgtcgatgct caccctgttg tttggtgtta cttctgcaga   2280
tgcagaaact cattaactca gtgcaaaact atgcctgggg cagcaaaacg gcgttgactg   2340
aactttatgg tatggaaaat ccgtccagcc agccgatggc cgagctgtgg atgggcgcac   2400
atccgaaaag cagttcacga gtgcagaatg ccgccggaga tatcgtttca ctgcgtgatg   2460
tgattgagag tgataaatcg actctgctcg gagaggccgt tgccaaacgc tttggcgaac   2520
tgcctttcct gttcaaagta ttatgcgcag cacagccact ctccattcag gttcatccaa   2580
```

```
acaaacacaa ttctgaaatc ggttttgcca aagaaaatgc cgcaggtatc ccgatggatg   2640
ccgccgagcg taactataaa gatcctaacc acaagccgga gctggttttt gcgctgacgc   2700
ctttccttgc gatgaacgcg tttcgtgaat tttccgagat tgtctcccta ctccagccgg   2760
tcgcaggtgc acatccggcg attgctcact ttttacaaca gcctgatgcc gaacgtttaa   2820
gcgaactgtt cgccagcctg ttgaatatgc agggtgaaga aaaatcccgc gcgctggcga   2880
ttttaaaatc ggccctcgat agccagcagg gtgaaccgtg gcaaacgatt cgtttaattt   2940
ctgaatttta cccggaagac agcggtctgt tctccccgct attgctgaat gtggtgaaat   3000
tgaaccctgg cgaagcgatg ttcctgttcg ctgaaacacc gcacgcttac ctgcaaggcg   3060
tggcgctgga agtgatggca aactccgata acgtgctgcg tgcgggtctg acgcctaaat   3120
acattgatat tccggaactg gttgccaatg tgaaattcga agccaaaccg gctaaccagt   3180
tgttgaccca gccggtgaaa caaggtgcag aactggactt cccgattcca gtggatgatt   3240
ttgccttctc gctgcatgac cttagtgata aagaaaccac cattagccag cagagtgccg   3300
ccattttgtt ctgcgtcgaa ggcgatgcaa cgttgtggaa aggttctcag cagttacagc   3360
ttaaaccggg tgaatcagcg tttattgccg ccaacgaatc accggtgact gtcaaaggcc   3420
acggccgttt agcgcgtgtt tacaacaagc tgtaagagct tactgaaaaa attaacatct   3480
cttgctaagc tgggagctct agatccccga atttccccga tcgttcaaac atttggcaat   3540
aaagtttctt aagattgaat cctgttgccg gtcttgcgat gattatcata taatttctgt   3600
tgaattacgt taagcatgta ataattaaca tgtaatgcat gacgttattt atgagatggg   3660
tttttatgat tagagtcccg caattataca tttaatacgc gatagaaaac aaaatatagc   3720
gcgcaaacta ggataaatta tcgcgcgcgg tgtcatctat gttactagat cgggaattgg   3780
cgagctcgaa ttaattcagt acattaaaaa cgtccgcaat gtgttattaa gttgtctaag   3840
cgtcaatttg tttacaccac aatatatcct gccaccagcc agccaacagc tccccgaccg   3900
gcagctcggc acaaaatcac cactcgatac aggcagccca tcagtccggg acggcgtcag   3960
cgggagagcc gttgtaaggc ggcagacttt gctcatgtta ccgatgctat tcggaagaac   4020
ggcaactaag ctgccgggtt tgaaacacgg atgatctcgc ggagggtagc atgttgattg   4080
taacgatgac agagcgttgc tgcctgtgat caaatatcat ctccctcgca gagatccgaa   4140
ttatcagcct tcttattcat ttctcgctta accgtgacag gctgtcgatc ttgagaacta   4200
tgccgacata ataggaaatc gctggataaa gccgctgagg aagctgagtg gcgctatttc   4260
tttagaagtg aacgttgacg atcgtcgacc gtaccccgat gaattaattc ggacgtacgt   4320
tctgaacaca gctggatact tacttgggcg attgtcatac atgacatcaa caatgtaccc   4380
gtttgtgtaa ccgtctcttg gaggttcgta tgacactagt ggttcccctc agcttgcgac   4440
tagatgttga ggcctaacat tttattagag agcaggctag ttgcttagat acatgatctt   4500
caggccgtta tctgtcaggg caagcgaaaa ttggccattt atgacgacca atgccccgca   4560
gaagctccca tctttgccgc catagacgcc gcgccccct tttggggtgt agaacatcct   4620
tttgccagat gtggaaaaga agttcgttgt cccattgttg gcaatgacgt agtagccggc   4680
gaaagtgcga gacccatttg cgctatatat aagcctacga tttccgttgc gactattgtc   4740
gtaattggat gaactattat cgtagttgct ctcagagttg tcgtaatttg atggactatt   4800
gtcgtaattg cttatggagt tgtcgtagtt gcttggagaa atgtcgtagt tggatgggga   4860
gtagtcatag ggaagacgag cttcatccac taaaacaatt ggcaggtcag caagtgcctg   4920
```

-continued

```
ccccgatgcc atcgcaagta cgaggcttag aaccaccttc aacagatcgc gcatagtctt   4980
ccccagctct ctaacgcttg agttaagccg cgccgcgaag cggcgtcggc ttgaacgaat   5040
tgttagacat tatttgccga ctaccttggt gatctcgcct ttcacgtagt gaacaaattc   5100
ttccaactga tctgcgcgcg aggccaagcg atcttcttgt ccaagataag cctgcctagc   5160
ttcaagtatg acgggctgat actgggccgg caggcgctcc attgcccagt cggcagcgac   5220
atccttcggc gcgattttgc cggttactgc gctgtaccaa atgcgggaca acgtaagcac   5280
tacatttcgc tcatcgccag cccagtcggg cggcgagttc catagcgtta aggtttcatt   5340
tagcgcctca aatagatcct gttcaggaac cggatcaaag agttcctccg ccgctggacc   5400
taccaaggca acgctatgtt ctcttgcttt tgtcagcaag atagccagat caatgtcgat   5460
cgtggctggc tcgaagatac ctgcaagaat gtcattgcgc tgccattctc caaattgcag   5520
ttcgcgctta gctggataac gccacggaat gatgtcgtcg tgcacaacaa tggtgacttc   5580
tacagcgcgg agaatctcgc tctctccagg ggaagccgaa gtttccaaaa ggtcgttgat   5640
caaagctcgc cgcgttgttt catcaagcct tacggtcacc gtaaccagca aatcaatatc   5700
actgtgtggc ttcaggccgc catccactgc ggagccgtac aaatgtacgg ccagcaacgt   5760
cggttcgaga tggcgctcga tgacgccaac tacctctgat agttgagtcg atacttcggc   5820
gatcaccgct tccctcatga tgtttaactc ctgaattaag ccgcgccgcg aagcggtgtc   5880
ggcttgaatg aattgttagg cgtcatcctg tgctcccgag aaccagtacc agtacatcgc   5940
tgtttcgttc gagacttgag gtctagtttt atacgtgaac aggtcaatgc cgccgagagt   6000
aaagccacat tttgcgtaca aattgcaggc aggtacattg ttcgtttgtg tctctaatcg   6060
tatgccaagg agctgtctgc ttagtgccca ctttttcgca aattcgatga gactgtgcgc   6120
gactcctttg cctcggtgcg tgtgcgacac aacaatgtgt tcgatagagg ctagatcgtt   6180
ccatgttgag ttgagttcaa tcttcccgac aagctcttgg tcgatgaatg cgccatagca   6240
agcagagtct tcatcagagt catcatccga gatgtaatcc ttccggtagg ggctcacact   6300
tctggtagat agttcaaagc cttggtcgga taggtgcaca tcgaacactt cacgaacaat   6360
gaaatggttc tcagcatcca atgtttccgc cacctgctca gggatcaccg aaatcttcat   6420
atgacgccta acgcctggca cagcggatcg caaacctggc gcggcttttg gcacaaaagg   6480
cgtgacaggt ttgcgaatcc gttgctgcca cttgttaacc cttttgccag atttggtaac   6540
tataatttat gttagaggcg aagtcttggg taaaaactgg cctaaaattg ctggggattt   6600
caggaaagta aacatcacct tccggctcga tgtctattgt agatatatgt agtgtatcta   6660
cttgatcggg ggatctgctg cctcgcgcgt ttcggtgatg acggtgaaaa cctctgacac   6720
atgcagctcc cggagacggt cacagcttgt ctgtaagcgg atgccgggag cagacaagcc   6780
cgtcagggcg cgtcagcggg tgttggcggg tgtcggggcg cagccatgac ccagtcacgt   6840
agcgatagcg gagtgtatac tggcttaact atgcggcatc agagcagatt gtactgagag   6900
tgcaccatat gcggtgtgaa ataccgcaca gatgcgtaag gagaaaatac cgcatcaggc   6960
gctcttccgc ttcctcgctc actgactcgc tgcgctcggt cgttcggctg cggcgagcgg   7020
tatcagctca ctcaaaggcg gtaatacggt tatccacaga atcaggggat aacgcaggaa   7080
agaacatgtg agcaaaaggc cagcaaaagg ccaggaaccg taaaaaggcc gcgttgctgg   7140
cgtttttcca taggctccgc ccccctgacg agcatcacaa aaatcgacgc tcaagtcaga   7200
ggtggcgaaa cccgacagga ctataaagat accaggcgtt tccccctgga agctccctcg   7260
tgcgctctcc tgttccgacc ctgccgctta ccggatacct gtccgccttt ctcccttcgg   7320
```

```
gaagcgtggc gctttctcat agctcacgct gtaggtatct cagttcggtg taggtcgttc   7380
gctccaagct gggctgtgtg cacgaacccc ccgttcagcc cgaccgctgc gccttatccg   7440
gtaactatcg tcttgagtcc aacccggtaa gacacgactt atcgccactg gcagcagcca   7500
ctggtaacag gattagcaga gcgaggtatg taggcggtgc tacagagttc ttgaagtggt   7560
ggcctaacta cggctacact agaaggacag tatttggtat ctgcgctctg ctgaagccag   7620
ttaccttcgg aaaaagagtt ggtagctctt gatccggcaa acaaaccacc gctggtagcg   7680
gtggtttttt tgtttgcaag cagcagatta cgcgcagaaa aaaaggatct caagaagatc   7740
ctttgatctt ttctacgggg tctgacgctc agtggaacga aaactcacgt taagggattt   7800
tggtcatgag attatcaaaa aggatcttca cctagatcct tttaaattaa aaatgaagtt   7860
ttaaatcaat ctaaagtata tatgagtaaa cttggtctga cagttaccaa tgcttaatca   7920
gtgaggcacc tatctcagcg atctgtctat ttcgttcatc catagttgcc tgactccccg   7980
tcgtgtagat aactacgata cgggagggct taccatctgg ccccagtgct gcaatgatac   8040
cgcgagaccc acgctcaccg gctccagatt tatcagcaat aaaccagcca gccggaaggg   8100
ccgagcgcag aagtggtcct gcaactttat ccgcctccat ccagtctatt aattgttgcc   8160
gggaagctag agtaagtagt tcgccagtta atagtttgcg caacgttgtt gccattgctg   8220
caggggggggg ggggggggggg ttccattgtt cattccacgg acaaaaacag agaaaggaaa   8280
cgacagaggc caaaaagctc gctttcagca cctgtcgttt cctttctttt cagagggtat   8340
tttaaataaa aacattaagt tatgacgaag aagaacggaa acgccttaaa ccggaaaatt   8400
ttcataaata gcgaaaaccc gcgaggtcgc cgccccgtaa cctgtcggat caccggaaag   8460
gacccgtaaa gtgataatga ttatcatcta catatcacaa cgtgcgtgga ggccatcaaa   8520
ccacgtcaaa taatcaatta tgacgcaggt atcgtattaa ttgatctgca tcaacttaac   8580
gtaaaaacaa cttcagacaa tacaaatcag cgacactgaa tacggggcaa cctcatgtcc   8640
cccccccccc cccccctgcag gcatcgtggt gtcacgctcg tcgtttggta tggcttcatt   8700
cagctccggt tcccaacgat caaggcgagt tacatgatcc cccatgttgt gcaaaaaagc   8760
ggttagctcc ttcggtcctc cgatcgttgt cagaagtaag ttggccgcag tgttatcact   8820
catggttatg gcagcactgc ataattctct tactgtcatg ccatccgtaa gatgcttttc   8880
tgtgactggt gagtactcaa ccaagtcatt ctgagaatag tgtatgcggc gaccgagttg   8940
ctcttgcccg gcgtcaacac gggataatac cgcgccacat agcagaactt taaaagtgct   9000
catcattgga aaacgttctt cggggcgaaa actctcaagg atcttaccgc tgttgagatc   9060
cagttcgatg taacccactc gtgcacccaa ctgatcttca gcatctttta ctttcaccag   9120
cgtttctggg tgagcaaaaa caggaaggca aaatgccgca aaaaagggaa taagggcgac   9180
acggaaatgt tgaatactca tactcttcct ttttcaatat tattgaagca tttatcaggg   9240
ttattgtctc atgagcggat acatatttga atgtatttag aaaaataaac aaataggggt   9300
tccgcgcaca tttccccgaa aagtgccacc tgacgtctaa gaaaccatta ttatcatgac   9360
attaacctat aaaaataggc gtatcacgag gccctttcgt cttcaagaat tggtcgacga   9420
tcttgctgcg ttcggatatt ttcgtggagt tcccgccaca gacccggatt gaaggcgaga   9480
tccagcaact cgcgccagat catcctgtga cggaactttg gcgcgtgatg actggccagg   9540
acgtcggccg aaagagcgac aagcagatca cgcttttcga cagcgtcgga tttgcgatcg   9600
aggatttttc ggcgctgcgc tacgtccgcg accgcgttga gggatcaagc cacagcagcc   9660
```

```
cactcgacct tctagccgac ccagacgagc caagggatct ttttggaatg ctgctccgtc   9720
gtcaggcttt ccgacgtttg ggtggttgaa cagaagtcat tatcgcacgg aatgccaagc   9780
actcccgagg ggaaccctgt ggttggcatg cacatacaaa tggacgaacg gataaacctt   9840
ttcacgccct tttaaatatc cgattattct aataaacgct cttttctctt aggtttaccc   9900
gccaatatat cctgtcaaac actgatagtt taaactgaag gcgggaaacg acaacctgat   9960
catgagcgga gaattaaggg agtcacgtta tgacccccgc cgatgacgcg ggacaagccg  10020
ttttacgttt ggaactgaca gaaccgcaac gttgaaggag ccactcagct taattaagtc  10080
taactcgagt tactggtacg taccaaatcc atggaatcaa ggtaccctgc agtgcagcgt  10140
gacccggtcg tgcccctctc tagagataat gagcattgca tgtctaagtt ataaaaaatt  10200
accacatatt ttttttgtca cacttgtttg aagtgcagtt tatctatctt tatacatata  10260
tttaaacttt actctacgaa taatataatc tatagtacta caataatatc agtgttttag  10320
agaatcatat aaatgaacag ttagacatgg tctaaaggac aattgagtat tttgacaaca  10380
ggactctaca gttttatctt tttagtgtgc atgtgttctc cttttttttt gcaaatagct  10440
tcacctatat aatacttcat ccattttatt agtacatcca tttagggttt agggttaatg  10500
gtttttatag actaattttt ttagtacatc tattttattc tattttagcc tctaaattaa  10560
gaaaactaaa actctatttt agttttttta tttaataatt tagatataaa atagaataaa  10620
ataaagtgac taaaaattaa acaaataccc tttaagaaat taaaaaaact aaggaaacat  10680
ttttcttgtt tcgagtagat aatgccagcc tgttaaacgc cgtcgacgag tctaacggac  10740
accaaccagc gaaccagcag cgtcgcgtcg ggccaagcga agcagacggc acggcatctc  10800
tgtcgctgcc tctggacccc tctcgagagt tccgctccac cgttggactt gctccgctgt  10860
cggcatccag aaattgcgtg gcggagcggc agacgtgagc cggcacggca ggcggcctcc  10920
tcctcctctc acggcacggc agctacgggg gattcctttc ccaccgctcc ttcgctttcc  10980
cttcctcgcc cgccgtaata aatagacacc ccctccacac cctctttccc caacctcgtg  11040
ttgttcggag cgcacacaca cacaaccaga tctcccccaa atccacccgt cggcacctcc  11100
gcttcaaggt acgccgctcg tcctcccccc cccccccctct ctaccttctc tagatcggcg  11160
ttccggtcca tggttagggc ccggtagttc tacttctgtt catgtttgtg ttagatccgt  11220
gtttgtgtta gatccgtgct gctagcgttc gtacacggat gcgacctgta cgtcagacac  11280
gttctgattg ctaacttgcc agtgtttctc tttggggaat cctgggatgg ctctagccgt  11340
tccgcagacg ggatcgattt catgattttt tttgtttcgt tgcatagggt ttggtttgcc  11400
cttttccttt atttcaatat atgccgtgca cttgtttgtc gggtcatctt ttcatgcttt  11460
tttttgtctt ggttgtgatg atgtggtctg gttgggcggt cgttctagat cggagtagaa  11520
ttctgtttca aactacctgg tggatttatt aattttggat ctgtatgtgt gtgccataca  11580
tattcatagt tacgaattga agatgatgga tggaaatatc gatctaggat aggtatacat  11640
gttgatgcgg gttttactga tgcatataca gagatgcttt ttgttcgctt ggttgtgatg  11700
atgtggtgtg gttgggcggt cgttcattcg ttctagatcg gagtagaata ctgtttcaaa  11760
ctacctggtg tatttattaa ttttggaact gtatgtgtgt gtcatacatc ttcatagtta  11820
cgagtttaag atggatggaa atatcgatct aggataggta tacatgttga tgtgggtttt  11880
actgatgcat atacatgatg gcatatgcag catctattca tatgctctaa ccttgagtac  11940
ctatctatta taataaacaa gtatgtttta taattatttt gatcttgata tacttggatg  12000
atggcatatg cagcagctat atgtggattt ttttagccct gccttcatac gctatttatt  12060
```

```
tgcttggtac tgtttctttt gtcgatgctc accctgttgt ttggtgttac ttctgcaggg  12120
atccatgtta cgtcctgtag aaaccccaac ccgtgaaatc aaaaaactcg acggcctgtg  12180
ggcattcagt ctggatcgcg aaaactgtgg aattggtcag cgttggtggg aaagcgcgtt  12240
acaagaaagc cgggcaattg ctgtgccagg cagttttaac gatcagttcg ccgatgcaga  12300
tattcgtaat tatgcgggca acgtctggta tcagcgcgaa gtctttatac cgaaaggttg  12360
ggcaggccag cgtatcgtgc tgcgtttcga tgcggtcact cattacggca aagtgtgggt  12420
caataatcag gaagtgatgg agcatcaggg cggctatacg ccatttgaag ccgatgtcac  12480
gccgtatgtt attgccggga aaagtgtacg taagtttctg cttctacctt tgatatatat  12540
ataataatta tcattaatta gtagtaatat aatatttcaa atattttttt caaaataaaa  12600
gaatgtagta tatagcaatt gcttttctgt agtttataag tgtgtatatt ttaatttata  12660
acttttctaa tatatgacca aaatttgttg atgtgcaggt atcaccgttt gtgtgaacaa  12720
cgaactgaac tggcagacta tcccgccggg aatggtgatt accgacgaaa acggcaagaa  12780
aaagcagtct tacttccatg atttctttaa ctatgccgga atccatcgca gcgtaatgct  12840
ctacaccacg ccgaacacct gggtggacga tatcaccgtg gtgacgcatg tcgcgcaaga  12900
ctgtaaccac gcgtctgttg actggcaggt ggtggccaat ggtgatgtca gcgttgaact  12960
gcgtgatgcg gatcaacagg tggttgcaac tggacaaggc actagcggga ctttgcaagt  13020
ggtgaatccg cacctctggc aaccgggtga aggttatctc tatgaactgt gcgtcacagc  13080
caaaagccag acagagtgtg atatctaccc gcttcgcgtc ggcatccggt cagtggcagt  13140
gaagggcgaa cagttcctga ttaaccacaa accgttctac tttactggct ttggtcgtca  13200
tgaagatgcg gacttacgtg gcaaaggatt cgataacgtg ctgatggtgc acgaccacgc  13260
attaatggac tggattgggg ccaactccta ccgtacctcg cattaccctt acgctgaaga  13320
gatgctcgac tgggcagatg aacatggcat cgtggtgatt gatgaaactg ctgctgtcgg  13380
ctttaacctc tctttaggca ttggtttcga agcgggcaac aagccgaaag aactgtacag  13440
cgaagaggca gtcaacgggg aaactcagca agcgcactta caggcgatta aagagctgat  13500
agcgcgtgac aaaaaccacc caagcgtggt gatgtggagt attgccaacg aaccggatac  13560
ccgtccgcaa ggtgcacggg aatatttcgc gccactggcg gaagcaacgc gtaaactcga  13620
cccgacgcgt ccgatcacct gcgtcaatgt aatgttctgc gacgctcaca ccgataccat  13680
cagcgatctc tttgatgtgc tgtgcctgaa ccgttattac ggatggtatg tccaaagcgg  13740
cgatttggaa acggcagaga aggtactgga aaaagaactt ctggcctggc aggagaaact  13800
gcatcagccg attatcatca ccgaatacgg cgtggatacg ttagccgggc tgcactcaat  13860
gtacaccgac atgtggagtg aagagtatca gtgtgcatgg ctggatatgt atcaccgcgt  13920
ctttgatcgc gtcagcgccg tcgtcggtga acaggtatgg aatttcgccg attttgcgac  13980
ctcgcaaggc atattgcgcg ttggcggtaa caagaaaggg atcttcactc gcgaccgcaa  14040
accgaagtcg gcggcttttc tgctgcaaaa acgctggact ggcatgaact tcggtgaaaa  14100
accgcagcag ggaggcaaac aatgac                                       14126
```

<210> SEQ ID NO 19
<211> LENGTH: 1991
<212> TYPE: DNA
<213> ORGANISM: Panicum virgatum
<220> FEATURE:
<221> NAME/KEY: promoter
<222> LOCATION: (1)..(1991)

<223> OTHER INFORMATION: PvUbi1 promoter

<400> SEQUENCE: 19

```
ccactggaga ggggcacaca cgtcagtgtt tggtttccac tagcacgagt agcgcaatca      60
gaaaattttc aatgcatgaa gtactaaacg aagtttattt agaaattttt ttaagaaatg     120
agtgtaattt tttgcgacga atttaatgac aataattaat cgatgattgc ctacagtaat     180
gctacagtaa ccaacctcta atcatgcgtc gaatgcgtca ttagattcgt ctcgcaaaat     240
agcacaagaa ttatgaaatt aattttacaa actattttta tttaatacta ataattaact     300
gtcaaagttt gtgctactcg caagagtagc gcgaaccaaa cacggcctgg aggagcacgg     360
taacggcgtc gacaaactaa cggccaccac ccgccaacgc aaaggagacg gatgagagtt     420
gacttcttga cggttctcca cccctctgtc tctctgtcac tgggccctgg gtccccctct     480
cgaaagttcc tctggccgaa attgcgcggc ggagacgagg cgggcggaac cgtcacggca     540
gaggattcct tccccaccct gcctggcccg gccatatata aacagccacc gcccctcccc     600
gttccccatc gcgtctcgtc tcgtgttgtt cccagaacac aaccaaaatc caaatcctcc     660
tcctcctccc gagcctcgtc gatccctcac ccgcttcaag gtacggcgat cctcctctcc     720
cttctcccct cgatcgatta tgcgtgttcc gtttccgttt ccgatcgagc gaatcgatgg     780
ttaggaccca tgggggaccc atggggtgtc gtgtggtggt ctggtttgat ccgcgatatt     840
tctccgttcg tagtgtagat ctgatcgaat ccctggtgaa atcgttgatc gtgctattcg     900
tgtgagggtt cttaggtttg gagttgtgga ggtagttctg atcggtttgt aggtgagatt     960
ttccccatga ttttgcttgg ctcgtttgtc ttggttagat tagatctgcc cgcattttgt    1020
tcgatatttc tgatgcagat atgatgaata atttcgtcct tgtatcccgc gtccgtatgt    1080
gtattaagtt tgcaggtgct agttaggttt ttcctactga tttgtcttat ccattctgtt    1140
tagcttgcaa ggtttggtaa tggtccggca tgtttgtctc tatagattag agtagaataa    1200
gattatctca acaagctgtt ggcttatcaa ttttggatct gcatgtgttt cgcatctata    1260
tctttgcaat taagatggta gatggacata tgctcctgtt gagttgatgt tgtacctttt    1320
acctgaggtc tgaggaacat gcatcctcct gctactttgt gcttatacag atcatcaaga    1380
ttatgcagct aatattcgat cagtttctag tatctacatg gtaaacttgc atgcacttgc    1440
tacttatttt tgatatactt ggatgataac atatgctgct ggttgattcc tacctacatg    1500
atgaacattt tacaggccat tagtgtctgt ctgtatgtgt tgttcctgtt tgcttcagtc    1560
tatttctgtt tcattcctag tttattggtt ctctgctaga tacttaccct gctgggctta    1620
gttatcatct tatctcgaat gcattttcat gtttatagat gaatatacac tcagataggt    1680
gtagatgtat gctactgttt ctctacgttg ctgtaggttt tacctgtggc aactgcatac    1740
tcctgttgct tcgctagata tgtatgtgct tatatagatt aagatatgtg tgatggttct    1800
ttagtatatc tgatgatcat gtatgctctt ttaacttctt gctacacttg gtaacatgct    1860
gtgatgctgt ttgttgattc tgtagcacta ccaatgatga ccttatctct ctttgtatat    1920
gatgtttctg tttgtttgag gcttgtgtta ctgctagtta cttaccctgt tgcctggcta    1980
atcttctgca g                                                          1991
```

<210> SEQ ID NO 20
<211> LENGTH: 1861
<212> TYPE: DNA
<213> ORGANISM: Panicum virgatum
<220> FEATURE:
<221> NAME/KEY: promoter
<222> LOCATION: (1)..(1861)
<223> OTHER INFORMATION: PvUbi2 promoter

<400> SEQUENCE: 20

```
gaagccaact aaacaagacc ataaccatgg tgacatttga catagttgtt tactacttgc     60
ttgagcccca cccttgctta tcggttgaac attacaagat acactgcggg tggcctaagg    120
cacaccgtcc gaaaccggca aaccaagcct gatcgccgaa atccaaaatc actaccggca    180
atctctaaag tttatttcat ccttatatga cgaggaaaga aaagaagaga gaaataatat    240
cttaacttct aaatcagtcg cgtcaacttt ctcggctaag aaagtgagca ctatcatttc    300
ggagaccatg tcatgagtgc cgacttgcca tatcttatta tattcttatt tatttaatta    360
taatcccatt gcaatacgtc tattctatca tggcctgcca ctaacgctcc gtctaacgtc    420
gttaagccat tgtcataagc ggctgctcaa aactcttccc ggtggaggcg aggcgttaac    480
ggcgtctaca aatctaacgg ccaccaacca tccagccgcc tctcgaaagc tccgctccga    540
tcgcggaaat tgcgtggcgg agacgagcgg gctcctctca cacggcccgg aaccgtcacg    600
gcacgggtgg gggattcctt ccccaaccct ccccacctct cctccccccg tcgcagccca    660
taaatacagg gccctccgcg cctcttccca caatctcaca tcgtctcatc gttcggagcg    720
cacaaccccc gggttccaaa tccaaattgc tcttctcgcg accctcggcg atccttcccc    780
cgcttcaagg tacggcgatc gtctcccccg tcctcttgcc ccatctcctc gctcggcgtg    840
gtttggtggt tctgcttggt ctgtggctag gaactaggct gaggcgttga cgaaatcatg    900
ctagatccgc gtgtttcctg atcgtgggtg gctgggaggt ggggttttcg tgtagatctg    960
atcggttccg ctgtttatcc tgtcatgctc atgtgatttg tggggatttt aggtcgtttg   1020
tccgggaatc gtggggttgc ttctaggctg ttcgtagatg agatcgttct cacgatctgc   1080
tgggtcgctg cctaggttca gctaggtctg ccctgttttt gggttcgttt tcgggatctg   1140
tacgtgcatc tattatctgg ttcgatggtg ctagctagga acaaacaact gattcgtccg   1200
atcgattgtt ttgttgccat gtgcaaggtt aggtcgttat ctgattgctg tagatcagag   1260
tagaataaga tcatcacaag ctagctcttg ggcttattat gaatctgcgt ttgttgcatg   1320
attaagatga ttatgctttt tcttatgctg ccgtttgtat atgatgcggt agcttttaac   1380
tgaatagcac acctttcctg tttagttaga ttagattaga ttgcatgata gatgaggata   1440
tatgctgcta catcagtttg atgattctct ggtacctcat aatcaactag ctcatgtgct   1500
taaattgaaa ctgcatgtgc cacatgatta agatgctaag attggtgaag atatatacgc   1560
tgctgttcct ataggatcct gtagctttta cctggtcaac atgcatcgtc ctgttatgga   1620
tagatatgca tgatagatga agatatgtac tgctacaatt tgatgattct tttgtgcacc   1680
tgatgatcat gcatgctctt tgcccttact ttgatatact tggatgatgg catgcttagt   1740
actaatgatg tgatgaacac acatgacctg ttggtatgaa tatgatgttg ctgtttgctt   1800
gtgatgagtt ctgtttgttt actgctaggc acttaccctg ttgtctggtt ctcttttgca   1860
g                                                                   1861
```

<210> SEQ ID NO 21
<211> LENGTH: 3802
<212> TYPE: DNA
<213> ORGANISM: Artificial Sequence
<220> FEATURE:
<223> OTHER INFORMATION: Synthetic construct, OsUbi3:HvAle:NtEGm:SEKDEL

<400> SEQUENCE: 21

```
gtcgactcta gtaacggccg ccagtgtgct ggaattaatt cggcttgtcg accacccaac      60
cccatatcga cagaggatgt gaagaacagg taaatcacgc agaagaaccc atctctgata     120
gcagctatcg attagaacaa cgaatccata ttgggtccgt gggaaatact tactgcacag     180
gaagggggcg atctgacgag gccccgccac cggcctcgac ccgaggccga ggccgacgaa     240
gcgccggcga gtacggcgcc gcggcggcct ctgcccgtgc cctctgcgcg tgggagggag     300
aggccgcggt ggtgggggcg cgcgcgcgcg cgcgcgcagc tggtgcggcg gcgcgggggt     360
cagccgccga gccggcggcg acggaggagc agggcggcgt ggacgcgaac ttccgatcgg     420
ttggtcagag tgcgcgagtt gggcttagcc aattaggtct caacaatcta ttgggccgta     480
aaattcatgg gccctggttt gtctaggccc aatatcccgt tcatttcagc ccacaaatat     540
ttccccagag gattattaag gcccacacgc agcttatagc agatcaagta cgatgtttcc     600
tgatcgttgg atcggaaacg tacggtcttg atcaggcatg ccgacttcgt caaagagagg     660
cggcatgacc tgacgcggag ttggttccgg gcaccgtctg gatggtcgta ccgggaccgg     720
acacgtgtcg cgcctccaac tacatggaca cgtgtggtgc tgccattggg ccgtacgcgt     780
ggcggtgacc gcaccggatg ctgcctcgca ccgccttgcc cacgctttat atagagaggt     840
tttctctcca ttaatcgcat agcgagtcga atcgaccgaa ggggaggggg agcgaagctt     900
tgcgttctct aatcgcctcg tcaaggtaac taatcaatca cctcgtccta atcctcgaat     960
ctctcgtggt gcccgtctaa tctcgcgatt ttgatgctcg tggtggaaag cgtaggagga    1020
tcccgtgcga gttagtctca atctctcagg gtttcgtgcg attttagggt gatccacctc    1080
ttaatcgagt tacggtttcg tgcgatttta gggtaatcct cttaatctct cattgattta    1140
gggtttcgtg agaatcgagg tagggatctg tgttatttat atcgatctaa tagatggatt    1200
ggttttgaga ttgttctgtc agatggggat tgtttcgata tattacccta atgatgtgtc    1260
agatggggat tgtttcgata tattacccta atgatgtgtc agatggggat tgtttcgata    1320
tattacccta atgatggata ataagagtag ttcacagtta tgttttgatc ctgccacata    1380
gtttgagttt tgtgatcaga tttagtttta cttatttgtg cttagttcgg atgggattgt    1440
tctgatattg ttccaataga tgaatagctc gttaggttaa aatctttagg ttgagttagg    1500
cgacacatag tttatttcct ctggatttgg attggaattg tgttcttagt tttttcccc     1560
tggatttgga ttggaattgt gtggagctgg gttagagaat tacatctgta tcgtgtacac    1620
ctacttgaac tgtagagctt gggttctaag gtcaatttaa tctgtattgt atctggctct    1680
ttgcctagtt gaactgtagt gctgatgttg tactgtgttt ttttacccgt tttatttgct    1740
ttactcgtgc aaatcaaatc tgtcagatgc tagaactagg tggctttatt ctgtgttctt    1800
acatagatct gttgtcctgt agttacttat gtcagttttg ttattatctg aagatatttt    1860
tggttgttgc ttgttgatgt ggtgtgagct gtgagcagcg ctcttatgat taatgatgct    1920
gtccaattgt agtgtagtat gatgtgattg atatgttcat ctattttgag ctgacagtac    1980
cgatatcgta ggatctggtg ccaacttatt ctccagctgc ttttttttac ctatgttaat    2040
tccaatcctt tcttgcctct tccagatcca gataatggcc cacgcccgcg tcctcctcct    2100
ggcgctcgcc gtcctggcca ccgccgccgt cgccgtcgcc tcctcctcct ccttcgccga    2160
ctccaacccg atccgcccgg tgaccgaccg cgccgcctcc accgcttacg actacaagca    2220
ggtgttgcgg gactcgctac tattctatga ggcccagaga tccggccggc tcccagccga    2280
ccagaaggtc acgtggagga aggatagcgc gctgaatgac cagggtgacc agggacaaga    2340
cttgaccggc ggctactttg acgctgggga cttcgtcaag ttcgggttcc ccatggctta    2400
```

```
taccgcaacc gtgctggcat ggggcctcat agattttgag gccggctaca gcagtgccgg   2460

ggccttggat gatggacgga aggctgtcaa atgggccacc gactatttca taaaggccca   2520

cacaagtcaa aatgagttct atggtcaggt cggccagggt gacgccgatc acgctttctg   2580

gggaagacca gaggatatga cgatggcgcg cccggcgtac aagatagaca cctcaaggcc   2640

tggctctgat ctggcaggcg agacagcggc tgctcttgcc gctgcttcaa tcgtgttccg   2700

gaacgtcgat ggcacttact caaataacct gttaacacac gctcgccagc tattcgactt   2760

cgcgaacaac taccggggaa agtatagtga ctctattact gacgcaagaa atttctacgc   2820

aagcgcagac tacagagacg agttggtttg ggctgctgcg tggttataca gagcgaccaa   2880

cgacaacacc tacctcaaca ctgctgagtc actgtacgat gagtttgggc tacagaactg   2940

gggggggggc ctgaactggg atagcaaggt gtctggcgtg caggtgttgt tggccaagct   3000

taccaataag caggcctaca aggacacggt gcagtcttac gtcaattacc taattaataa   3060

ccagcagaag actcccaagg gcctcctcta catcgacatg tggggcaccc ttcgccacgc   3120

tgccaacgcc gcattcatca tgctcgaagc cgccgagctg ggcttgtccg cctcctctta   3180

tagacagttc gcgcaaacgc aaatcgacta cgccctgggc gatggtggcc gctcctttgt   3240

gtgcgggttc gggagtaatc ctcctacgag accgcaccac agatcctcgt cgtgcccgcc   3300

agctcccgct acttgcgact ggaatacatt caactcacct gacccaaact accacgtcct   3360

ctctggggcc ctagtgggcg gacctgatca gaatgacaac tacgtcgatg accgttcaga   3420

ctatgttcac aacgaagtcg ccactgatta caacgcgggt ttccagtccg cgttagctgc   3480

tttggtggcc cttggttaca gcgagaagga cgagctgtga cctaggtccc cgaatttccc   3540

cgatcgttca aacatttggc aataaagttt cttaagattg aatcctgttg ccggtcttgc   3600

gatgattatc atataatttc tgttgaatta cgttaagcat gtaataatta acatgtaatg   3660

catgacgtta tttatgagat gggtttttat gattagagtc ccgcaattat acatttaata   3720

cgcgatagaa aacaaaatat agcgcgcaaa ctaggataaa ttatcgcgcg cggtgtcatc   3780

tatgttacta gatcgggaat tg                                            3802
```

<210> SEQ ID NO 22
<211> LENGTH: 3741
<212> TYPE: DNA
<213> ORGANISM: Artificial Sequence
<220> FEATURE:
<223> OTHER INFORMATION: Synthetic construct,
ZmUbi:Kozak:HvAle:NtEGm:SEKDEL

<400> SEQUENCE: 22

```
ctgcagtgca gcgtgacccg gtcgtgcccc tctctagaga taatgagcat tgcatgtcta     60

agttataaaa aattaccaca tatttttttt gtcacacttg tttgaagtgc agtttatcta    120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480

taaaatagaa taaaataaag tgactaaaaa ttaaacaaat accctttaag aaattaaaaa    540

aactaaggaa acatttttct tgtttcgagt agataatgcc agcctgttaa acgccgtcga    600
```

```
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaattg cgtggcggag cggcagacgt gagccggcac    780
ggcaggcggc ctcctcctcc tctcacggca cggcagctac gggggattcc tttcccaccg    840
ctccttcgct ttcccttcct cgcccgccgt aataaataga cacccccctcc acaccctctt    900
tccccaacct cgtgttgttc ggagcgcaca cacacacaac cagatctccc ccaaatccac    960
ccgtcggcac ctccgcttca aggtacgccg ctcgtcctcc cccccccccc ctctctacct   1020
tctctagatc ggcgttccgg tccatggtta gggcccggta gttctacttc tgttcatgtt   1080
tgtgttagat ccgtgtttgt gttagatccg tgctgctagc gttcgtacac ggatgcgacc   1140
tgtacgtcag acacgttctg attgctaact tgccagtgtt tctctttggg gaatcctggg   1200
atggctctag ccgttccgca gacgggatcg atttcatgat tttttttgtt tcgttgcata   1260
gggtttggtt tgcccttttc ctttatttca atatatgccg tgcacttgtt tgtcgggtca   1320
tcttttcatg cttttttttg tcttggttgt gatgatgtgg tctggttggg cggtcgttct   1380
agatcggagt agaattctgt ttcaaactac ctggtggatt tattaatttt ggatctgtat   1440
gtgtgtgcca tacatattca tagttacgaa ttgaagatga tggatggaaa tatcgatcta   1500
ggataggtat acatgttgat gcgggtttta ctgatgcata tacagagatg ctttttgttc   1560
gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg   1740
ttgatgtggg ttttactgat gcatatacat gatggcatat gcagcatcta ttcatatgct   1800
ctaaccttga gtacctatct attataataa acaagtatgt tttataatta ttttgatctt   1860
gatatacttg gatgatggca tatgcagcag ctatatgtgg atttttttag ccctgccttc   1920
atacgctatt tatttgcttg gtactgtttc ttttgtcgat gctcaccctg ttgtttggtg   1980
ttacttctgc agatccagat cggatcctaa accatggccc acgcccgcgt cctcctcctg   2040
gcgctcgccg tcctggccac cgccgccgtc gccgtcgcct cctcctcctc cttcgccgac   2100
tccaacccga tccgcccggt gaccgaccgc gccgcctcca ccgcttacga ctacaagcag   2160
gtgttgcggg actcgctact attctatgag gcccagagat ccggccggct cccagccgac   2220
cagaaggtca cgtggaggaa ggatagcgcg ctgaatgacc agggtgacca gggacaagac   2280
ttgaccggcg gctactttga cgctggggac ttcgtcaagt tcgggttccc catggcttat   2340
accgcaaccg tgctggcatg gggcctcata gattttgagg ccggctacag cagtgccggg   2400
gccttggatg atggacggaa ggctgtcaaa tgggccaccg actatttcat aaaggcccac   2460
acaagtcaaa atgagttcta tggtcaggtc ggccagggtg acgccgatca cgctttctgg   2520
ggaagaccag aggatatgac gatggcgcgc ccggcgtaca agatagacac ctcaaggcct   2580
ggctctgatc tggcaggcga gacagcggct gctcttgccg ctgcttcaat cgtgttccgg   2640
aacgtcgatg gcacttactc aaataacctg ttaacacacg ctcgccagct attcgacttc   2700
gcgaacaact accggggaaa gtatagtgac tctattactg acgcaagaaa tttctacgca   2760
agcgcagact acagagacga gttggtttgg gctgctgcgt ggttatacag agcgaccaac   2820
gacaacacct acctcaacac tgctgagtca ctgtacgatg agtttgggct acagaactgg   2880
ggggggggcc tgaactggga tagcaaggtg tctggcgtgc aggtgttgtt ggccaagctt   2940
```

```
accaataagc aggcctacaa ggacacggtg cagtcttacg tcaattacct aattaataac   3000

cagcagaaga ctcccaaggg cctcctctac atcgacatgt ggggcaccct tcgccacgct   3060

gccaacgccg cattcatcat gctcgaagcc gccgagctgg gcttgtccgc ctcctcttat   3120

agacagttcg cgcaaacgca aatcgactac gccctgggcg atggtggccg ctcctttgtg   3180

tgcgggttcg ggagtaatcc tcctacgaga ccgcaccaca gatcctcgtc gtgcccgcca   3240

gctcccgcta cttgcgactg gaatacattc aactcacctg acccaaacta ccacgtcctc   3300

tctggggccc tagtgggcgg acctgatcag aatgacaact acgtcgatga ccgttcagac   3360

tatgttcaca acgaagtcgc cactgattac aacgcgggtt tccagtccgc gttagctgct   3420

ttggtggccc ttggttacag cgagaaggac gagctgtgac ctaggtcccc gaatttcccc   3480

gatcgttcaa acatttggca ataaagtttc ttaagattga atcctgttgc cggtcttgcg   3540

atgattatca tataatttct gttgaattac gttaagcatg taataattaa catgtaatgc   3600

atgacgttat ttatgagatg ggtttttatg attagagtcc cgcaattata catttaatac   3660

gcgatagaaa acaaaatata gcgcgcaaac taggataaat tatcgcgcgc ggtgtcatct   3720

atgttactag atcgggaatt g                                             3741
```

<210> SEQ ID NO 23
<211> LENGTH: 5330
<212> TYPE: DNA
<213> ORGANISM: Artificial Sequence
<220> FEATURE:
<223> OTHER INFORMATION: Synthetic construct, PvUbi4:HvAle:NtEGm:SEKDEL

<400> SEQUENCE: 23

```
ctggcctaac ctaaaatcag ttcttgctgc tgggtggttg ggtacattat ctgacaacta     60

ggatccacat caaaaaaaaa aagactacta cgatcatcat ggagtccttc gcaacggcag    120

ctgggcagac accttcagag ttcagagtcc acgcacacac taataaaggg gtccatttgc    180

ctgcttcgtt ccggctgaaa tttttacgaa ccggtcatcc gtaaccacga taatcgatat    240

ggaccaagag agacaaaaat aatctcggaa catcgttagc aagtccaaat ggaacgcaac    300

cagagacatg ttgtttgcct tcatccttca tacacaaccc acctggccac ctccatgtcc    360

atgatttttt ttccccaatc gaccttggac aaccaccaag gaattccttg tcagttgtta    420

gcatggatga cagttcaagc cgggcagctg gcgtgtccgt tcagacatca tcgtcctgcc    480

agaactccat ccacgcgagc ccgctgaacc aagggagcct ttgcgtttgc cctttggcca    540

cggcatcgtt cagctcattc cctcaacaga tcaactgaac ccagcgcgcg aagttagcac    600

cggagcgcaa tgcgagccgt gcccgtgtct tcctcccagc tcctccagcg caagcaagac    660

gacgaccgga ggagagattc tttgctttgc ttgtggctgc gaaggaggag gagaaaccac    720

gcagcggata agaaggaagc cgcctttgca aaaccagagc atcttttctg atgaagaaat    780

ccgcgttgcc tcctgtgaga agaatgcgac cctttttttta tactctattc tatctttatt   840

attattgtca atttgtcatg tcactgagaa atggccctga tacgaacgct aagatccaat    900

catacacctt ttatttattt atacataagt acgtaaataa gatgaaaata aaaaaaatgt    960

catggacgaa aacaacgtcc acaaggacgg caaagatgga ggaccgcagg agcacaacgg   1020

atggatgttc tttttttgtt atcaaacaac ggatggatgt ttccgagcag gtgcagcgtc   1080

tcctccgttt actcgccgtg cacatcacgg cgtccaaacg ggcgtttgcc ggcgaggaca   1140

cggtagattt tgccgacatg gtagatttta tcaagatatt ccggtcgagt ttggagtact   1200

agctccatca tgtataacca ccaatgattg agtggtgacc atatcataat cgttggtcag   1260
```

```
ctttccttcc attacttttt aattcagtaa taataatccc taaagcctaa tcaagtaaat   1320
tcaacttccg aattcaatag ggatcatcag ggcacgacct gattgtaaag acatacaata   1380
gctttcaaac aacattttca cttatggtaa aatcttaatt aaggtcttaa tattataatt   1440
atttttttca ctgccgtgag ggaatggaga tttcagaaag ggactttttg gtatcatcat   1500
tgtatatgat ccacggtttt tagttagggc gactttaatt tcttattttt gataattctt   1560
gtttctattg tcttgacgat tctaatgcca tgtccttttg tcttgacagc tctagtgcca   1620
tgtctatttg tcatgttatc atttgttctt tttatttcaa ggaaaattat tacatcaaaa   1680
aattgatttt cgaagttcac ggtcatcttc accatcactc tctatcgcat tggtggcgag   1740
aagcatatct agtggtttca ttctggtaag cctcgctcaa atgaaatttg taataaaata   1800
ctatatttct ttatcaaggt tataagatat ggagagaaat ggtctgcttc ataaatttga   1860
cttacctaga gcctttaaaa aggaatacca tgtaatctaa actctataac ataaagagct   1920
ttgcgctttt aaaaatatgc taacctatat aaatcgcttt tgctagagac aggtcatgta   1980
tgattgaagc gtcaccataa cgccgttaat cttccgtcca gccattaacg gccacctacc   2040
gcaggaaaca aacggcgtca ccatcctcga tatctccgcg gcggccgctg gctttttttcg  2100
gagaaattgc gcggtgggga cggagtccac gagagcctct cgccgctggg ccccacaatc   2160
aatggcgtga cctcacggga cggctccctc cctctaccct ccccccgtgt ataaatagca   2220
cccctccctc gcctcttccg catccagtat tccagtcccc aatccgtcga gaaattctcg   2280
cgagcgatcg aaatctaagc gaagcgaaga ggcctcccca gatcctctca aggtatgcga   2340
gagcatcgat ccccttccga tctatatcgc gtgtcctccc tgttcttgtt cttcgtcgat   2400
ctagtttagg gtttgatttg gttctgaatc gaacccttttt cctgcttgcg ttcgatttgt  2460
actcgatcct cgggtagagg tgtggatctg cggggcgtga tgaggtagtt tggtgtagat   2520
ttgttctggg cgttcgattt gccactaggg ttcggctgct gttggcattc ctgatcgagc   2580
ggccggatag gattgttttt cccttttttat atgttggatg cgtgatggtt cctgtgtgtt  2640
gggttagatt gctggtacga ttcatctagg tggtgatttg cagaggaaca actttgctgt   2700
tgaatattgg taggtctatc tagatttatt acttttgatt atcgcctgat aaggatcacc   2760
gattcgtgta gaataaatta tttcattgtt gggtcatgta gatatagctg cacaatttct   2820
tacttggctc cttactgtgt gaattgtaga ataaactgtg ttactctatg agtttttctg   2880
gattgctgga tccagttagg ccagtgctgt caatttgtta tggctgttaa tgtaataatt   2940
ttctggattg ttggcctgct tctcttcatg tttaatcacg tgatggttca tgatgcctgt   3000
tgggttagat tgtttgttca attcatctag gcagtgctgt gcagagtaca actcgattga   3060
tgtttaatct tggtagcttc atctagattt gtacaaattt tggtcacctg atgatgatca   3120
ccgattgttg tggaattatt tcttaactgg ttcgttgtta gtcaccacct tacttgtaga   3180
ataacctgtg gtactgcttt tctgttctgt tttaggccac atcatatgat tgtcaaaaat   3240
ttacatggta gtttaatgat aaaattagtt cagcttactt cagtttgatt tgcttcatat   3300
tttgttttct gttctattaa tgatacttca tgaaatgttt gtttttctc tgttcagatt    3360
tgacatgttt cagtatcata ataataatat tctgtatcct ttatagtttg ttggcatgat   3420
ttgctttgaa tttagttagc ctattctgtt aatataggat gataagctgt gaggcgttca   3480
ttctcttcag tccagagtta tcattttcag tgttttaatg ttgtttatca agctggatgt   3540
atatggtggt ttaactcttt tctgtttctt actgtttgca gatccagatc ggatcctaaa   3600
```

```
ccatggccca cgcccgcgtc ctcctcctgg cgctcgccgt cctggccacc gccgccgtcg   3660
ccgtcgcctc ctcctcctcc ttcgccgact ccaacccgat ccgcccggtg accgaccgcg   3720
ccgcctccac cgcttacgac tacaagcagg tgttgcggga ctcgctacta ttctatgagg   3780
cccagagatc cggccggctc ccagccgacc agaaggtcac gtggaggaag gatagcgcgc   3840
tgaatgacca gggtgaccag ggacaagact tgaccggcgg ctactttgac gctggggact   3900
tcgtcaagtt cgggttcccc atggcttata ccgcaaccgt gctggcatgg ggcctcatag   3960
attttgaggc cggctacagc agtgccgggg ccttggatga tggacggaag gctgtcaaat   4020
gggccaccga ctatttcata aaggcccaca caagtcaaaa tgagttctat ggtcaggtcg   4080
gccagggtga cgccgatcac gctttctggg gaagaccaga ggatatgacg atggcgcgcc   4140
cggcgtacaa gatagacacc tcaaggcctg gctctgatct ggcaggcgag acagcggctg   4200
ctcttgccgc tgcttcaatc gtgttccgga acgtcgatgg cacttactca aataacctgt   4260
taacacacgc tcgccagcta ttcgacttcg cgaacaacta ccggggaaag tatagtgact   4320
ctattactga cgcaagaaat ttctacgcaa gcgcagacta cagagacgag ttggtttggg   4380
ctgctgcgtg gttatacaga gcgaccaacg acaacaccta cctcaacact gctgagtcac   4440
tgtacgatga gtttgggcta cagaactggg gggggggcct gaactgggat agcaaggtgt   4500
ctggcgtgca ggtgttgttg gccaagctta ccaataagca ggcctacaag gacacggtgc   4560
agtcttacgt caattaccta attaataacc agcagaagac tcccaagggc ctcctctaca   4620
tcgacatgtg ggcacccttt cgccacgctg ccaacgccgc attcatcatg ctcgaagccg   4680
ccgagctggg cttgtccgcc tcctcttata gacagttcgc gcaaacgcaa atcgactacg   4740
ccctgggcga tggtggccgc tcctttgtgt gcgggttcgg gagtaatcct cctacgagac   4800
cgcaccacag atcctcgtcg tgcccgccag ctcccgctac ttgcgactgg aatacattca   4860
actcacctga cccaaactac cacgtcctct ctggggccct agtgggcgga cctgatcaga   4920
atgacaacta cgtcgatgac cgttcagact atgttcacaa cgaagtcgcc actgattaca   4980
acgcgggttt ccagtccgcg ttagctgctt tggtggccct tggttacagc gagaaggacg   5040
agctgtgacc taggtccccg aatttccccg atcgttcaaa catttggcaa taaagtttct   5100
taagattgaa tcctgttgcc ggtcttgcga tgattatcat ataatttctg ttgaattacg   5160
ttaagcatgt aataattaac atgtaatgca tgacgttatt tatgagatgg gtttttatga   5220
ttagagtccc gcaattatac atttaatacg cgatagaaaa caaaatatag cgcgcaaact   5280
aggataaatt atcgcgcgcg gtgtcatcta tgttactaga tcgggaattg              5330
```

<210> SEQ ID NO 24
<211> LENGTH: 10
<212> TYPE: DNA
<213> ORGANISM: Artificial Sequence
<220> FEATURE:
<223> OTHER INFORMATION: Synthetic construct, LR element

<400> SEQUENCE: 24

```
aatctaaact                                                             10
```

<210> SEQ ID NO 25
<211> LENGTH: 10
<212> TYPE: DNA
<213> ORGANISM: Artificial Sequence
<220> FEATURE:
<223> OTHER INFORMATION: Synthetic construct, TATA box

<400> SEQUENCE: 25

```
tatataaatc                                                          10


<210> SEQ ID NO 26
<211> LENGTH: 10
<212> TYPE: DNA
<213> ORGANISM: Artificial Sequence
<220> FEATURE:
<223> OTHER INFORMATION: Synthetic construct, SA responsive element

<400> SEQUENCE: 26

gagaagcata                                                          10


<210> SEQ ID NO 27
<211> LENGTH: 12
<212> TYPE: DNA
<213> ORGANISM: Artificial Sequence
<220> FEATURE:
<223> OTHER INFORMATION: Synthetic construct, protein binding site

<400> SEQUENCE: 27

aacattttca ct                                                       12


<210> SEQ ID NO 28
<211> LENGTH: 10
<212> TYPE: DNA
<213> ORGANISM: Artificial Sequence
<220> FEATURE:
<223> OTHER INFORMATION: Synthetic construct, heat stress response
      element

<400> SEQUENCE: 28

aaaaaatgtc                                                          10


<210> SEQ ID NO 29
<211> LENGTH: 10
<212> TYPE: DNA
<213> ORGANISM: Artificial Sequence
<220> FEATURE:
<223> OTHER INFORMATION: Synthetic construct, SA responsive motif

<400> SEQUENCE: 29

cagaaaggga                                                          10


<210> SEQ ID NO 30
<211> LENGTH: 20
<212> TYPE: DNA
<213> ORGANISM: Artificial Sequence
<220> FEATURE:
<223> OTHER INFORMATION: Synthetic construct, GUS PCR forward primer

<400> SEQUENCE: 30

tcaggaagtg atggagcatc                                               20


<210> SEQ ID NO 31
<211> LENGTH: 21
<212> TYPE: DNA
<213> ORGANISM: Artificial Sequence
<220> FEATURE:
<223> OTHER INFORMATION: Synthetic construct, GUS PCR reverse primer

<400> SEQUENCE: 31

cacacaaacg gtgatacgta c                                             21


<210> SEQ ID NO 32
<211> LENGTH: 20
```

<212> TYPE: DNA
<213> ORGANISM: Artificial Sequence
<220> FEATURE:
<223> OTHER INFORMATION: Synthetic construct, Actin PCR forward primer

<400> SEQUENCE: 32
caactgccca gcaatgtatg 20

<210> SEQ ID NO 33
<211> LENGTH: 20
<212> TYPE: DNA
<213> ORGANISM: Artificial Sequence
<220> FEATURE:
<223> OTHER INFORMATION: Synthetic construct, Actin PCR reverse primer

<400> SEQUENCE: 33
cgtagatagg gacggtgtgg 20

<210> SEQ ID NO 34
<211> LENGTH: 20
<212> TYPE: DNA
<213> ORGANISM: Artificial Sequence
<220> FEATURE:
<223> OTHER INFORMATION: Synthetic construct, GAPDH PCR forward primer

<400> SEQUENCE: 34
cgctgagtat gtcgtggagt 20

<210> SEQ ID NO 35
<211> LENGTH: 20
<212> TYPE: DNA
<213> ORGANISM: Artificial Sequence
<220> FEATURE:
<223> OTHER INFORMATION: Synthetic construct, GAPDH PCR reverse primer

<400> SEQUENCE: 35
aacaaccttc ttggcaccac 20

<210> SEQ ID NO 36
<211> LENGTH: 6
<212> TYPE: PRT
<213> ORGANISM: Artificial Sequence
<220> FEATURE:
<223> OTHER INFORMATION: Synthetic construct, SEKDEL

<400> SEQUENCE: 36

Ser Glu Lys Asp Glu Leu
1 5

<210> SEQ ID NO 37
<211> LENGTH: 4
<212> TYPE: PRT
<213> ORGANISM: Artificial Sequence
<220> FEATURE:
<223> OTHER INFORMATION: Synthetic construct, KDEL

<400> SEQUENCE: 37

Lys Asp Glu Leu
1

STRONG CONSTITUTIVE PROMOTERS FOR HETEROLOGOUS EXPRESSION OF PROTEINS IN PLANTS

This application is a 35 U.S.C. §371 national phase application of PCT/US2013/043148, which was filed May 29, 2013, and claims the benefit of U.S. provisional application No. 61/652,628 filed May 29, 2012, both of which are incorporated herein by reference as if fully set forth.

The sequence listing electronically filed with this application titled "Sequence Listing," created on May 29, 2013, and having a file size of 190,213 bytes is incorporated herein by reference as if fully set forth. The substitute sequence listing electronically filed Apr. 28, 2015 titled "Substitute Sequence Listing," created on Apr. 28, 2015, and having a file size of 190,617 bytes is incorporated herein by reference as if fully set forth.

FIELD OF INVENTION

The disclosure relates to nucleic acid promoters isolated from *Panicum virgatum*; genetic constructs, vectors and transformed plants that include nucleic acid promoters; and methods for producing heterologous proteins by engineering plants to include nucleic acid promoters and genetic constructs.

BACKGROUND

Genetic transformation can be used to engineer plants with altered characteristics by introducing heterologous nucleic acid molecules into plant genomes. Such altered plants may have a variety of applications. Genetically engineered plants may be used in a traditional plant breeding to generate improved crops or as lignocellulosic biomass for the production of biofuels, chemicals, and bioproducts, or as factories to produce pharmaceuticals. The prerequisite for genetic engineering of plants is creation of a reliable transformation and expression systems for introduction of heterologous nucleic acid molecules.

SUMMARY

In an aspect, the invention relates to an isolated nucleic acid promoter. The isolated nucleic acid promoter has a sequence with at least 90% identity to a reference sequence selected from the group consisting of: SEQ ID NO: 1 (PvUbi3), SEQ ID NO: 2 (PvUbi4) or SEQ ID NO: 3 (PvUbi4s).

In an aspect, the invention relates to an isolated nucleic acid promoter that includes a sequence of DNA element. The sequence of the DNA element has at least 90% sequence identity to a reference sequence selected from the group consisting of: SEQ ID NO: 4 (2037 bp downstream PvUbi3), SEQ ID NO: 5 (2037 bp downstream PvUbi4), SEQ ID NO: 6 (230 bp region of PvUbi3, position −927 to −698), SEQ ID NO: 7 (230 bp region of PvUbi4/PvUbi4s; position −1580 to −1351), SEQ ID NO: 8 (653 bp Unique SEQ of PvUbi4/PvUbi4s), SEQ ID NO: 9 (91 bp non-coding exon) and SEQ ID NO: 10 (1249 bp intron).

In an aspect, the invention relates to a genetic construct that includes any isolated nucleic acid promoter herein operably linked to a heterologous nucleic acid.

In an aspect, the invention relates to a method for producing a heterologous protein in a plant. The method includes contacting a plant with a genetic construct. The genetic construct includes an isolated nucleic acid promoter operably linked to a polynucleotide encoding a heterologous protein. The isolated nucleic acid promoter has a sequence with at least 90% identity to a reference sequence selected from the group consisting of: SEQ ID NO: 1 (PvUbi3), SEQ ID NO: 2 (PvUbi4) and SEQ ID NO: 3 (PvUbi4s). The method includes selecting a transformed plant containing the genetic construct. The method also includes cultivating the transformed plant under conditions suitable for production of the heterologous protein.

In an aspect, the invention relates to a method for producing a heterologous protein. The method includes obtaining a transgenic plant that includes a genetic construct. The genetic construct includes an isolated nucleic acid promoter operably linked to a polynucleotide encoding a heterologous protein. The isolated nucleic acid promoter has a sequence with at least 90% identity to a reference sequence selected from the group consisting of: SEQ ID NO: 1 (PvUbi3), SEQ ID NO: 2 (PvUbi4), and SEQ ID NO: 3 (PvUbi4s). The heterologous protein is expressed in the transgenic plant. The method also includes isolating the heterologous protein.

In an aspect, the invention relates to a transformed plant that includes an isolated nucleic acid promoter. The isolated nucleic acid promoter has a sequence with at least 90% identity to a reference sequence selected from the group consisting of: SEQ ID NO: 1 (PvUbi3), SEQ ID NO: 2 (PvUbi4), and SEQ ID NO: 3 (PvUbi4s).

In an aspect, the invention relates to a vector that includes an isolated nucleic acid promoter. The isolated nucleic acid promoter has a sequence with at least 90% identity to a reference sequence selected from the group consisting of: SEQ ID NO: 1 (PvUbi3), SEQ ID NO: 2 (PvUbi4), and SEQ ID NO: 3 (PvUbi4s).

BRIEF DESCRIPTION OF THE DRAWINGS

The following detailed description of the preferred embodiments will be better understood when read in conjunction with the appended drawings. For the purpose of illustration, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENTS

Figure 1:
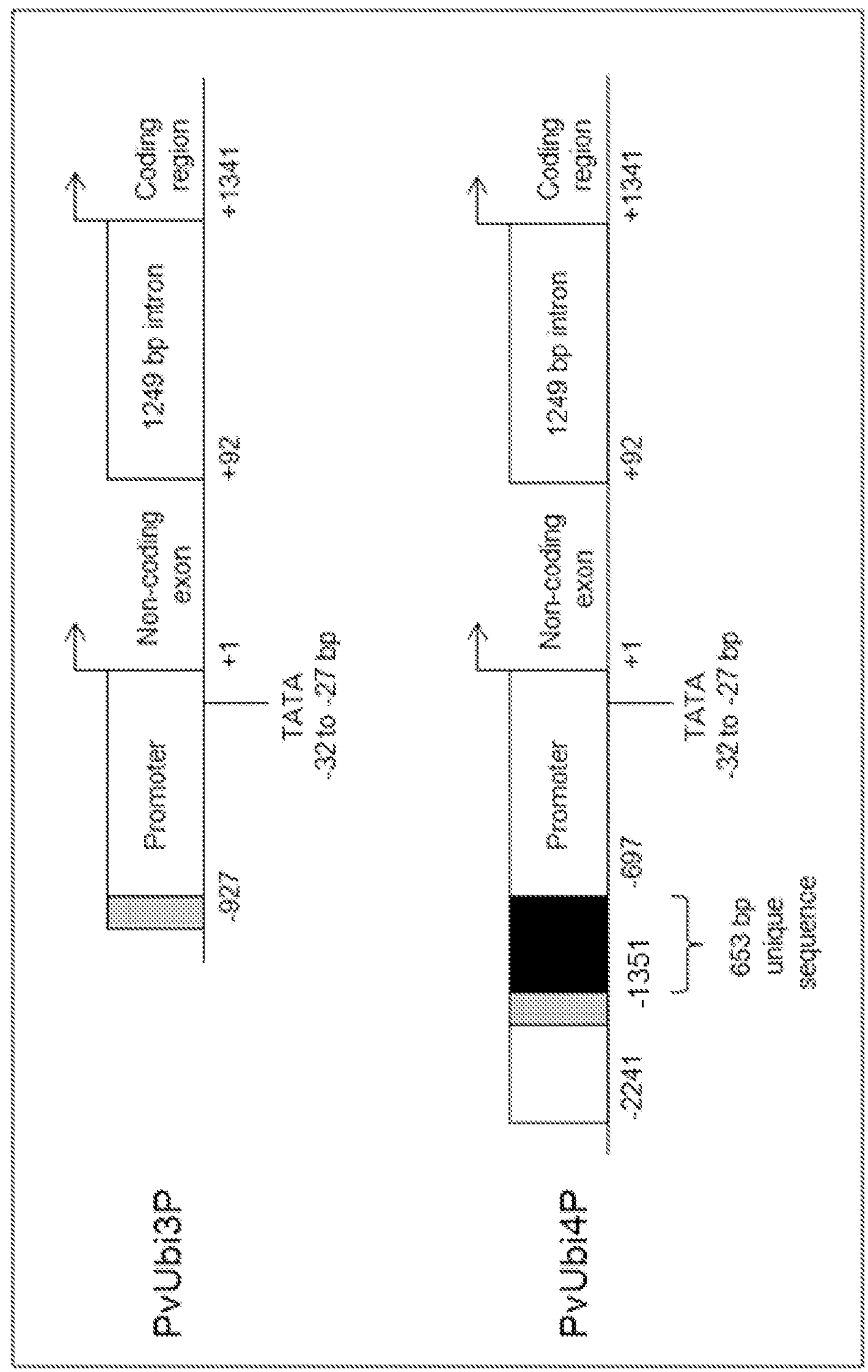
FIG. 1 illustrates diagrams of genomic structures of isolated PvUbi3 and PvUbi4 promoters.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

As used herein in reference to an isolated nucleic acid, isolated nucleic acid promoter, isolated polynucleotide sequence, isolated oligonucleotide sequence, isolated nucleotide sequence, or the like, refers to nucleic acid, nucleic acid promoter, polynucleotide sequence, oligonucleotide sequence, nucleotide sequence, or the like separated from the source in which it was discovered. An isolated nucleic acid, isolated nucleic acid promoter, isolated polynucleotide sequence, isolated oligonucleotide sequence, isolated nucleotide sequence, or the like may lack covalent bonds to sequences with which it was associated in the source (e.g., an isolated DNA may lack covalent bonds to the sequences that it neighbored in the genome it was discovered in).

As used herein, an "operably connected" isolated nucleic acid promoter is capable of activating transcription of another sequence.

An embodiment provides isolated novel Ubiquitin-based promoters from switchgrass *Panicum virgatum* L., cv. Alamo.

An embodiment provides an isolated nucleic acid promoter comprising, consisting essentially of, or consisting of a sequence with at least 70, 72, 75, 80, 85, 90, 91, 92, 93, 94, 95, 96, 97, 98, 99, or 100% identity to a reference sequence selected from the group consisting of: SEQ ID NO: 1 (PvUbi3), SEQ ID NO: 2 (PvUbi4), and SEQ ID NO: 3 (PvUbi4s). The isolated nucleic acid promoter may be capable of transcriptionally activating a second nucleic acid. The second nucleic acid may be a heterologous nucleic acid.

The isolated nucleic acid promoter may be operably connected with a heterologous nucleic acid and may transcriptionally activate the heterologous nucleic acid. As a result of transcriptional activation, the heterologous nucleic acid may be expressed constitutively in a plant. Constitutive expression means that the promoter provides transcription of polynucleotide sequences throughout the plant in most cells, tissues and organs and during many but not necessarily all stages of development. The isolated nucleic acid promoter may include a DNA element. The DNA element may regulate gene expression. The DNA element may be but is not limited to an enhancer, an activator, or a repressor. The DNA element may be a cis-acting regulatory element. The cis-acting regulatory element may be but is not limited to an elicitor-mediated activation element, an anaerobic induction element (ARE), a light responsive element, a meristem specific expression element, a methyl jasmonate responsive element, an anoxic specific inducibility element, a MYB transcription binding site, a gibberellin responsive element, an endosperm specific expression motif, a salicylic acid responsive element, or a TATA-box sequence. The DNA element may be a non-coding exon sequence or an intron sequence. The DNA element may comprise, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 4 (2037 bp downstream PvUbi3); SEQ ID NO: 5 (2037 bp downstream PvUbi4); SEQ ID NO: 6 (230 bp region of PvUbi3; position −927 to −698), SEQ ID NO: 7 (230 bp region of PvUbi4/PvUbi4s; position −1580 to −1351), SEQ ID NO: 8 (653 bp Unique SEQ of PvUbi4/PvUbi4s), SEQ ID NO: 9 (91 bp non-coding exon), and SEQ ID NO: 10 (1249 bp intron) (FIG. 1 and sequences shown in Example 2).

Determining percent identity of two nucleic acid sequences or two amino acid sequences may include aligning and comparing the nucleotides the amino acid residues at corresponding positions in the two sequences. If all positions in two sequences are occupied by identical amino acid residues or nucleotides then the sequences are said to be 100% identical. Percent identity may be measured by the Smith Waterman algorithm (Smith T F, Waterman M S 1981 "Identification of Common Molecular Subsequences," J Mol Biol 147: 195-197, which is incorporated herein by reference as if fully set forth).

An embodiment provides an isolated nucleic acid promoter comprising, consisting essentially of, or consisting of a polynucleotide sequence capable of hybridizing under conditions of one of low, moderate, or high stringency to nucleic acid consisting of a reference sequence selected from the group consisting of: SEQ ID NO: 1 (PvUbi3), SEQ ID NO: 2 (PvUbi4), and SEQ ID NO: 3 (PvUbi4s). The isolated nucleic acid promoter may include a DNA element. The isolated nucleic acid promoter may be operably connected with a heterologous nucleic acid and may transcriptionally activate the heterologous nucleic acid. As a result of transcriptional activation, the heterologous nucleic acid may be expressed constitutively in a plant. Constitutive expression means that the heterologous nucleic acid may be expressed in many but not necessarily all tissues and/or in many but not necessarily all stages of development of the plant. The DNA element may be any one of the DNA elements listed above. The DNA element may comprise, consists essentially of, or consists of a polynucleotide sequence capable of hybridizing under conditions of one of low, moderate, or high stringency to nucleic acid consisting of a reference sequence selected from the group consisting of: SEQ ID NO: 4 (2037 bp downstream PvUbi3), SEQ ID NO: 5 (2037 bp downstream PvUbi4), SEQ ID NO: 6 (230 bp region of PvUbi3; position −927 to −698), SEQ ID NO: 7 (230 bp region of PvUbi4/PvUbi4s; position −1580 to −1351), SEQ ID NO: 8 (653 bp Unique SEQ of PvUbi4/PvUbi4s), SEQ ID NO: 9 (91 bp non-coding exon), and SEQ ID NO: 10 (1249 bp intron).

Methods of hybridization and stringency conditions are known in the art and are described the following books: Molecular Cloning, T. Maniatis, E. F. Fritsch and J. Sambrook, Cold Spring Harbor Laboratory, 1982, and Current Protocols in Molecular Biology, F. M. Ausubel, R. Brent, R. E. Kingston, D. D. Moore, J. G. Siedman, J. A. Smith, K. Struhl, Volume 1, John Wiley & Sons, 2000, which are incorporated hereby by reference as if fully set forth.

Moderate conditions may be as follows: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), 5×Denhardt's solution (Amresco, Inc., Solon, Ohio), and denatured salmon sperm (Invitrogen Life Technologies, Inc. Carlsbad, Calif.). Hybridization is in the same solution with the following modifications: 0.01 M EDTA (Amresco, Inc., Solon, Ohio), 100 μg/ml salmon sperm DNA, and 5-20×$10^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.). $Tm=81.5+16.61 \text{ Log}_{10}([Na^+]/(1.0+0.7[Na^+]))+0.41(\%[G+C])-(500/n)-P-F$. [Na+]=Molar concentration of sodium ions. %[G+C]=percent of G+C bases in DNA sequence. n=length of DNA sequence in bases. P=a temperature correction for % mismatched base pairs (~1° C. per 1% mismatch). F=correction for formamide concentration (=0.63° C. per 1% formamide). Filters are exposed for development in an imager or by autoradiography. Low stringency conditions refers to hybridization conditions at low temperatures, for example, between 37° C. and 60° C., and the second wash with higher [$Na^+$] (up to 0.825M) and at a temperature 40° C. to 48° C. below Tm. High stringency refers to hybridization conditions at high temperatures, for example, over 68° C., and the second wash with [Na+]=0.0165 to 0.0330M at a temperature 5° C. to 10° C. below Tm.

An embodiment provides a fragment of any of the above isolated nucleic acid promoters. The fragment may be implemented as a hybridization probe or primer. The probe or primer may have any length. The probe or primer may be 6, 10, 15, 20, 25, 30, 35, 40, 45, or 50 nucleotides in length along any corresponding length of the reference isolated nucleic acid promoter, or may have a length in a range between any two of the foregoing lengths (endpoints inclusive). A fragment may have a length less than the full length reference sequence and/or include substitutions or deletions in comparison to the cited reference sequence. A fragment may have a length of 6, 7, 8, 9, 10 . . . or n nucleotides (where n is the one nucleotide less than full length) along any corresponding length of the reference isolated nucleic acid, or may have a length in a range between any two of the foregoing lengths (endpoints inclusive). The fragment may be a variant of the cited reference sequence. A variant may be capable of transcriptionally activating the heterologous nucleic acid operably connected to the variant.

In an embodiment, a variant of a nucleic acid promoter is provided. The fragment or the variant may be obtained by any method. The fragment or the variant may be obtained through mutations, insertions, deletions and/or substitutions of one or more nucleotides introduced into the polynucleotide sequence of the nucleic acid promoter.

In an embodiment, a variant or a fragment of an isolated nucleic acid promoter herein may be operably linked to a heterologous nucleic acid. To test a biological activity of an isolated nucleic acid promoter, or a variant or a fragment thereof, a polynucleotide sequence of the promoter, the variant, or the fragment thereof may be operably linked to a screenable marker and introduced into a host cell. The expression level of the screenable marker may be assessed and the promoter activity may be determined based on the level of expression of the screenable marker. For example, the isolated nucleic acid promoter, or the variant, or the fragment thereof may be operably linked to the GUS gene. The isolated nucleic acid promoter, or the variant, or the fragment thereof and the GUS gene may be introduced into a host cell. The biological activity of the isolated nucleic acid promoter, or the variant, or the fragment thereof may be determined either visually or quantitatively based on levels of GUS expression in host cells. High levels of GUS expression may correlate with high activity of the isolated nucleic acid promoter, or the variant, or the fragment thereof.

In an embodiment, a genetic construct is provided. The genetic construct may include an isolated nucleic acid promoter herein. The isolated nucleic acid promoter herein may be operably linked to a heterologous nucleic acid. The heterologous nucleic acid may encode a heterologous protein. The heterologous nucleic acid may encode any heterologous protein. The heterologous nucleic acid may encode an agronomic trait. The agronomic trait may be but is not limited to insect resistance, disease resistance, virus resistance, herbicide tolerance, drought tolerance, salt tolerance, cold tolerance or a quality trait for an improved nutritional value. The heterologous nucleic acid may encode a selectable marker. The selectable marker may be but is not limited to a phosphomannose isomerase gene (PMI) conferring ability to metabolize mannose, a neomycin phosphotransferase (npt) gene conferring resistance to kanamycin, a hygromycin phosphotransferase (hpt) gene conferring resistance to hygromycin, an enolpyruvylshikimate-3-phosphate synthase (EPSPS) gene conferring resistance to glyphosate, or a bar (BAR) gene conferring resistance to phosphinothricin.

The heterologous nucleic acid may encode a cell wall degrading enzyme. The cell wall degrading enzyme may be but is not limited to an endoglucanase, an exoglucanase, a xylanase, or a feruloyl esterase. The heterologous nucleic acid molecule may encode an intein-modified cell wall degrading enzyme. The intein-modified cell wall degrading enzyme may be inactive. The cell-wall degrading enzyme may re-gain activity upon splicing of the intein. The intein may be inducible to splice by providing induction conditions. Intein modified enzymes and conditions for inducing splicing of the inteins, which could be used as activation conditions, were described in U.S. application Ser. No. 10/886,393 filed Jul. 7, 2004 and PCT/US10/55746 filed Nov. 5, 2010, and PCT/US10/55669 filed Nov. 5, 2010 and PCT/US10/55751 filed Nov. 5, 2010, which are incorporated herein by reference as if fully set forth. The intein-modified cell wall degrading enzyme may be but is not limited to an intein-modified endoglucanase, an intein-modified exoglucanase, an intein-modified xylanase or an intein-modified feruloyl esterase. For example, the isolated nucleic acid promoter, or the variant, or the fragment thereof may be operably linked to the endoglucanase gene from *Nasutitermus takasogoensis* (NtEGm). The isolated nucleic acid promoter, or the variant, or the fragment thereof and the NtEGm gene may be introduced into a host cell. The biological activity of the isolated nucleic acid promoter, or the variant, or the fragment thereof may be determined quantitatively based on levels of NtEGm expression in host cells. NtEGm expression may be assessed using quantitative Cellazyme assays for detection of endoglucanase protein expression described in Example 6 of this application. High levels of NtEGm expression may correlate with high activity of the isolated nucleic acid promoter, or the variant, or the fragment thereof.

The heterologous nucleic acid encoding a heterologous protein may further include one or more DNA sequences encoding a targeting peptide. The targeting peptide may be fused to the heterologous protein. The targeting peptide may be fused to a cell wall degrading. The cell wall degrading enzyme may be fused to more than one targeting peptide. The cell wall degrading enzyme may be fused to two targeting peptides. The heterologous nucleic acid acid may encode more than one cell wall degrading enzyme. A targeting peptide may be independently selected for each of the cell wall degrading enzymes. Each targeting peptide may be independently selected from but is not limited to an amyloplast targeting signal, a cell wall targeting peptide, a mitochondrial targeting peptide, a cytosol localization signal, a chloroplast targeting signal, a nuclear targeting peptide, and a vacuole targeting peptide.

A DNA sequence may encode an amino targeting peptide. The DNA sequence encoding the amino targeting peptide may be upstream of the heterologous nucleic acid. The DNA sequence encoding the amino targeting peptide may be downstream of the isolated nucleic acid promoter. The DNA sequence encoding the amino targeting peptide may be operably linked and between the heterologous nucleic acid and the isolated nucleic acid promoter. The amino targeting peptide may be selected but is not limited to a sequence of BAASS, the barley aleurone vacuoalr targeting sequence {HvAle], or the gamma-zein sequence [xGZein27ss-02]. The amino terminus of the cell wall degrading enzyme may be fused to the amino targeting peptide.

A DNA sequence may encode a carboxy targeting peptide. The DNA sequence encoding the carboxy targeting peptide may be downstream of the heterologous nucleic acid. A carboxy targeting peptide may be selected from but is not limited to a sequence of SEKDEL (SEQ ID NO: 36) endoplasmic reticulum retention signal, KDEL (SEQ ID NO: 37), or the barley vacuolar sorting determinant [HvVSD-01]. The carbxy terminus of the cell wall degrading enzyme may be fused to the carboxy targeting peptide.

The amino terminus of the cell wall degrading enzyme may be fused to the amino targeting peptide and the carboxy terminus of the cell wall degrading enzyme may be fused to the carboxy terminus of the carboxy targeting peptide. For example, the amino terminus of endoglucanase NtEGm may be fused to the HvAle and the carboxy terminus may be fused to SEKDEL (SEQ ID NO: 36).

In an embodiment, the genetic contruct may include a sequence with at least 70, 72, 75, 80, 85, 90, 91, 92, 93, 94, 95, 96, 97, 98, 99, or 100% identity to a reference sequence of SEQ ID NO: 23 (PvUbi4:HvAleNtEGm:SEKDEL).

In an embodiment, a method for producing a heterologous protein in a plant is provided. The method may include contacting a plant with a genetic construct. The genetic construct may include an isolated nucleic acid promoter operably linked to a polynucleotide encoding a heterologous protein. The isolated nucleic acid promoter may have a sequence that may comprise, consist essentially of, or consists of a nucleic acid with at least 70, 72, 75, 80, 85, 90, 91, 92, 93, 94, 95, 96, 97, 98, 99, or 100% identity to a reference sequence selected from the group consisting of: SEQ ID NO: 1 (PvUbi3), SEQ ID NO: 2 (PvUbi4), and SEQ ID NO: 3 (PvUbi4s). The isolated nucleic acid promoter may include a sequence that may comprise, consist essentially of, or consist of a nucleic acid that hybridizes under conditions of one of low, moderate, or high stringency to a nucleic acid consisting of a reference sequence selected from the group consisting of: SEQ ID NO: 1 (PvUbi3), SEQ ID NO: 2 (PvUbi4) and SEQ ID NO: 3 (PvUbi4s). The method may include selecting a transformed plant comprising the genetic construct. The method may include cultivating the transformed plant under conditions suitable for production of the heterologous protein.

In an embodiment, a method for producing a heterologous protein is provided. The method may include obtaining a transgenic plant that includes a genetic construct. The genetic construct may include an isolated nucleic acid promoter operably linked to a polynucleotide encoding a heterologous protein. The isolated nucleic acid promoter may have a sequence that may comprise, consist essentially of, or consists of a nucleic acid with at least 70, 72, 75, 80, 85, 90, 91, 92, 93, 94, 95, 96, 97, 98, 99, or 100% identity to a reference sequence selected from the group consisting of: SEQ ID NO: 1 (PvUbi3), SEQ ID NO: 2 (PvUbi4), and SEQ ID NO: 3 (PvUbi4s). The isolated nucleic acid promoter may include a sequence that may comprise, consist essentially of, or consist of a nucleic acid that hybridizes under conditions of one of low, moderate, or high stringency to a nucleic acid consisting of a reference sequence selected from the group consisting of: SEQ ID NO: 1 (PvUbi3), SEQ ID NO: 2 (PvUbi4) and SEQ ID NO: 3 (PvUbi4s). The heterologous protein may be expressed in the transgenic plant. The method may also include isolating the heterologous protein.

In an embodiment of any of the method, the genetic construct may be stably integrated into a genome of the transformed plant. In an embodiment of any of the method, the genetic construct may be expressed transiently in the transformed plant.

The transformed plant may be any type of plant. The transformed plant may be a monocotyledonous plant. The transformed plant may be a dicotyledonous plant.

An embodiment of any of the method may further include breeding the transformed plant and obtaining its progeny, or its descendant. The progeny or the descendant may include the genetic construct.

In an embodiment of any of the method, the transformed plant may be selected from but is not limited to maize, switchgrass, miscanthus, sorghum, sugar beet, sugar cane, rice, wheat or poplar.

In an embodiment, any of the method further may include obtaining a seed of the transformed plant. The seed may include the genetic construct that includes the genetic construct.

In an embodiment, a transformed plant that includes an isolated nucleic acid promoter of any one of embodiments herein is provided. The transformed plant may be created by known methods to express a heterologous nucleic acid under control of the nucleic acid promoter. The plant may be created by *Agrobacterium*-mediated transformation using a vector that includes a heterologous nucleic acid operably linked to an isolated nucleic acid promoter herein. The transformed plant may be created by other methods for modifying plants, for example, particle bombardment or direct DNA uptake. The transformed plant may be stably transformed. The stably transformed plant may incorporate the heterologous nucleic acid under control of the isolated nucleic acid promoter into the genome of the plant.

The plant may be transformed with a viral vector for transient expression of one or more heterologous proteins in a plant. The viral vector may be a T-DNA vector. The T-DNA vector may be delivered to a plant by any method. Plants may be infiltrated with a diluted *Agrobacterium* suspension carrying T-DNAs encoding viral replicons. The resulting plants may have a high copy number of RNA molecules that encode one or more heterologous proteins. One or more heterologous proteins may be produced in plants rapidly. One or more heterologous proteins may be produced in the transformed plant in 1, 2, 3, 4, 5, 6, 7, 8, 9, 10, 11, 12, 13, 14 or more days after transformation. The plant transformed with a viral vector may not integrate heterologous nucleic acid molecules into the plant genome.

In an embodiment, a vector that includes an isolated nucleic acid promoter is provided for expressing heterologous proteins in a plant. The vector may comprise, consist essentially of, or consist of a polynucleotide sequence with at least 70, 72, 75, 80, 85, 90, 91, 92, 93, 94, 95, 96, 97, 98, 99 or 100% identity to a reference sequence selected from the group consisting of: SEQ ID NO: 1 (PvUbi3), SEQ ID NO: 2 (PvUbi4), and SEQ ID NO: 3 (PvUbi4s). The vector may further include a heterologous nucleic acid operably linked to the isolated nucleic acid promoter. The vector may comprise, consist essentially of, or consist of a polynucleotide sequence with at least 70, 72, 75, 80, 85, 90, 91, 92, 93, 94, 95, 96, 97, 98, 99 or 100% identity to a reference sequence selected from the group consisting of: SEQ ID NO: 11 (pAG 4008), SEQ ID NO: 12 (pAG4009), and SEQ ID NO: 13 (pAG 4010). The vector may comprise, consist essentially of, or consist of a polynucleotide sequence with at least 70, 72, 75, 80, 85, 90, 91, 92, 93, 94, 95, 96, 97, 98, 99 or 100% identity to a reference sequence selected from the group consisting of: SEQ ID NO:14 (pAG 4008b), SEQ ID NO: 15 (pAG 4009b), and SEQ ID NO: 16 (pAG 4010b). The vector may comprise, consist essentially of, or consist of a polynucleotide sequence that hybridizes under conditions of one of low, moderate, or high stringency to a nucleic acid consisting of a reference sequence selected from the group consisting of: SEQ ID NO: 11 (pAG 4008), SEQ ID NO: 12 (pAG4009), and SEQ ID NO: 13 (pAG 4010). The vector may comprise, consist essentially of, or consists of a polynucleotide sequence that hybridizes under conditions of one of low, moderate, or high stringency to a nucleic acid consisting of a reference sequence selected from the group consisting of: SEQ ID NO:14 (pAG 4008b), SEQ ID NO: 15 (pAG4009b), and SEQ ID NO: 16 (pAG4010b).

The vector may comprise an expression cassette that may comprise, consist essentially of, or consist of a polynucleotide sequence with at least 70, 72, 75, 80, 85, 90, 91, 92, 93, 94, 95, 96, 97, 98, 99 or 100% identity to a reference sequence of SEQ ID NO:23 (PvUbi4:HvAle:NtEGm:SEKDEL). The vector may comprise an expression cassette that may comprise, consist essentially of, or consist of a polynucleotide sequence that hybridizes under conditions of one of low, moderate, or high stringency to a nucleic acid consisting of a reference sequence SEQ ID NO:23 (PvUbi4:HvAle:NtEGm:SEKDEL).

The vector may include the polynucleotide sequence of a nucleic acid promoter isolated from *Panicum virgatum*.

In an embodiment, a vector herein may be a vector for expressing heterologous proteins in a plant. The vector may be a plant transformation vector. The plant transformation vector may be a vector for stable transformation of a plant. The plant transformation vector may be but is not limited to a T-DNA vector, a binary vector or a cointegrate vector. The plant transformation vector may be a vector for a transient expression of heterologous proteins in a plant. The plant transformation vector for transient expression of heterologous proteins in a plant may be a viral-based vector. The viral-based vector may be based on viruses belonging to any genus. The viruses may be but are not limited to potyviruses, tobamoviruses, cucumoviruses or bromoviruses. For example, the viral-based vector may be a tobacco mosaic virus (TMV)-based vector or potato virus X (PVX)-based.

An embodiment provides a vector herein having fragment of any of the above isolated nucleic acid promoters. The probe or primer may have any length. The probe or primer may be 6, 10, 15, 20, 25, 30, 35, 40, 45, or 50 nucleotides in length along any corresponding length of the reference isolated nucleic acid promoter, or may have a length in a range between any two of the foregoing lengths (endpoints inclusive). A fragment may have a length less than the full length and/or include substitutions or deletions in comparison to cited reference sequence. A fragment may have a length of 6, 7, 8, 9, 10 . . . or n nucleotides (where n is the one nucleotide less than full length) along any corresponding length of the reference isolated nucleic acid, or may have a length in a range between any two of the foregoing lengths (endpoints inclusive). The fragment may be a variant of the cited reference sequence. A variant may be capable of transcriptionally activating the heterologous nucleic acid operably connected to the variant.

Vectors containing isolated nucleic acid promoters herein may also include at least one of genetic elements, multiple cloning sites to facilitate molecular cloning, or selection markers to facilitate selection. A selectable marker that may be included in a vector may be but is not limited to PMI, npt, hpt, EPSPS or BAR genes. The selectable marker included in the vector may be operably linked to a second promoter. The second promoter may be any promoter. The second promoter may be a constitutive promoter, which provides transcription of the polynucleotide sequences throughout the plant in most cells, tissues and organs and during many but not necessarily all stages of development. The second promoter may be an inducible promoter, which initiates transcription of the polynucleotide sequences only when exposed to a particular chemical or environmental stimulus. The second promoter may be specific to a particular developmental stage, organ or tissue. A tissue specific promoter may be capable of initiating transcription in a particular plant tissue. The second promoter may be a constitutive promoter selected from Cestrum Yellow Leaf Curling Virus promoter (CMP) or the CMP short version (CMPS). The second promoter may be selected from other known constitutive promoters, including but not limited to the rice Ubiquitin 3 promoter (OsUbi3P), rice Actin 1 promoter, Cauliflower Mosaic Virus (CAMV) 35S promoter, the Rubisco small subunit promoter, the maize phosphoenolpyruvate carboxylase (PepC) promoter and the maize ubiquitin promoter.

A vector herein may include a terminator sequence. A terminator sequence may be included at the 3' end of a transcriptional unit of the genetic construct. The terminator may be derived from a variety of plant genes. The terminator may be a terminator sequence from the nopaline synthase or octopine synthase genes of *Agrobacterium tumefaciens*.

In an embodiment, the vector may be constructed to include polynucleotide sequences encoding multiple heterologous nucleic acids. A vector herein may further include a heterologous nucleic acid designed to silence a gene or genes in a plant.

Further embodiments herein may be formed by supplementing an embodiment with one or more element from any one or more other embodiment herein, and/or substituting one or more element from one embodiment with one or more element from one or more other embodiment herein. Further embodiments herein may be described by reference to any one of the appended claims following claim 1 and reading the chosen claim to depend from any one or more preceding claim.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1: Isolation of Upstream Sequences Containing Novel Ubiquitin Promoters from the Switchgrass Genome A combination of different PCR approaches has been applied to isolate the upstream region of TC44841 (The Gene Index Databases, Dana Farber Cancer Institute, Boston Mass. 02115 (URL: httn://danafarber.otg); EST sequences (450) expressed in various switchgrass tissue and developmental stages) using genomic DNA prepared from switchgrass cultivar Alamo. Initially, a series of primers was designed, based on the TC44841 5' end sequence to amplify a putative intron localized within a first non-coding exon. Four PCR fragments longer than 1 kb were amplified, cloned and completely sequenced. All isolated sequences were subsequently validated by PCR on switchgrass genomic DNA with the new forward primers designed at 5' ends of the isolated PCR fragments and reverse primers designed at 5' end of TC44841. This work allowed assigning the 1291 bp OB-1413 sequence as an extension of EST TC44841 into its 5' genomic region.

A series of reverse primers was further designed at the 5' end of the OB-1413. These primers were used in a genome walking PCR approach to extend OB-1413 farther into the 5' region. Using these primers, additional 855 bp (OB-1693) and 1624 bp (OB-1731) sequences were isolated and proved to be an extension of OB-1413 sequence.

The sequences compiled during genome walk were amplified and validated by PCR and designated as PvUbi3 and PvUbi4. The PCR yielded the 2267 bp PvUbi3 and 3581 bp PvUbi4 upstream regions, which were completely sequenced in both directions. These validated sequences were subsequently used to develop GUS expression cassettes to assess promoter functionality of the isolated PvUbi3 and PvUbi4 upstream regions.

Example 2: Characterization of the PvUbi3 and PvUbi4 Sequences

The PvUbi3 promoter consists of a 927 bp sequence upstream of the predicted transcription initiation site, a 91 bp sequence of the non-coding exon and a 1249 bp of the 5' UTR intron. The PvUbi4 promoter is contained within the 2241 bp sequence upstream of the transcription initiation site. Similar to the PvUbi3 promoter, it has the 91 bp non-coding exon and 1249 bp intron sequences within its 5'UTR region. Both promoters are predicted to contain various cis-acting elements.

Various sequence motifs resembling potential cis-acting regulatory elements were identified in isolated candidate promoter regions of PvUbi3 and PvUbi4. The sequences motifs common to both PvUbi3 and PvUbi4 are represented by an elicitor-mediated activation element (TAAAATACT, position −448 to −440), a putative anaerobic induction element ARE (TGGTTT, position −489 to −484), light responsive elements (LREs) (AATCTAAACT (SEQ ID NO: 24), position −348 to −339; CTTTATCA, position −433 to −426; GATATGG, position −416 to −410), a meristem specific expression element (CCGTCC, position −228 to −223), three methyl jasmonate responsive elements (TGACG, position −668 to −664; CGTCA, positions −252 to −248, −186 to −182), an anoxic specific inducibility element (CCCCCG, position −40 to −35), the MYB transcription factor binding site (CGGTCA, position −542 to −537), a gibberellin-responsive element (CCTTTTG, position −648 to −642), endosperm-specific expression motifs (GTCAT, positions −1387 to −1383, −612 to −608, −540 to −536), TATA-box sequences (taTATAAAtc (SEQ ID NO: 25), position −296 to −287; TATAAAT, position −32 to −26), a salicylic acid responsive element (GAGAAGCATA (SEQ ID NO: 26), position −504 to −495), and the promoter enhancer element site (CAAT, position −1393 to −1390).

A unique 653 bp sequence in PvUbi4 contains several additional cis-elements compared to PvUbi3. These elements are comprised of the leaf morphology development site (CAAT(G/C)ATTG, position −1020 to −1012), two extra LREs (CACGAC, position −889 to 884; TTTCAAA, position −859 to −853), a protein-binding site (AACATTTTCACT (SEQ ID NO: 27), position −851 to −840), four putative promoter enhancers (CAAT, positions −1345 to −1342, −1020 to −1017, −907 to −904, −866 to −863), two extra MYB transcription factor binding sites (CAACGG, position −1227 to −1222 and −1195 to −1190), the heat stress response element (AAAAAATGTC, (SEQ ID NO: 28), position −1290 to −1281), an endosperm-specific expression element (GTCAT, positions −1283 to −1279), and a salicylic acid responsive motif (CAGAAAGGGA, (SEQ ID NO: 29), position −768 to −759).

The polynucleotide sequences of both PvUbi3 (SEQ ID NO: 1) and PvUbi4 (SEQ ID NO: 2) are shown below. Both sequences contain a 1249 bp intron indicated by low case letters. Putative TATA sequences (TATATAAA, TATAAAT) are shown as the boxed sequences. The predicted transcription initiation site is shown as a boxed A nucleotide. The sequence for PvUbi4 (SEQ ID NO: 2) shows the unique 653 bp sequence underlined in the PvUbi4 upstream region. This sequence in PvUbi4 appears as an extra 653 bp sequence upstream of the 2037 bp downstream sequence, which is almost identical in PvUbi3 and PvUbi4. PvUbi3 and PvUbi4 contain highly homologous 230 bp 5' sequences shown as bold and italicized nucleotide sequences. The highly homologous 230 bp sequence in PvUbi4 is located upstream of the unique 653 bp sequence, while in PvUbi3 it is directly adjacent to the 2037 bp downstream sequence.

PvUbi3

(SEQ ID NO: 1)

*ACGACCGGAGGAGAGATTCTTTGCTTTGCTTGTGGCTGCGAAGGAGG*

*AGGAGAAACCACGCCGCGGATAAGAAGGAAACCGCCTTTGCAAAACC*

*AGAACATCTTTTCTGATGAAGAAATCCGCGTTGCCTCCTGTGAGAAGA*

*ATGCGACCCTTTTTTTATACTCTATTATATCTTTATTATTATTGTCAAT*

*TTGTCATGTCACTGAGAAATGACCCTGATACGAACGGTC*ATTTTTGAT

AATTCTTGTTTCTATTGTCTTGACGATTCTAATGCCATGTCCTTTTGTCT

TGACAGCTCTAGTGCCATGTCTATTTGTCATGTTATCATTTGTTCTTTTT

ATTTCAAGGAAAATTATTACATCAAAAAATTGATTTTCGAAGTTCACGGT

CATCTTCACCATCACTCTCTACCGCATTGGTGGCGAGAAGCATATCTAGT

GGTTTCATTCTGGTAAGCCTCGCTCAAATGAAATTTGTAATAAAATACTA

TATTTCTTTATCAAGGTTATAAGATATGGAGAGAAATGGTCTGCTTCATA

AATTTGACTTACATAGAGCCTTTAAAAAGGAATACCATGTAATCTAAACT

CTATAA

CATAAAGAGCTTTGCGCTTTTAAAAATATGCTAACCTATATAAATCGCTTT

TGCTAGAGACAGGTCATGTATGATTGAAGCGTCACCATAACGCCGTTAAT

CTTCCGTCCAGCCATTAACGGCCACCTACCGCAGGAAACAAACGGCGTCA

CCATCCTCGATATCTCCGCGGCGGCCGCTGGCTTTTTTCGGAGAAATTGC

GCGGTGGGGACGGAGTCCACGAGAGCCTCTCGCCGCTGGGCCCCACAATC

AATGGCGTGACCTCACGGGACGCCTCCCTCCCTCTACCCTCCCCCCGTG

TATAAATAGCACCCCTCCCTCGCCTCTTCCGCATCCAGTATTCCAGTCCC

CAATCCGTCGAGAAATTCTCGCGAGCGATCGAAATCTAAGCGAAGCGAAG

AGGCCTCCCCAGATCCTCTCAAGgtatgcgagagcatcgatccccttccg atctatatcgcgtgtcctccctgttcttgttcttcgtcgatctagtttag ggtttgatttggttctgaatcgaacccttttcctgcttgcgttcgatttg tactcgatcctcgggtagaggtgtggatctgcggggcgtgatgaggtagt ttggtgtagatttgttctgggcgttcgatttgccactagggttcggctgc tgttggcattcctgatcgagcggccggataggattgtttttccattttat atgttggatgcgtgatggttcctgtgtgttgggttagattgctggtacga ttcatctaggtggtgatttgcagaggaacaactttgctgttgaatattgg taggtctatctagatttattactttgattatcgcctgataaggatcacc gattcgtgtagaataaattatttcattgttgggtcatgtagatatagctg cacaatttcttacttggctccttactgtgtgaattgtagaataaactgtg ttactctatgagtttttctggattgctggatccagttaggccagtgctgt caatttgttatggctgttaatgtaataattttctggattgttggcctgct tctcttcatgtttaatcacgtgatggttcatgatgcctgttgggttagat tgtttgttcaattcatctaggcagtgctgtgcagagtacaactcgattga tgtttaatcttggtagcttcatctagatttgtacaaattttggtcacctg -continued atgatgatcaccgattgttgtggaattatttcttaactggttcgttgtta gtcaccaccttacttgtagaataacctgtggtactgatttctgttctgtt ttaggccacatcatatgattgtcaaaaatttacatggtagtttaatgata aaattagttcagcttacttcagtttgatttgcttcatatttgttttctg ttctattaatgatacttcatgaaatgtttgtttttttctctgttcagattt gacatgtttcagtatcataataataatattctgtatcctttatagtttgt tggcatgatttgctttgaatttagttagcctattctgttaatataggatg ataagctgtgaggcgttcattctcttcagtccagagttatcattttcagt gttttaatgttgtttatcaagctggatgtatatggtggtttaactctttt ctgtttcttactgtttgcag >PvUbi4

CTGGCCTAACCTAAAATCAGTTCTTGCTGCTGGGTGGTTGGGTACATTAT

CTGACAACTAGGATCCACATCAAAAAAAAAAAGACTACTACGATCATCAT

GGAGTCCTTCGCAACGGCAGCTGGGCAGACACCTTCAGAGTTCAGAGTCC

ACGCACACACTAATAAAGGGGTCCATTTGCCTGCTTCGTTCCGGCTGAAA

TTTTTACGAACCGGTCATCCGTAACCACGATAATCGATATGGACCAAGAG

AGACAAAAAATAATCTCGGAACATCGTTAGCAAGTCCAAATGGAACGCAAC

CAGAGACATGTTGTTTGCCTTCATCCTTCATACACAACCCACCTGGCCAC

CTCCATGTCCATGATTTTTTTTCCCCAATCGACCTTGGACAACCACCAAG

GAATTCCTTGTCAGTTGTTAGCATGGATGACAGTTCAAGCCGGGCAGCTG

GCGTGTCCGTTCAGACATCATCGTCCTGCCAGAACTCCATCCACGCGAGC

CCGCTGAACCAAGGGAGCCTTTGCGTTTGCCCTTTGGCCACGGCATCGTT

CAGCTCATTCCCTCAACAGATCAACTGAACCCAGCGCGCGAAGTTAGCAC

CGGAGCGCAATGCGAGCCGTGCCCGTGTCTTCCTCCCAGCTCCTCCAGCG

CAAGCAAGACG*ACGACCGGAGGAGAGATTCTTTGCTTTGCTTGTGGCT*

*GCGAAGGAGGAGGAGAAACCACGCAGCGGATAAGAAGGAAGCCGCCT*

*TTGCAAAACCAGAGCATCTTTTCTGATGAAGAAATCCGCGTTGCCTCC*

*TGTGAGAAGAATGCGACCCTTTTTTTATACTCTATTCTATCTTTATTA*

*TTATTGTCAATTTGTCATGTCACTGAGAAATGGCCCTGATACGAACGC*

*TA*AGATCCAATCATACACCTTTTATTTATTTATACATAAGTACGTAAATAA

GATGAAAATAAAAAAAATGTCATGGACGAAAACAACGTCCACAAGGACGG

CAAAGATGGAGGACCGCAGGAGCACAACGGATGGATGTTCTTTTTTTGTT

ATCAAACAACGGATGGATGTTTCCGAGCAGGTGCAGCGTCTCCTCCGTTT

ACTCGCCGTGCACATCACGGCGTCCAAACGGGCGTTTGCCGGCGAGGACA

CGGTAGATTTTGCCGACATGGTAGATTTTATCAAGATATTCCGGTCGAGT

TTGGAGTACTAGCTCCATCATGTATAACCACCAATGATTGAGTGGTGACC

ATATCATAATCGTTGGTCAGCTTTCCTTCCATTACTTTTTAATTCAGTAA

TAATAATCCCTAAAGCCTAATCAAGTAAATTCAACTTCCGAATTCAATAG

GGATCATCAGGGCACGACCTGATTGTAAAGACATACAATAGCTTTCAAAC

AACATTTTCACTTATGGTAAAATCTTAATTAAGGTCTTAATATTATAATT

ATTTTTTTCACTGCCGTGAGGGAATGGAGATTTCAGAAAGGGACTTTTTG

-continued

GTATCATCATTGTATATGATCCACGGTTTTTAGTTAGGGCGACTTTAATT
TCTTATTTTTGATAATTCTTGTTTCTATTGTCTTGACGATTCTAATGCCA
TGTCCTTTTGTCTTGACAGCTCTAGTGCCATGTCTATTTGTCATGTTATC
ATTTGTTCTTTTTATTTCAAGGAAAATTATTACATCAAAAAATTGATTTT
CGAAGTTCACGGTCATCTTCACCATCACTCTCTATCGCATTGGTGGCGAG
AAGCATATCTAGTGGTTTCATTCTGGTAAGCCTCGCTCAAATGAAATTTG
TAATAAAATACTATATTTCTTTATCAAGGTTATAAGATATGGAGAGAAAT
GGTCTGCT (SEQ ID NO: 2)

TCATAAATTTGACTTACCTAGAGCCTTTAAAAAGGAATACCATGTAATCT
AAACTCTATAACATAAAGAGCTTTGCGCTTTTAAAAATATGCTAACCTAT
ATAAATCGCTTTTGCTAGAGACAGGTCATGTATGATTGAAGCGTCACCAT
AACGCCGTTAATCTTCCGTCCAGCCATTAACGGCCACCTACCGCAGGAAA
CAAACGGCGTCACCATCCTCGATATCTCCGCGGCGGCCGCTGGCTTTTTT
CGGAGAAATTGCGCGGTGGGGACGGAGTCCACGAGAGCCTCTCGCCGCTG
GGCCCCACAATCAATGGCGTGACCTCACGGGACGGCTCCCTCCCTCTACC
CTCCCCCCGTGTATAAATAGCACCCCTCCCTCGCCTCTTCCGCATCCAGT
ATTCCAGTCCCCAATCCGTCGAGAAATTCTCGCGAGCGATCGAAATCTAA
GCGAAGCGAAGAGGCCTCCCCAGATCCTCTCAAGgtatgcgagagcatcg
atccccttccgatctatatcgcgtgtcctccctgttcttgttcttcgtcg
atctagtttagggtttgatttggttctgaatcgaaccccttttcctgcttg
cgttcgatttgtactcgatcctcgggtagaggtgtggatctgcggggcgt
gatgaggtagtttggtgtagatttgttctgggcgttcgatttgccactag
ggttcggctgctgttggcattcctgatcgagcggccggataggattgttt
ttcccttttttatatgttggatgcgtgatggttcctgtgtgttgggttaga
ttgctggtacgattcatctaggtggtgatttgcagaggaacaactttgct
gttgaatattggtaggtctatctagatttattacttttgattatcgcctg
ataaggatcaccgattcgtgtagaataaattatttcattgttgggtcatg
tagatatagctgcacaatttcttacttggctccttactgtgtgaattgta
gaataaactgtgttactctatgagtttttctggattgctggatccagtta
ggccagtgctgtcaatttgttatggctgttaatgtaataattttctggat
tgttggcctgcttctcttcatgtttaatcacgtgatggttcatgatgcct
gttgggttagattgtttgttcaattcatctaggcagtgctgtgcagagta
caactcgattgatgtttaatcttggtagcttcatctagatttgtacaaat
tttggtcacctgatgatgatcaccgattgttgtggaattatttcttaact
ggttcgttgttagtcaccaccttacttgtagaataacctgtggtactgct
tttctgttctgttttaggccacatcatatgattgtcaaaaatttacatgg
tagtttaatgataaaattagttcagcttacttcagtttgatttgcttcat
attttgttttctgttctattaatgatacttcatgaaatgtttgtttttc
tctgttcagatttgacatgtttcagtatcataataataatattctgtatc
ctttatagtttgttggcatgatttgctttgaatttagttagcctattctg
ttaatataggatgataagctgtgaggcgttcattctcttcagtccagagt
tatcattttcagtgttttaatgttgtttatcaagctggatgtatatggtg
gtttaactcttttctgtttcttactgtttgcag The nucleotide sequence of the PvUbi4s promoter is shown below. PvUbi4s is a short version of the PvUbi4 sequence in which the 661 bp upstream of the bold and italicized nucleotide sequence in PvUbi4s (SEQ ID NO: 2), above, was truncated. Other regions of the PvUbi4s are identical to the full-length PvUbi4 sequence and include the bold and italicized 230 bp 5' sequence, the underlined 653 bp unique sequence, a 91 bp non-coding exon, and a 1249 bp intron indicated by low case letters. The putative TATA sequences and the predicted transcription initiation site A are shown as boxed nucleotides.

>PvUbi4Ps ("s"stands for "short")

(SEQ ID NO: 3)

*ACGACCGGAGGAGAGATTCTTTGCTTTGCTTGTGGCTGCGAAGGAGG*
*AGGAGAAACCACGCAGCGGATAAGAAGGAAGCCGCCTTTGCAAAACC*
*AGAGCATCTTTTCTGATGAAGAAATCCGCGTTGCCTCCTGTGAGAAGA*
*ATGCGACCCTTTTTTTATACTCTATTCTATCTTTATTATTATTGTCAAT*
*TTGTCATGTCACTGAGAAATGGCCCTGATACGAACGCTA*AGATCCAAT
CATACACCTTTTATTTATTTATACATAAGTACGTAAATAAGATGAAAATA
AAAAAAATGTCATGGACGAAAACAACGTCCACAAGGACGGCAAAGATGGA
GGACCGCAGGAGCACAACGGATGGATGTTCTTTTTTTGTTATCAAACAAC
GGATGGATGTTTCCGAGCAGGTGCAGCGTCTCCTCCGTTTACTCGCCGTG
CACATCACGGCGTCCAAACGGGCGTTTGCCGGCGAGGACACGGTAGATTT
TGCCGACATGGTAGATTTTATCAAGATATTCCGGTCGAGTTTGGAGTACT
AGCTCCATCATGTATAACCACCAATGATTGAGTGGTGACCATATCATAAT
CGTTGGTCAGCTTTCCTTCCATTACTTTTTAATTCAGTAATAATAATCCC
TAAAGCCTAATCAAGTAAATTCAACTTCCGAATTCAATAGGGATCATCAG
GGCACGACCTGATTGTAAAGACATACAATAGCTTTCAAACAACATTTTCA
CTTATGGTAAAATCTTAATTAAGGTCTTAATATTATAATTATTTTTTTCA
CTGCCGTGAGGGAATGGAGATTTCAGAAAGGGACTTTTTGGTATCATCAT
TGTATATGATCCACGGTTTTTAGTTAGGGCGACTTTAATTTCTTATTTTT
GATAATTCTTGTTTCTATTGTCTTGACGATTCTAATGCCATGTCCTTTTG
TCTTGACAGCTCTAGTGCCATGTCTATTTGTCATGTTATCATTTGTTCTT
TTTATTTCAAGGAAAATTATTACATCAAAAAATTGATTTTCGAAGTTCAC
GGTCATCTTCACCATCACTCTCTATCGCATTGGTGGCGAGAAGCATATCT
AGTGGTTTCATTCTGGTAAGCCTCGCTCAAATGAAATTTGTAATAAAATA
CTATATTTCTTTATCAAGGTTATAAGATATGGAGAGAAATGGTCTGCTTC
ATAAATTTGACTTACCTAGAGCCTTTAAAAAGGAATACCATGTAATCTAA
ACTCTATAA

-continued

```
CATAAAGAGCTTTGCGCTTTTAAAAATATGCTAACCTATATAAATCGCTTT

TGCTAGAGACAGGTCATGTATGATTGAAGCGTCACCATAACGCCGTTAAT

CTTCCGTCCAGCCATTAACGGCCACCTACCGCAGGAAACAAACGGCGTCA

CCATCCTCGATATCTCCGCGGCGGCCGCTGGCTTTTTTCGGAGAAATTGC

GCGGTGGGGACGGAGTCCACGAGAGCCTCTCGCCGCTGGGCCCCACAATC

AATGGCGTGACCTCACGGGACGGCTCCCTCCCTCTACCCTCCCCCCGTG

TATAAATAGCACCCCTCCCTCGCCTCTTCCGCATCCAGTATTCCAGTCCC

CAATCCGTCGAGAAATTCTCGCGAGCGATCGAAATCTAAGCGAAGCGAAG

AGGCCTCCCCAGATCCTCTCAAGgtatgcgagagcatcgatccuttccga

tctatatcgcgtgtcctccctgttcttgttcttcgtcgatctagtttagg

gtttgatttggttctgaatcgaaccccttttcctgcttgcgttcgatttgt

actcgatcctcgggtagaggtgtggatctgcggggcgtgatgaggtagtt

tggtgtagatttgttctgggcgttcgatttgccactagggttcggctgct

gttggcattcctgatcgagcggccggatagatgattgtttttcccttttttat

atgttggatgcgtgatggttcctgtgtgttgggttagattgctggtacga

ttcatctaggtggtgatttgcagaggaacaactttgctgttgaatattgg

taggtctatctagatttattacttttgattatcgcctgataaggatcacc

gattcgtgtagaataaattatttcattgttgggtcatgtagatatagctg

cacaatttcttacttggctccttactgtgtgaattgtagaataaactgtg

ttactctatgagtttttctggattgctggatccagttaggccagtgctgt

caatttgttatggctgttaatgtaataatttctggattgttggcctgct

tctcttcatgtttaatcacgtgatggttcatgatgcctgttgggttagat

tgtttgttcaattcatctaggcagtgctgtgcagagtacaactcgattga

tgtttaatcttggtagcttcatctagatttgtacaaattttggtcacctg

atgatgatcaccgattgttgtggaattatttcttaactggttcgttgtta

gtcaccaccttacttgtagaataacctgtggtactgatttctgttctgtt
```

-continued

```
ttaggccacatcatatgattgtcaaaaatttacatggtagtttaatgata

aaattagttcagcttacttcagtttgatttgcttcatattttgttttctg

ttctattaatgatacttcatgaaatgtttgtttttttctctgttcagattt

gacatgtttcagtatcataataataatattctgtatcctttatagtttgt

tggcatgatttgctttgaatttagttagcctattctgttaatataggatg

ataagctgtgaggcgttcattctcttcagtccagagttatcattttcagt

gttttaatgttgtttatcaagctggatgtatatggtggtttaactctttt

ctgtttcttactgtttgcag
```

FIG. 1 demonstrates the genomic structure of the isolated PvUbi3 (upper diagram) and PvUbi4 (lower diagram) gene regions containing functional promoters. The PvUbi3 promoter (upper diagram) includes a (−927) region upstream of the transcription initiation site (+1) shown as a Promoter box, a 91 bp region of a non-coding exon and a 1249 bp Intron box which starts at +92 position downstream of the transcription initiation site and ends at +1341 position immediately adjacent to a coding region of a transcribable polynucleotide sequence. PvUbi4P (lower diagram) includes −2241 region upstream of the transcription initiation site (+1) shown as Promoter box. This region includes the unique 653 bp sequence shown as the black box (corresponds to the underlined sequence in the annotated sequence of PvUbi3 and PvUbi4, above.). The unique 653 bp sequence starts at −1353 and ends at −697. The unique 653 bp region includes the putative TATA box which starts at −32 and ends at −27. The 230 bp highly homologous sequence is shown as a gray box in diagrams of PvUbi3 and PvUbi4 and corresponds to gray colored nucleotides in FIGS. 1 and 2. Similar to PvUbi3P, the PvUbi4P sequence includes a 91 bp non-coding exon and a 1249 bp Intron (shown as a box) which starts at +92 and ends at +1341 respective nucleotide position.

An alignment is shown below for the 2037 bp nucleotide sequences downstream of the bold and italicized nucleotides shown in the annotated PvUbi3 and PvUBi4 sequences above, and the gray boxes shown on the diagrams of promoter constructs in FIG. 1. The 2037 bp downstream sequences within the isolated PvUbi3 and PvUbi4 sequences differ by only two bold and italicized nucleotides at positions 322 and 639 as shown below.

```
MSF: 2037 Type: N Check: 32 ..
Name: 2037sPvUbi3 Len: 2037 Check: 9870 Weight: 0
Name: 2037sPvUbi4 Len: 2037 Check: 162 Weight: 0
//
            1                                                  50
2037sPvUbi3 ATTTTTGATA ATTCTTGTTT CTATTGTCTT GACGATTCTA ATGCCATGTC
2037sPvUbi4 ATTTTTGATA ATTCTTGTTT CTATTGTCTT GACGATTCTA ATGCCATGTC

            51                                                100
2037sPvUbi3 CTTTTGTCTT GACAGCTCTA GTGCCATGTC TATTTGTCAT GTTATCATTT
2037sPvUbi4 CTTTTGTCTT GACAGCTCTA GTGCCATGTC TATTTGTCAT GTTATCATTT

            101                                               150
2037sPvUbi3 GTTCTTTTTA TTTCAAGGAA AATTATTACA TCAAAAAATT GATTTTCGAA
2037sPvUbi4 GTTCTTTTTA TTTCAAGGAA AATTATTACA TCAAAAAATT GATTTTCGAA

            151                                               200
2037sPvUbi3 GTTCACGGTC ATCTTCACCA TCACTCTCTA CCGCATTGGT GGCGAGAAGC
2037sPvUbi4 GTTCACGGTC ATCTTCACCA TCACTCTCTA TCGCATTGGT GGCGAGAAGC

            201                                               250
2037sPvUbi3 ATATCTAGTG GTTTCATTCT GGTAAGCCTC GCTCAAATGA AATTTGTAAT
2037sPvUbi4 ATATCTAGTG GTTTCATTCT GGTAAGCCTC GCTCAAATGA AATTTGTAAT
```

-continued

```
             251                                                300
2037sPvUbi3 AAAATACTAT ATTTCTTTAT CAAGGTTATA AGATATGGAG AGAAATGGTC
2037sPvUbi4 AAAATACTAT ATTTCTTTAT CAAGGTTATA AGATATGGAG AGAAATGGTC

             301                                                350
2037sPvUbi3 TGCTTCATAA ATTTGACTTA CATAGAGCCT TTAAAAAGGA ATACCATGTA
2037sPvUbi4 TGCTTCATAA ATTTGACTTA CCTAGAGCCT TTAAAAAGGA ATACCATGTA

             351                                                400
2037sPvUbi3 ATCTAAACTC TATAACATAA AGAGCTTTGC GCTTTTAAAA ATATGCTAAC
2037sPvUbi4 ATCTAAACTC TATAACATAA AGAGCTTTGC GCTTTTAAAA ATATGCTAAC

             401                                                450
2037sPvUbi3 CTATATAAAT CGCTTTTGCT AGAGACAGGT CATGTATGAT TGAAGCGTCA
2037sPvUbi4 CTATATAAAT CGCTTTTGCT AGAGACAGGT CATGTATGAT TGAAGCGTCA

             451                                                500
2037sPvUbi3 CCATAACGCC GTTAATCTTC CGTCCAGCCA TTAACGGCCA CCTACCGCAG
2037sPvUbi4 CCATAACGCC GTTAATCTTC CGTCCAGCCA TTAACGGCCA CCTACCGCAG

             501                                                550
2037sPvUbi3 GAAACAAACG GCGTCACCAT CCTCGATATC TCCGCGGCGG CCGCTGGCTT
2037sPvUbi4 GAAACAAACG GCGTCACCAT CCTCGATATC TCCGCGGCGG CCGCTGGCTT

             551                                                600
2037sPvUbi3 TTTTCGGAGA AATTGCGCGG TGGGGACGGA GTCCACGAGA GCCTCTCGCC
2037sPvUbi4 TTTTCGGAGA AATTGCGCGG TGGGGACGGA GTCCACGAGA GCCTCTCGCC

             601                                                650
2037sPvUbi3 GCTGGGCCCC ACAATCAATG GCGTGACCTC ACGGGACGCC TCCCTCCCTC
2037sPvUbi4 GCTGGGCCCC ACAATCAATG GCGTGACCTC ACGGGACGGC TCCCTCCCTC

             651                                                700
2037sPvUbi3 TACCCTCCCC CCGTGTATAA ATAGCACCCC TCCCTCGCCT CTTCCGCATC
2037sPvUbi4 TACCCTCCCC CCGTGTATAA ATAGCACCCC TCCCTCGCCT CTTCCGCATC

             701                                                750
2037sPvUbi3 CAGTATTCCA GTCCCCAATC CGTCGAGAAA TTCTCGCGAG CGATCGAAAT
2037sPvUbi4 CAGTATTCCA GTCCCCAATC CGTCGAGAAA TTCTCGCGAG CGATCGAAAT

             751                                                800
2037sPvUbi3 CTAAGCGAAG CGAAGAGGCC TCCCCAGATC CTCTCAAGGT ATGCGAGAGC
2037sPvUbi4 CTAAGCGAAG CGAAGAGGCC TCCCCAGATC CTCTCAAGGT ATGCGAGAGC

             801                                                850
2037sPvUbi3 ATCGATCCCC TTCCGATCTA TATCGCGTGT CCTCCCTGTT CTTGTTCTTC
2037sPvUbi4 ATCGATCCCC TTCCGATCTA TATCGCGTGT CCTCCCTGTT CTTGTTCTTC

             851                                                900
2037sPvUbi3 GTCGATCTAG TTTAGGGTTT GATTTGGTTC TGAATCGAAC CCTTTTCCTG
2037sPvUbi4 GTCGATCTAG TTTAGGGTTT GATTTGGTTC TGAATCGAAC CCTTTTCCTG

             901                                                950
2037sPvUbi3 CTTGCGTTCG ATTTGTACTC GATCCTCGGG TAGAGGTGTG GATCTGCGGG
2037sPvUbi4 CTTGCGTTCG ATTTGTACTC GATCCTCGGG TAGAGGTGTG GATCTGCGGG

             951                                               1000
2037sPvUbi3 GCGTGATGAG GTAGTTTGGT GTAGATTTGT TCTGGGCGTT CGATTTGCCA
2037sPvUbi4 GCGTGATGAG GTAGTTTGGT GTAGATTTGT TCTGGGCGTT CGATTTGCCA

             1001                                              1050
2037sPvUbi3 CTAGGGTTCG GCTGCTGTTG GCATTCCTGA TCGAGCGGCC GGATAGGATT
2037sPvUbi4 CTAGGGTTCG GCTGCTGTTG GCATTCCTGA TCGAGCGGCC GGATAGGATT

             1051                                              1100
2037sPvUbi3 GTTTTTCCCT TTTTATATGT TGGATGCGTG ATGGTTCCTG TGTGTTGGGT
2037sPvUbi4 GTTTTTCCCT TTTTATATGT TGGATGCGTG ATGGTTCCTG TGTGTTGGGT

             1101                                              1150
2037sPvUbi3 TAGATTGCTG GTACGATTCA TCTAGGTGGT GATTTGCAGA GGAACAACTT
2037sPvUbi4 TAGATTGCTG GTACGATTCA TCTAGGTGGT GATTTGCAGA GGAACAACTT

             1151                                              1200
2037sPvUbi3 TGCTGTTGAA TATTGGTAGG TCTATCTAGA TTTATTACTT TTGATTATCG
2037sPvUbi4 TGCTGTTGAA TATTGGTAGG TCTATCTAGA TTTATTACTT TTGATTATCG
```

-continued

```
             1201                                                1250
2037sPvUbi3 CCTGATAAGG ATCACCGATT CGTGTAGAAT AAATTATTTC ATTGTTGGGT
2037sPvUbi4 CCTGATAAGG ATCACCGATT CGTGTAGAAT AAATTATTTC ATTGTTGGGT

             1251                                                1300
2037sPvUbi3 CATGTAGATA TAGCTGCACA ATTTCTTACT TGGCTCCTTA CTGTGTGAAT
2037sPvUbi4 CATGTAGATA TAGCTGCACA ATTTCTTACT TGGCTCCTTA CTGTGTGAAT

             1301                                                1350
2037sPvUbi3 TGTAGAATAA ACTGTGTTAC TCTATGAGTT TTTCTGGATT GCTGGATCCA
2037sPvUbi4 TGTAGAATAA ACTGTGTTAC TCTATGAGTT TTTCTGGATT GCTGGATCCA

             1351                                                1400
2037sPvUbi3 GTTAGGCCAG TGCTGTCAAT TTGTTATGGC TGTTAATGTA ATAATTTTCT
2037sPvUbi4 GTTAGGCCAG TGCTGTCAAT TTGTTATGGC TGTTAATGTA ATAATTTTCT

             1401                                                1450
2037sPvUbi3 GGATTGTTGG CCTGCTTCTC TTCATGTTTA ATCACGTGAT GGTTCATGAT
2037sPvUbi4 GGATTGTTGG CCTGCTTCTC TTCATGTTTA ATCACGTGAT GGTTCATGAT

             1451                                                1500
2037sPvUbi3 GCCTGTTGGG TTAGATTGTT TGTTCAATTC ATCTAGGCAG TGCTGTGCAG
2037sPvUbi4 GCCTGTTGGG TTAGATTGTT TGTTCAATTC ATCTAGGCAG TGCTGTGCAG

             1501                                                1550
2037sPvUbi3 AGTACAACTC GATTGATGTT TAATCTTGGT AGCTTCATCT AGATTTGTAC
2037sPvUbi4 AGTACAACTC GATTGATGTT TAATCTTGGT AGCTTCATCT AGATTTGTAC

             1551                                                1600
2037sPvUbi3 AAATTTTGGT CACCTGATGA TGATCACCGA TTGTTGTGGA ATTATTTCTT
2037sPvUbi4 AAATTTTGGT CACCTGATGA TGATCACCGA TTGTTGTGGA ATTATTTCTT

             1601                                                1650
2037sPvUbi3 AACTGGTTCG TTGTTAGTCA CCACCTTACT TGTAGAATAA CCTGTGGTAC
2037sPvUbi4 AACTGGTTCG TTGTTAGTCA CCACCTTACT TGTAGAATAA CCTGTGGTAC

             1651                                                1700
2037sPvUbi3 TGCTTTTCTG TTCTGTTTTA GGCCACATCA TATGATTGTC AAAAATTTAC
2037sPvUbi4 TGCTTTTCTG TTCTGTTTTA GGCCACATCA TATGATTGTC AAAAATTTAC

             1701                                                1750
2037sPvUbi3 ATGGTAGTTT AATGATAAAA TTAGTTCAGC TTACTTCAGT TTGATTTGCT
2037sPvUbi4 ATGGTAGTTT AATGATAAAA TTAGTTCAGC TTACTTCAGT TTGATTTGCT

             1751                                                1800
2037sPvUbi3 TCATATTTTG TTTTCTGTTC TATTAATGAT ACTTCATGAA ATGTTTGTTT
2037sPvUbi4 TCATATTTTG TTTTCTGTTC TATTAATGAT ACTTCATGAA ATGTTTGTTT

             1801                                                1850
2037sPvUbi3 TTTCTCTGTT CAGATTTGAC ATGTTTCAGT ATCATAATAA TAATATTCTG
2037sPvUbi4 TTTCTCTGTT CAGATTTGAC ATGTTTCAGT ATCATAATAA TAATATTCTG

             1851                                                1900
2037sPvUbi3 TATCCTTTAT AGTTTGTTGG CATGATTTGC TTTGAATTTA GTTAGCCTAT
2037sPvUbi4 TATCCTTTAT AGTTTGTTGG CATGATTTGC TTTGAATTTA GTTAGCCTAT

             1901                                                1950
2037sPvUbi3 TCTGTTAATA TAGGATGATA AGCTGTGAGG CGTTCATTCT CTTCAGTCCA
2037sPvUbi4 TCTGTTAATA TAGGATGATA AGCTGTGAGG CGTTCATTCT CTTCAGTCCA

             1951                                                2000
2037sPvUbi3 GAGTTATCAT TTTCAGTGTT TTAATGTTGT TTATCAAGCT GGATGTATAT
2037sPvUbi4 GAGTTATCAT TTTCAGTGTT TTAATGTTGT TTATCAAGCT GGATGTATAT

             2001                                 2037
2037sPvUbi3 GGTGGTTTAA CTCTTTTCTG TTTCTTACTG TTTGCAG (SEQ ID NO: 4)
2037sPvUbi4 GGTGGTTTAA CTCTTTTCTG TTTCTTACTG TTTGCAG (SEQ ID NO: 5)
```

The highly homologous 230 bp 5' nucleotide sequences of PvUbi3 and PvUbi4 are aligned below. (shown as a gray box in the diagrams of FIG. 1 and as bold and italicized nucleotides in the annotated versions of PvUbi3 and PvUbi4, above). The upstream 230 bp sequence in the isolated PvUbi3 fragment has high degree of sequence identity (97%) to the 230 bp sequence located upstream of the unique 653 bp sequence of the PvUbi4. The identified nucleotide differences in homologous upstream 230 bp sequences of PvUbi3 and PvUbi4 are indicated by bold and italicized at positions 62, 78, 98, 169, 213, 228 and 230.

```
MSF: 230 Type: N Check: 3896 ..
Name: 5'PvUbi3 Len: 230 Check: 6702 Weight: 0
Name: 5'PvUbi4 Len: 230 Check: 7194 Weight: 0
//
        1                                                50
5'PvUbi3 ACGACCGGAG GAGAGATTCT TTGCTTTGCT TGTGGCTGCG AAGGAGGAGG
5'PvUbi4 ACGACCGGAG GAGAGATTCT TTGCTTTGCT TGTGGCTGCG AAGGAGGAGG

        51                                              100
5'PvUbi3 AGAAACCACG CCGCGGATAA GAAGGAACC GCCTTTGCAA AACCAGAACA
5'PvUbi4 AGAAACCACG CAGCGGATAA GAAGGAAGCC GCCTTTGCAA AACCAGAGCA

        101                                             150
5'PvUbi3 TCTTTTCTGA TGAAGAAATC CGCGTTGCCT CCTGTGAGAA GAATGCGACC
5'PvUbi4 TCTTTTCTGA TGAAGAAATC CGCGTTGCCT CCTGTGAGAA GAATGCGACC

        151                                             200
5'PvUbi3 CTTTTTTTAT ACTCTATTAT ATCTTTATTA TTATTGTCAA TTTGTCATGT
5'PvUbi4 CTTTTTTTAT ACTCTATTCT ATCTTTATTA TTATTGTCAA TTTGTCATGT

        201                            230
5'PvUbi3 CACTGAGAAA TGACCCTGAT ACGAACGGTC (SEQ ID NO: 6)
5'PvUbi4 CACTGAGAAA TGGCCCTGAT ACGAACGCTA (SEQ ID NO: 7)
```

The unique 653 bp sequence identified in the upstream region of PvUbi4 is shown below. The 653 bp sequence appears as an insertion into the sequence of PvUbi3 that is flanked by the highly conserved 2037 bp downstream and less conserved 230 bp upstream sequences that appear in both PvUbi3 and PvUbi4.

```
>unique 653 bp sequence in PvUbi4 upstream region
                                       (SEQ ID NO: 8)
AGATCCAATCATACACCTTTTATTTATTTATACATAAGTACGT

AAATAAGATGAAAATAAAAAAAATGTCATGGACGAAAACAACGTCCACAA

GGACGGCAAAGATGGAGGACCGCAGGAGCACAACGGATGGATGTTCTTT

TTTTGTTATCAAACAACGGATGGATGTTTCCGAGCAGGTGCAGCGTCTCC

TCCGTTTACTCGCCGTGCACATCACGGCGTCCAAACGGGCGTTTGCCGGC

GAGGACACGGTAGATTTTGCCGACATGGTAGATTTTATCAAGATATTCCG

GTCGAGTTTGGAGTACTAGCTCCATCATGTATAACCACCAATGATTGAGT

GGTGACCATATCATAATCGTTGGTCAGCTTTCCTTCCATTACTTTTTAAT

TCAGTAATAATAATCCCTAAAGCCTAATCAAGTAAATTCAACTTCCGAAT

TCAATAGGGATCATCAGGGCACGACCTGATTGTAAAGACATACAATAGCT

TTCAAACAACATTTTCACTTATGGTAAAATCTTAATTAAGGTCTTAATAT

TATAATTATTTTTTTCACTGCCGTGAGGGAATGGAGATTTCAGAAAGGGA
```

-continued

```
CTTTTTGGTATCATCATTGTATATGATCCACGGTTTTTAGTTAGGGCGAC

TTTAATTTCTT
```

Example 3: Nucleotide Sequence Alignments Between PvUbi4, PvUbi1, and PvUbi2 Switchgrass Promoters In order to demonstrate the uniqueness of the isolated PvUbi4 promoter, its nucleotide sequence including the first intron was compared to the known switchgrass promoters PvUbi1 (Gene Bank Accession HM209467) and PvUbi2 (Gene Bank Accession HM209468), which also contain their corresponding first intron sequences. The PvUbi1 and PvUbi2 promoter sequences have been isolated and disclosed by Mann. See Mann et al. 2011 BMC Biotechnol. 11, 74 and U.S. patent application Ser. No. 12/797,248. The nucleotide sequence alignments between the PvUbi4 and PvUbi1 or PvUbi2 promoters were performed using AlignX function of the VectorNTI software (Invitrogen, Carlsbad, USA). The aligned sequences are presented in the PileUp format below. In the alignments, the intron sequences are italicized. The nucleotide sequence identity between PvUbi4 and PvUbi1 promoters is 62.4%, while it is 65.2% between PvUbi4 and PvUbi2 promoters. These levels of sequence similarities confirm that the PvUbi4 switchgrass promoter significantly diverged in its nucleotide sequence composition from the already known sequences of PvUbi1 and PvUbi2 switchgrass promoters. Furthermore, the sequence length of the predicted first intron in PvUbi4 promoter is 1249 bp, which differs from the length of the reported first introns in both PvUbi1 and PvUbi2 promoters (1291 bp and 1072 bp accordingly).

```
PileUp
MSF: 3704 Type: N Check: 2556 ..
Name: PvUbi1P Len: 3704 Check: 2362 Weight: 0
Name: PvUbi4P Len: 3704 Check: 194 Weight: 0
//
         1                                                  50
PvUbi1P  .......... .......... .......... .......... ..........
PvUbi4P  CTGGCCTAAC CTAAAATCAG TTCTTGCTGC TGGGTGGTTG GGTACATTAT

         51                                                100
PvUbi1P  .......... .......... .......... .......... ..........
PvUbi4P  CTGACAACTA GGATCCACAT CAAAAAAAAA AAGACTACTA CGATCATCAT

         101                                               150
PvUbi1P  .......... .......... .......... .......... ..........
PvUbi4P  GGAGTCCTTC GCAACGGCAG CTGGGCAGAC ACCTTCAGAG TTCAGAGTCC

         151                                               200
PvUbi1P  .......... .......... .......... .......... ..........
PvUbi4P  ACGCACACAC TAATAAAGGG GTCCATTTGC CTGCTTCGTT CCGGCTGAAA

         201                                               250
PvUbi1P  .......... .......... .......... .......... ..........
PvUbi4P  TTTTTACGAA CCGGTCATCC GTAACCACGA TAATCGATAT GGACCAAGAG

         251                                               300
PvUbi1P  .......... .......... .......... .......... ..........
PvUbi4P  AGACAAAAAT AATCTCGGAA CATCGTTAGC AAGTCCAAAT GGAACGCAAC

         301                                               350
PvUbi1P  .......... .......... .......... .......... ..........
PvUbi4P  CAGAGACATG TTGTTTGCCT TCATCCTTCA TACACAACCC ACCTGGCCAC

         351                                               400
PvUbi1P  .......... .......... .......... .......... ..........
PvUbi4P  CTCCATGTCC ATGATTTTTT TTCCCCAATC GACCTTGGAC AACCACCAAG

         401                                               450
PvUbi1P  .......... .......... .......... .......... ..........
PvUbi4P  GAATTCCTTG TCAGTTGTTA GCATGGATGA CAGTTCAAGC CGGGCAGCTG

         451                                               500
PvUbi1P  .......... .......... .......... .......... ..........
PvUbi4P  GCGTGTCCGT TCAGACATCA TCGTCCTGCC AGAACTCCAT CCACGCGAGC

         501                                               550
PvUbi1P  .......... .......... .......... .......... ..........
PvUbi4P  CCGCTGAACC AAGGGAGCCT TTGCGTTTGC CCTTTGGCCA CGGCATCGTT

         551                                               600
PvUbi1P  .......... .......... .......... .......... ..........
PvUbi4P  CAGCTCATTC CCTCAACAGA TCAACTGAAC CCAGCGCGCG AAGTTAGCAC

         601                                               650
PvUbi1P  .......... .......... .......... .......... ..........
PvUbi4P  CGGAGCGCAA TGCGAGCCGT GCCCGTGTCT TCCTCCCAGC TCCTCCAGCG

         651                                               700
PvUbi1P  .......... .......... .......... .......... ..........
PvUbi4P  CAAGCAAGAC GACGACCGGA GGAGAGATTC TTTGCTTTGC TTGTGGCTGC

         701                                               750
PvUbi1P  .......... .......... .......... .......... ..........
PvUbi4P  GAAGGAGGAG GAGAAACCAC GCAGCGGATA AGAAGGAAGC CGCCTTTGCA

         751                                               800
PvUbi1P  .......... .......... .......... .......... ..........
PvUbi4P  AAACCAGAGC ATCTTTTCTG ATGAAGAAAT CCGCGTTGCC TCCTGTGAGA

         801                                               850
PvUbi1P  .......... .......... .......... .......... ..........
PvUbi4P  AGAATGCGAC CCTTTTTTTA TACTCTATTC TATCTTTATT ATTATTGTCA

         851                                               900
PvUbi1P  .......... .......... .......... .......... ..........
PvUbi4P  ATTTGTCATG TCACTGAGAA ATGGCCCTGA TACGAACGCT AAGATCCAAT

         901                                               950
PvUbi1P  .......... .......... .......... .......... ..........
PvUbi4P  CATACACCTT TTATTTATTT ATACATAAGT ACGTAAATAA GATGAAAATA
```

-continued

```
         951                                                1000
PvUbi1P  .......... .......... .......... .......... ..........
PvUbi4P  AAAAAAATGT CATGGACGAA AACAACGTCC ACAAGGACGG CAAAGATGGA

         1001                                               1050
PvUbi1P  .......... .......... .......... .......... ..........
PvUbi4P  GGACCGCAGG AGCACAACGG ATGGATGTTC TTTTTTTGTT ATCAAACAAC

         1051                                               1100
PvUbi1P  .......... .......... .......... .......... ..........
PvUbi4P  GGATGGATGT TTCCGAGCAG GTGCAGCGTC TCCTCCGTTT ACTCGCCGTG

         1101                                               1150
PvUbi1P  .......... .......... .......... .......... ..........
PvUbi4P  CACATCACGG CGTCCAAACG GGCGTTTGCC GGCGAGGACA CGGTAGATTT

         1151                                               1200
PvUbi1P  .......... .......... .......... .......... ..........
PvUbi4P  TGCCGACATG GTAGATTTTA TCAAGATATT CCGGTCGAGT TTGGAGTACT

         1201                                               1250
PvUbi1P  .......... .......... .......... .......... ..........
PvUbi4P  AGCTCCATCA TGTATAACCA CCAATGATTG AGTGGTGACC ATATCATAAT

         1251                                               1300
PvUbi1P  .......... .......... .......... .......... ..........
PvUbi4P  CGTTGGTCAG CTTTCCTTCC ATTACTTTTT AATTCAGTAA TAATAATCCC

         1301                                               1350
PvUbi1P  .......... .......... .......... .......... ..........
PvUbi4P  TAAAGCCTAA TCAAGTAAAT TCAACTTCCG AATTCAATAG GGATCATCAG

         1351                                               1400
PvUbi1P  .......... .......... .......... .......... ..........
PvUbi4P  GGCACGACCT GATTGTAAAG ACATACAATA GCTTTCAAAC AACATTTTCA

         1401                                               1450
PvUbi1P  .......... .......... .......... .......... ..........
PvUbi4P  CTTATGGTAA AATCTTAATT AAGGTCTTAA TATTATAATT ATTTTTTTCA

         1451                                               1500
PvUbi1P  .......... .......... .......... .......... ..........
PvUbi4P  CTGCCGTGAG GGAATGGAGA TTTCAGAAAG GGACTTTTTG GTATCATCAT

         1501                                               1550
PvUbi1P  .......... .......... .......... .......... ..........
PvUbi4P  TGTATATGAT CCACGGTTTT TAGTTAGGGC GACTTTAATT TCTTATTTTT

         1551                                               1600
PvUbi1P  .......... .......... .......... .......... ..........
PvUbi4P  GATAATTCTT GTTTCTATTG TCTTGACGAT TCTAATGCCA TGTCCTTTTG

         1601                                               1650
PvUbi1P  .......... .......... ...CCACTGG AGAGGGGCAC ACACGTCAGT
PvUbi4P  TCTTGACAGC TCTAGTGCCA TGTCTATTTG TCATGTTATC ATTTGTTCTT

         1651                                               1700
PvUbi1P  GTTTGGTTTC CACTAGCACG AGTAGCGCAA TCAGAAAATT TTCAATG..C
PvUbi4P  TTTA..TTTC AAGGAAAATT ATTACATCAA AAAATTGATT TTCGAAGTTC

         1701                                               1750
PvUbi1P  ATGAAGTACT AAACGA..AG TTTATTTAGA AATTTTTTTA AGAAATGAGT
PvUbi4P  ACGGTCATCT TCACCATCAC TCTCTATCGC ATTGGTGGCG AGAAGCATAT

         1751                                               1800
PvUbi1P  GTAATTTTTT GCGAC..GAA TTTAATGACA ATAATTAATC GATGATTGCC
PvUbi4P  CTAGTGGTTT CATTCTGGTA AGCCTCGCTC AAATGAAATT TGTAATAAAA

         1801                                               1850
PvUbi1P  TACAGTAATG CTACAGTAAC C....AACCT CTAATCATGC GTCGAATGCG
PvUbi4P  TACTATATTT CTTTATCAAG GTTATAAGAT ATGGAGAGAA ATGGTCTGCT

         1851                                               1900
PvUbi1P  TCATTAGATT CGTCT..... .....CGCAA AATAGCA... .CAAGAATTA
PvUbi4P  TCATAA.ATT TGACTTACCT AGAGCCTTTA AAAAGGAATA CCATGTAATC

         1901                                               1950
PvUbi1P  TGAAATTAAT TTTACAAACT ATTTTT..AT TTAATACTAA TAATTAACTG
PvUbi4P  TAAACTCTAT AACATAAAGA GCTTTGCGCT TTTAAAAATA TGCTAACCTA
```

-continued

```
         1951                                              2000
PvUbi1P  TCAAAGT... TTGTGCTACT CGCAAGAGTA GCGCGAACCA AACACGGCCT
PvUbi4P  TATAAATCGC TTTTGCTAGA GACAGGTCAT GTATGATTGA AGCGTCACCA

         2001                                              2050
PvUbi1P  GGAGGAGCAC GGTAACG..G CGTCGACAAA CTAACGGCCA CCACCCGC..
PvUbi4P  TAACGC...C GTTAATCTTC CGTCCAGCCA TTAACGGCCA CCTACCGCAG

         2051                                              2100
PvUbi1P  CAACGCAAAG GAGACGGATG AGAGTTGACT TCTTGACGGT TCTCCACCCC
PvUbi4P  GAAACAAACG GCGTC..ACC ATCCTCGATA TCTCCGCGGC GGCCGCTGGC

         2101                                              2150
PvUbi1P  TCTGTCTCTC TGTCACTGGG CCCTGGGTCC CCCTCTCGAA AGTTCCTCTG
PvUbi4P  TTTTT.TCGG AGAAATTGCG CGGTGGGGAC GGAGTCCACG AGAGCCTCTC

         2151                                              2200
PvUbi1P  GCCGAAATTG CGCGGCGGAG ACGAGGCGGG CGGAACCGTC ACGGCAGAGG
PvUbi4P  GCCGC...TG GGCCCCACAA TCAATG...G CGTGACC.TC ACGG..GACG

         2201                                              2250
PvUbi1P  ATTCCTTCCC CACCCTGCCT GGCCCGGCCA TATATAAACA GCCACCGCCC
PvUbi4P  GCTCCCTCCC T...CTACCC TCCCC..CCG TGTATAAATA GCACCCCTCC

         2251                                              2300
PvUbi1P  CTCCCCG.TT CCCCATCGCG TCTC...GTC TCGTGTTGTT CCCAGAACAC
PvUbi4P  CTCGCCTCTT CCGCATCCAG TATTCCAGTC CCCAATCCGT CGAGAAATTC

         2301                                              2350
PvUbi1P  AACCAAA..A TCCAAATCCT CCTCCTCCTC CCGAGCCTCG TCGATCCCTC
PvUbi4P  TCGCGAGCGA TCGAAATCTA AGCGAAGCGA AGAGGCCTC. .....CCCAG

         2351                                              2400
PvUbi1P  ACCCGCTTCA AGGTACG.GC GATCCTCCTC TCCCTTCTCC CCTCGATCGA
PvUbi4P  ATCCTCT.CA AGGTATGCGA GAGCATCGAT CCCCTTC... ...CGATCTA

         2401                                              2450
PvUbi1P  TTATGCGTGT ..TCCGTTTC CGTTTCCG.. ATCGAGCGAA TCGATGGTTA
PvUbi4P  TATCGCGTGT CCTCCCTGTT CTTGTTCTTC GTCGATCTAG TTTAGGGTTT

         2451                                              2500
PvUbi1P  GGACCCATGG GGGACCCATG GGGTGTCGTG TGGTGGTCTG GTTTGATCCG
PvUbi4P  GATTTGGTTC TGAATCGAAC CCTTTTCCTG CTTGCGTTCG ATTTG.TACT

         2501                                              2550
PvUbi1P  CGATATTTCT CCGTTCGTAG TGTAGATCTG ATCGAATCCC TGGTGAAATC
PvUbi4P  CGATC...CT CGGGTAGAGG TGTGGATCTG CGGGG...CG TGATGAGGTA

         2551                                              2600
PvUbi1P  GTTGATCGTG CTATTCGTGT GAGGGTTCT. ........TA GGTTTGGAGT
PvUbi4P  GTTTGGTGTA GATTTGTTCT GGGCGTTCGA TTTGCCACTA GGGTTCGGCT

         2601                                              2650
PvUbi1P  TGTGGAGGTA GTTCTGATCG GTTTG..... TAGGTGAGAT TTTCCCCATG
PvUbi4P  GCTGTTGGCA TTCCTGATCG AGCGGCCGGA TAGGATTGTT TTTCCCTTTT

         2651                                              2700
PvUbi1P  ...ATTTTGC TTG...GCTC GTTTGTCTTG GTTAGATTAG ATCTGCCCGC
PvUbi4P  TATATGTTGG ATGCGTGATG GTTCCTGTGT GTTGGGTTAG AT.TGC....

         2701                                              2750
PvUbi1P  ATTTTGTTCG ATATTTCT.G ATGCAGATAT G...ATGAAT AATTTCGTCC
PvUbi4P  ...TGGTACG ATTCATCTAG GTGGTGATTT GCAGAGGAAC AACTTTGCTG

         2751                                              2800
PvUbi1P  TTGTATCCCG CGTCCGTATG TGTATTAAGT TTGCAGGTGC TAGTTAGGTT
PvUbi4P  TTGAATATTG .....GTAGG TCTATCTAGA TT.....TAT TACTTTTGAT

         2801                                              2850
PvUbi1P  TTTCCTACTG ATTTGTCTTA TCCATTCTGT TTAGCTTGCA AGGTTTGGTA
PvUbi4P  TATCGC.CTG ATAAGGATCA CCGATTC.GT GTAGAATAAA TTATTTCAT.

         2851                                              2900
PvUbi1P  ATGGTCCGGC ATGTTTGTCT CTATAGATTA GAGTAGAATA AGATTATCTC
PvUbi4P  .TGTTGGGTC ATGT...... ....AGAT.A TAGCTGCACA A...TTTCTT

         2901                                              2950
PvUbi1P  AACAAGCTGT TGGCT.TATC AATTTTGGAT CTGCATGTGT TTCGCATCTA
PvUbi4P  ACTTGGCTCC TTACTGTGTG AATTGTAGAA TAAACTGTGT TAC...TCTA
```

-continued

```
        2951                                            3000
PvUbi1P TATCTTTGCA ATTAAGATGG TAGATGGACA TATGCTCCTG TTGAGTTGAT
PvUbi4P TGAGTTTTTC TGGAT..TGC TGGATCCAGT TAGGCCAGTG CTGTCAATTT

        3001                                            3050
PvUbi1P GTTGTACCTT TTACCTGAG. .GTCTGAGGA ACATGCATCC TCCTGCTACT
PvUbi4P GTTATGGCTG TTAATGTAAT AATTTTCTGG ATTGTTGGCC TGCTTCT.CT

        3051                                            3100
PvUbi1P TTGTGCTTAT ACAGATCATC AAGATTATGC AGCTAATATT CGATCAGTTT
PvUbi4P TCATGTTTAA TCACGTGATG ..GTTCATGA TGCC..TGTT GGGTTAGATT

        3101                                            3150
PvUbi1P CTAGTATCTA CATGGTAAAC TTGCA.TGCA CTTGCTACTT ATTTTTGATA
PvUbi4P ...GTTTGTT CAATTCATCT AGGCAGTGCT GTGCAGAGTA CAACTCGATT

        3151                                            3200
PvUbi1P TACTTGGATG ATAACATATG CTGCTGGTTG ATTCCTACCT ACATGATGAA
PvUbi4P GA..TGTTTA ATCTTGGTAG CTTCATCTAG ATTTGTAC.. AAATTTTGGT

        3201                                            3250
PvUbi1P CATTTTACAG GCCATTAGTG TCTGTCTGTA TGTGTTGTTC CTGTTTGCTT
PvUbi4P CACCTGAT.G ATGATCACCG ATTGT.TGTG GAATTATTTC TTAACTGGTT

        3251                                            3300
PvUbi1P CAGTCTATTT CTGTTTCATT CCTAGTTTAT TGGTTCTCTG CTAGATACTT
PvUbi4P CGTTGTTAGT CACCACC.TT ACTTGTAGAA TAAC.CTGTG GTACTGCTTT

        3301                                            3350
PvUbi1P ACCCTGCTGG GCTTAGTTAT CATCTTAT.. CTCGAATGCA TTTTCATGTT
PvUbi4P TCTGTTCTGT T.TTAGGCCA CATCATATGA TTGTCAAAAA TTTACATGGT

        3351                                            3400
PvUbi1P TATAGATGAA T.ATACACTC AGATAGGTGT AGATGTATGC TACTGTTTCT
PvUbi4P ...AGTTTAA TGATAAAATT AGTTCAGCTT ACTTCAGTTT GATTTGCTTC

        3401                                            3450
PvUbi1P CTACGTTGCT GTAGGTTTTA CCTGTGGCAA CTGCAT...A CTCCTGTTGC
PvUbi4P ATATTTTGTT TTCTGTTCTA TTAATGATA. CTTCATGAAA TGTTTGTTTT

        3451                                            3500
PvUbi1P TTCGCT.... AGATATGTAT GTGCTTATAT AGATTAAGAT ATGTGTGATG
PvUbi4P TTCTCTGTTC AGATTTG.AC ATGTTTCAGT ATCATAATAA TAATATTCTG

        3501                                            3550
PvUbi1P GTTCTTTAGT ATATCTGATG ATCATGTATG CTCTTTTAAC TTC..TTGCT
PvUbi4P TATCCTT..T ATAGTTTGTT GGCATG.ATT TGCTTTGAAT TTAGTTAGCC

        3551                                            3600
PvUbi1P ACACTTGGTA ACAT..GCTG TGATGCTGTT TG...TTGAT TCTGTAGCAC
PvUbi4P TATTCTGTTA ATATAGGATG ATAAGCTGTG AGGCGTTCAT TCTCTT.CAG

        3601                                            3650
PvUbi1P TACCAATGAT GACCTTATCT CTCTTTGTAT ATGATGTTTC TGTTTGTTTG
PvUbi4P T.CCAGAGTT ATCATTTTCA GTGTTT.TA. ATGTTGTTTA TC........

        3651                                            3700
PvUbi1P AGGCTTG.TG TTACTGCTAG TTACTTACCC TGTTGCCTGG CTAATCTTCT
PvUbi4P AAGCTGGATG TATATGGTGG TT..TAACTC TTTTCTGTTT CTTACTGTTT

        3701
PvUbi1P GCAG (SEQ ID NO: 19)
PvUbi4P GCAG (SEQ ID NO: 2)

PileUp
MSF: 3616 Type: N Check: 2736 ..
Name: PvUbi2P Len: 3616 Check: 5921 Weight: 0
Name: PvUbi4P Len: 3616 Check: 6815 Weight: 0
//
        1                                               50
PvUbi2P .......... .......... .......... .......... ..........
PvUbi4P CTGGCCTAAC CTAAAATCAG TTCTTGCTGC TGGGTGGTTG GGTACATTAT

        51                                              100
PvUbi2P .......... .......... .......... .......... ..........
PvUbi4P CTGACAACTA GGATCCACAT CAAAAAAAAA AAGACTACTA CGATCATCAT

        101                                             150
PvUbi2P .......... .......... .......... .......... ..........
PvUbi4P GGAGTCCTTC GCAACGGCAG CTGGGCAGAC ACCTTCAGAG TTCAGAGTCC
```

-continued

```
         151                                                200
PvUbi2P  .......... .......... .......... .......... ..........
PvUbi4P  ACGCACACAC TAATAAAGGG GTCCATTTGC CTGCTTCGTT CCGGCTGAAA

         201                                                250
PvUbi2P  .......... .......... .......... .......... ..........
PvUbi4P  TTTTTACGAA CCGGTCATCC GTAACCACGA TAATCGATAT GGACCAAGAG

         251                                                300
PvUbi2P  .......... .......... .......... .......... ..........
PvUbi4P  AGACAAAAAT AATCTCGGAA CATCGTTAGC AAGTCCAAAT GGAACGCAAC

         301                                                350
PvUbi2P  .......... .......... .......... .......... ..........
PvUbi4P  CAGAGACATG TTGTTTGCCT TCATCCTTCA TACACAACCC ACCTGGCCAC

         351                                                400
PvUbi2P  .......... .......... .......... .......... ..........
PvUbi4P  CTCCATGTCC ATGATTTTTT TTCCCCAATC GACCTTGGAC AACCACCAAG

         401                                                450
PvUbi2P  .......... .......... .......... .......... ..........
PvUbi4P  GAATTCCTTG TCAGTTGTTA GCATGGATGA CAGTTCAAGC CGGGCAGCTG

         451                                                500
PvUbi2P  .......... .......... .......... .......... ..........
PvUbi4P  GCGTGTCCGT TCAGACATCA TCGTCCTGCC AGAACTCCAT CCACGCGAGC

         501                                                550
PvUbi2P  .......... .......... .......... .......... ..........
PvUbi4P  CCGCTGAACC AAGGGAGCCT TTGCGTTTGC CCTTTGGCCA CGGCATCGTT

         551                                                600
PvUbi2P  .......... .......... .......... .......... ..........
PvUbi4P  CAGCTCATTC CCTCAACAGA TCAACTGAAC CCAGCGCGCG AAGTTAGCAC

         601                                                650
PvUbi2P  .......... .......... .......... .......... ..........
PvUbi4P  CGGAGCGCAA TGCGAGCCGT GCCCGTGTCT TCCTCCCAGC TCCTCCAGCG

         651                                                700
PvUbi2P  .......... .......... .......... .......... ..........
PvUbi4P  CAAGCAAGAC GACGACCGGA GGAGAGATTC TTTGCTTTGC TTGTGGCTGC

         701                                                750
PvUbi2P  .......... .......... .......... .......... ..........
PvUbi4P  GAAGGAGGAG GAGAAACCAC GCAGCGGATA AGAAGGAAGC CGCCTTTGCA

         751                                                800
PvUbi2P  .......... .......... .......... .......... ..........
PvUbi4P  AAACCAGAGC ATCTTTTCTG ATGAAGAAAT CCGCGTTGCC TCCTGTGAGA

         801                                                850
PvUbi2P  .......... .......... .......... .......... ..........
PvUbi4P  AGAATGCGAC CCTTTTTTTA TACTCTATTC TATCTTTATT ATTATTGTCA

         851                                                900
PvUbi2P  .......... .......... .......... .......... ..........
PvUbi4P  ATTTGTCATG TCACTGAGAA ATGGCCCTGA TACGAACGCT AAGATCCAAT

         901                                                950
PvUbi2P  .......... .......... .......... .......... ..........
PvUbi4P  CATACACCTT TTATTTATTT ATACATAAGT ACGTAAATAA GATGAAAATA

         951                                               1000
PvUbi2P  .......... .......... .......... .......... ..........
PvUbi4P  AAAAAAATGT CATGGACGAA AACAACGTCC ACAAGGACGG CAAAGATGGA

         1001                                              1050
PvUbi2P  .......... .......... .......... .......... ..........
PvUbi4P  GGACCGCAGG AGCACAACGG ATGGATGTTC TTTTTTTGTT ATCAAACAAC

         1051                                              1100
PvUbi2P  .......... .......... .......... .......... ..........
PvUbi4P  GGATGGATGT TTCCGAGCAG GTGCAGCGTC TCCTCCGTTT ACTCGCCGTG

         1101                                              1150
PvUbi2P  .......... .......... .......... .......... ..........
PvUbi4P  CACATCACGG CGTCCAAACG GGCGTTTGCC GGCGAGGACA CGGTAGATTT
```

-continued

```
         1151                                               1200
PvUbi2P  .......... .......... .......... .......... ..........
PvUbi4P  TGCCGACATG GTAGATTTTA TCAAGATATT CCGGTCGAGT TTGGAGTACT

         1201                                               1250
PvUbi2P  .......... .......... .......... .......... ..........
PvUbi4P  AGCTCCATCA TGTATAACCA CCAATGATTG AGTGGTGACC ATATCATAAT

         1251                                               1300
PvUbi2P  .......... .......... .......... .......... ..........
PvUbi4P  CGTTGGTCAG CTTTCCTTCC ATTACTTTTT AATTCAGTAA TAATAATCCC

         1301                                               1350
PvUbi2P  .......... .......... .......... .......... ..........
PvUbi4P  TAAAGCCTAA TCAAGTAAAT TCAACTTCCG AATTCAATAG GGATCATCAG

         1351                                               1400
PvUbi2P  .......... .......... .......... .......... ..........
PvUbi4P  GGCACGACCT GATTGTAAAG ACATACAATA GCTTTCAAAC AACATTTTCA

         1401                                               1450
PvUbi2P  .......... .......... .......... .......... ..........
PvUbi4P  CTTATGGTAA AATCTTAATT AAGGTCTTAA TATTATAATT ATTTTTTTCA

         1451                                               1500
PvUbi2P  .......... .......... .......... .......... ..........
PvUbi4P  CTGCCGTGAG GGAATGGAGA TTTCAGAAAG GGACTTTTTG GTATCATCAT

         1501                                               1550
PvUbi2P  .......... ....GAAGCC AACTAAACAA GACCATAACC ATGGTGACAT
PvUbi4P  TGTATATGAT CCACGGTTTT TAGTTAGGGC GACTTTAAT. .TTCTTATTT

         1551                                               1600
PvUbi2P  TTGACA.TAG TTGTTTACTA CTTGCTTGAG CCCCACCCTT GCTTATCGGT
PvUbi4P  TTGATAATTC TTGTTT.CTA TTGTCTTGAC GATTCTAATG CCATGTCCTT

         1601                                               1650
PvUbi2P  TGAACATTAC AAGATACACT GCGGGTGGCC TAAGGCA... CACCGTCCGA
PvUbi4P  TTGTCTTGAC A.GCTCTAGT GCCATGTCTA TTTGTCATGT TATCATTTGT

         1651                                               1700
PvUbi2P  AACCGGCAAA CCAAGCCTGA TCGCCGAAAT CCAAAA..TC ACTACCGGCA
PvUbi4P  TCTTTTTATT TCAAGGAAAA TTATT.ACAT CAAAAAATTG ATTTTCGAAG

         1701                                               1750
PvUbi2P  ATCTCTAAAG TTTATTTCAT CCTTATATGA CG.AGGAAAG AAAAGAAGAG
PvUbi4P  TTCACGGTCA TCTTCACCAT CACTCTCTAT CGCATTGGTG GCGAGAAGC.

         1751                                               1800
PvUbi2P  AGAAATAATA TCTTAACTTC TAAATCAGTC GCG.TCAACT TTCTCGGCTA
PvUbi4P  ATATCTAGTG GTTTCA.TTC TGG.TAAGCC TCGCTCAAAT GAAATTTGTA

         1801                                               1850
PvUbi2P  AGAAAGTGAG CACTATCATT TCGGAGACCA TGTCATGAGT GCCGACTTGC
PvUbi4P  ATAAAATACT ATATTTCTTT ATCAAGGTTA TAAGATATGG AGAGAAATGG

         1851                                               1900
PvUbi2P  CATATCTTAT TATATT..CT TATTTA.... .TTTAATTAT .AATCCCATT
PvUbi4P  TCTGCTTCAT AAATTTGACT TACCTAGAGC CTTTAAAAAG GAATACCAT.

         1901                                               1950
PvUbi2P  GCAAT...AC GTCTATTCTA TCATGGCCT. ...GCCACTA ACGCTCCGTC
PvUbi4P  GTAATCTAAA CTCTATAACA TAAAGAGCTT TGCGCTTTTA AAAATATG.C

         1951                                               2000
PvUbi2P  TAACGTCGTT AAGCCATTGT CATAAGCGGC TGCTCAAAAC TCTTCCCGGT
PvUbi4P  TAACCTATAT AAATCGCTTT TGCTAGAGAC AGGTCATGTA TGATTGAAGC

         2001                                               2050
PvUbi2P  GGAGGC...G AGGCGTTAAC G..GCGTCTA CAAATCTAAC GGCCACCAAC
PvUbi4P  GTCACCATAA CGCCGTTAAT CTTCCGTCCA GCCAT.TAAC GGCCACCTAC

         2051                                               2100
PvUbi2P  C..AT....C CAGCCGCCTC .......TCG AAAGCTCCGC TCCGATCGCG
PvUbi4P  CGCAGGAAAC AAACGGCGTC ACCATCCTCG ATATCTCCGC GGCGGCCGCT

         2101                                               2150
PvUbi2P  GAAATTGCGT GGCGGAGACG AGCGGGCTCC TCTCACACGG CCCGGAACCG
PvUbi4P  GGCTTTTTTC GGAGAAATTG CGCGGTGGGG ACGGAGTC.. CACGAGAGCC
```

-continued

```
         2151                                               2200
PvUbi2P  TCACGGCAC. GGGTGGGGGA TTCCTTCCCC AACCCTCCCC ..ACCTCTCC
PvUbi4P  TCTCGCCGCT GGGCCCCACA ATCAATGGCG TGACCTCACG GGACGGCTCC

         2201                                               2250
PvUbi2P  TCCCCCCGTC GCAGCCC... ...ATAAATA CAGGGCCCTC CGCGCCTCTT
PvUbi4P  CTCCCTCTAC CCTCCCCCCG TGTATAAATA GCACCCCTCC CTCGCCTCTT

         2251                                               2300
PvUbi2P  CC.CA..CAA TCTCACATCG TCTCATCGTT CGGAGCGCAC AACCCCCGGG
PvUbi4P  CCGCATCCAG TATTCCAGTC CCCAATCCGT CG.AGAAATT CTCGCGAGCG

         2301                                               2350
PvUbi2P  TTCCAAATCC AA........ ATTGCTCTTC TCGCGACCCT CGGCGATCCT
PvUbi4P  ATCGAAATCT AAGCGAAGCG AAGAGGCCTC CCCAGATCCT CTCAAGGTAT

         2351                                               2400
PvUbi2P  TCCCCCGCTT CAAGGTACGG C.GATCG.TC TCCCCCGTCC TCTTGCCCCA
PvUbi4P  GCGAGAGCAT CGATCCCCTT CCGATCTATA TCGCGTGTCC TCCCTGTTCT

         2401                                               2450
PvUbi2P  TCTCCTCGCT CGGCGTGGTT TGGTGGTTCT GCTTGGTCTG TGGCTAGGAA
PvUbi4P  TGTTCTTCGT CGATCTAGTT TAGGGTTTGA TTTGGTTCTG AATCGAACCC

         2451                                               2500
PvUbi2P  CTAGGCTGAG .GCGTTGACG AAATCATGCT AGATCCGCGT GTT....TCC
PvUbi4P  TTTTCCTGCT TGCGTT..CG ATTTG.TACT CGATCCTCGG GTAGAGGTGT

         2501                                               2550
PvUbi2P  TGATCGTGGG TGGCTGGGAG GTGGGGTTTT CGTGTAGATC TGATCGGTTC
PvUbi4P  GGATC.TGCG GGGC.GTGAT GAGGTAGTTT GGTGTAGATT TGTTCTGGGC

         2551                                               2600
PvUbi2P  CGCTGTTTAT CCTGTCATGC TCATGTGATT TGTGGGGATT TTAGGTCGTT
PvUbi4P  GTTCGATTTG CCACTAGGGT TCGGCTGCT. .GTTGGCATT CCTGATCGAG

         2601                                               2650
PvUbi2P  TGTCCGGGAA TCGTGGGGTT GC..TTCTAG GCTGTTCGTA GATGAGATCG
PvUbi4P  CGGCCGGATA GGATTGTTTT TCCCTTTTTA TATGTTGGAT GC.GTGATGG

         2651                                               2700
PvUbi2P  TTCTCACGA. .TCTGCTGGG TCGCTGCCTA GGTTCAGCTA GGTC......
PvUbi4P  TTCCTGTGTG TTGGGTTAGA TTGCTGGTAC GATTCATCTA GGTGGTGATT

         2701                                               2750
PvUbi2P  TGCCCTGTTT TTGGGTTCGT TTTCGGGATC TGTACGTGCA TCTA...TTA
PvUbi4P  TGCAGAGGAA CAACTTTGCT GTTGAATATT GGTAGGTCTA TCTAGATTTA

         2751                                               2800
PvUbi2P  TCTGGTTCGA TGGT.GCTAG CTAGGAACAA ACAACTGATT CGTCCGATCG
PvUbi4P  TTACTTTTGA TTATCGCCTG ATAAGGATCA CCGATTCGT. .GTAGAATAA

         2801                                               2850
PvUbi2P  ATTGTTT... TGTTG..CCA TGT....... ...GCAAGGT TAGGTCGTTA
PvUbi4P  ATTATTTCAT TGTTGGGTCA TGTAGATATA GCTGCACAAT TTCTTACTTG

         2851                                               2900
PvUbi2P  TCTGATTGCT GTAGATCAGA GTAGAATAAG ATCA.TCACA AGCT.AGCTC
PvUbi4P  GCTCCTTACT GT.GTGAATT GTAGAATAAA CTGTGTTACT CTATGAGTTT

         2901                                               2950
PvUbi2P  TTG.GGCTTA TT..ATGAAT CT..GCGTTT GTTGCATGAT TAAGATGATT
PvUbi4P  TTCTGGATTG CTGGATCCAG TTAGGCCAGT GCTGTCAATT TGTTATGGCT

         2951                                               3000
PvUbi2P  ATGCTTTTTC TTATGCTGCC GTTTGTATA. .TGATGCGGT AGCTTTTAAC
PvUbi4P  GTTAATGTAA TAATTTTCTG GATTGTTGGC CTGCTTCTCT TCATGTTTAA

         3001                                               3050
PvUbi2P  TGA....ATA GCACACCTTT CCTGTTTAGT TAGATTAGAT TAGATTGCAT
PvUbi4P  TCACGTGATG GTTCATGATG CCTGTTGGGT TAGATTG..T TTGTTCAATT

         3051                                               3100
PvUbi2P  GATAGATGAG GATATATGCT GC.TACATCA .GTTTGATGA TTC.TCT.GG
PvUbi4P  CATCTAGGCA GTGCTGTGCA GAGTACAACT CGATTGATGT TTAATCTTGG
```

-continued

```
        3101                                              3150
PvUbi2P TACCTCATAA TCAACTAGCT CATGTGCTTA AATTGA..AA CTGCATGTGC
PvUbi4P TAGCT..... TCATCTAGAT T.TGTACAAA TTTTGGTCAC CTGATGATGA

        3151                                              3200
PvUbi2P CACATGATTA AGATGCTAAG ATTGGTGAA. .G.....ATA T.ATACGCTG
PvUbi4P TCACCGATTG TTGTGGAATT ATTTCTTAAC TGGTTCGTTG TTAGTCACCA

        3201                                              3250
PvUbi2P CTGTTCCTAT AGGAT..CCT GTAG..CTT. TTACCTGGTC AAC...ATGC
PvUbi4P CCTTACTTGT AGAATAACCT GTGGTACTGC TTTTCTGTTC TGTTTTAGGC

        3251                                              3300
PvUbi2P ATCGTCCTGT TATGG..ATA GATATGCATG ATAG....AT GAAGATAT..
PvUbi4P CACATCATAT GATTGTCAAA AATTTACATG GTAGTTTAAT GATAAAATTA

        3301                                              3350
PvUbi2P GTACTGCT.. ..ACAATTTG AT..GATTC. .....T.... TTTGTGCACC
PvUbi4P GTTCAGCTTA CTTCAGTTTG ATTTGCTTCA TATTTTGTTT TCTGTTCTAT

        3351                                              3400
PvUbi2P TGATGATCAT GCATG..CTC TTTGCCCTTA CTTTGAT.AT ACTTGGATGA
PvUbi4P TAATGATACT TCATGAAATG TTTGTTTTTT CTCTGTTCAG ATTTGACATG

        3401                                              3450
PvUbi2P TGGCATGCTT AGTACTAATG ATGTGATGAA CACAC.ATGA CCTGTTGGTA
PvUbi4P TTTCAGTATC A.TAATAATA ATATTCTGTA TCCTTTATAG TTTGTTGGCA

        3451                                              3500
PvUbi2P TGAATATGAT GT...TGCTG TTTGC...TT GTGATGAGTT CTGTTTGTTT
PvUbi4P TGATT.TGCT TTGAATTTAG TTAGCCTATT CTGTTAATAT AGGATGATAA

        3501                                              3550
PvUbi2P ACTGCTAGGC ACTTACCCTG TT..GTCTGG ..TTCTCTTT TGCAG.....
PvUbi4P GCTGTGAGGC GTTCATTCTC TTCAGTCCAG AGTTATCATT TTCAGTGTTT

        3551                                              3600
PvUbi2P .......... .......... .......... .......... ..........
PvUbi4P TAATGTTGTT TATCAAGCTG GATGTATATG GTGGTTTAAC TCTTTTCTGT

        3601        3616
PvUbi2P .......... ...... (SEQ ID NO: 20)
PvUbi4P TTCTTACTGT TTGCAG (SEQ ID NO: 2)
```

Example 4: Expression Vectors

Figure 5:
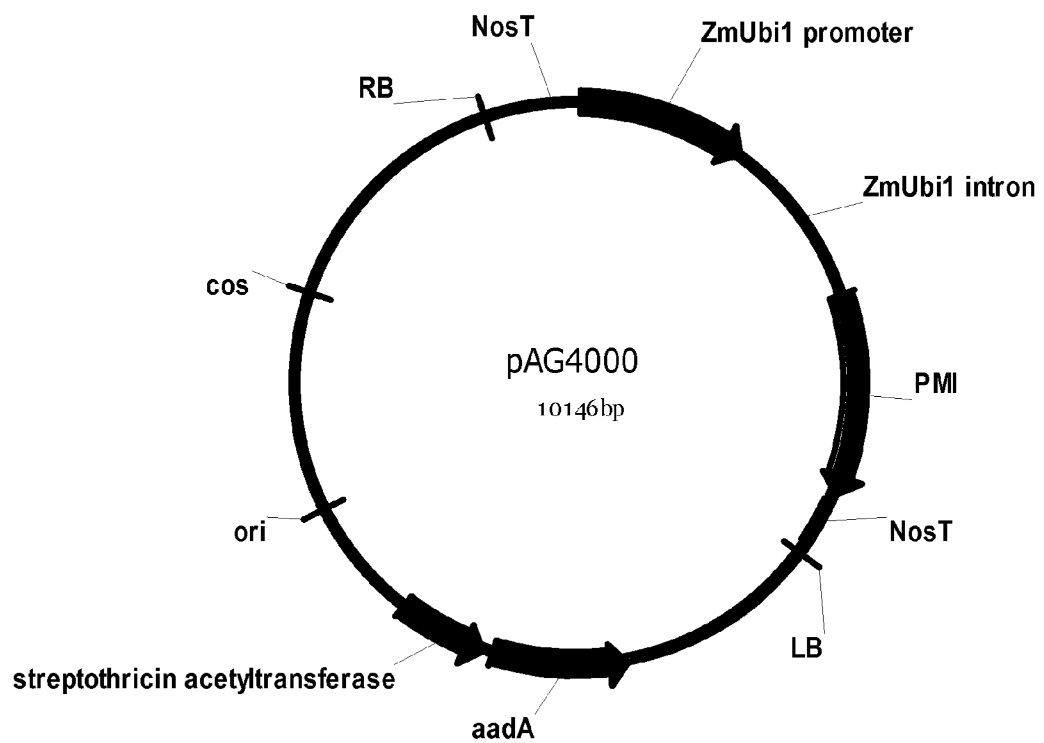
FIG. 5 illustrates a map of the plasmid pAG4000.

All vectors that include promoter sequences were developed in pAG4000 (SEQ ID NO: 17). A map of pAG4000 is shown in FIG. 5. The GUS cassettes for the pAG4008, pAG4009 and pAG4010 can be cloned into the pAG4000 as the KpnI-AvrII fragments. Both sites are underlined in the pAG4000 sequence as shown below.

```
>pAG4000
                                               (SEQ ID NO: 17)
AATTCCTGCAGTGCAGCGTGACCCGGTCGTGCCCCTCTCTAGAGATAATG
AGCATTGCATGTCTAAGTTATAAAAAATTACCACATATTTTTTTTGTCAC
ACTTGTTTGAAGTGCAGTTTATCTATCTTTATACATATATTTAAACTTTA
CTCTACGAATAATATAATCTATAGTACTACAATAATATCAGTGTTTTAGA
GAATCATATAAATGAACAGTTAGACATGGTCTAAAGGACAATTGAGTATT
TTGACAACAGGACTCTACAGTTTTATCTTTTTAGTGTGCATGTGTTCTCC
TTTTTTTTTGCAAATAGCTTCACCTATATAATACTTCATCCATTTTATTA
GTACATCCATTTAGGGTTTAGGGTTAATGGTTTTTATAGACTAATTTTTT
TAGTACATCTATTTTATTCTATTTTAGCCTCTAAATTAAGAAAACTAAAA
CTCTATTTTAGTTTTTTTATTTAATAATTTAGATATAAAATAGAATAAAA
TAAAGTGACTAAAAATTAAACAAATACCCTTTAAGAAATTAAAAAAACTA
```

-continued

```
AGGAAACATTTTTCTTGTTTCGAGTAGATAATGCCAGCCTGTTAAACGCC
GTCGACGAGTCTAACGGACACCAACCAGCGAACCAGCAGCGTCGCGTCGG
GCCAAGCGAAGCAGACGGCACGGCATCTCTGTCGCTGCCTCTGGACCCCT
CTCGAGAGTTCCGCTCCACCGTTGGACTTGCTCCGCTGTCGGCATCCAGA
AATTGCGTGGCGGAGCGGCAGACGTGAGCCGGCACGGCAGGCGGCCTCCT
CCTCCTCTCACGGCACGGCAGCTACGGGGGATTCCTTTCCCACCGCTCCT
TCGCTTTCCCTTCCTCGCCCGCCGTAATAAATAGACACCCCCTCCACACC
CTCTTTCCCCAACCTCGTGTTGTTCGGAGCGCACACACACACAACCAGAT
CTCCCCCAAATCCACCCGTCGGCACCTCCGCTTCAAGGTACGCCGCTCGT
CCTCCCCCCCCCCCCCTCTCTACCTTCTCTAGATCGGCGTTCCGGTCCAT
GGTTAGGGCCCGGTAGTTCTACTTCTGTTCATGTTTGTGTTAGATCCGTG
TTTGTGTTAGATCCGTGCTGCTAGCGTTCGTACACGGATGCGACCTGTAC
GTCAGACACGTTCTGATTGCTAACTTGCCAGTGTTTCTCTTTGGGGAATC
CTGGGATGGCTCTAGCCGTTCCGCAGACGGGATCGATTTCATGATTTTTT
TTGTTTCGTTGCATAGGGTTTGGTTTGCCCTTTTCCTTTATTTCAATATA
TGCCGTGCACTTGTTTGTCGGGTCATCTTTTCATGCTTTTTTTTGTCTTG
GTTGTGATGATGTGGTCTGGTTGGGCGGTCGTTCTAGATCGGAGTAGAAT
```

-continued

TCTGTTTCAAACTACCTGGTGGATTTATTAATTTTGGATCTGTATGTGTG
TGCCATACATATTCATAGTTACGAATTGAAGATGATGGATGGAAATATCG
ATCTAGGATAGGTATACATGTTGATGCGGGTTTTACTGATGCATATACAG
AGATGCTTTTTGTTCGCTTGGTTGTGATGATGTGGTGTGGTTGGGCGGTC
GTTCATTCGTTCTAGATCGGAGTAGAATACTGTTTCAAACTACCTGGTGT
ATTTATTAATTTTGGAACTGTATGTGTGTGTCATACATCTTCATAGTTAC
GAGTTTAAGATGGATGGAAATATCGATCTAGGATAGGTATACATGTTGAT
GTGGGTTTTACTGATGCATATACATGATGGCATATGCAGCATCTATTCAT
ATGCTCTAACCTTGAGTACCTATCTATTATAATAAACAAGTATGTTTTAT
AATTATTTTGATCTTGATATACTTGGATGATGGCATATGCAGCAGCTATA
TGTGGATTTTTTTAGCCCTGCCTTCATACGCTATTTATTTGCTTGGTACT
GTTTCTTTTGTCGATGCTCACCCTGTTGTTTGGTGTTACTTCTGCAGATG
CAGAAACTCATTAACTCAGTGCAAAACTATGCCTGGGGCAGCAAAACGGC
GTTGACTGAACTTTATGGTATGGAAAATCCGTCCAGCCAGCCGATGGCCG
AGCTGTGGATGGGCGCACATCCGAAAAGCAGTTCACGAGTGCAGAATGCC
GCCGGAGATATCGTTTCACTGCGTGATGTGATTGAGAGTGATAAATCGAC
TCTGCTCGGAGAGGCCGTTGCCAAACGCTTTGGCGAACTGCCTTTCCTGT
TCAAAGTATTATGCGCAGCACAGCCACTCTCCATTCAGGTTCATCCAAAC
AAACACAATTCTGAAATCGGTTTTGCCAAAGAAAATGCCGCAGGTATCCC
GATGGATGCCGCCGAGCGTAACTATAAAGATCCTAACCACAAGCCGGAGC
TGGTTTTTGCGCTGACGCCTTTCCTTGCGATGAACGCGTTTCGTGAATTT
TCCGAGATTGTCTCCCTACTCCAGCCGGTCGCAGGTGCACATCCGGCGAT
TGCTCACTTTTTACAACAGCCTGATGCCGAACGTTTAAGCGAACTGTTCG
CCAGCCTGTTGAATATGCAGGGTGAAGAAAAATCCCGCGCGCTGGCGATT
TTAAAATCGGCCCTCGATAGCCAGCAGGGTGAACCGTGGCAAACGATTCG
TTTAATTTCTGAATTTACCCGGAAGACAGCGGTCTGTTCTCCCCGCTAT
TGCTGAATGTGGTGAAATTGAACCCTGGCGAAGCGATGTTCCTGTTCGCT
GAAACACCGCACGCTTACCTGCAAGGCGTGGCGCTGGAAGTGATGGCAAA
CTCCGATAACGTGCTGCGTGCGGGTCTGACGCCTAAATACATTGATATTC
CGGAACTGGTTGCCAATGTGAAATTCGAAGCCAAACCGGCTAACCAGTTG
TTGACCCAGCCGGTGAAACAAGGTGCAGAACTGGACTTCCCGATTCCAGT
GGATGATTTTGCCTTCTCGCTGCATGACCTTAGTGATAAAGAAACCACCA
TTAGCCAGCAGAGTGCCGCCATTTTGTTCTGCGTCGAAGGCGATGCAACG
TTGTGGAAAGGTTCTCAGCAGTTACAGCTTAAACCGGGTGAATCAGCGTT
TATTGCCGCCAACGAATCACCGGTGACTGTCAAAGGCCACGGCCGTTTAG
CGCGTGTTTACAACAAGCTGTAAGAGCTTACTGAAAAAATTAACATCTCT
TGCTAAGCTGGGAGCTCTAGATCCCCGAATTTCCCCGATCGTTCAAACAT
TTGGCAATAAAGTTTCTTAAGATTGAATCCTGTTGCCGGTCTTGCGATGA
TTATCATATAATTTCTGTTGAATTACGTTAAGCATGTAATAATTAACATG
TAATGCATGACGTTATTTATGAGATGGGTTTTTATGATTAGAGTCCCGCA
ATTATACATTTAATACGCGATAGAAAACAAAATATAGCGCGCAAACTAGG

-continued

ATAAATTATCGCGCGCGGTGTCATCTATGTTACTAGATCGGGAATTGGCG
AGCTCGAATTAATTCAGTACATTAAAAACGTCCGCAATGTGTTATTAAGT
TGTCTAAGCGTCAATTTGTTTACACCACAATATATCCTGCCACCAGCCAG
CCAACAGCTCCCCGACCGGCAGCTCGGCACAAAATCACCACTCGATACAG
GCAGCCCATCAGTCCGGGACGGCGTCAGCGGGAGAGCCGTTGTAAGGCGG
CAGACTTTGCTCATGTTACCGATGCTATTCGGAAGAACGGCAACTAAGCT
GCCGGGTTTGAAACACGGATGATCTCGCGGAGGGTAGCATGTTGATTGTA
ACGATGACAGAGCGTTGCTGCCTGTGATCAAATATCATCTCCCTCGCAGA
GATCCGAATTATCAGCCTTCTTATTCATTTCTCGCTTAACCGTGACAGGC
TGTCGATCTTGAGAACTATGCCGACATAATAGGAAATCGCTGGATAAAGC
CGCTGAGGAAGCTGAGTGGCGCTATTTCTTTAGAAGTGAACGTTGACGAT
CGTCGACCGTACCCCGATGAATTAATTCGGACGTACGTTCTGAACACAGC
TGGATACTTACTTGGGCGATTGTCATACATGACATCAACAATGTACCCGT
TTGTGTAACCGTCTCTTGGAGGTTCGTATGACACTAGTGGTTCCCCTCAG
CTTGCGACTAGATGTTGAGGCCTAACATTTTATTAGAGAGCAGGCTAGTT
GCTTAGATACATGATCTTCAGGCCGTTATCTGTCAGGGCAAGCGAAAATT
GGCCATTTATGACGACCAATGCCCCGCAGAAGCTCCCATCTTTGCCGCCA
TAGACGCCGCGCCCCCCTTTTGGGGTGTAGAACATCCTTTTGCCAGATGT
GGAAAAGAAGTTCGTTGTCCCATTGTTGGCAATGACGTAGTAGCCGGCGA
AAGTGCGAGACCCATTTGCGCTATATATAAGCCTACGATTTCCGTTGCGA
CTATTGTCGTAATTGGATGAACTATTATCGTAGTTGCTCTCAGAGTTGTC
GTAATTTGATGGACTATTGTCGTAATTGCTTATGGAGTTGTCGTAGTTGC
TTGGAGAAATGTCGTAGTTGGATGGGGAGTAGTCATAGGGAAGACGAGCT
TCATCCACTAAAACAATTGGCAGGTCAGCAAGTGCCTGCCCCGATGCCAT
CGCAAGTACGAGGCTTAGAACCACCTTCAACAGATCGCGCATAGTCTTCC
CCAGCTCTCTAACGCTTGAGTTAAGCCGCGCCGCGAAGCGGCGTCGGCTT
GAACGAATTGTTAGACATTATTTGCCGACTACCTTGGTGATCTCGCCTTT
CACGTAGTGAACAAATTCTTCCAACTGATCTGCGCGCGAGGCCAAGCGAT
CTTCTTGTCCAAGATAAGCCTGCCTAGCTTCAAGTATGACGGGCTGATAC
TGGGCCGGCAGGCGCTCCATTGCCCAGTCGGCAGCGACATCCTTCGGCGC
GATTTTGCCGGTTACTGCGCTGTACCAAATGCGGGACAACGTAAGCACTA
CATTTCGCTCATCGCCAGCCCAGTCGGGCGGCGAGTTCCATAGCGTTAAG
GTTTCATTTAGCGCCTCAAATAGATCCTGTTCAGGAACCGGATCAAAGAG
TTCCTCCGCCGCTGGACCTACCAAGGCAACGCTATGTTCTCTTGCTTTTG
TCAGCAAGATAGCCAGATCAATGTCGATCGTGGCTGGCTCGAAGATACCT
GCAAGAATGTCATTGCGCTGCCATTCTCCAAATTGCAGTTCGCGCTTAGC
TGGATAACGCCACGGAATGATGTCGTCGTGCACAACAATGGTGACTTCTA
CAGCGCGGAGAATCTCGCTCTCTCCAGGGGAAGCCGAAGTTTCCAAAAGG
TCGTTGATCAAAGCTCGCCGCGTTGTTTCATCAAGCCTTACGGTCACCGT
AACCAGCAAATCAATATCACTGTGTGGCTTCAGGCCGCCATCCACTGCGG

-continued

AGCCGTACAAATGTACGGCCAGCAACGTCGGTTCGAGATGGCGCTCGATG

ACGCCAACTACCTCTGATAGTTGAGTCGATACTTCGGCGATCACCGCTTC

CCTCATGATGTTTAACTCCTGAATTAAGCCGCGCCGCGAAGCGGTGTCGG

CTTGAATGAATTGTTAGGCGTCATCCTGTGCTCCCGAGAACCAGTACCAG

TACATCGCTGTTTCGTTCGAGACTTGAGGTCTAGTTTTATACGTGAACAG

GTCAATGCCGCCGAGAGTAAAGCCACATTTTGCGTACAAATTGCAGGCAG

GTACATTGTTCGTTTGTGTCTCTAATCGTATGCCAAGGAGCTGTCTGCTT

AGTGCCCACTTTTTCGCAAATTCGATGAGACTGTGCGCGACTCCTTTGCC

TCGGTGCGTGTGCGACACAACAATGTGTTCGATAGAGGCTAGATCGTTCC

ATGTTGAGTTGAGTTCAATCTTCCCGACAAGCTCTTGGTCGATGAATGCG

CCATAGCAAGCAGAGTCTTCATCAGAGTCATCATCCGAGATGTAATCCTT

CCGGTAGGGGCTCACACTTCTGGTAGATAGTTCAAAGCCTTGGTCGGATA

GGTGCACATCGAACACTTCACGAACAATGAAATGGTTCTCAGCATCCAAT

GTTTCCGCCACCTGCTCAGGGATCACCGAAATCTTCATATGACGCCTAAC

GCCTGGCACAGCGGATCGCAAACCTGGCGCGGCTTTTGGCACAAAAGGCG

TGACAGGTTTGCGAATCCGTTGCTGCCACTTGTTAACCCTTTTGCCAGAT

TTGGTAACTATAATTTATGTTAGAGGCGAAGTCTTGGGTAAAAACTGGCC

TAAAATTGCTGGGGATTTCAGGAAAGTAAACATCACCTTCCGGCTCGATG

TCTATTGTAGATATATGTAGTGTATCTACTTGATCGGGGGATCTGCTGCC

TCGCGCGTTTCGGTGATGACGGTGAAAACCTCTGACACATGCAGCTCCCG

GAGACGGTCACAGCTTGTCTGTAAGCGGATGCCGGGAGCAGACAAGCCCG

TCAGGGCGCGTCAGCGGGTGTTGGCGGGTGTCGGGGCGCAGCCATGACCC

AGTCACGTAGCGATAGCGGAGTGTATACTGGCTTAACTATGCGGCATCAG

AGCAGATTGTACTGAGAGTGCACCATATGCGGTGTGAAATACCGCACAGA

TGCGTAAGGAGAAAATACCGCATCAGGCGCTCTTCCGCTTCCTCGCTCAC

TGACTCGCTGCGCTCGGTCGTTCGGCTGCGGCGAGCGGTATCAGCTCACT

CAAAGGCGGTAATACGGTTATCCACAGAATCAGGGGATAACGCAGGAAAG

AACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAA

ATCGACGCTCAAGTCAGAGGTGGCGAAACCCGACAGGACTATAAAGATAC

CAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGC

TTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGC

CTTATCCGGTAACTATCGTCTTGAGTCCAACCCGGTAAGACACGACTTAT

CGCCACTGGCAGCAGCCACTGGTAACAGGATTAGCAGAGCGAGGTATGTA

GGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAA

AAAGAGTTGGTAGCTCTTGATCCGGCAAACAAACCACCGCTGGTAGCGGT

GGTTTTTTTGTTTGCAAGCAGCAGATTACGCGCAGAAAAAAAGGATCTCA

AGAAGATCCTTTGATCTTTTCTACGGGGTCTGACGCTCAGTGGAACGAAA

-continued

ACTCACGTTAAGGGATTTTGGTCATGAGATTATCAAAAAGGATCTTCACC

TAGATCCTTTTAAATTAAAAATGAAGTTTTAAATCAATCTAAAGTATATA

TGAGTAAACTTGGTCTGACAGTTACCAATGCTTAATCAGTGAGGCACCTA

TCTCAGCGATCTGTCTATTTCGTTCATCCATAGTTGCCTGACTCCCCGTC

GTGTAGATAACTACGATACGGGAGGGCTTACCATCTGGCCCCAGTGCTGC

AATGATACCGCGAGACCCACGCTCACCGGCTCCAGATTTATCAGCAATAA

ACCAGCCAGCCGGAAGGGCCGAGCGCAGAAGTGGTCCTGCAACTTTATCC

GCCTCCATCCAGTCTATTAATTGTTGCCGGGAAGCTAGAGTAAGTAGTTC

GCCAGTTAATAGTTTGCGCAACGTTGTTGCCATTGCTGCAGGGGGGGGGG

GGGGGGGGTTCCATTGTTCATTCCACGGACAAAAACAGAGAAAGGAAACG

ACAGAGGCCAAAAAGCTCGCTTTCAGCACCTGTCGTTTCCTTTCTTTTCA

GAGGGTATTTTAAATAAAAACATTAAGTTATGACGAAGAAGAACGGAAAC

GCCTTAAACCGGAAAATTTTCATAAATAGCGAAAACCCGCGAGGTCGCCG

CCCCGTAACCTGTCGGATCACCGGAAAGGACCCGTAAAGTGATAATGATT

ATCATCTACATATCACAACGTGCGTGGAGGCCATCAAACCACGTCAAATA

ATCAATTATGACGCAGGTATCGTATTAATTGATCTGCATCAACTTAACGT

AAAAACAACTTCAGACAATACAAATCAGCGACACTGAATACGGGGCAACC

TCATGTCCCCCCCCCCCCCCCCCCTGCAGGCATCGTGGTGTCACGCTCGTC

GTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGC

AGCACTGCATAATTCTCTTACTGTCATGCCATCCGTAAGATGCTTTTCTG

TGACTGGTGAGTACTCAACCAAGTCATTCTGAGAATAGTGTATGCGGCGA

CCGAGTTGCTCTTGCCCGGCGTCAACACGGGATAATACCGCGCCACATAG

CAGAACTTTAAAAGTGCTCATCATTGGAAAACGTTCTTCGGGGCGAAAAC

TCTCAAGGATCTTACCGCTGTTGAGATCCAGTTCGATGTAACCCACTCGT

GCACCCAACTGATCTTCAGCATCTTTTACTTTCACCAGCGTTTCTGGGTG

AGCAAAAACAGGAAGGCAAAATGCCGCAAAAAAGGGAATAAGGGCGACAC

GGAAATGTTGAATACTCATACTCTTCCTTTTTCAATATTATTGAAGCATT

TATCAGGGTTATTGTCTCATGAGCGGATACATATTTGAATGTATTTAGAA

AAATAAACAAATAGGGGTTCCGCGCACATTTCCCCGAAAAGTGCCACCTG

ACGTCTAAGAAACCATTATTATCATGACATTAACCTATAAAAATAGGCGT

ATCACGAGGCCCTTTCGTCTTCAAGAATTGGTCGACGATCTTGCTGCGTT

CGGATATTTTCGTGGAGTTCCCGCCACAGACCCGGATTGAAGGCGAGATC

CAGCAACTCGCGCCAGATCATCCTGTGACGGAACTTTGGCGCGTGATGAC

TGGCCAGGACGTCGGCCGAAAGAGCGACAAGCAGATCACGCTTTTCGACA

GCGTCGGATTTGCGATCGAGGATTTTTCGGCGCTGCGCTACGTCCGCGAC

CGCGTTGAGGGATCAAGCCACAGCAGCCCACTCGACCTTCTAGCCGACCC

AGACGAGCCAAGGGATCTTTTTGGAATGCTGCTCCGTCGTCAGGCTTTCC

GACGTTTGGGTGGTTGAACAGAAGTCATTATCGCACGGAATGCCAAGCAC

-continued

```
TCCCGAGGGGAACCCTGTGGTTGGCATGCACATACAAATGGACGAACGGA

TAAACCTTTTCACGCCCTTTTAAATATCCGATTATTCTAATAAACGCTCT

TTTCTCTTAGGTTTACCCGCCAATATATCCTGTCAAACACTGATAGTTTA

AACTGAAGGCGGGAAACGACAACCTGATCATGAGCGGAGAATTAAGGGAG

TCACGTTATGACCCCCGCCGATGACGCGGGACAAGCCGTTTTACGTTTGG

AACTGACAGAACCGCAACGTTGAAGGAGCCACTCAGCTTAATTAAGTCTA

ACTCGAGTTACTGGTACGTACCAAATCCATGGAATCAAGGTACCATCAAT

CCCGGGTATTCATCCTAGGTCCCCGAATTTCCCCGATCGTTCAAACATTT

GGCAATAAAGTTTCTTAAGATTGAATCCTGTTGCCGGTCTTGCGATGATT

ATCATATAATTTCTGTTGAATTACGTTAAGCATGTAATAATTAACATGTA

ATGCATGACGTTATTTATGAGATGGGTTTTTATGATTAGAGTCCCGCAAT

TATACATTTAATACGCGATAGAAAACAAAATATAGCGCGCAAACTAGGAT

AAATTATCGCGCGCGGTGTCATCTATGTTACTAGATCGGGAATTGG
```

Figure 2:
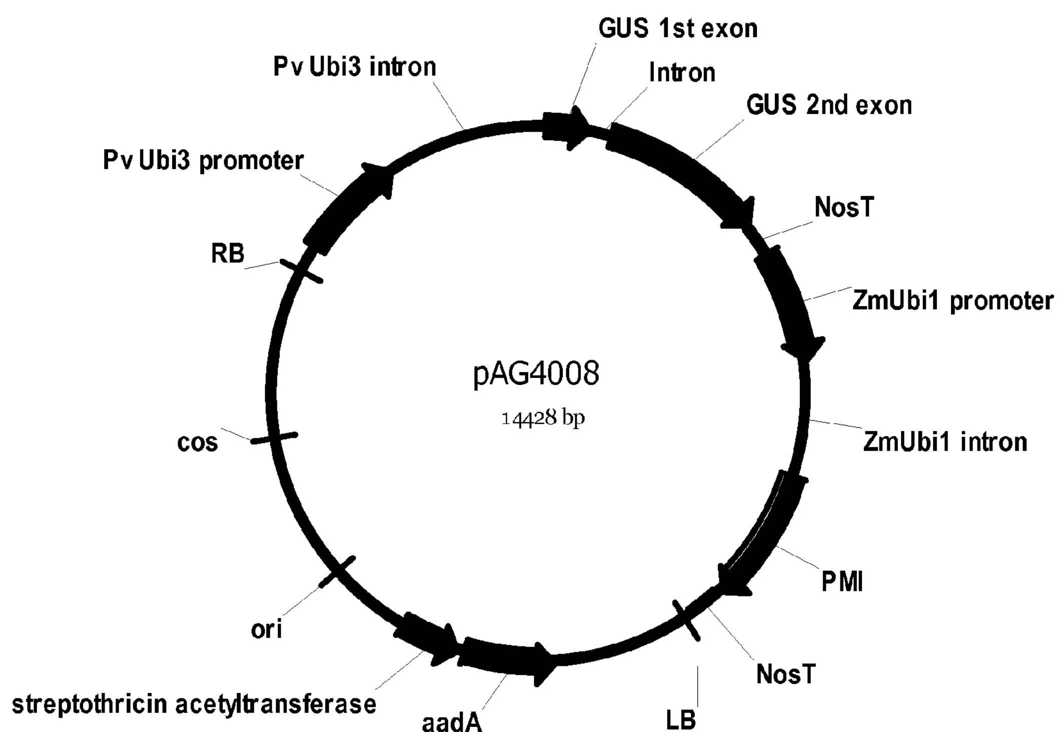
FIG. 2 illustrates a map of the plasmid pAG4008.
Figure 3:
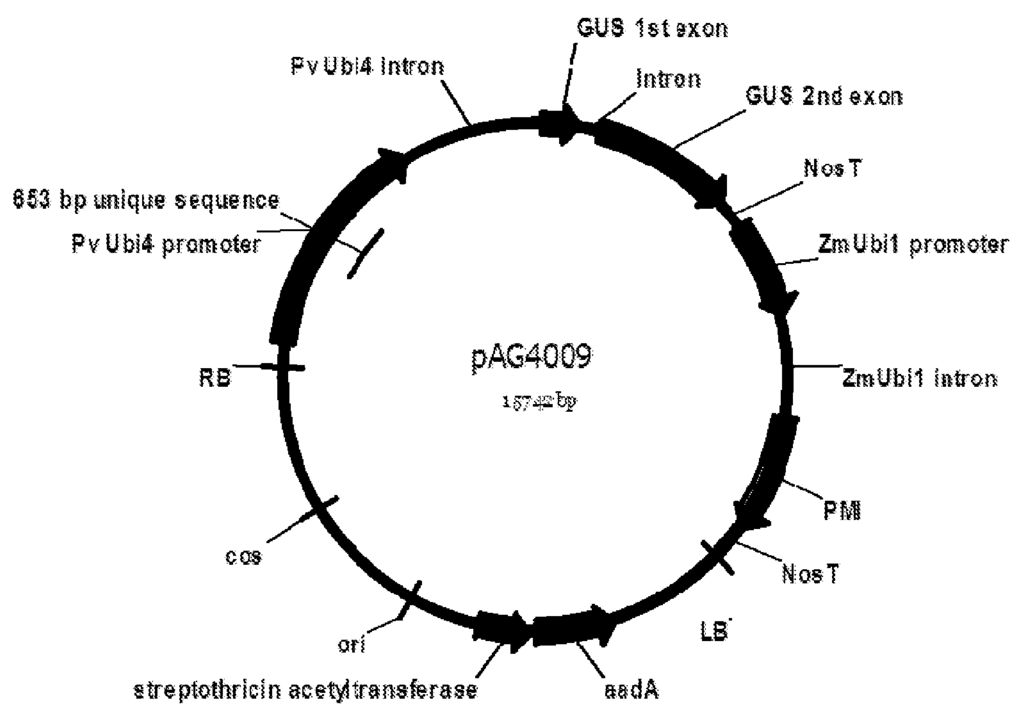
FIG. 3 illustrates a map of the plasmid pAG4009.
Figure 4:
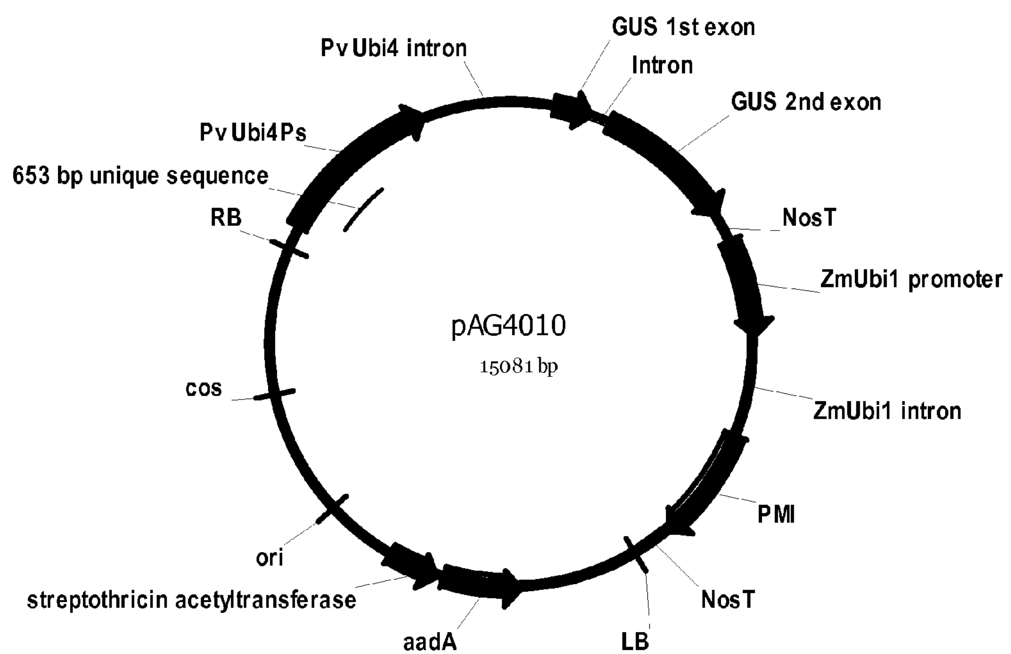
FIG. 4 illustrates a map of the plasmid pAG4010.

PvUbi3, PvUbi4 and PvUbi4s promoter sequences were cloned into the pAG4000 to create the expression constructs pAG4008 (SEQ ID NO: 11), pAG4009 (SEQ ID NO: 12) and pAG4010 (SEQ ID NO: 13), respectively, to validate promoter activity in plants. Maps of pAG4008, pAG4009 and pAG2010 are shown in FIGS. 2-4, respectively. In the figures, pAG2008 (FIG. 2), pAG2009 (FIG. 3) and pAG4010 (FIG. 4) include expression cassettes containing PvUbi3, PvUbi4 and PvUbi4s promoters, respectively, operably linked to the GUS gene and the Nos terminator. The constructs also include selection cassettes containing the phosphomannose isomerase (PMI) gene between the *Zea mays* Ubiquitin 1(ZmUbi1) promoter and the Nos terminator. The pAG4008 vector contains the entire upstream PvUbi3 sequence fused to GUS. The pAG4009 vector contains entire upstream PvUbi4 sequence fused to GUS. The pAG4010 vector contains the upstream PvUbi4 sequence, which was truncated at its 5' end to the resulting 2920 bp sequence designated as PvUbi4Ps (SEQ ID NO: 3) fused to GUS. This sequence at its 5' end has 230 bp region of homology to PvUbi3. With exception of the dispersed 9 nt differences between PvUbi3P and PvUbi4Ps, the major difference between both promoter regions is to the unique 653 bp sequence in PvUbi4.

Figure 9:
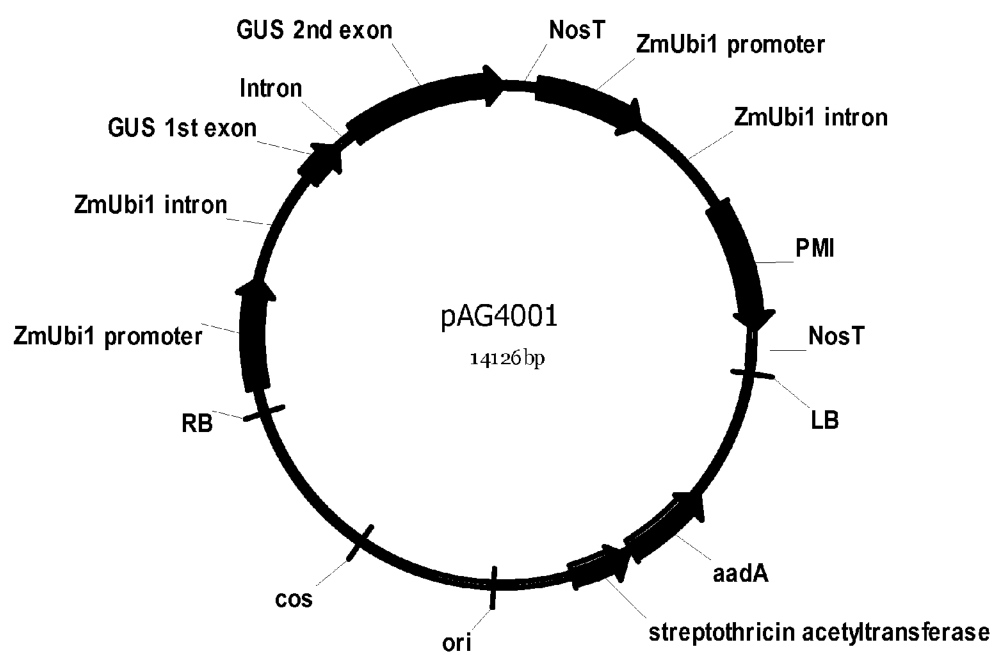
FIG. 9 illustrates a map of the plasmid pAG4001.

Promoter activity of PvUbi3, PvUbi4 and PvUbi4s was compared to the activity of ZmUbi1 promoter driving GUS expression from the pAG4001 expression vector, which is shown in FIG. 9. pAG4001 also contains a PMI cassette for selection of transgenic plants.

Figure 6:
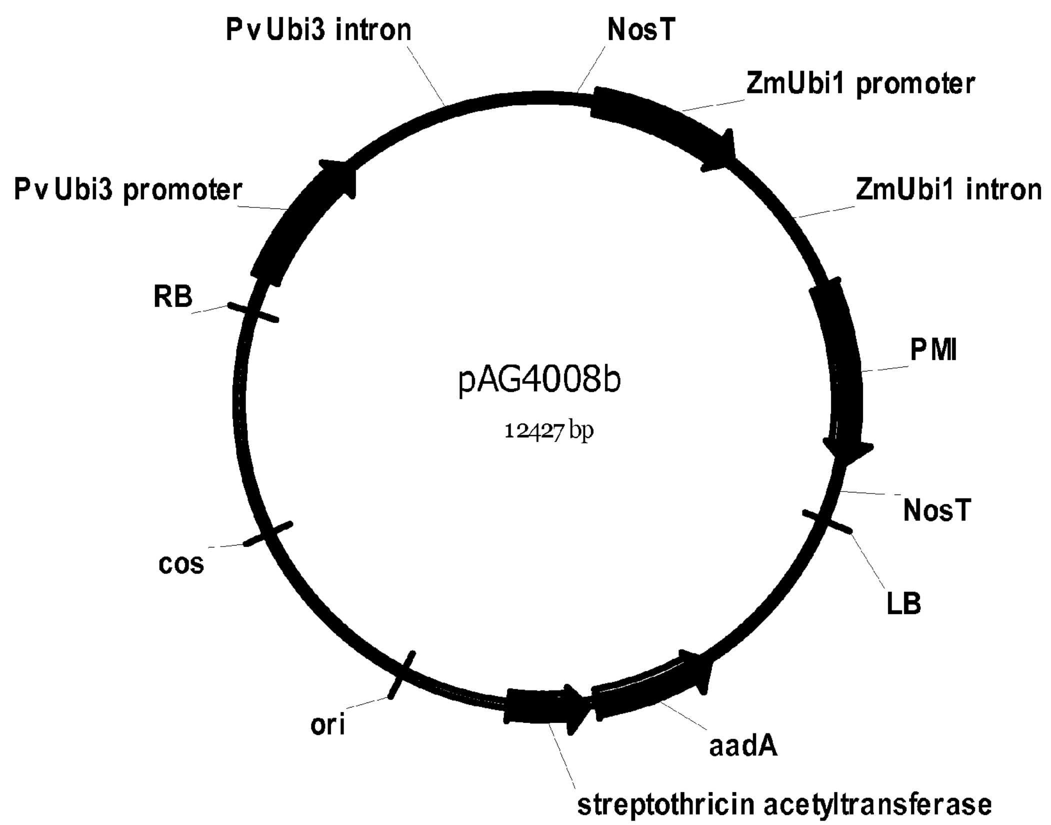
FIG. 6 illustrates a map of the plasmid pAG4008b.
Figure 7:
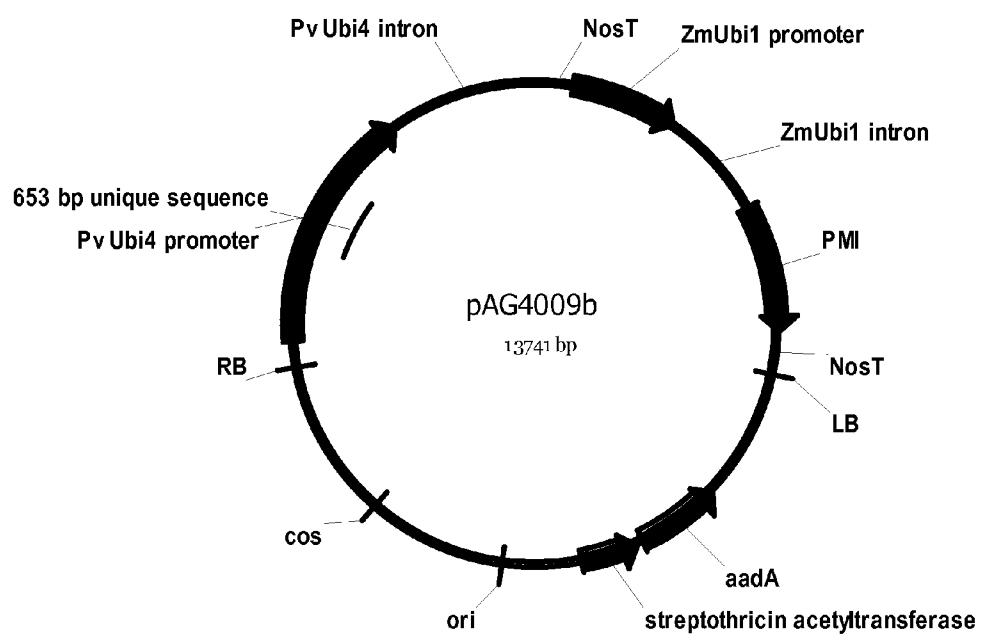
FIG. 7 illustrates a map of the plasmid pAG4009b.
Figure 8:
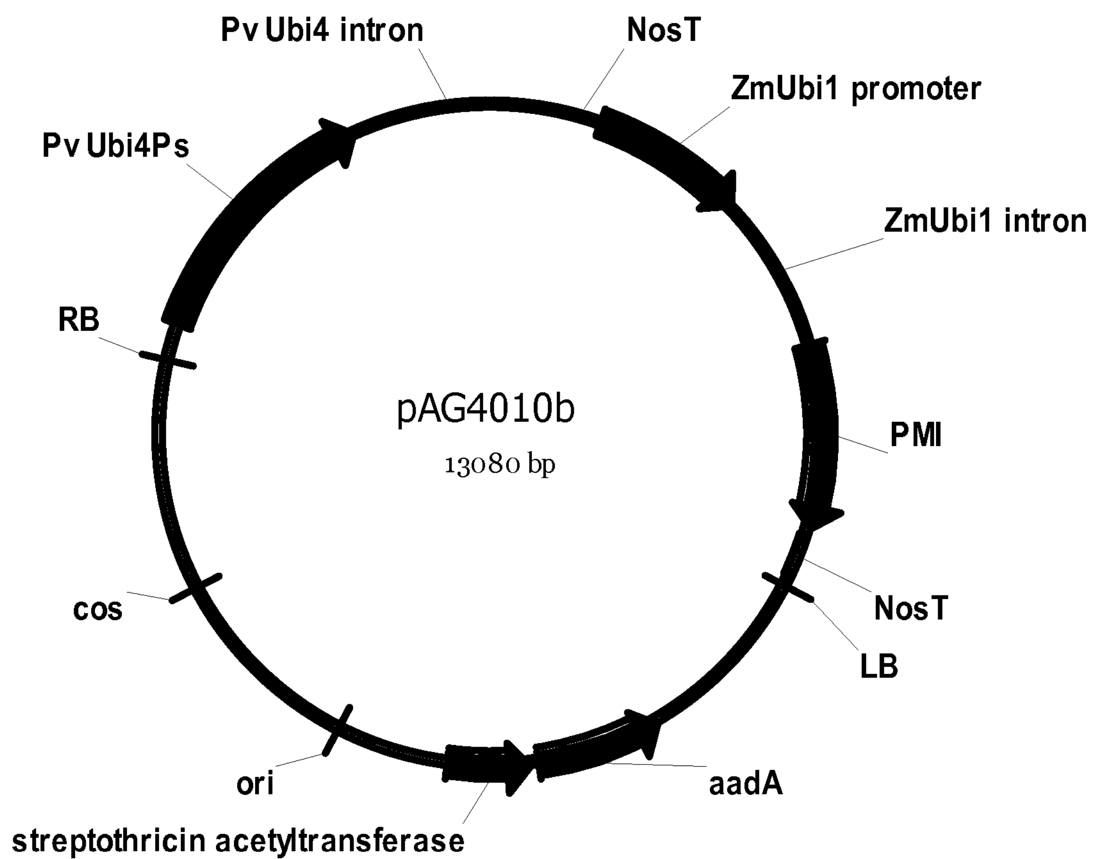
FIG. 8 illustrates a map of the plasmid pAG4010b.

PvUbi3, PvUbi4 and PvUbi4s promoter sequences were cloned into pAG4000 (FIG. 5) to create the expression cassettes pAG4008b, pAG4009b and pAG4010b. Maps of pAG4008b, pAG4009b and pAG4010b are shown in FIGS. 6-8, respectively. A gene of interest may be cloned into each of the expression cassette to be operably linked to the respective promoter and Nos terminator.

Example 5: GUS Expression Data

Maize immature embryos were infected with LBA4404 *Agrobacterium* strains carrying expression vectors pAG4008, pAG4009, and pAG4010, in which the isolated switchgrass promoters PvUbi3, PvUbi4, and PvUbi4s, respectively, were fused to the gene encoding beta-glucuronidase (GUS). The strain containing pAG4001 vector, where GUS expression is driven by the strong constitutive maize Ubi1 promoter, was used for generating control plants that served as benchmark controls for GUS expression from the PvUbi3, PvUbi4, and PvUbi4s promoters. Stably transformed maize plants were generated and efficiency of switchgrass promoters was assessed using histochemical (visual) or MUG (quantitative) assays for detection of GUS protein expression.

A. Histochemical GUS Staining in Maize Leaf Tissues.

Figure 10:
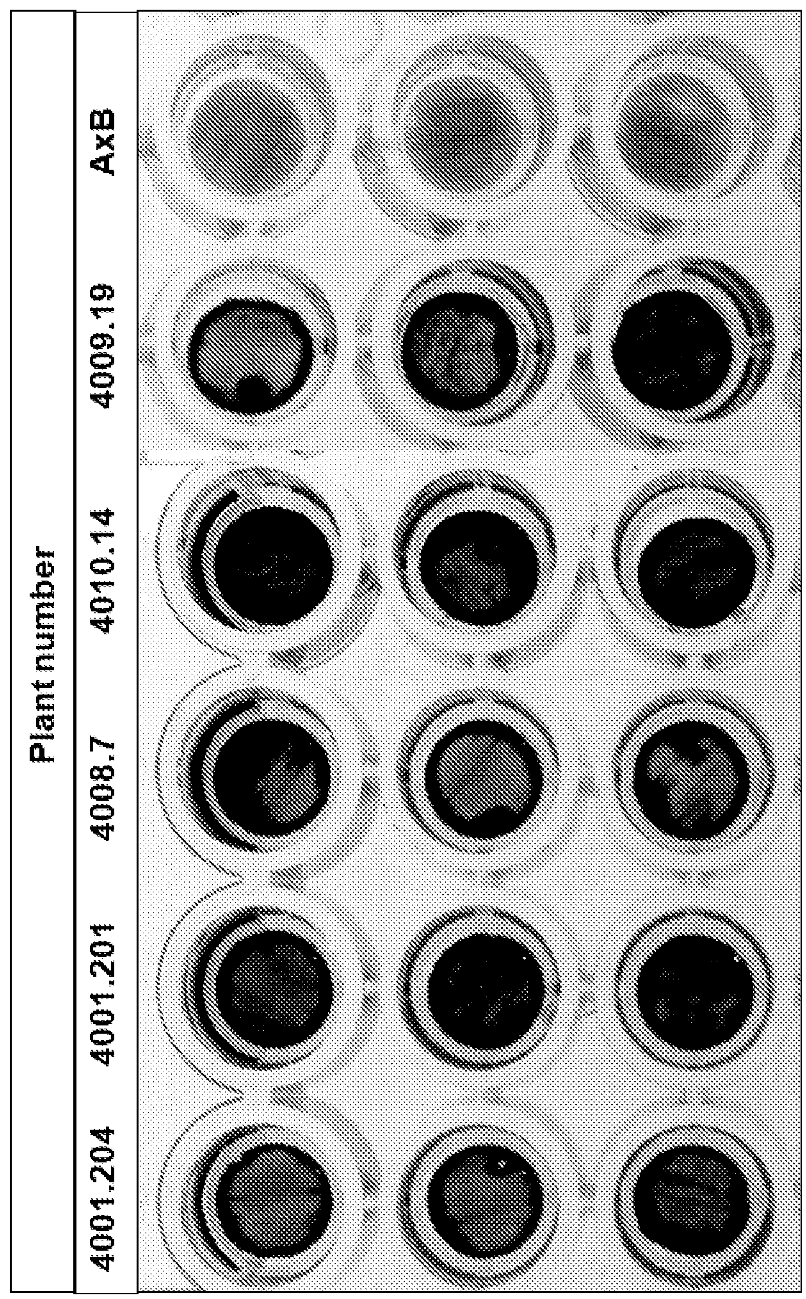
FIG. 10 illustrates histochemical GUS staining of maize leaf tissues expressing GUS gene under control of the switchgrass promoters.
Figure 11:
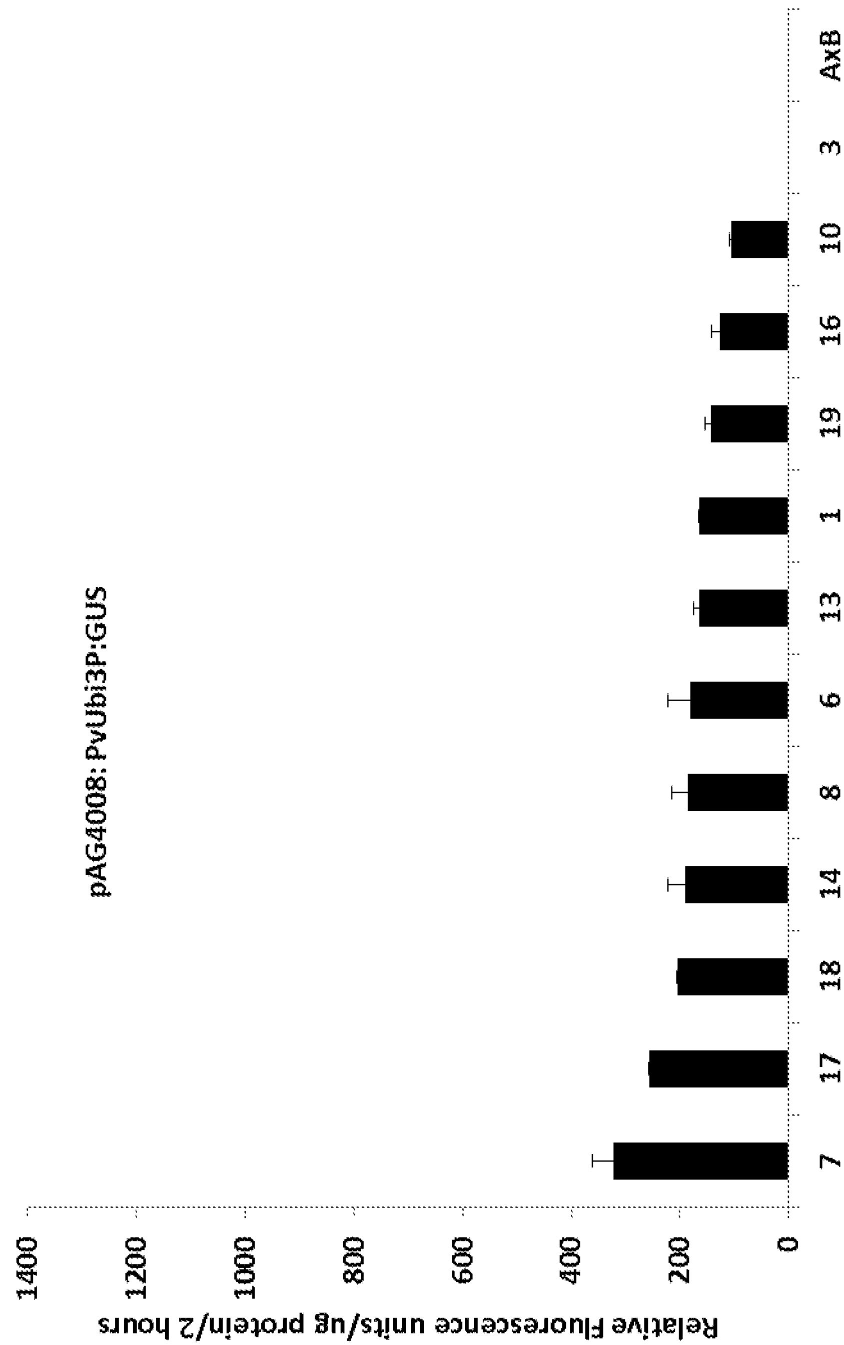
FIG. 11 illustrates distributions of the GUS protein activity values determined by the fluorescent β-glucoronidase assay (MUG) in populations of transgenic maize plants transformed with the construct pAG4008 (PvUbi3P:GUS).
Figure 12:
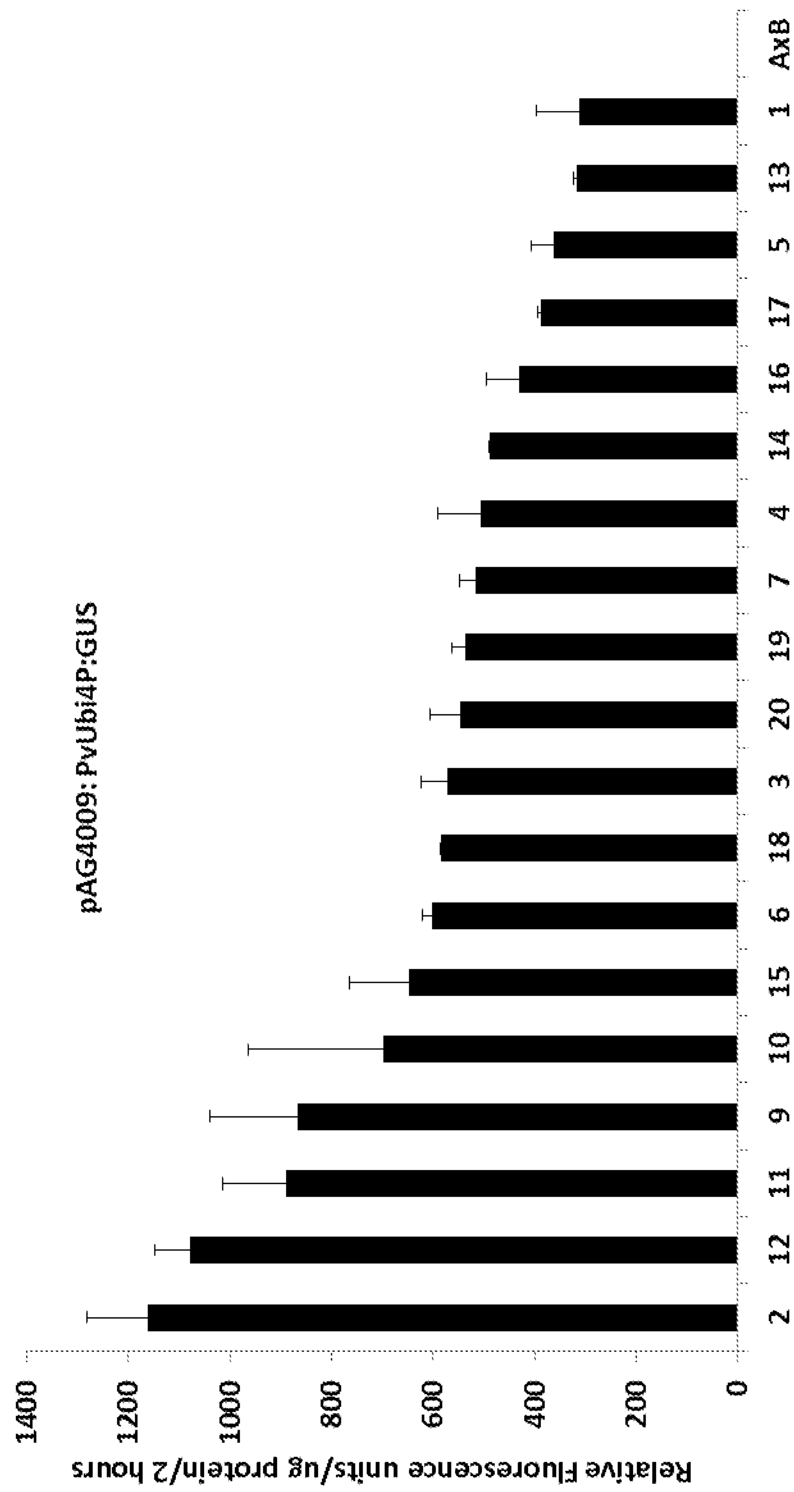
FIG. 12 illustrates distributions of the GUS protein activity values determined by the fluorescent β-glucoronidase assay (MUG) in populations of transgenic maize plants transformed with the construct pAG4009 (PvUbi4P:GUS)
Figure 13:
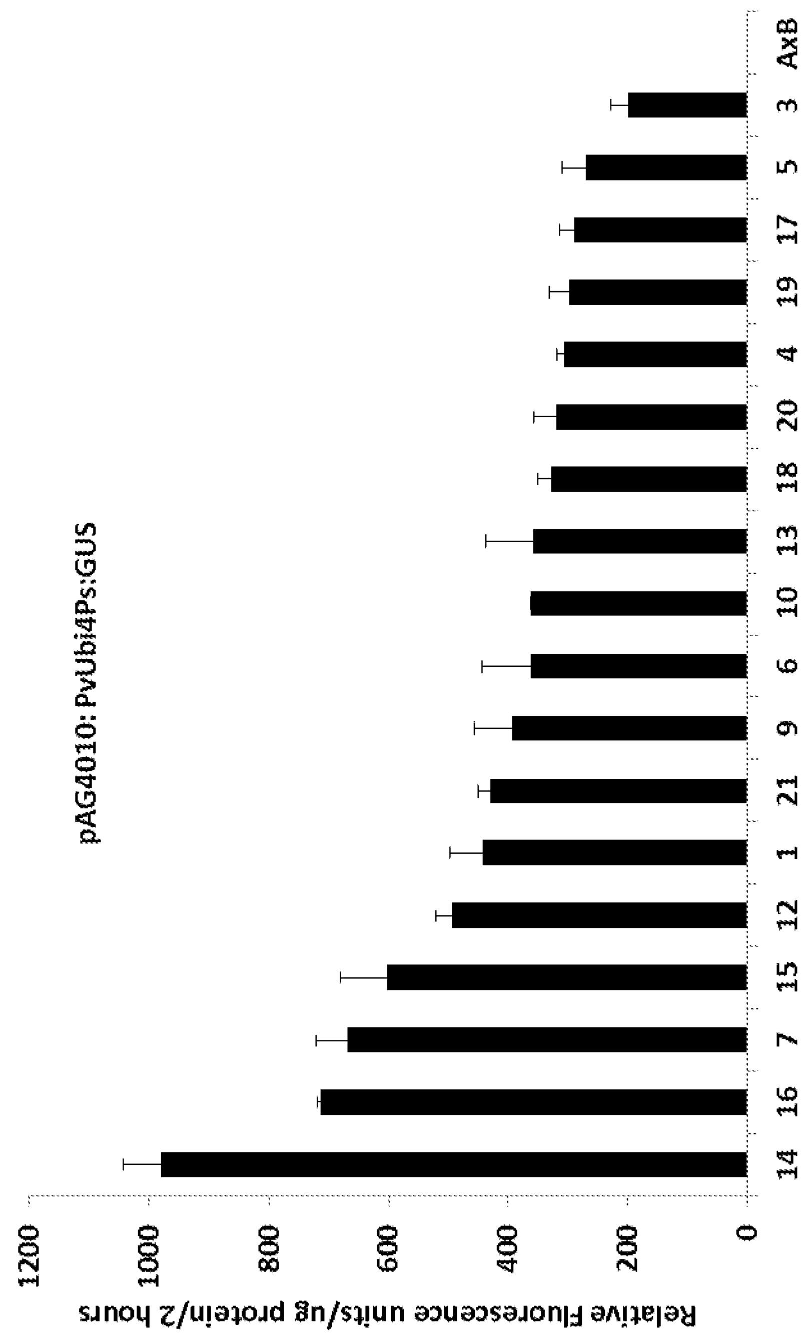
FIG. 13 illustrates distributions of the GUS protein activity values determined by the fluorescent β-glucoronidase assay (MUG) in populations of transgenic maize plants transformed with constructs pAG4010 (PvUbi4Ps:GUS).
Figure 14:
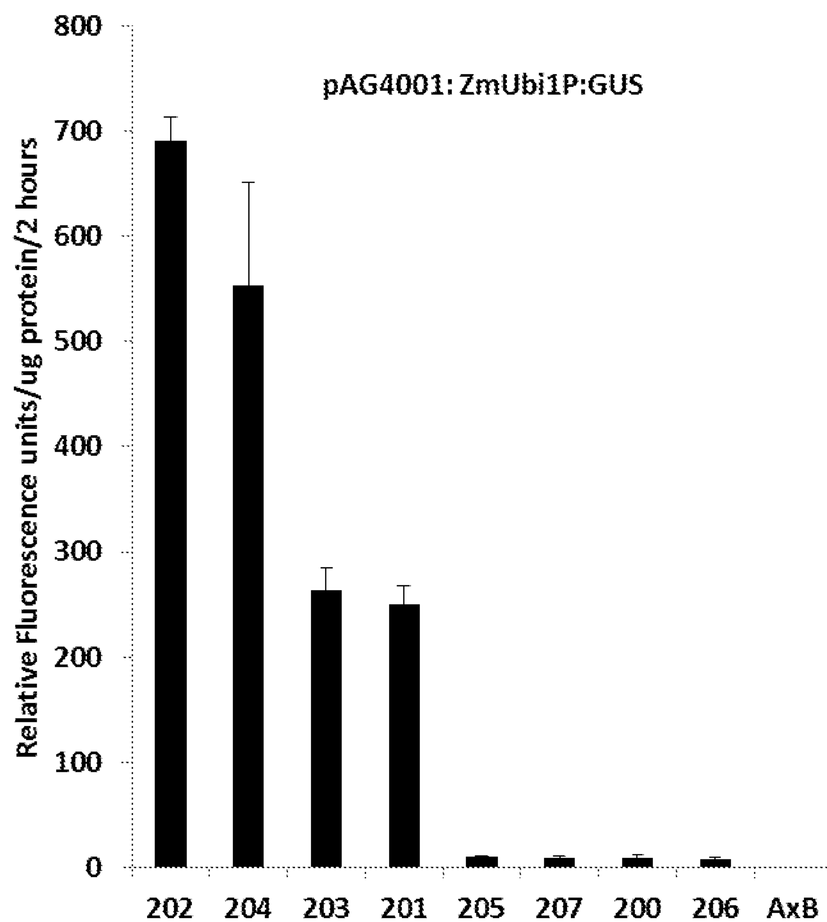
FIG. 14 illustrates distributions of the GUS protein activity values determined by the fluorescent β-glucoronidase assay (MUG) in populations of transgenic maize plants transformed with the construct pAG4001 (ZmUbi1P:GUS).

FIG. 10 shows data from histochemical GUS staining of leaf tissues from the transgenic maize events 4008.7 (derived from transformation with pAG4008), 4010.14 (derived from transformation with pAG4010) and 4009.19 (derived from transformation with pAG4009) containing PvUbi3, PvUbi4s, and PvUbi4 promoters, respectively, in comparison to a) positive control, maize events 4001.204 and 4001.201 (both from pAG4001) containing ZmUbi1 promoter and negative control, and b) a wild type maize plant A×B. As shown, samples refer to the plasmid used to make the transgenic event but with the omitted "pAG" portion of the plasmid identifier, and include the number of the sampled transgenic event. For example, sample 4008.7 indicates that the transgenic event was produced using plasmid pAG4008 and that transgenic event number 8 was sampled. The data show that the level of GUS staining of tissues samples collected from 4008.7, 4010.14, and 4009.1 maize events containing GUS genes driven by PvUbi3, PvUbi4s, and PvUbi4 promoters, respectively, is comparable to that of tissues collected from 4001.204 and 4001.201 positive control plants containing GUS genes under control of strong constitutive promoter ZmUbi1.

B. Quantitative GUS Expression in Maize Leaf Tissues Determined by MUG Assay.

β-glucoronidase activity in samples of the transgenic maize plants was determined using the fluorescent β-glucoronidase assay (MUG). FIGS. 11-14 show data assessing relative fluorescence in samples obtained from a population of plants transformed with pAG4008 containing PvUbi3P:GUS (FIG. 11), pAG4009 containing PvUbi4P:GUS (FIG. 12), pAG4010 containing PvUbi4Ps:GUS (FIG. 13) in comparison to plants transformed with pAG4001 containing ZmUbi1P:GUS (FIG. 14) used as positive controls. Based on the data obtained from MUG GUS assay, the relative promoter efficiency of switchgrass promoter sequences can be ranked as PvUbi4P>PvUbi4Ps>ZmUbi1P>PvUbi3P. The highest expressors transformed with pAG4009 (PvUbi4P) and pAG4010 (PvUbi4Ps) provide approximately 42-64% enhancement of GUS expression activity compared to the highest control expresser transformed with pAG4001 (ZmUbi1P).

C. Tissue-Specific Expression Profiles of PvUbi3 and PvUbi4 Promoters

Figure 15:
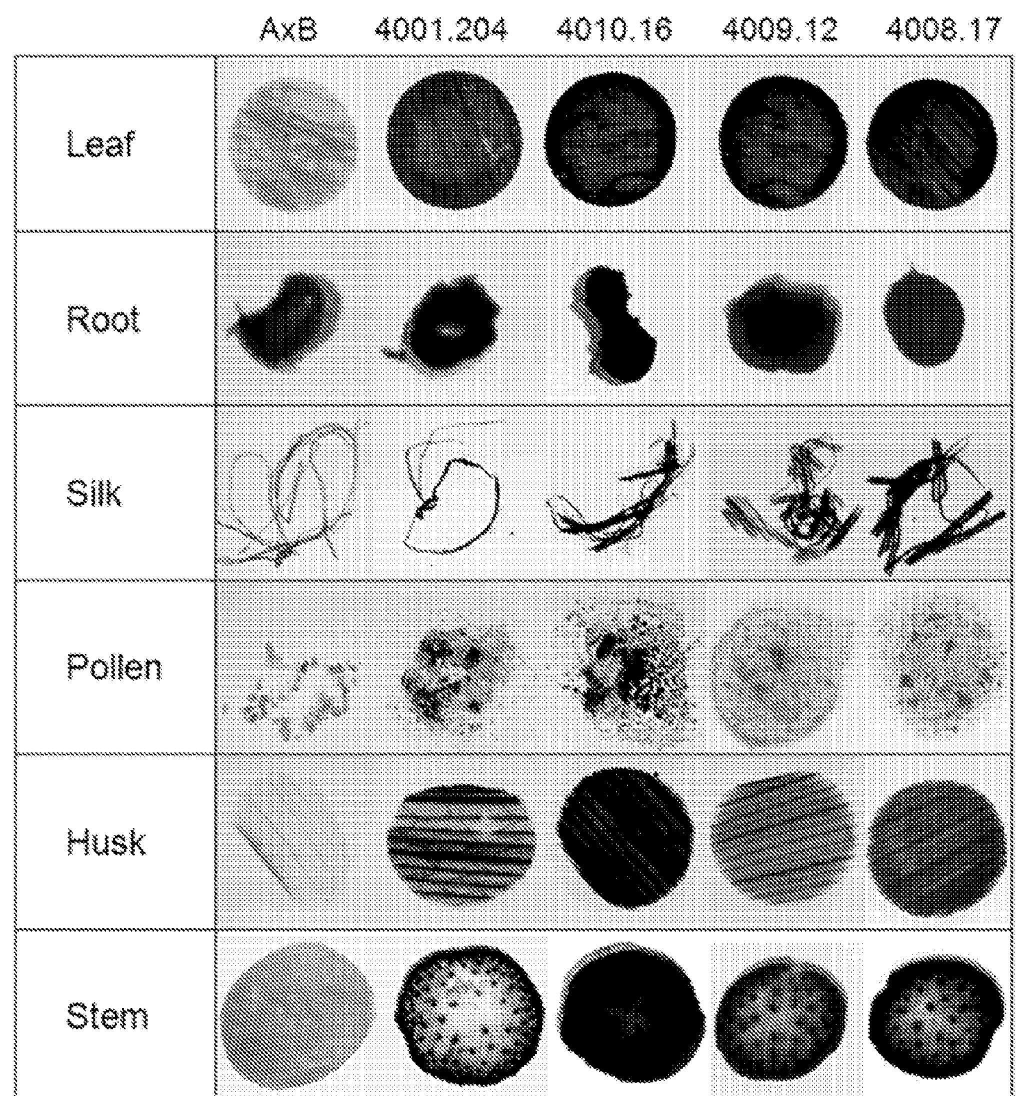
FIG. 15 illustrates tissue-specific expression of PvUbi3 and PvUbi4 promoters.

Samples of various tissues were collected from the earlier identified high expressors 4010.16 (derived from transformation with pAG2010), 4009.12 (derived from transformation with pAG2009) and 4008.17 (derived from transformation with pAG2008); and from control plants 4001.204 (derived from transformation with pAG2001) and A×B. Histochemical GUS assays were performed on each sample to assess tissue-specific GUS expression from the isolated switchgrass promoters. FIG. 15 shows results of GUS assays. Strong GUS staining, indicating expression from PvUbi3P (pAG4008), PvUbi4P (pAG4009), and PvUbi4Ps (pAG4010) in tested samples, was detected in leaf, root, silk, pollen, husk, and stem tissues. The levels of GUS staining intensity provided by PvUbi3P, PvUbi4P, and PvUbi4Ps promoter fragments were at least as high or better than those provided by strong maize Ubi1 promoter. The differences in levels of GUS staining intensity indicate potential differences in activity levels of evaluated promoters.

Example 6: Cellulase Expression

Figure 16:
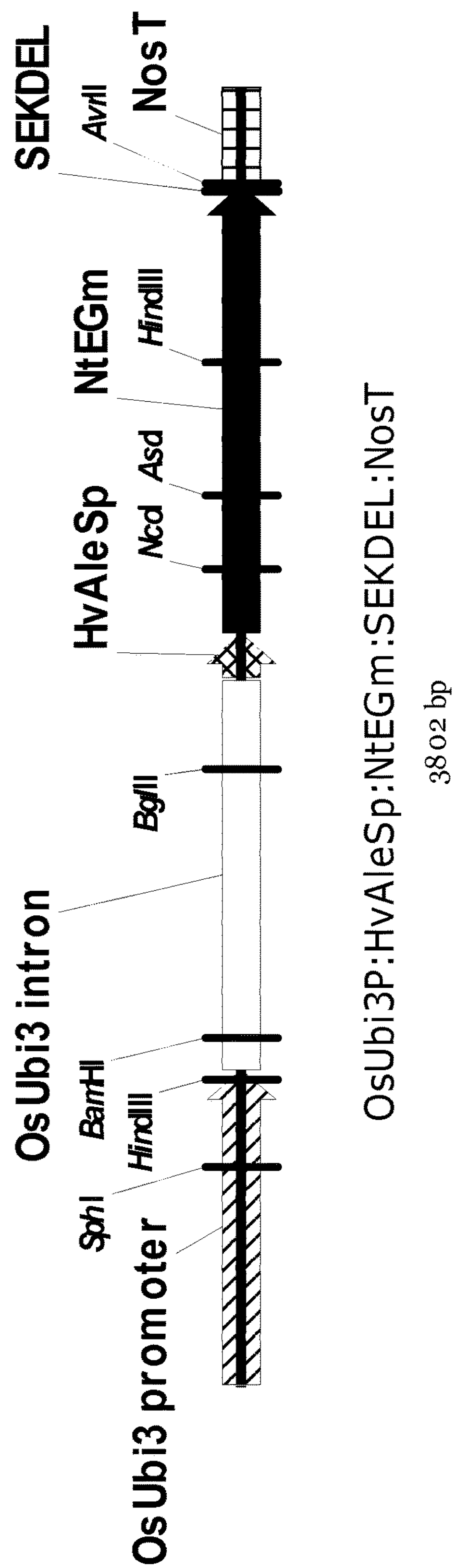
FIG. 16 illustrates a schematic drawing of the NtEGm expression cassette driven by the OsUbi3 promoter.
Figure 17:
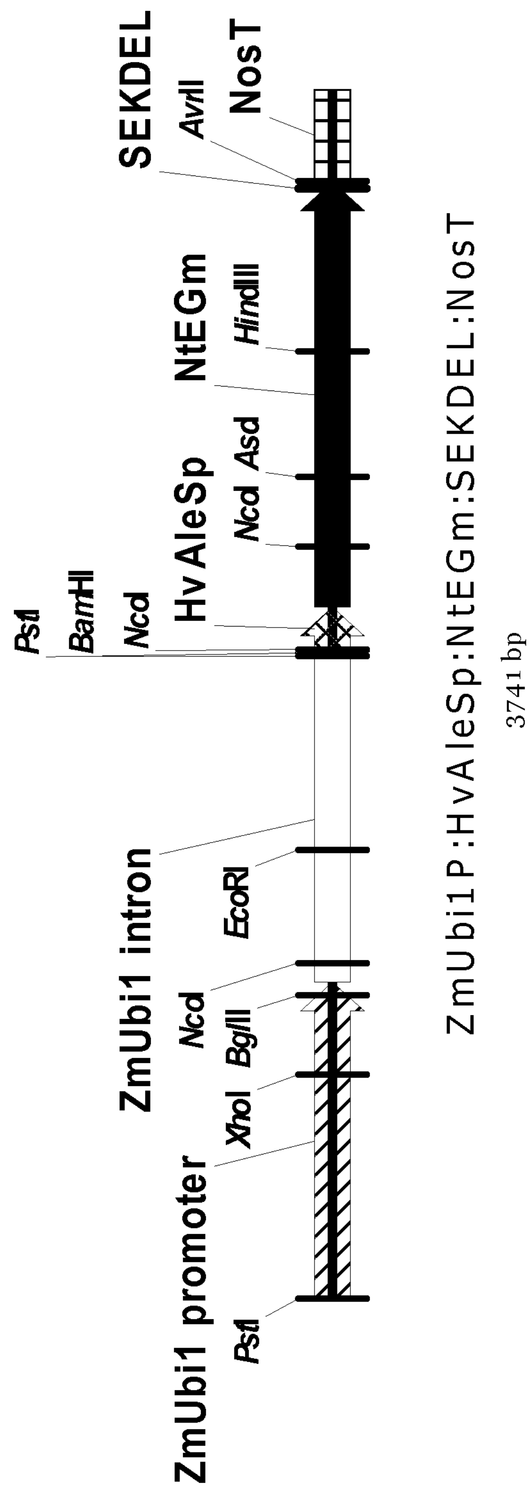
FIG. 17 illustrates a schematic drawing of the NtEGm expression cassette driven by the ZmUbi1 promoter.
Figure 18:
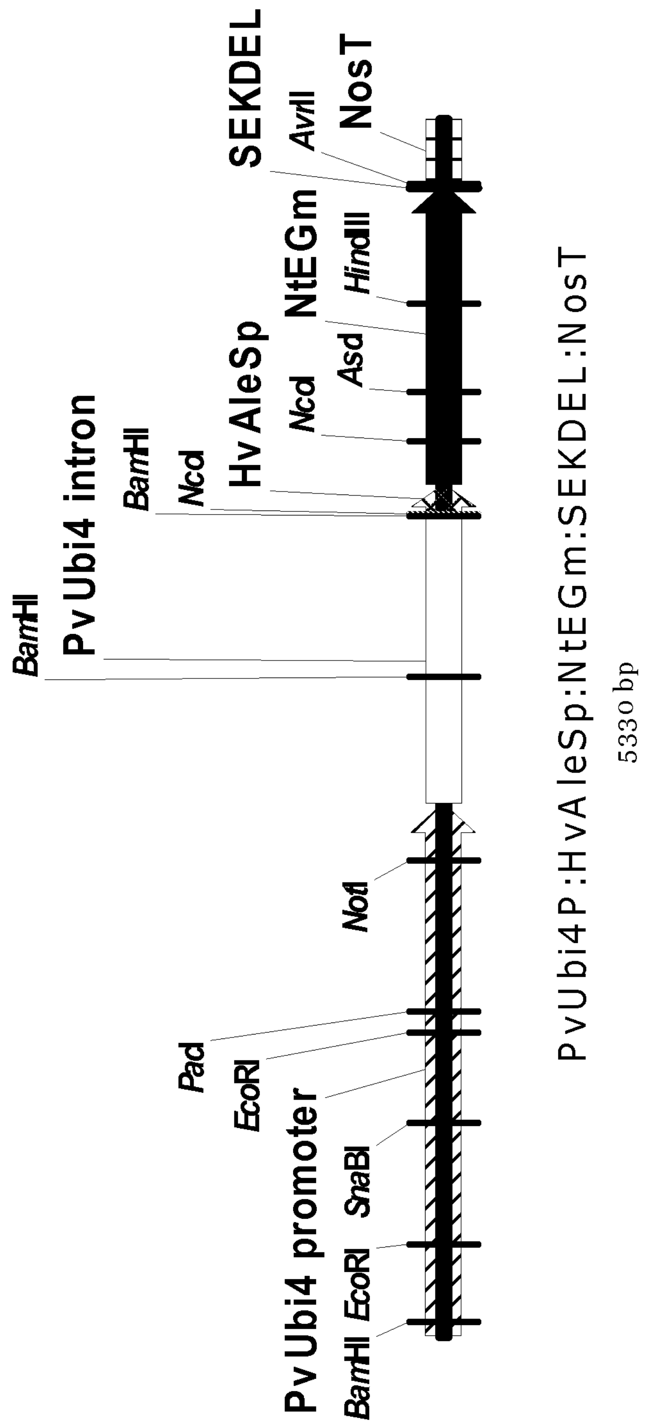
FIG. 18 illustrates a schematic drawing of the NtEGm expression cassette driven by the Pv4Ubi4 promoter.

Maize immature embryos were infected with LBA4404 *Agrobacterium* strains carrying expression pAG400—based vectors carrying endoglucanse expression cassettes. In the OsUbi3-NtEGm expression cassette, the rice ubiquitin (OsUbi3) promoter is fused to the coding sequence for the endoglucanase from *Nasutitermes takasagoensis* (NtEGm), which in turn is fused to the HvAle N-terminal targeting signal and the C-terminal SEKDEL (SEQ ID NO: 36) signal (FIG. 16; SEQ ID NO: 21). In the ZmUbi1-NtEGm expression cassette, the maize ubiquitin promoter (ZmUbi1) is fused to the coding sequence for NtEGm, which in turn is fused to the barley aleuron vacuolar N-terminal targeting signal (HvAle) and the C-terminal SEKDEL (SEQ ID NO: 36) endoplasmic reticulum retention signal (FIG. 17; SEQ ID NO: 22). In the PvUbi4-NtEGm expression cassette, the isolated switchgrass promoter, PvUbi4, is fused to the coding sequence for NtEGm, which in turn is fused to the HvAle N-terminal targeting signal and the C-terminal SEKDEL (SEQ ID NO: 36) signal (FIG. 18; SEQ ID NO: 23). Stably transformed maize plants were generated and efficiency of the promoters was assessed using quantitative Cellazyme assays for detection of endoglucanase protein expression.

A. Expression of Endoglucanase Enzyme in Immature Maize Leaf Tissue.

Leaf samples were collected from transgenic plants approximately one week before pollination. Leaf tissues were also collected from several similarly-aged untransformed (wild type) maize plants (A×B). Protein was extracted from ground leaf tissue in extraction buffer (100 mM sodium phosphate buffer, pH 6.5, 10 mM EDTA, and 0.1% Triton X-100), incubated for 10 minutes at room temperature with gentle shaking, then spun down by centrifugation. Protein concentration in the supernatant was determined using Bradford reagent (Bio-Rad, Hercules, Calif.). For enzyme assays, 10 μl protein extract was diluted in 400 μl 100 mM NaOAc, pH 4.5. Cellazyme tablets (Megazyme, Wicklow, Ireland) were added to each sample. The reactions were incubated at approximately 50° C. for 3 hours, then stopped with 500 μl of 2% Tris base solution. Following centrifugation, the amount of Remazol Brilliant Blue dye that had been released from the Cellazyme tablets into the soluble (supernatant) fraction was quantified by measuring absorbance at 590 nm.

Figure 19:
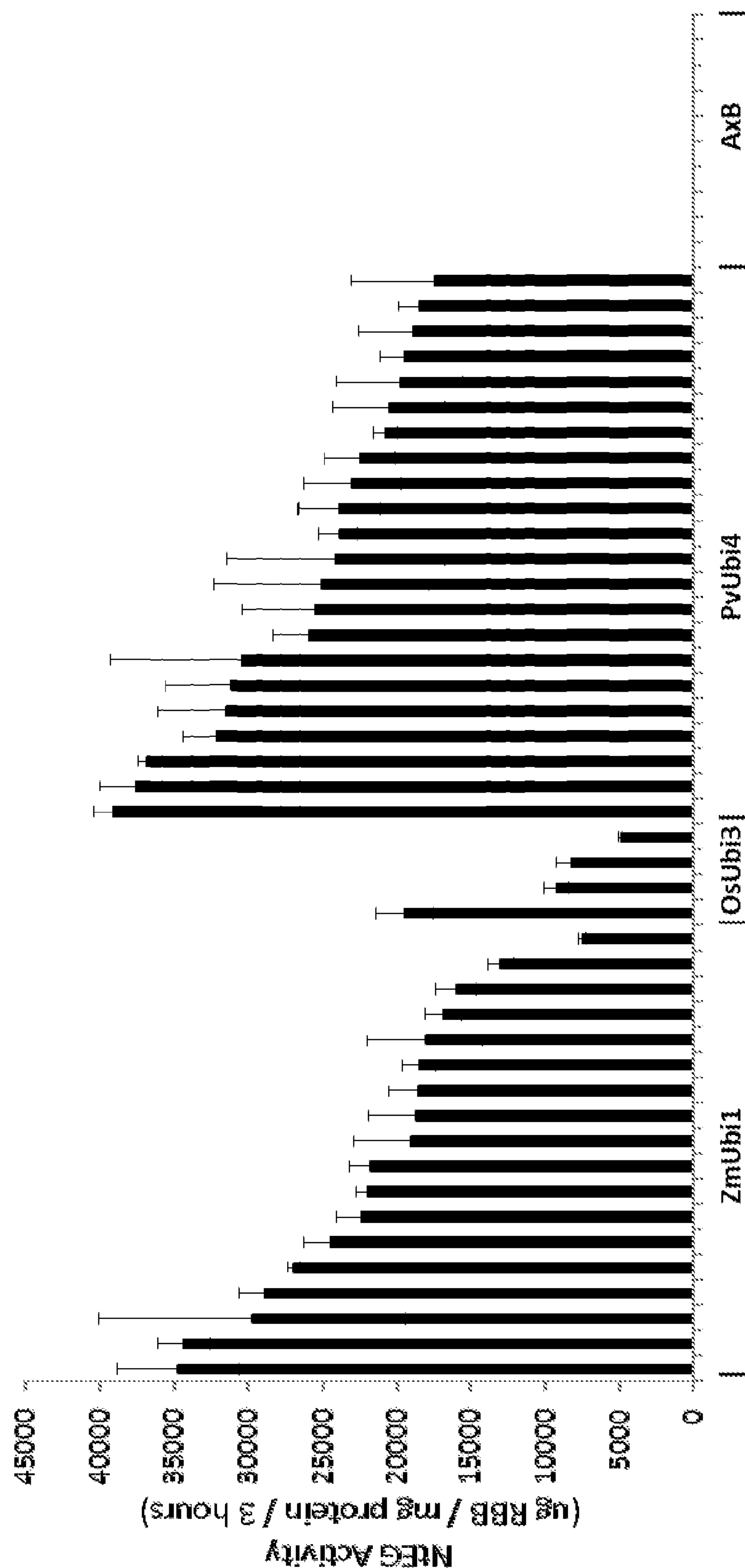
FIG. 19 illustrates NtEGm activity in the samples of green tissue collected one week before pollination from the transgenic maize plants harboring the ZmUbi1-NtEGm (ZmUbi1), OsUbi3-NtEGm (OsUbi3) or PvUbi4-NtEGm (PvUbi4) expression cassettes.

FIG. 19 shows the level of endoglucanase (NtEGm) activity that was detected in leaf tissues from several independently-generated transgenic maize events derived from transformation with vectors carrying NtEGm expression cassettes driven by ZmUb1, OsUbi3 and PvUb4 promoters. The data show that all three promoters support significant levels of the enzyme expression. Examining the enzyme activity across the three populations of plants carrying the three expression cassettes, it appears that the PvUbi4 promoter in the PvUbi4-NtEGm expression cassette supports at least as much and perhaps slightly higher expression of the endoglucanase than does the ZmUbi1 promoter in the ZmUbi1-NtEGm expression cassette, and that both of these promoters outperform the OsUbi3 promoter in the OsUbi3-NtEGm expression cassette.

B. Endoglucanase Enzyme in Corn Stover.

Once plants had matured and senesced, each was dried down, cobs, husks and tassles were removed, and the remaining stover was milled to a fine powder. Protein was extracted from 15 mg milled stover in 500 μl extraction buffer after incubation for 30 minutes at room temperature. The stover was spun down by centrifugation. The supernatant was collected and transferred to a new Eppendorf tube. For enzyme assays, 50 μl protein extract was resuspended in 100 mM NaOAc, pH 4.5, and Cellazyme tablets were added to each enzyme assay tube. The reactions were incubated at 50-60° C. Following a suitable enzyme incubation time, reactions were stopped by adding 1 ml of 2% Tris base to each assay tube. The amount of blue dye was quantified by measuring absorbance of the reaction at 590 nm.

Figure 20:
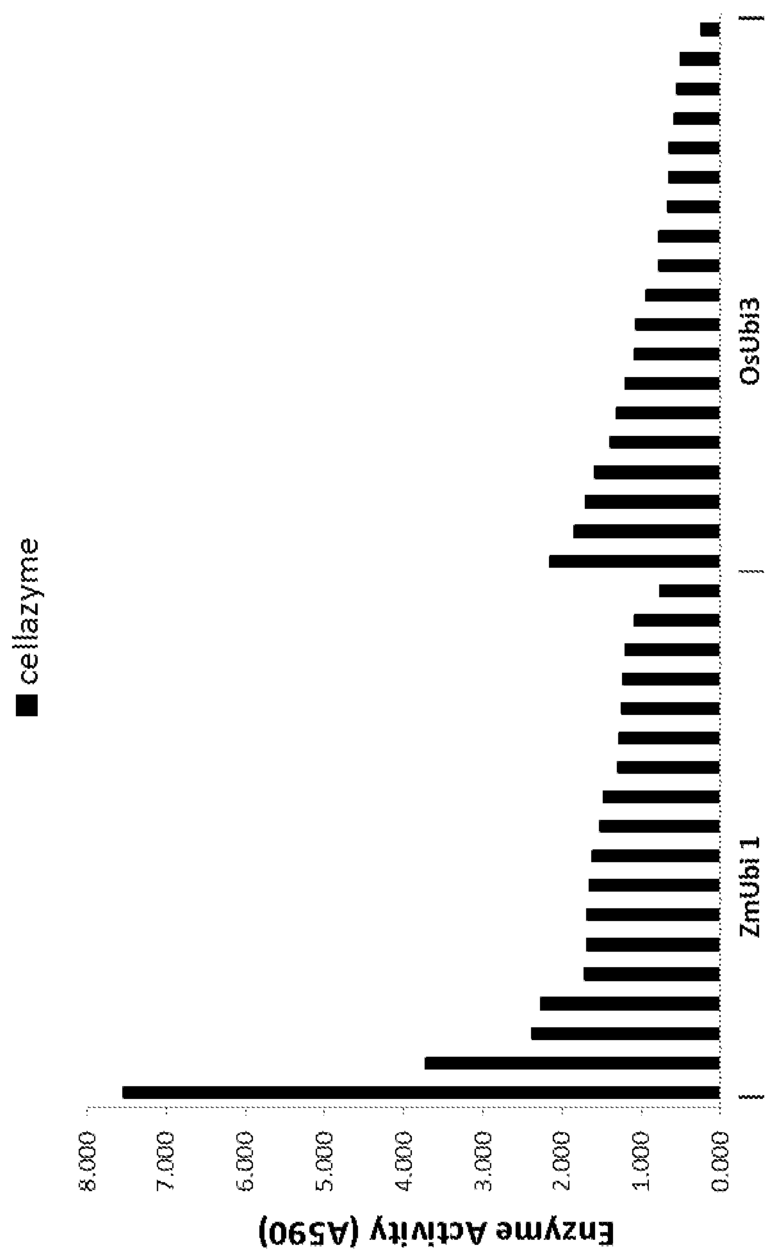
FIG. 20 illustrates NtEGm expression in stover prepared from the transgenic maize plants harboring the ZmUbi1-NtEGm (ZmUbi1) or OsUbi3-NtEGm (OsUbi3) expression cassettes.

FIG. 20 shows the amount of endoglucanase activity that had accumulated in stover from plants that had been transformed with the ZmUbi1-NtEGm and OsUbi3-NtEGm expression cassettes driven by the ZmUbi1, and OsUbi3 promoters, respectively. The range of enzyme accumulation levels among independent transgenic plants appears to have been greater when endoglucanase expression was driven by the ZmUbi1 promoter (ZmUbi1-NtEGm) than when driven by the OsUbi3 promoter (OsUbi3-NtEGm). Stover from plants that had been transformed with ZmUbi1-NtEGm had somewhat higher endoglucanase activity overall (population median=1.58 A590 units) than did stover from plants that had been transformed with OsUbi3-NtEGm (population median=0.95 A590 units). Subsequently, stover samples from plants that had been transformed with PvUbi4-NtEGm were assayed alongside select stover samples from representative ZmUbi1-NtEGm and OsUbi3-NtEGm plants. In these assays, enzyme incubation time was decreased to accommodate the more rapid accumulation of blue dye from the PvUbi4-NtEGm samples.

Figure 21:
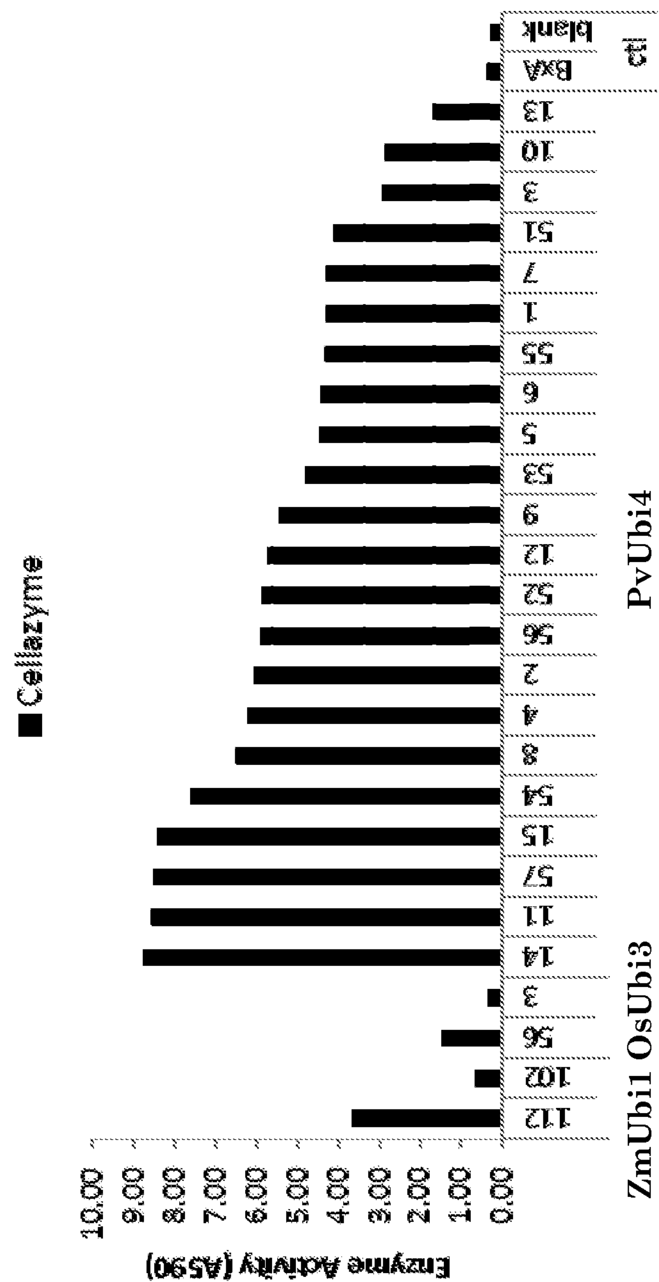
FIG. 21 illustrates NtEGm expression in stover from the transgenic maize plants harboring the ZmUbi1-NtEGm (ZmUbi1), OsUbi3-NtEGm (OsUbi3) and PvUbi4-NtEGm (PvUbi4) expression cassettes.

FIG. 21 shows the amount of endoglucanase activity that had accumulated in stover from representative plants that had been transformed with ZmUbi1-NtEGm and OsUbi3-NtEGm, containing the ZmUbi1, and OsUbi promoters, respectively, an entire population of plants that had been transformed with PvUbi4-NtEGm, containing the PvUbi4 promoter, and a single untransformed (wild-type) plant (B×A). Significant diversity in enzyme accumulation levels was observed among the PvUbi4-NtEGm stover samples. However, the majority of the stover samples in the PvUbi4-NtEGm population had higher enzyme activity than was observed in stover samples from plants that had been transformed with either ZmUbi1-NtEGm or OsUbi3-NtEGm. This suggests that the PvUbi4 promoter can direct higher enzyme expression in maize tissue than can either the ZmUbi1 or OsUbi3 promoters.

Example 7: Isolation of Total RNA and RT-qPCR Analysis of GUS Expression in Transgenic Maize Untransformed maize (wild type A×B) or transgenic maize plants (TO) derived from A×B transformation experiments with the plasmid constructs carrying expression cassettes of the isolated PvUbi3, PvUbi4, PvUbi4s, or maize Ubi1 promoter sequences operably fused to the beta-glucuronidase (GUS) reporter gene containing intron sequence (PvUbi3:GUS in pAG4008, PvUbi4:GUS in pAG4009, PvUbi4s:GUS in pAG4010, and ZmUbi1:GUS in pAG4001 vectors) were sources of green leaf material for total RNA isolation. Collected in the green house and immediately frozen in liquid nitrogen maize green leaf tissues were subsequently disrupted with the TissueLyser instrument (QIAGEN, Valencia, Calif., USA) and used for total RNA isolation using TRIZOL reagent method (Invitrogen, Carlsbad, Calif., USA). Residual genomic DNA in RNA preparations was removed with TURBO DNase using TURBO DNA-free Kit (Invitrogen) and RNA samples were further purified with the RNeasy MinElute Cleanup Kit (QIAGEN). RNA quality and quantity were confirmed spectrophotometrically and 1 μg of total RNA preparation was converted into cDNA with iScript Reverse Transcriptase according to the supplied protocol (Bio-Rad, Hercules, Calif., USA).

Primers for RT-qPCR assays were designed for GUS gene sequence and maize internal control genes using available online Primer3 software (http://fokker.wi.mit.edu/primer3/input.htm). Several maize internal control genes were initially selected from the literature sources and evaluated in regular RT-PCR with the agarose gel electrophoresis analysis. See Coll et al. 2008 Plant Mol. Biol. 68:105; Vyroubalova et al. 2009 Plant Physiol. 151: 433; Sytykiewicz H 2011 Int. J. Mol. Sci. 12: 7982; Manoli et al. 2012 J. Plant Physiol. 169: 807, all of which are incorporated herein by reference as if fully set forth. Limited number of primer combinations for internal control genes were further validated in real time quantitative reverse transcription PCR (RT-qPCR) reactions using standard curve and melt point analysis to ensure specificity of primers and qPCR amplification efficiencies above 90%. Based on the results of these experiments, two maize genes Actin (Gene Bank Accession U60508) and cytosolic GAPDH (GapC) glyceraldehyde-3-phosphate dehydrogenase (Gene Bank Accession X07156) were selected as internal gene controls for RT-qPCR based GUS gene expression analysis. The following forward and reverse primers at 300 nM final concentration were used in all subsequent RT-qPCR experiments: a) ob1576: 5'-TCAGGAAGTGATGGAGCATC-3' (SEQ ID NO: 30) and ob1580 5'-CACACAAACGGTGATACGTAC-3' (SEQ ID NO: 31) for GUS; b) ob1555 5'-CAACTGCCCAGCAATGTATG-3' (SEQ ID NO: 32) and ob1556 5'-CGTAGATAGGGACGGTGTGG-3' (SEQ ID NO: 33) for Actin; c) ob1567 5'-CGCTGAGTATGTCGTGGAGT-3' (SEQ ID NO: 34) and ob1568 5'-AACAACCTTCTTGGCACCAC-3' (SEQ ID NO: 35) for GAPDH.

RT-qPCR reactions to assess relative GUS expression levels from the isolated PvUbi3 and PvUbi4 promoters were performed in 96-well plates using CFX96 instrument (Bio-Rad). Each 12.5 μl reaction contained 1 ng of corresponding cDNA template and was performed in triplicates using iQ™ SYBR® Green Supermix according to manufacturer's recommendations (Bio-Rad). Relative GUS gene expression levels in experimental samples were subsequently normalized against expression of maize internal control genes Actin and GADPH and compared to the level of GUS gene expression in a reference sample pAG4001.201 (ZmUbi1P:GUS), which was set to 1. All calculations for relative GUS gene expression levels were performed by ΔΔCt method using the CFX Manager Software Version 2.1 (Bio-Rad).

Figure 22:
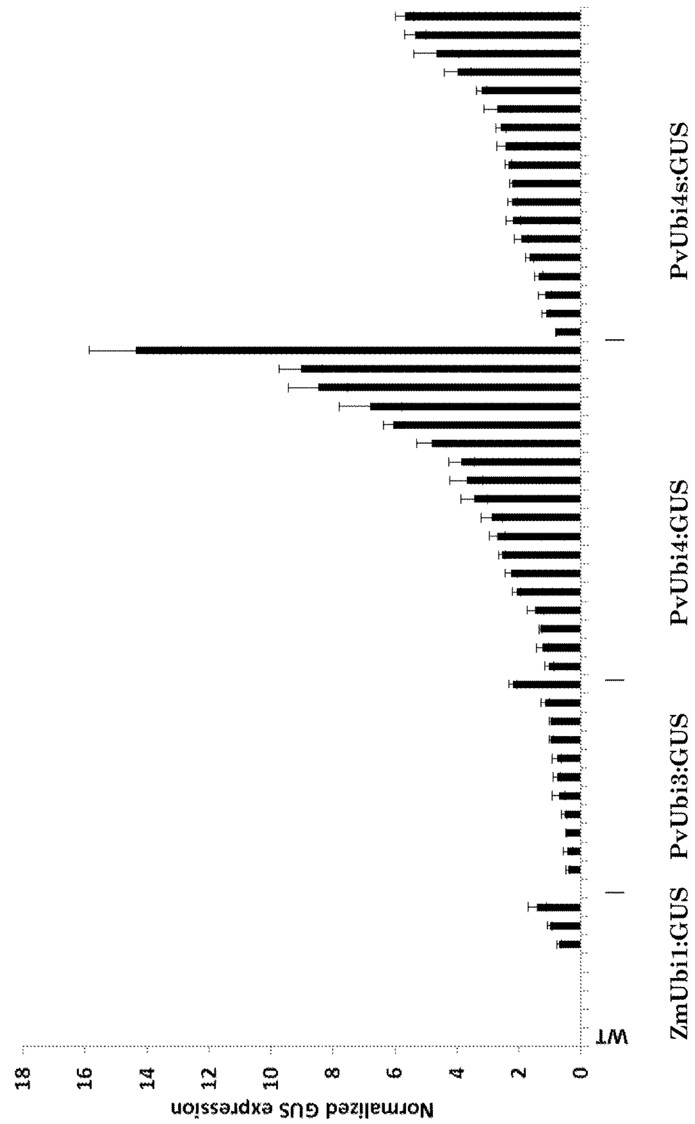
FIG. 22 illustrates gene expression from switchgrass promoters based on the RT-qPCR analysis.

Relative GUS gene expression levels from the isolated switchgrass promoters PvUbi3, PvUbi4 and PvUbi4s are summarized in FIG. 22 in comparison to the GUS gene expression conditioned by the maize Ubi1 promoter, which is a known strong and commonly used promoter for gene expression studies in monocotyledonous plant species. The switchgrass PvUbi3 promoter provided GUS gene expression levels similar to those of maize Ubi1 promoter, while both the PvUbi4 and PvUbi4s switchgrass promoters were superior to the Ubi1 promoter driving GUS gene expression up to 7- or 3-fold higher respectively. The PvUbi3 and PvUbi4s (shortened version of the PvUbi4) promoters have almost identical nucleotide sequences with the exception of the "unique" 653 bp sequence that is present in the PvUbi4s promoter. This "unique" sequence originates from the PvUbi4 promoter and contains several putative promoter enhancing CAAT elements (positions −1345 to −1342, −1020 to −1017, −907 to −904, −866 to −863) as well as predicted cis-acting motifs that could be functionally important such as protein-binding site AACATTTTCACT (SEQ ID NO; 27; position −851 to −840) and two extra MYB transcription factor binding sites CAACGG (positions −1227 to −1222 and −1195 to −1190). Further expression analysis studies involving the "unique" 653 bp sequence should shed additional light on its functional importance and possible role for the significant enhancement of the strength of the PvUbi4s and PvUbi4 switchgrass promoters.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A genetic construct comprising an isolated nucleic acid promoter comprising a sequence selected from the group consisting of: SEQ ID NO: 1 (PvUbi3), SEQ ID NO: 2 (PvUbi4), and SEQ ID NO: 3 (PvUbi4s), operably linked to a heterologous nucleic acid.

2. The genetic construct of claim 1, wherein the heterologous nucleic acid encodes a polypeptide that confers an agronomic trait.

3. The genetic construct of claim 1, wherein the heterologous nucleic acid encodes a selectable marker.

4. The genetic construct of claim 1, wherein the heterologous nucleic acid encodes a cell wall degrading enzyme.

5. The genetic construct of claim 4, wherein the cell wall degrading enzyme is an intein-modified cell wall degrading enzyme.

6. The genetic construct of claim 4, wherein the cell wall degrading enzyme is selected from the group consisting of: an endoglucanase, an exoglucanase, a xylanase, and a feruloyl esterase.

7. The genetic construct of claim 5, wherein the intein-modified cell wall degrading enzyme is selected from the group consisting of: an intein-modified endoglucanase, an intein-modified exoglucanase, an intein-modified xylanase and an intein-modified feruloyl esterase.

8. The genetic construct of claim 4, wherein the heterologous nucleic acid further comprises at least one DNA sequence encoding a targeting peptide fused to the cell wall degrading enzyme.

9. The genetic construct of claim 8, wherein the genetic construct comprises SEQ ID NO: 23.

10. A method for producing a heterologous protein in a plant comprising:

contacting a plant with a genetic construct comprising an isolated nucleic acid promoter operably linked to a heterologous polynucleotide encoding a protein, wherein the isolated nucleic acid promoter comprises a sequence selected from the group consisting of: SEQ ID NO: 1 (PvUbi3), SEQ ID NO: 2 (PvUbi4), and SEQ ID NO: 3 (PvUbi4s);

selecting a transformed plant comprising the genetic construct;

cultivating the transformed plant under conditions suitable for production of the heterologous protein.

11. The method of claim 10, wherein the protein is a cell wall degrading enzyme.

12. The method of claim 11, wherein the cell wall degrading enzyme is an intein-modified cell wall degrading enzyme.

13. The method of claim 11, wherein the cell wall degrading enzyme is selected from the group consisting of: an endoglucanase, an exoglucanase, a xylanase, and a feruloyl esterase.

14. The method of claim 12, wherein the intein-mothfied cell wall degrading enzyme is selected from the group consisting of: an intein-modified endoglucanase, an intein-modified exoglucanase, an intein-modified xylanase and an intein-modified feruloyl esterase.

15. The method of claim 10, wherein the genetic construct is stably integrated into a genome of the transformed plant.

16. The method of claim 10, wherein the genetic construct is expressed transiently in the transformed plant.

17. The method of claim 10, the method further comprising obtaining a progeny or a descendant of the transformed plant, wherein the genetic construct is stably integrated into the genome of the transformed plant and the progeny or descendant comprises the genetic construct.

18. The method of claim 10, the method further comprising obtaining a seed of the transformed plant, wherein the genetic construct is stably integrated into the genome of the transformed plant and the seed includes comprises the genetic construct.

19. A method for producing a heterologous protein comprising:

obtaining a transgenic plant that comprises a genetic construct comprising an isolated nucleic acid promoter operably linked to a heterologous polynucleotide encoding a protein, wherein the isolated nucleic acid promoter comprises a sequence selected from the group consisting of: SEQ ID NO: 1 (PvUbi3), SEQ ID NO: 2 (PvUbi4), and SEQ ID NO: 3 (PvUbi4s), wherein the protein is expressed in the transgenic plant; and isolating the protein.

20. The method of claim 19, wherein the protein is a cell wall degrading enzyme.

21. The method of claim 20, wherein the cell wall degrading enzyme is an intein-modified cell wall degrading enzyme.

22. A transformed plant comprising a genetic construct that comprises an isolated nucleic acid promoter comprising a sequence selected from the group consisting of: SEQ ID NO: 1 (PvUbi3), SEQ ID NO: 2 (PvUbi4), and SEQ ID NO: 3 (PvUbi4s) operably linked to a heterologous nucleic acid to be expressed.

23. The transformed plant of claim 22, wherein the promoter further comprises a DNA element selected from the group consisting of: SEQ ID NO: 4, SEQ ID NO: 5, SEQ ID NO: 6, SEQ ID NO: 7, SEQ ID NO: 9, and SEQ ID NO: 10.

24. The transformed plant of claim 22, wherein the heterologous nucleic acid encodes a polypeptide that confers an agronomic trait.

25. The transformed plant of claim 22, wherein the heterologous nucleic acid encodes a cell wall degrading enzyme.

26. The transformed plant of claim 25, wherein the cell wall degrading enzyme is an intein-modified cell wall degrading enzyme.

27. The transformed plant of claim 25, wherein the cell wall degrading enzyme is selected from the group consisting of: an endoglucanase, an exoglucanase, a xylanase, and a feruloyl esterase.

28. The transformed plant of claim 26, wherein the intein-modified cell wall degrading enzyme is selected from the group consisting of: an intein-modified endoglucanase, an intein-modified exoglucanase, an intein-modified xylanase and an intein-modified feruloyl esterase.

* * * * *